(12) United States Patent
Montierth et al.

(10) Patent No.: US 7,238,085 B2
(45) Date of Patent: Jul. 3, 2007

(54) METHOD AND APPARATUS TO PROCESS SUBSTRATES WITH MEGASONIC ENERGY

(75) Inventors: Garry L. Montierth, Fremont, CA (US); Henry R. Miranda, Fremont, CA (US); Sharyl L. Maraviov, Pleasanton, CA (US); Ahmed A. Busnaina, Ashland, MA (US)

(73) Assignee: P.C.T. Systems, Inc., Fremont, CA (US)

( * ) Notice: Subject to any disclaimer, the term of this patent is extended or adjusted under 35 U.S.C. 154(b) by 0 days.

(21) Appl. No.: 10/861,793

(22) Filed: Jun. 4, 2004

(65) Prior Publication Data

US 2005/0003737 A1 Jan. 6, 2005

Related U.S. Application Data

(60) Provisional application No. 60/476,845, filed on Jun. 6, 2003, provisional application No. 60/476,527, filed on Jun. 6, 2003, provisional application No. 60/530,194, filed on Dec. 16, 2003, provisional application No. 60/510,054, filed on Oct. 8, 2003, provisional application No. 60/546,383, filed on Feb. 20, 2004, provisional application No. 60/517,255, filed on Nov. 3, 2003, provisional application No. 60/528,941, filed on Dec. 10, 2003, provisional application No. 60/525,435, filed on Nov. 26, 2003.

(51) Int. Cl.
*B24B 1/00* (2006.01)
(52) U.S. Cl. .............................. 451/36; 451/37; 451/910
(58) Field of Classification Search ................... 451/5, 451/165, 910; 134/1, 1.3, 920, 1.2

See application file for complete search history.

(56) References Cited

U.S. PATENT DOCUMENTS 3,973,152 A    8/1976   Karplus (Continued)

FOREIGN PATENT DOCUMENTS

JP           05-013396           1/1993

(Continued)

OTHER PUBLICATIONS

Ting, Aili; "The Influence of Wafer Elasticity on Acoustic Waves During LIGA Development" Fluid and Thermal Science Department, Sandia National Laboratories; Aug. 2003.

(Continued)

*Primary Examiner*—Dung Van Nguyen
(74) *Attorney, Agent, or Firm*—Townsend and Townsend and Crew LLP

(57) ABSTRACT

A variety of techniques may be employed, alone or in combination, to enhance contact between a processed substrate and applied megasonic energy. In accordance with one embodiment of the new invention, the vibration plate is brought into intimate contact with one surface of the substrate, while cleaning or processing fluid contacts the other. In accordance with an alternative embodiment of the present invention, a reflecting surface may be provided to cause emanated energy to be reflected back into the near field and make it more uniform. In accordance with another alternative embodiment of the present invention, energy may be transferred across a substrate bounded on both sides by liquid with incidence of megasonic energy that is either normal to the substrate surface or within a critical range of incident angles. In yet another embodiment, generated dilatational waves may be converted to surface waves prior to contacting the substrate.

55 Claims, 70 Drawing Sheets

U.S. PATENT DOCUMENTS

| | | | |
|---|---|---|---|
| 3,983,515 A | 9/1976 | Mitchell et al. | |
| 4,326,553 A | 4/1982 | Hall | |
| 4,336,719 A | 6/1982 | Lynnworth | |
| 4,373,401 A | 2/1983 | Baumoel | |
| 4,602,184 A | 7/1986 | Meitzler | |
| 4,836,684 A * | 6/1989 | Javorik et al. | 366/114 |
| 4,979,994 A | 12/1990 | Dusault et al. | |
| 5,013,366 A | 5/1991 | Jackson et al. | |
| 5,037,481 A | 8/1991 | Bran | |
| 5,090,432 A | 2/1992 | Bran | |
| 5,148,823 A | 9/1992 | Bran | |
| 5,203,798 A | 4/1993 | Watanabe et al. | |
| 5,279,316 A | 1/1994 | Miranda | |
| 5,337,446 A | 8/1994 | Smith et al. | |
| 5,379,785 A * | 1/1995 | Ohmori et al. | 134/184 |
| 5,462,604 A * | 10/1995 | Shibano et al. | 134/1 |
| 5,497,662 A | 3/1996 | Dykes | |
| 5,560,362 A | 10/1996 | Sliwa et al. | |
| 5,625,249 A | 4/1997 | Grant | |
| 5,734,588 A | 3/1998 | Rose et al. | |
| 5,865,894 A | 2/1999 | Reynolds | |
| 5,894,092 A | 4/1999 | Lindgren | |
| 5,927,308 A * | 7/1999 | Kim | 134/172 |
| 5,931,173 A * | 8/1999 | Schiele | 134/57 R |
| 5,932,077 A | 8/1999 | Reynolds | |
| 6,016,821 A | 1/2000 | Puskas | |
| 6,021,789 A | 2/2000 | Akatsu et al. | |
| 6,026,832 A | 2/2000 | Sato et al. | |
| 6,039,059 A | 3/2000 | Bran | |
| 6,041,799 A | 3/2000 | Aoki | |
| 6,041,938 A | 3/2000 | Senn | |
| 6,098,643 A | 8/2000 | Miranda | |
| 6,119,367 A * | 9/2000 | Kamikawa et al. | 34/401 |
| 6,136,724 A | 10/2000 | Hansen | |
| 6,138,694 A | 10/2000 | Hansen | |
| 6,138,698 A | 10/2000 | Tanaka et al. | |
| 6,140,744 A | 10/2000 | Bran | |
| 6,148,833 A | 11/2000 | Tang | |
| 6,153,533 A | 11/2000 | Senn | |
| 6,209,555 B1 | 4/2001 | Struven | |
| 6,220,259 B1 | 4/2001 | Brown et al. | |
| 6,241,162 B1 | 6/2001 | Takahashi et al. | |
| 6,269,511 B1 | 8/2001 | Andreas | |
| 6,273,100 B1 | 8/2001 | Andreas | |
| 6,276,370 B1 * | 8/2001 | Fisch et al. | 134/1.3 |
| 6,295,999 B1 | 10/2001 | Bran | |
| 6,314,974 B1 * | 11/2001 | Schuler et al. | 134/184 |
| 6,343,609 B1 | 2/2002 | Kim | |
| 6,385,805 B2 | 5/2002 | Konishi et al. | |
| 6,395,096 B1 | 5/2002 | Madanshetty | |
| 6,398,937 B1 | 6/2002 | Menini | |
| 6,412,499 B1 | 7/2002 | Tang | |
| 6,460,551 B1 * | 10/2002 | Fishkin et al. | 134/147 |
| 6,463,938 B2 | 10/2002 | Bran | |
| 6,513,365 B1 | 2/2003 | Bruetting | |
| 6,523,557 B2 | 2/2003 | Struven | |
| 6,539,952 B2 | 4/2003 | Itzkowitz | |
| 6,554,003 B1 * | 4/2003 | Birang et al. | 134/1.3 |
| 6,554,688 B2 | 4/2003 | Lacy | |
| 6,582,525 B2 | 6/2003 | Bergman | |
| 6,585,898 B1 | 7/2003 | Ekberg | |
| 6,591,845 B1 | 7/2003 | Bergman | |
| 6,595,224 B2 | 7/2003 | Miranda | |
| 6,599,402 B2 | 7/2003 | Dordi | |
| 6,619,301 B2 | 9/2003 | Kobayashi | |
| 6,619,305 B1 | 9/2003 | Sharma | |
| 6,745,494 B2 | 6/2004 | Bergman | |
| 6,880,560 B2 * | 4/2005 | Ching et al. | 134/1.3 |
| 6,904,637 B2 * | 6/2005 | Sugarman | 15/77 |
| 7,004,016 B1 * | 2/2006 | Puskas | 73/64.53 |
| 2001/0013355 A1 | 8/2001 | Busnania | |
| 2001/0017146 A1 | 8/2001 | Berman | |
| 2001/0027797 A1 | 10/2001 | Yoskioka | |
| 2001/0047810 A1 | 12/2001 | Farber | |
| 2002/0011257 A1 | 1/2002 | Degendt | |
| 2002/0025760 A1 | 2/2002 | Lee | |
| 2002/0043893 A1 | 4/2002 | Puskas | |
| 2002/0086620 A1 | 7/2002 | Lacy | |
| 2002/0086622 A1 | 7/2002 | Radman | |
| 2002/0088478 A1 | 7/2002 | Degendt | |
| 2002/0108631 A1 | 8/2002 | Madanshetty | |
| 2002/0115024 A1 | 8/2002 | Oya | |
| 2002/0115025 A1 | 8/2002 | Noda | |
| 2002/0139390 A1 | 10/2002 | Okano | |
| 2002/0144708 A1 | 10/2002 | Kashkoush | |
| 2002/0153806 A1 | 10/2002 | Beck | |
| 2002/0157685 A1 | 10/2002 | Hayamizu | |
| 2002/0157686 A1 | 10/2002 | Kenny | |
| 2002/0173156 A1 | 11/2002 | Yates | |
| 2002/0173166 A1 | 11/2002 | Christenson | |
| 2002/0195133 A1 | 12/2002 | Miranda et al. | |
| 2003/0024547 A1 | 2/2003 | Bran | |
| 2003/0028287 A1 | 2/2003 | Puskas | |
| 2003/0061675 A1 | 4/2003 | Sugarman | |
| 2003/0062071 A1 | 4/2003 | Sorbo | |
| 2003/0064586 A1 | 4/2003 | Merchant | |
| 2003/0088995 A1 | 5/2003 | Bergman | |
| 2003/0106566 A1 | 6/2003 | Danese | |
| 2003/0106572 A1 | 6/2003 | Nishiki | |
| 2003/0106846 A1 | 6/2003 | Shaw | |
| 2003/0111092 A1 | 6/2003 | Kashkoush | |
| 2003/0116174 A1 | 6/2003 | Park | |
| 2003/0116176 A1 | 6/2003 | Rothman | |
| 2003/0116491 A1 | 6/2003 | Yamazaki | |
| 2003/0133851 A1 | 7/2003 | Kitahara | |
| 2003/0134518 A1 | 7/2003 | Novak | |
| 2003/0136334 A1 | 7/2003 | Novak | |
| 2003/0136422 A1 | 7/2003 | Scranton | |
| 2003/0136429 A1 | 7/2003 | Scranton | |
| 2003/0139057 A1 | 7/2003 | Novak | |
| 2003/0141784 A1 | 7/2003 | Bran | |
| 2003/0168946 A1 | 9/2003 | Beck | |
| 2003/0178049 A1 | 9/2003 | Yoon | |
| 2003/0183246 A1 | 10/2003 | Boyd | |
| 2003/0192571 A1 | 10/2003 | Yeo | |
| 2003/0196679 A1 | 10/2003 | Cotte | |
| 2003/0200986 A1 | 10/2003 | Yeo | |
| 2003/0205240 A1 | 11/2003 | Bergman | |
| 2003/0205559 A1 | 11/2003 | Hansen | |
| 2003/0234029 A1 | 12/2003 | Bergman | |
| 2004/0007257 A1 | 1/2004 | Park | |
| 2004/0009740 A1 | 1/2004 | Verhaverke | |
| 2004/0016442 A1 | 1/2004 | Cawlfield | |
| 2004/0020512 A1 | 2/2004 | Hosack | |
| 2004/0020781 A1 | 2/2004 | Dordi | |
| 2004/0020898 A1 | 2/2004 | Uziel | |
| 2004/0025911 A1 * | 2/2004 | Yeo et al. | 134/113 |
| 2004/0053503 A1 | 3/2004 | Brask | |
| 2004/0055621 A1 | 3/2004 | McDermott | |
| 2004/0061199 A1 | 4/2004 | Brask | |
| 2004/0062874 A1 | 4/2004 | Kim | |
| 2004/0067639 A1 | 4/2004 | Pai | |
| 2004/0069319 A1 | 4/2004 | Boyd | |
| 2004/0072448 A1 | 4/2004 | Brask | |
| 2004/0074521 A1 | 4/2004 | Shih | |
| 2004/0077172 A1 | 4/2004 | Brask | |
| 2004/0084318 A1 | 5/2004 | Cohen | |
| 2004/0103919 A1 | 6/2004 | Kenny | |
| 2004/0149308 A1 | 8/2004 | Korbler | |

| | | |
|---|---|---|
| 2004/0152319 A1 | 8/2004 | Kanagawa et al. |
| 2004/0168706 A1* | 9/2004 | Boyd et al. .................. 134/1.3 |
| 2004/0178476 A1 | 9/2004 | Brask |

FOREIGN PATENT DOCUMENTS

JP  07-211684  11/1995

OTHER PUBLICATIONS

Buckin et al., Ultrasonic Waves and Material Analysis: Recent Advances and Future Trends, LabPlus International, Jun. 2002.

McClements, Ultrasonic Measurements in Particle Size Analysis, Ultrasonic Measurements in Particle Size Analysis, Encyclopedia of Analytical Chemistry, pp. 1-8.

* cited by examiner

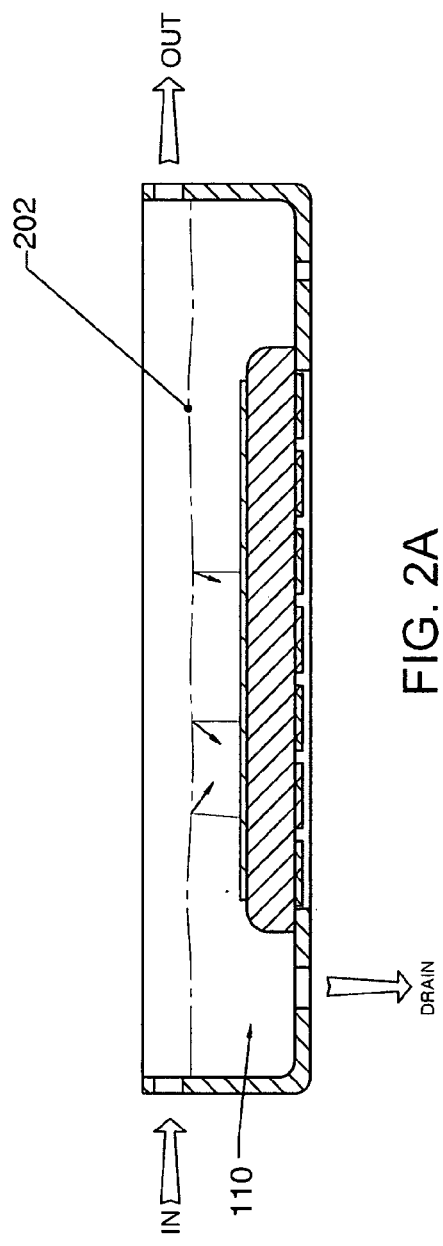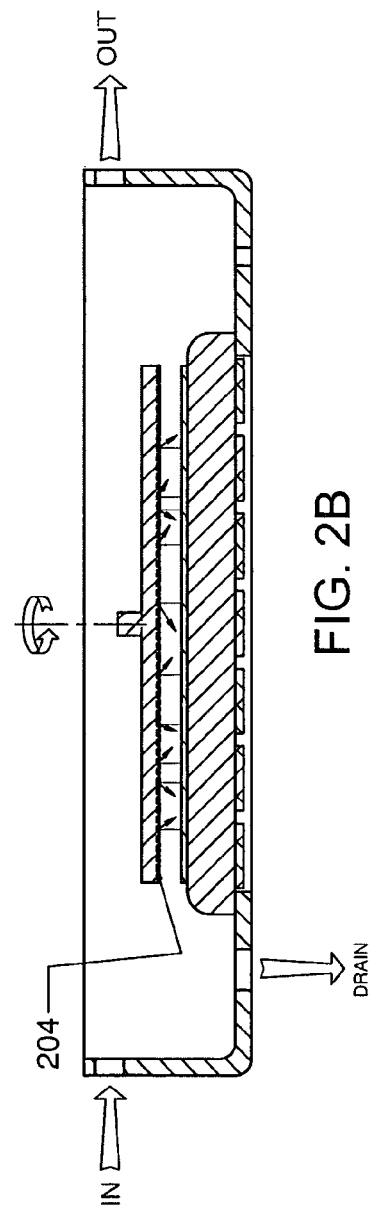

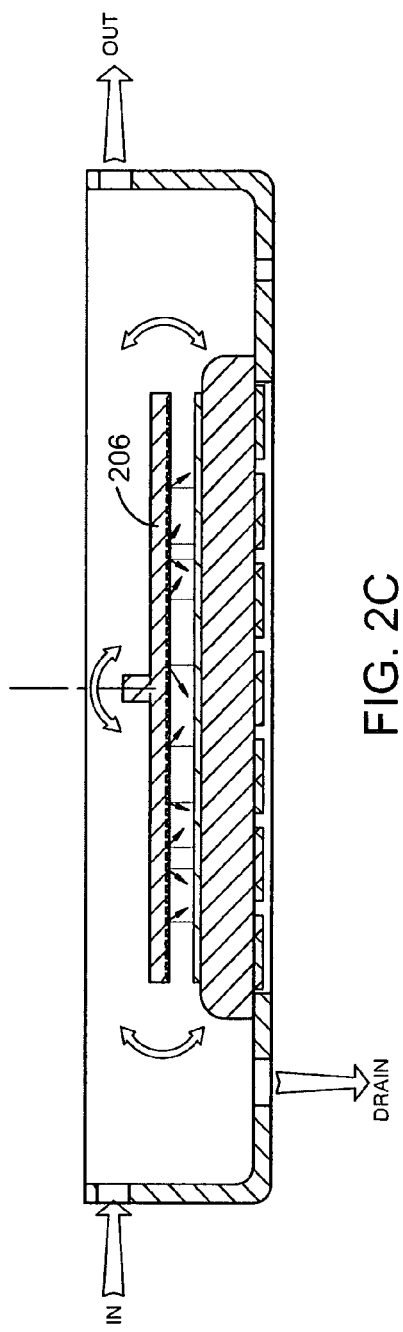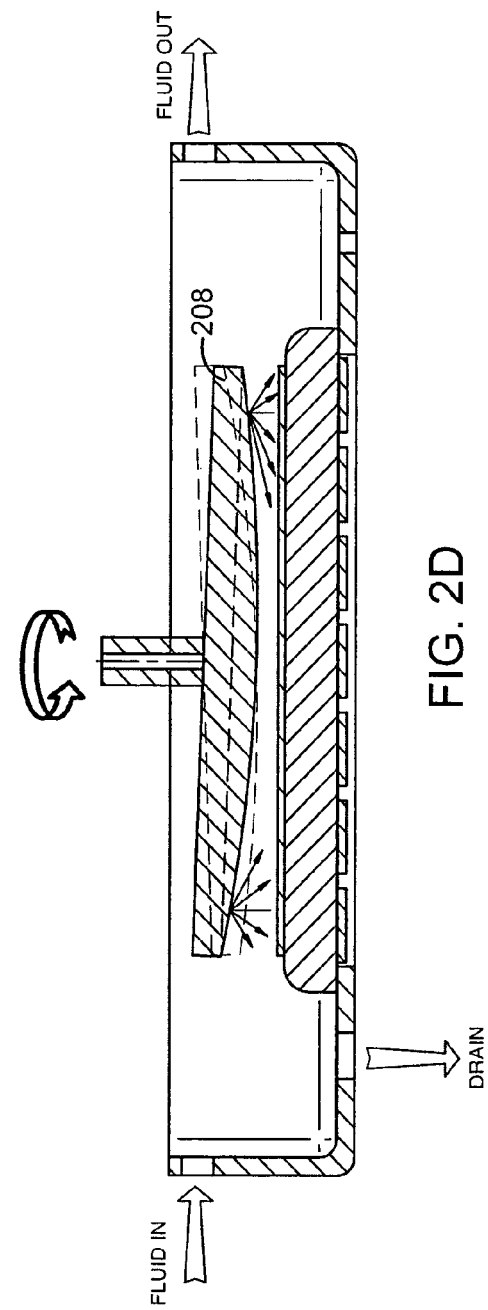

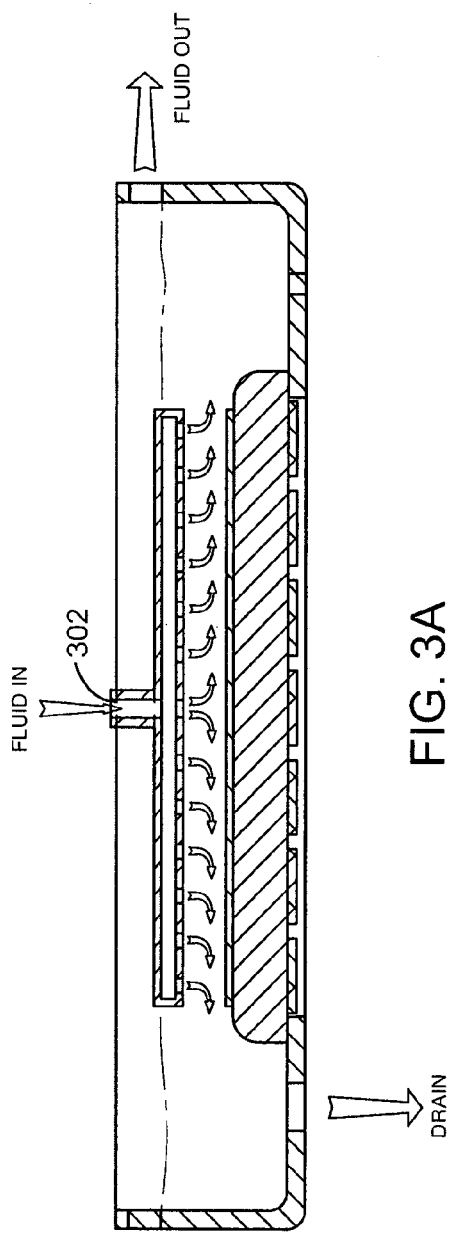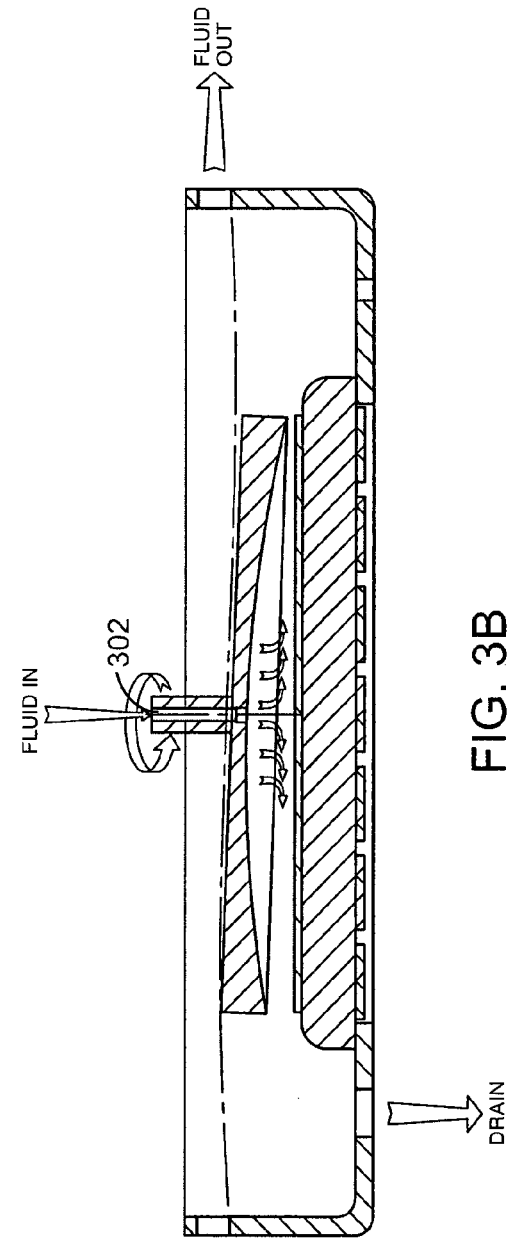

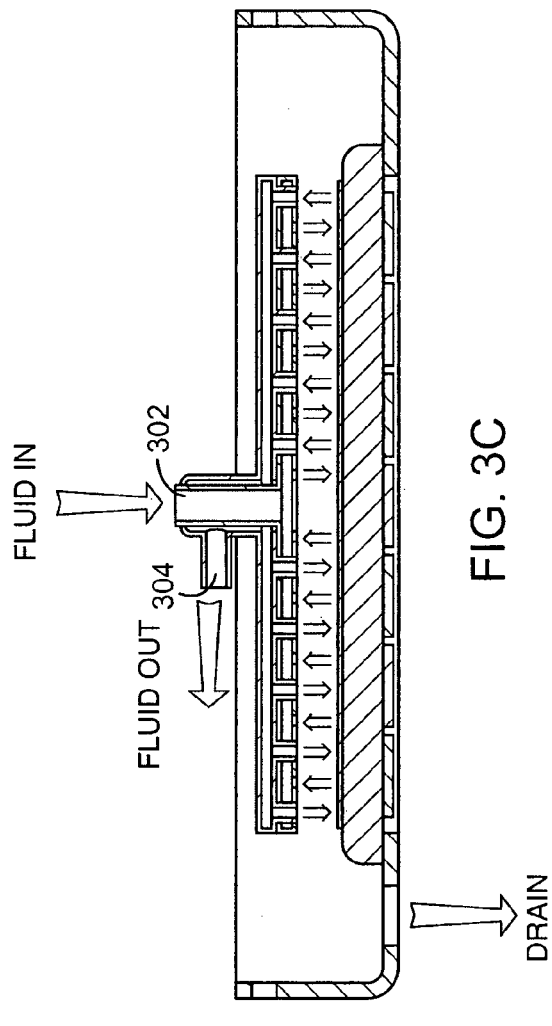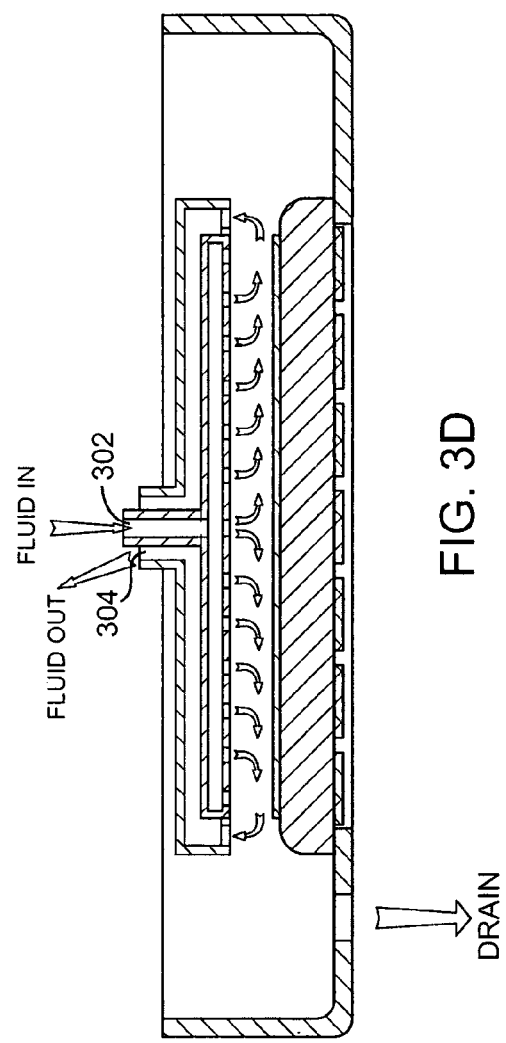

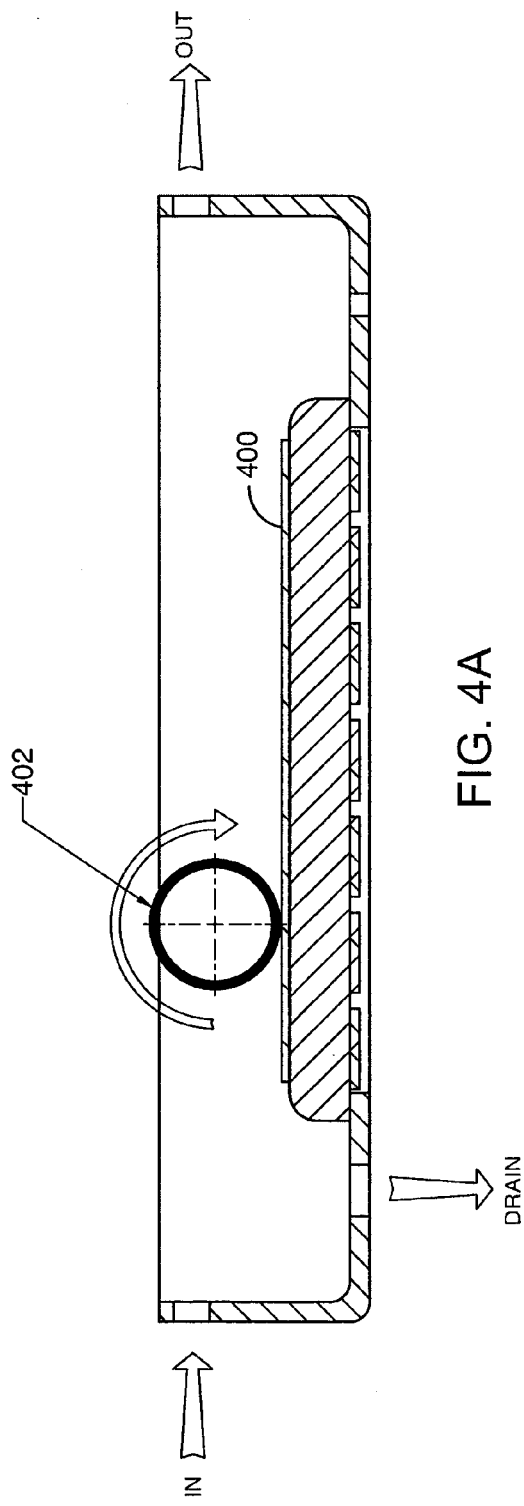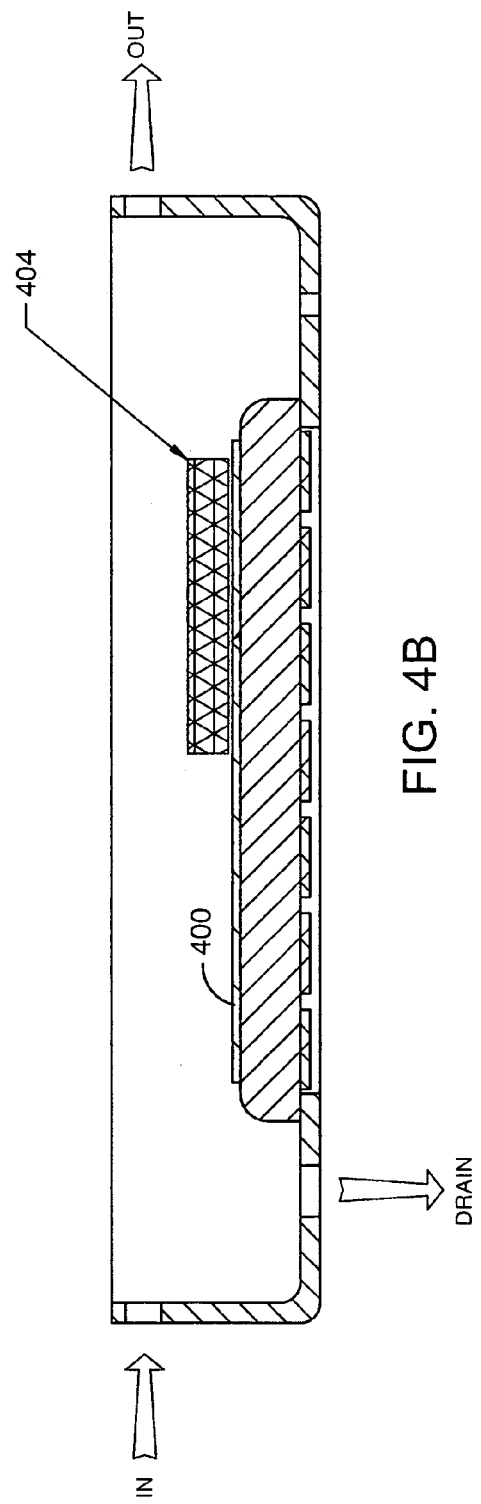

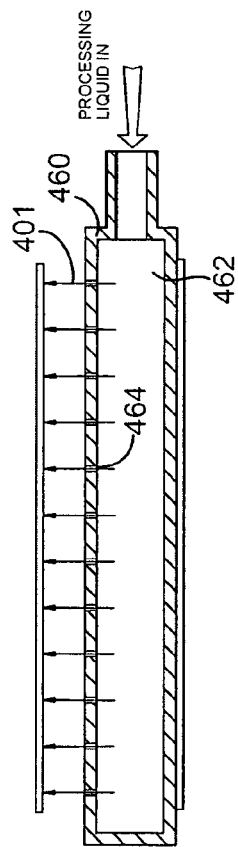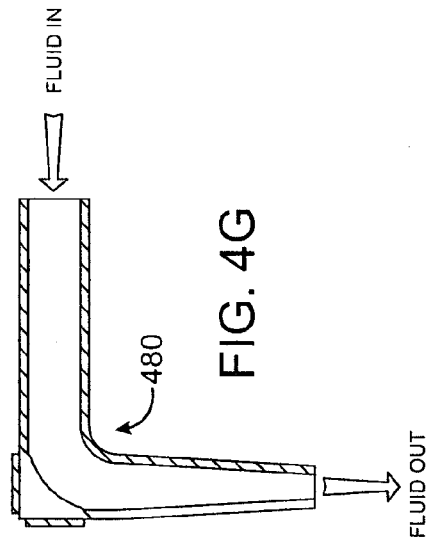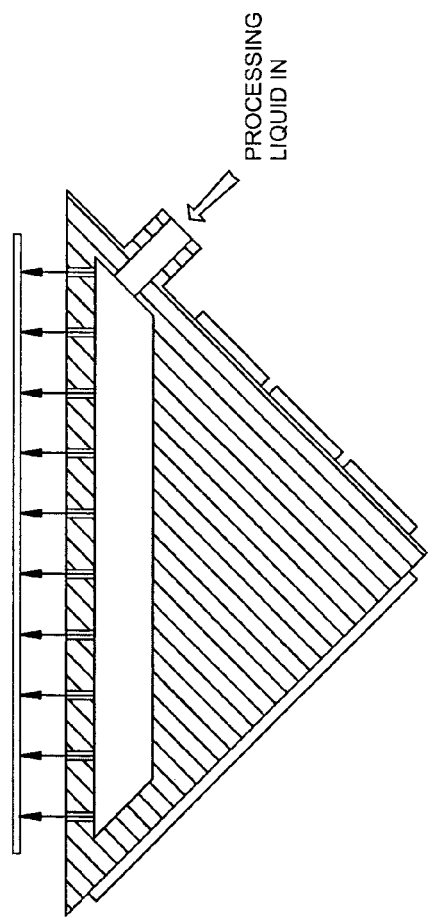

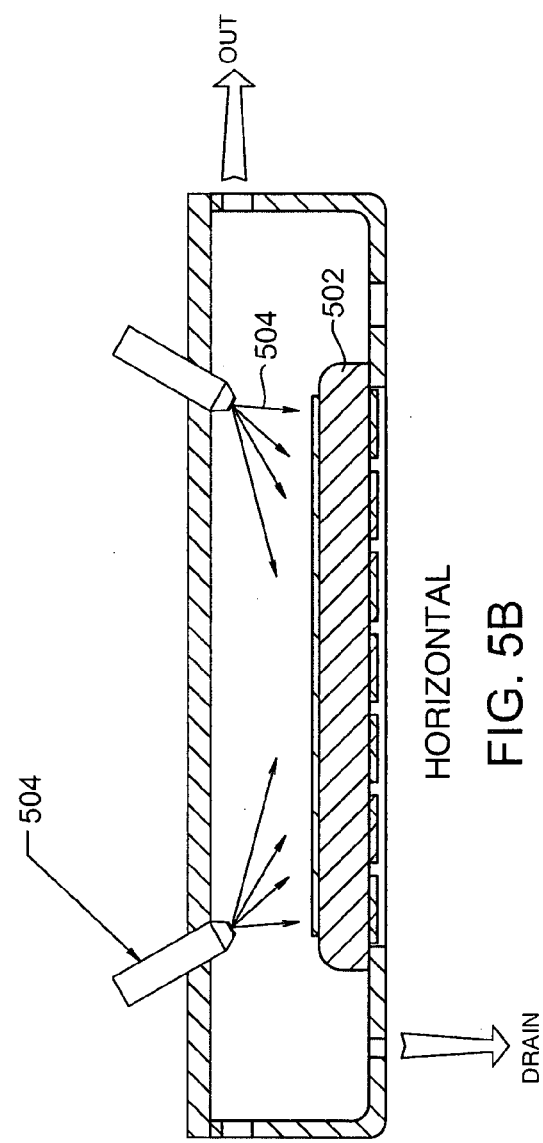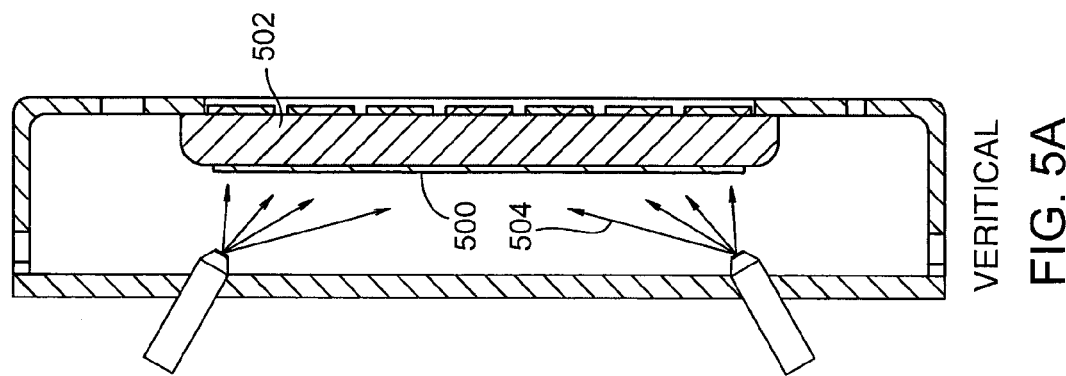
FIG. 5A VERTICAL
FIG. 5B HORIZONTAL

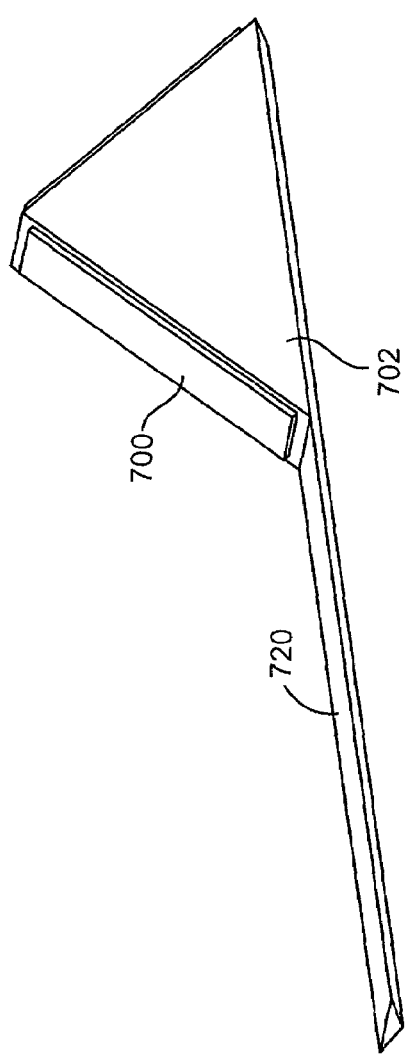
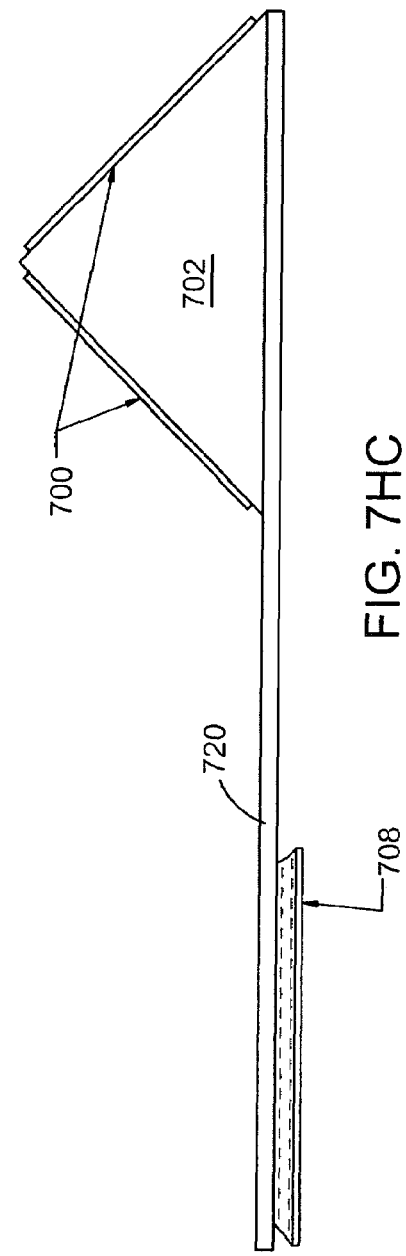
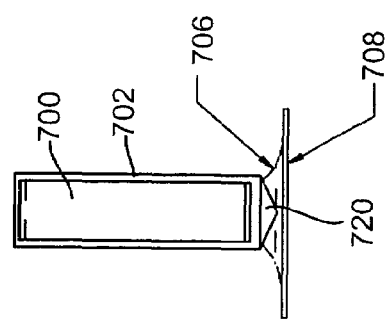

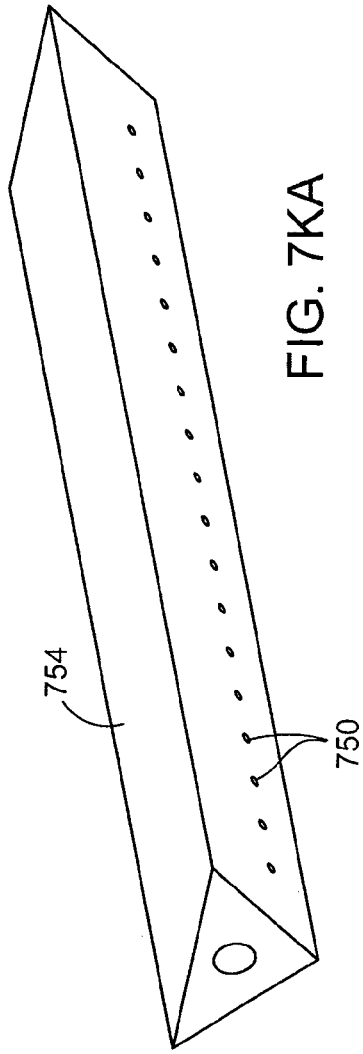
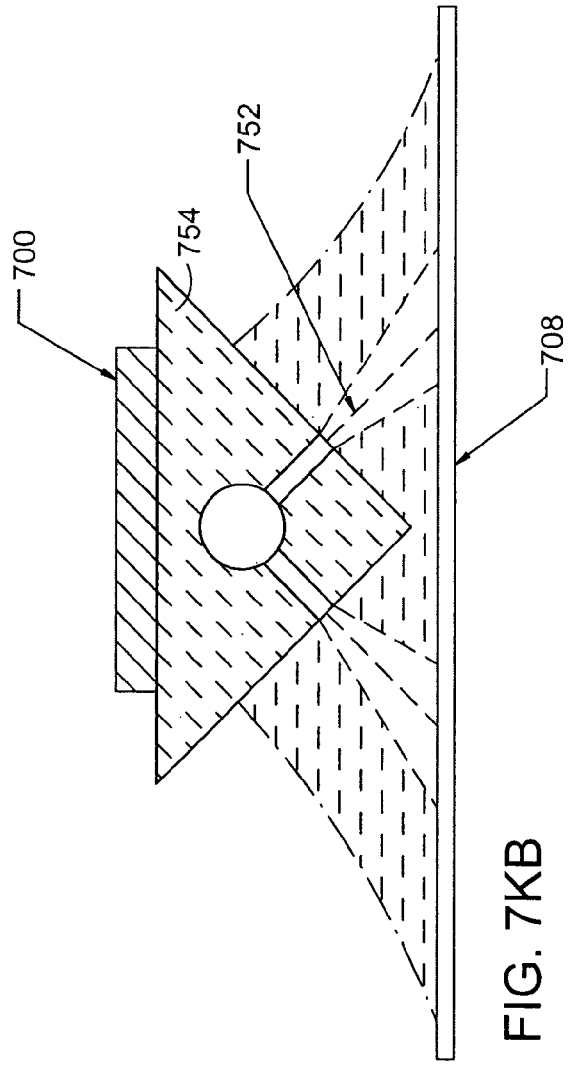

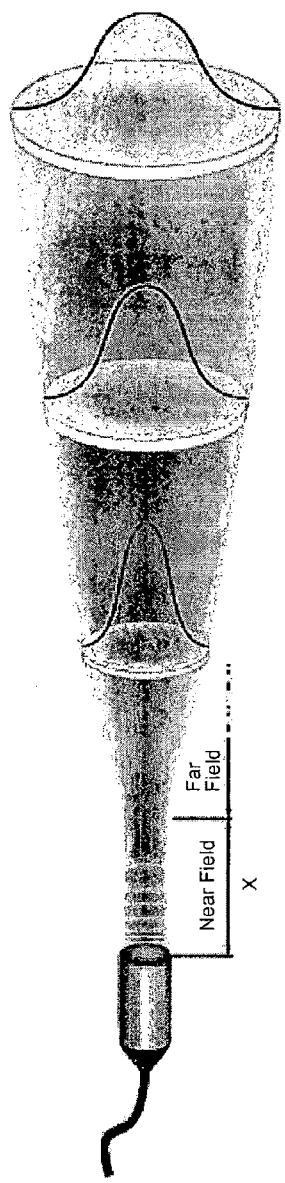
FIG. 29A
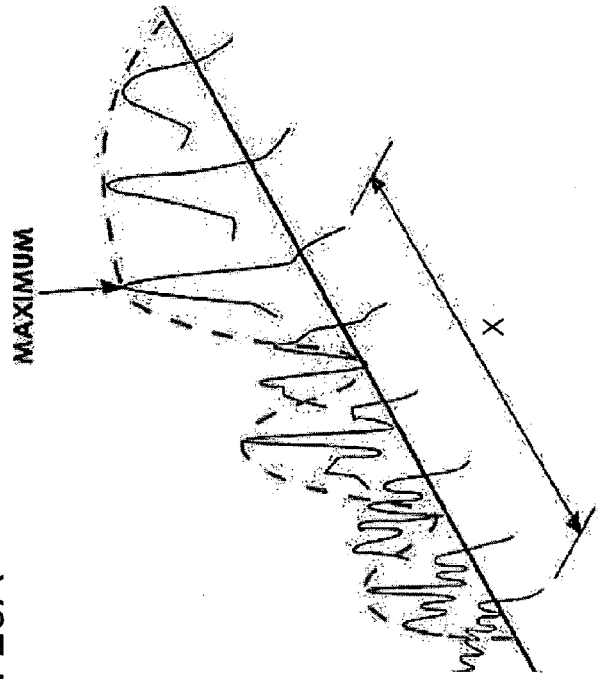
FIG. 29B

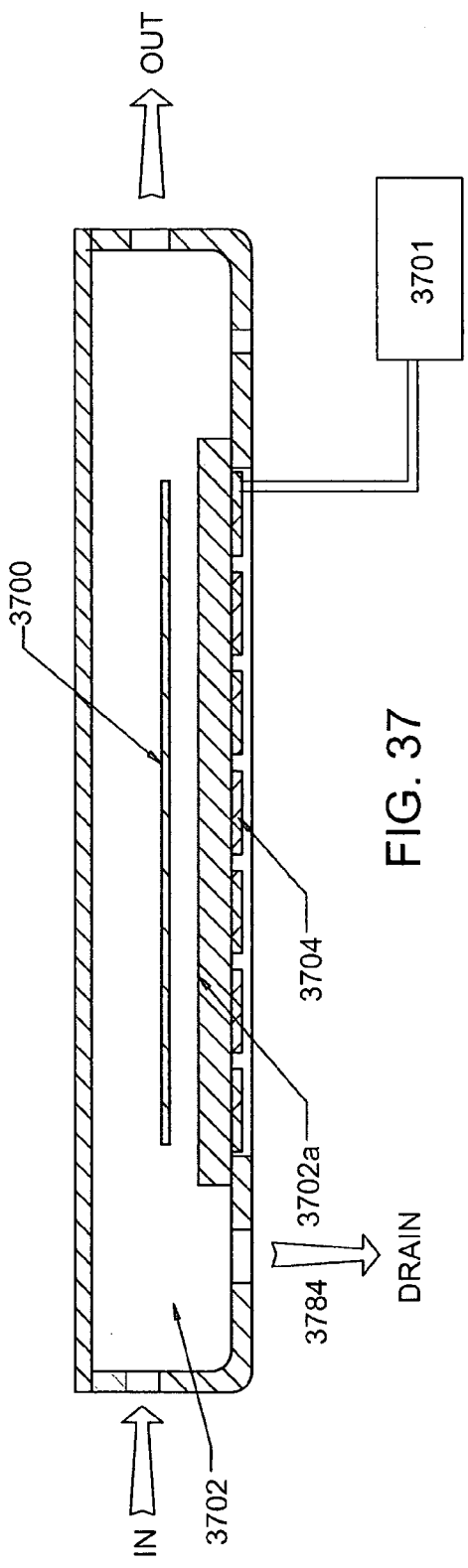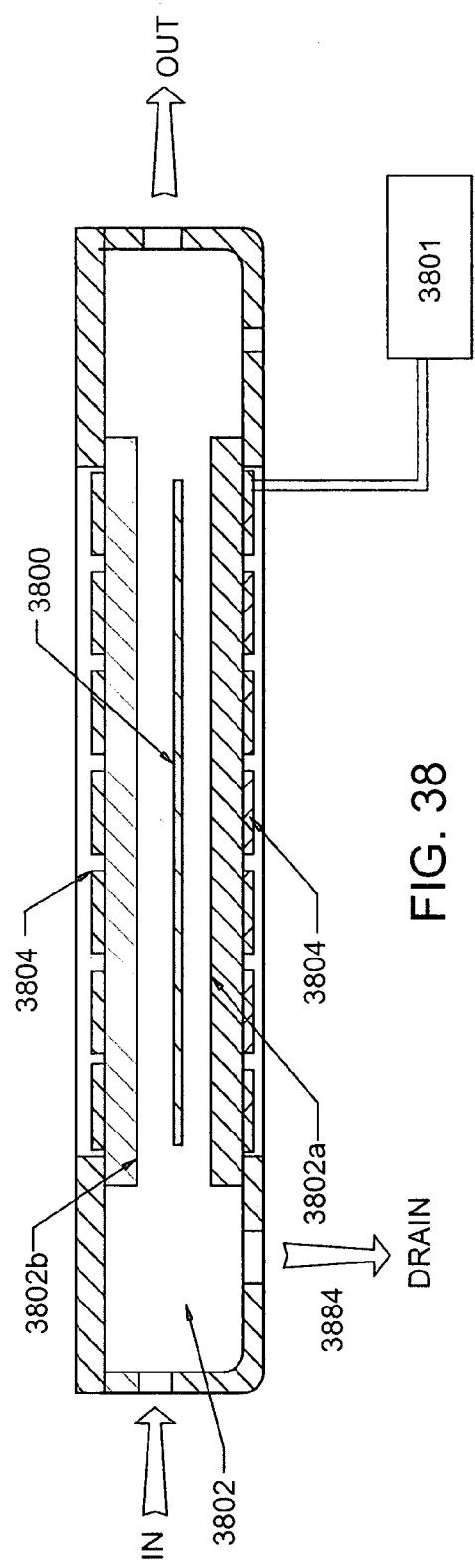

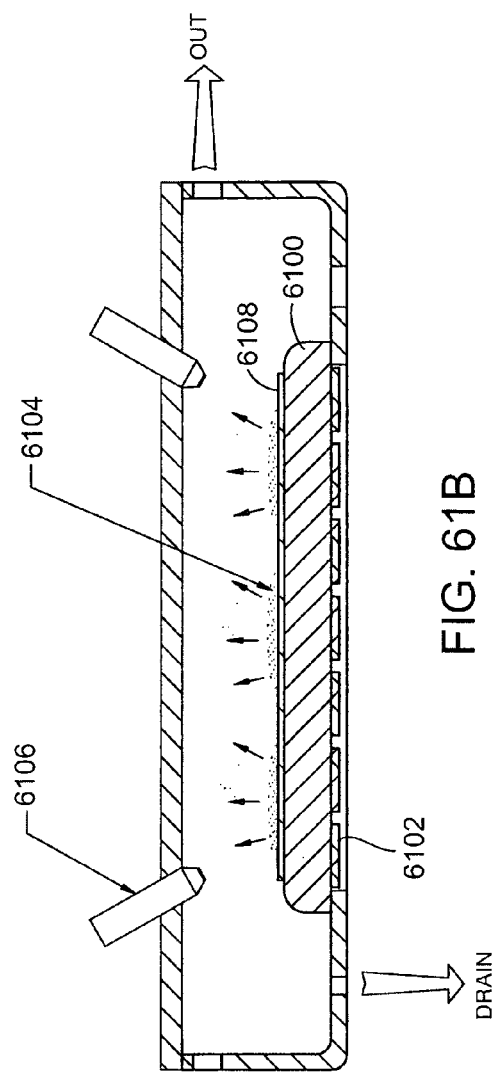
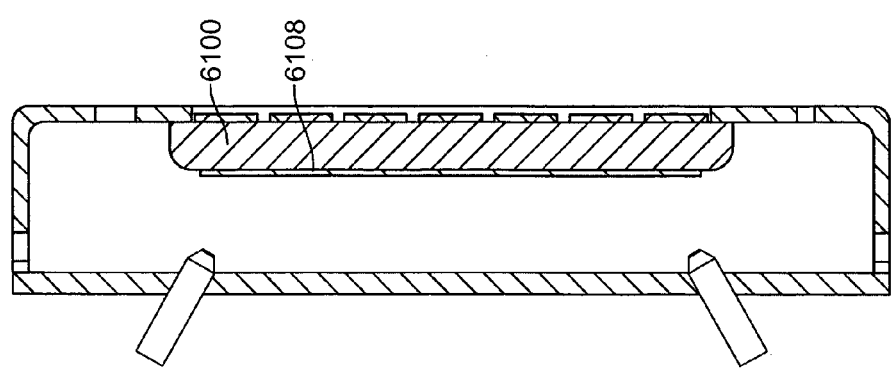
FIG. 61B
FIG. 61A

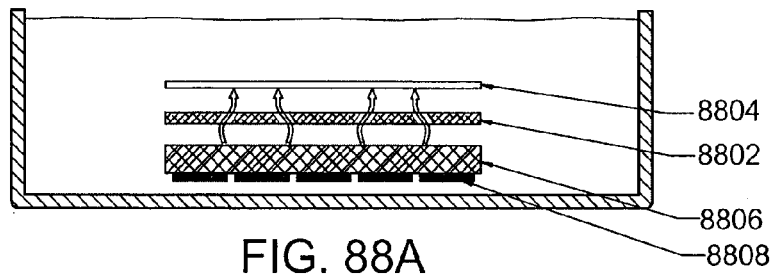
FIG. 88A
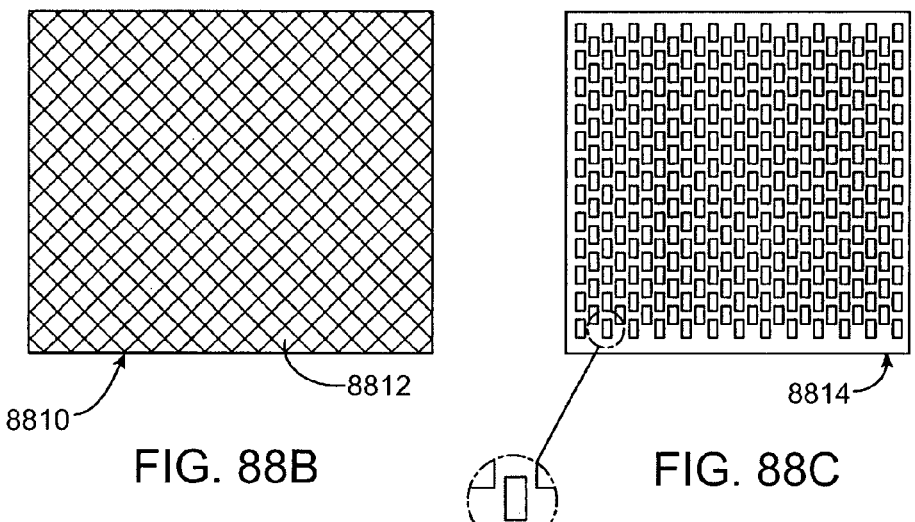
FIG. 88B    FIG. 88C
FIG. 88D
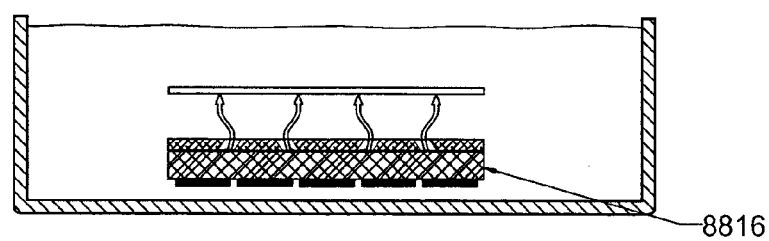
FIG. 88E

METHOD AND APPARATUS TO PROCESS SUBSTRATES WITH MEGASONIC ENERGY

CROSS-REFERENCE TO RELATED APPLICATIONS

The instant nonprovisional patent application claims priority from the following provisional patent applications, each of which is also incorporated by reference herein for all purposes: 60/476,845, filed Jun. 6, 2003; 60/476,527, filed Jun. 6, 2003; 60/530,194, filed Dec. 16, 2003; 60/510,054, filed Oct. 8, 2003; 60/546,383, filed Feb. 20, 2004; 60/517,255, filed Nov. 3, 2003; 60/528,941, filed Dec. 10, 2003; and 60/525,435, filed Nov. 26, 2003.

BACKGROUND OF THE INVENTION

The application of megasonic energy to substrate wet processing has become widely accepted, especially in semiconductor fabrication. As device/feature size has shrunk, and as substrate structures have become more vulnerable to damage, the frequency of megasonic systems have increased and have trended towards the megahertz range.

The application of sonic energy having frequencies approaching and exceeding one megahertz are often referred to as megasonic processing. These higher frequencies are used in an attempt to dislodge smaller contaminant particles and to reduce the localized energy release associated with bubble formation/collapse (cavitation and possible microcavitation) that some have theorized can lead to substrate damage as has been observed with lower frequency ultrasonic cleaners.

Historically, batch-processing systems have been designed to introduce megasonic energy parallel to substrate surfaces. In the quest for faster processing, particularly with the push for single wafer processing, megasonic designs have tended towards high-energy systems with introduction of energy perpendicular to substrate surfaces. This has led to concerns regarding megasonic damage to sensitive structures.

Therefore it is desirable to find gentler ways of applying megasonic energy that will rapidly remove ever-smaller contaminants.

BRIEF SUMMARY OF THE INVENTION

A variety of techniques may be employed, alone or in combination, to enhance contact between a processed substrate and applied megasonic energy. In accordance with one embodiment of the new invention, the vibration plate is brought into intimate contact with one surface of the substrate, while cleaning or processing fluid contacts the other. In accordance with an alternative embodiment of the present invention, a reflecting surface may be provided to cause emanated energy to be reflected back into the near field and make it more uniform. In accordance with another alternative embodiment of the present invention, energy may be transferred across a substrate bounded on both sides by liquid with incidence of megasonic energy that is either normal to the substrate surface or within a critical range of incident angles. In accordance with yet another embodiment of the present invention, generated dilatational waves may be converted to surface waves prior to contacting the substrate. In accordance with still another embodiment of the present invention, generated dilatational waves may be converted into surface waves after contacting the substrate, or within the substrate itself.

An apparatus in accordance with an embodiment of the present invention, configured to process a substrate with megasonic energy, comprises a processing region configured to receive a processing fluid, a megasonic energy source, and a vibration member in physical contact with the megasonic energy source and with at least a portion of an element proximate to the processing region. A combined thickness of the element and the vibration member being about +/−30% of an odd one-quarter wavelength of a megasonic energy applied by the source in order to transfer the megasonic energy across the element.

An embodiment of a method in accordance with the present invention of processing a substrate, comprises, placing at least one substrate into a process vessel, making contact between at least a part of the substrate and at least a part of a vibration member, and introducing at least one processing fluid into the processing vessel. At least a part of the substrate is contacted with at least one of the processing fluids and megasonic energy is applied, wherein the applying megasonic energy step occurs at least one of before, during and after the introducing processing fluid step.

An embodiment of an apparatus in accordance with the present invention configured to process a substrate with megasonic energy, comprises, a processing region configured to receive a processing fluid, a megasonic energy source, and a vibration member in contact with the megasonic energy source and oriented within a critical angle range of between about 18–58° relative to an element positioned within the processing region, in order to transfer the megasonic energy across the element.

An embodiment of a method in accordance with the present invention for processing a substrate, comprises, placing at least one substrate into a processing vessel, introducing at least one processing fluid into the processing vessel to contact at least a part of the substrate, and applying megasonic energy at between about 18–58° relative to a surface of the substrate, such that a substantial portion of the megasonic energy is transferred across the substrate. The introducing of a processing fluid step may occur before, during, or after the applying megasonic energy step.

An alternative embodiment of an apparatus in accordance with the present invention configured to process a substrate with megasonic energy, comprises, a processing region configured to receive a processing fluid, a flow member configured to control a path of the processing fluid within the tank, and a megasonic energy source configured to apply megasonic energy to the tank, such that a direction of the megasonic energy conforms to the path.

An alternative embodiment of a method in accordance with the present invention for processing a substrate with megasonic energy, comprises, flowing a processing fluid within a tank containing a substrate, and applying megasonic energy to the tank such that a direction of the megasonic energy conforms to a path of the processing fluid.

Another alternative embodiment of an apparatus in accordance with the present invention configured to process a substrate with megasonic energy, comprises, a processing region configured to receive a processing fluid, a megasonic energy source, and a wedge vibration member having a first face in contact with and configured to receive energy from the megasonic energy source. The wedge vibration member having a second face oriented at an angle relative to the first face and configured to emit energy received from the megasonic energy source to a substrate positioned within the processing region.

An alternative embodiment of a method in accordance with the present invention for processing a substrate, comprises the steps of placing a substrate into a processing region, introducing at least one processing fluid to the substrate, and contacting at least a part of a vibration member comprising a plate to at least part of a first face of a wedged shaped vibration member. Megasonic energy is applied to the substrate from a second face of the wedge shaped vibration member, wherein the applying megasonic energy step occurs at least one of before, during and after the introducing a processing fluid step.

Another alternative embodiment of an apparatus in accordance with the present invention configured to process a substrate with megasonic energy, comprises, a processing region configured to receive a processing fluid, a vibration member in physical contact with a megasonic energy source and configured to support a substrate in the processing region within a near field of megasonic energy incident in a first direction from the vibration member, and an element configured to direct megasonic energy to the near field from a second direction different from the first direction.

Another embodiment of an apparatus in accordance with the present invention configured to process a substrate with megasonic energy, comprises, a processing region configured to receive a processing fluid, and a megasonic energy source configured to output megasonic energy having at least one of a user-controlled and variable frequency, power, and pulse width, to a substrate present within the processing region.

An embodiment of a method in accordance with the present invention for processing a substrate, comprises, varying at least one of frequency, power, and pulse width of ultrasonic energy applied from a first energy source to a substrate in contact with a processing fluid, such that a uniformity of energy in near field regions is improved by at least one of moving high energy node points and low energy null points, minimizing a difference between a magnitude of the high and low energy points, and retarding formation of high and low energy points.

An embodiment of a method in accordance with the present invention for processing a substrate with megasonic energy, comprises, disposing a substrate in contact with a processing fluid, applying megasonic energy to the substrate to establish points of constructive and destructive interference proximate to a substrate surface, and changing a position of the points of constructive and destructive interference in order to enhance uniformity of exposure of the substrate to sonic energy.

An embodiment of a method in accordance with the present invention for processing a substrate, comprises the steps of supporting a substrate in a holder, positioning the substrate adjacent to a portion of a processing member, and causing relative motion between the substrate and the processing member at least one of before, during, or after a substrate processing step. The substrate is brought into at least one of into contact with and closely spaced apart from, the processing member surface. One of a solid, a fluid, and a mixture is between the substrate and the processing member, and energy is transmitted to an interface between the substrate and the processing member to modify processing of a surface of the substrate.

An embodiment of a processing apparatus in accordance with the present invention comprises a vessel configured to contain an electrochemical fluid, a voltage supply, and a support configured to position a substrate in contact with the electrochemical fluid, one of the support and the substrate in electrical communication with a first terminal of the voltage supply. An electrode is in electrical communication with the electrochemical bath and with a second terminal of the voltage supply, and a sonic energy source is in communication with the substrate one of across the electrode, across the substrate, and along a face of the substrate.

An embodiment of a method in accordance with the present invention for processing a substrate, comprises the steps of, providing an electrode in electronic communication with an electrochemical bath, disposing a substrate within the electrochemical bath, applying a potential difference between the substrate and the electrode across the electrochemical bath, and applying sonic energy across one of the electrode and the substrate, to a surface of the substrate.

An embodiment of a liquid for processing a substrate with sonic energy, comprises, a gas dissolved in a liquid component, the gas exhibiting a solubility in the liquid component at least as great as a solubility of the gas in deionized water under equivalent temperature and pressure conditions.

An alternative embodiment of a liquid for processing a substrate with sonic energy, comprises, a gas dissolved in a liquid component, the gas exhibiting a solubility in the liquid component at least as great as a solubility of air in deionized water under equivalent temperature and pressure conditions.

An embodiment of a method in accordance with the present invention for processing a substrate with sonic energy, comprises, causing a gas to be dissolved in a component of a liquid, the component exhibiting a solubility of the gas that is at least as great as a solubility of the gas in deionized water under equivalent temperature and pressure conditions. A substrate is exposed to the liquid component, and sonic energy is applied to the substrate within the liquid component.

An embodiment of a processing apparatus in accordance with the present invention comprises a vessel configured to support a substrate, a source configured to direct a jet comprising energy or matter against a surface of the substrate, and a vibration energy source in communication with the substrate.

An embodiment of a method in accordance with the present invention for processing a substrate, comprises, disposing a substrate within a processing vessel, directing a jet comprising energy or matter against a surface of the substrate, and applying sonic energy to the substrate at least one of before, during or after application of the jet.

An embodiment of an apparatus in accordance with the present invention for processing a substrate utilizing ultrasound energy, comprises, a tank having walls configured to contain a liquid bath, an energy source in sonic communication with the liquid bath, and a substrate holder configured to support a substrate within the liquid bath, at least one of a member of the substrate holder and a feature of the tank lying between the energy source and a portion of the substrate. A reflecting surface is in contact with the liquid bath and configured to receive ultrasound energy incident from the source at an angle of greater than 26°, and to reflect the ultrasound energy to the substrate portion.

An embodiment of a method in accordance with the present invention for processing a substrate utilizing ultrasound energy, comprises, providing a liquid bath within a tank having walls, supporting a substrate within the liquid bath on a holder, and directing ultrasound energy to the substrate, such that at least one of a portion of the tank and a portion of the substrate holder lies between the energy source and a portion of the substrate. The ultrasound energy incident at an angle of greater than 260° to a surface is reflected to contact the substrate portion.

An embodiment of a method in accordance with the present invention for drying a substrate, comprises, positioning a substrate within a processing chamber, pressurizing the processing chamber by at least one of introducing a gas and a vapor and a processing liquid into the chamber, and wetting at least part of the substrate surface comprising one of submerging, spraying and condensing liquid onto the substrate. A surface tension lowering component is concentrated at a gas-liquid interface, one of the substrate and the processing liquid level are moved relative to one of the substrate and the gas-liquid interface such that a surface tension gradient is created between the liquid comprising a meniscus on the substrate surface and a remaining portion of the processing liquid, wherein the surface tension gradient draws liquid from the substrate surface into the bulk processing liquid. Radiation is applied to at least one of a part of the substrate and at least one of the processing liquid on the substrate surface. The pressurizing step may occur before, after, or during the radiation applying step, and the applying radiation step may occur before, after, or during the moving step.

A further understanding of the nature and advantages of the inventions disclosed herein may be realized by reference to the remaining portions of the specification and the attached drawings.

BRIEF DESCRIPTION OF THE DRAWINGS

FIG. 2A shows a simplified cross-sectional view of an embodiment of an apparatus in accordance with the present invention utilizing an air-liquid interface as a reflecting surface.

FIG. 2B shows a simplified cross-sectional view of an embodiment of an apparatus in accordance with the present invention utilizing a randomly pitted surface facing the substrate as a reflecting surface.

FIG. 2C shows a simplified cross-sectional view of an embodiment of an apparatus in accordance with the present invention utilizing a vibrating plate as a reflecting surface.

FIG. 2D shows a simplified cross-sectional view of an embodiment of an apparatus in accordance with the present invention utilizing a rotating plate as a reflecting surface.

FIGS. 3A–B show simplified cross-sectional views of embodiments of apparatuses in accordance with the present invention utilizing fluid introduction coupled with reflection of megasonic energy.

FIGS. 3C–D show simplified cross-sectional views of embodiments of apparatuses in accordance with the present invention utilizing fluid introduction and removal coupled with reflection of megasonic energy.

FIG. 4A shows a simplified cross-sectional view of an embodiment of an apparatus in accordance with the present invention for performing brush scrubbing.

FIG. 4B shows a simplified cross-sectional view of an embodiment of an apparatus in accordance with the present invention for performing chemical mechanical polishing.

FIG. 4E shows a simplified cross-sectional view of an embodiment of an apparatus in accordance with the present invention showing a wide area megasonic nozzle based on a flat plate vibration member design.

FIG. 4F shows a simplified cross-sectional view of an embodiment of an apparatus in accordance with the present invention showing a wide area megasonic nozzle based on a wedge element design with multiple piezoelectric crystals or vibration elements.

FIG. 4G shows a simplified cross-sectional view of an embodiment of an apparatus in accordance with the present invention showing a narrow area megasonic nozzle based on a small wedge element with curved fluid contact face.

FIG. 5A shows a simplified cross-sectional view of a vertical embodiment of an apparatus in accordance with the present invention where processing fluid is introduced through spray nozzles.

FIG. 5B shows a simplified cross-sectional view of a horizontal embodiment of an apparatus in accordance with the present invention where processing fluid is introduced through spray nozzles.

FIGS. 7HA–C shows a simplified perspective, end, and side views of an alternative embodiment of an apparatus in accordance with the present invention, where energy is transferred from piezoelectric crystals through a solid wedge device into a transfer member having a triangular cross section, into a substrate across a gap filled with liquid.

FIG. 7KA shows a shows a simplified perspective view of one embodiment of a wedge structure in accordance with the present invention, featuring a hollow wedge filled with liquid, which exits through multiple holes or nozzles.

FIG. 7 KB shows a cross-sectional view of the megasonic nozzle structure of FIG. 7KA, where energy is transferred from piezoelectric crystals through the wedge to the substrate.

FIGS. 29A–B show simplified cross-sectional and schematic views, respectively, illustrating nonuniformity in the resulting energy field of the near field.

FIG. 37 shows a simplified cross-sectional view of another embodiment of an apparatus in accordance with the present invention featuring the vibration member separated from the substrate by a distance.

FIG. 38 shows a simplified cross-sectional view of another embodiment n accordance with the present invention including two vibration members aligned parallel to each other and spaced apart with a substrate inserted between them.

FIGS. 61A–B shows simplified cross-sectional views of vertically- and horizontally-oriented embodiments, respectively, of an apparatus in accordance with the present invention wherein ultrasonic energy is transferred directly from the vibration member through the substrate into residual liquid on another surface.

FIG. 82 shows a simplified cross-sectional view of an alternative embodiment of a substrate processing apparatus in accordance with the present invention, having vibration members oriented for cross-substrate energy transfer while providing substrate rotation.

FIG. 83 shows a simplified cross-sectional view of an alternative embodiment of a substrate processing apparatus in accordance with the present invention, having multiple vibration members in the form of transducers spaced about the height of the tank.

FIG. 84 shows a simplified cross-sectional view of an alternative embodiment of a substrate processing apparatus in accordance with the present invention, featuring multiple vibration members in the form of transducer pairs in physical contact with a wedge having a triangle cross-section.

FIG. 85 shows a simplified cross-sectional view of an alternative embodiment of a substrate processing apparatus in accordance with the present invention, featuring multiple vibration members in the form of a plurality of transducers in physical contact with a wedge having a polygonal cross-section.

FIG. 86 shows a simplified cross-sectional view of an alternative embodiment of a substrate processing apparatus in accordance with the present invention, wherein multiple vibration members are configured to perform processing of a substrate supported horizontally.

FIG. 87 shows a simplified cross-sectional view of an alternative embodiment of a substrate processing apparatus in accordance with the present invention, utilizing a single processing liquid jet spray and multiple sources of vibration from a flat plate wide area sonic nozzle design with multiple sonic nozzles elements.

FIG. 88A shows a simplified cross-section of an embodiment of an apparatus in accordance with the present invention featuring a diffraction grating between the sonic energy source and the substrate.

FIG. 88B shows a plan view of one example of a diffraction grating for use in accordance with embodiments of the present invention.

FIG. 88C shows a plan view of another example of a diffraction grating for use in accordance with embodiments of the present invention.

FIG. 88D shows an enlarged view of a portion of FIG. 88C.

FIG. 88E shows a simplified cross-sectional view of an alternative embodiment of an apparatus in accordance with the present invention utilizing a diffraction grating.

DETAILED DESCRIPTION OF THE INVENTION

Figure 1A:
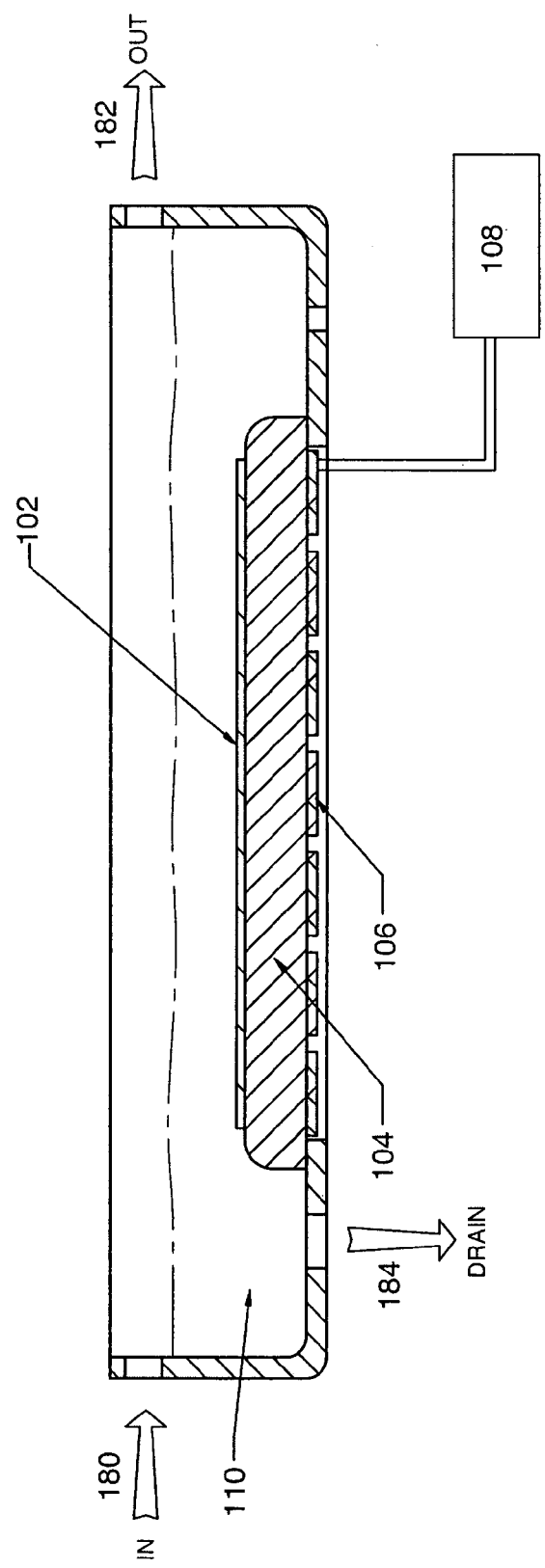
FIG. 1A shows a cross-sectional view of an embodiment of an apparatus in accordance with the present invention wherein megasonic energy is transferred directly from the vibration member through the substrate into the cleaning or processing liquid on the other surface.

A pressurized processing system incorporating megasonic energy is disclosed in U.S. nonprovisional patent application Ser. No. 10/150,748, incorporated hereby for all purposes. A technique for rapid, effective and efficient substrate heating in pressurized systems is disclosed in U.S. nonprovisional patent application Ser. No. 10/456,995, also incorporated by reference herein for all purposes. Incorporated also by reference herein for all purposes is published U.S. patent application no. 2001/0013355 A1.

Apparatuses in accordance with embodiments of the present invention relate generally to the application of megasonic energy to enhance processing of a substrate with a fluid. The substrate is disposed within a processing region configured to receive a processing fluid, and is exposed to megasonic energy.

The substrate need not be immersed in the processing fluid, which can be present on a substrate surface in the form of droplets or a thin film (meniscus). In addition, the processing region may, but need not be, partially or completely enclosed by walls or a tank in order to contain the fluid. Furthermore, the processing region can, but need not be, enclosed within a processing vessel to allow for processing at elevated or reduced pressures.

Conventionally, the term "megasonic" was used to describe ultrasonic acoustic energy having a frequency of about 700–1800 kHz, while the term ultrasonic has been used to describe a lower frequency range of about 20–200 kHz when applied to semiconductor substrate processing. For purposes of the instant application, the term "megasonic" is utilized to describe acoustic energy having a frequency of about 10–10,000 kHz and higher that may be applied to process a variety of substrates. Therefore, the term "megasonic" is used interchangeably with "ultrasonic" in the instant patent application.

In general, to achieve effective and efficient cleaning and processing of substrates, it is important that the megasonic energy be applied uniformly. Historically, piezoelectric crystals have been attached to vibration plates, or directly onto tank walls. The vibration plates or active tank walls have then been acoustically or sonically coupled with process or cleaning solutions. These vibration members were generally located in the bottom of process tanks or more recently on sidewalls. When the piezoelectric crystals were excited with a RF frequency, they caused the vibration plates to vibrate, which in turn caused a series of pressure or dilatational waves to propagate through the solution. The substrate to be processed or cleaned was suspended within the solution. With semiconductor substrates, the pressure waves flowed up both sides, parallel to the wafer surface causing cleaning or reactions to occur.

In order to efficiently transfer energy from a vibration member to a substrate, effective sonic coupling between the vibration member and the substrate should occur. This generally had been accomplished by transferring energy from the vibration plate to the solution, and then from the solution to the substrate. With better coupling, more of the energy input into the piezoelectric crystal is transferred to the process vessel and ultimately to the substrate. With poor energy coupling, more energy is wasted as it is reflected back to the generator or converted to heat, necessitating cooling of crystals and more robust generator designs. As a consequence of poor coupling, less actual energy could be applied to a given substrate, which led to longer cleaning and processing times.

Embodiments in accordance with the present invention provide for designs that introduce megasonic energy to substrate surfaces in ways that address the concerns and limitations mentioned with conventional designs. The multiple embodiments of this invention provide great flexibility in delivering a very uniform energy field to a variety of substrate surfaces, as well as providing alternative energy wave patterns, especially on the surface of the substrate. For example, most megasonic designs are based on dilatational waves (also known as longitudinal or pressure waves) being generated and transmitted through fluid boundaries to substrate surfaces. Some of the embodiments of the new invention disclosed herein are based on generating and using shear and surface waves as well. Wave modes generated in substrates by these different wave types can impact contamination particles on substrate surfaces differently than previously seen with traditional megasonic systems where only longitudinal waves emanated from vibration members.

In one embodiment of the new invention, the vibration plate is brought into intimate contact with one surface of the substrate, while cleaning or processing fluid contacts the other. This embodiment is shown in FIG. 1A, where the megasonic energy is transferred directly from the vibration member 104 through the substrate 102 into the cleaning or processing liquid 110 on the other surface.

Figure 1B:
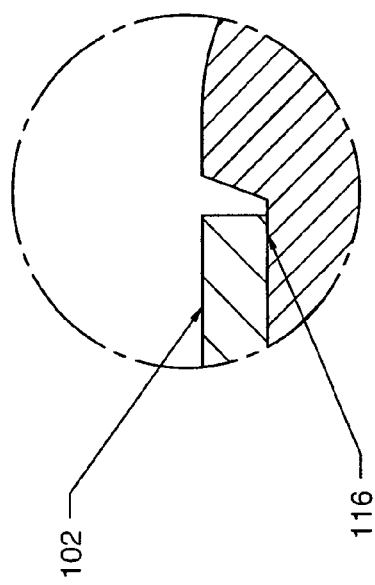
FIG. 1B shows a simplified cross-sectional view of an embodiment of an apparatus in accordance with the present invention wherein the substrate may be held tightly against a vibration member in contact with crystals by vacuum through a series of small holes in the vibration member FIG. 1BA shows an enlarged view of the embodiment of FIG. 1B.

Many methods of ensuring adequate contact between the substrate 102 and a vibration member to provide reasonable energy transfer are possible. For example, with a smooth substrate surface and a smooth vibration member surface, the substrate 102 may be held tightly against a vibration member 115 in contact with crystals 106 by vacuum through a series of small holes in the vibration member and a vacuum tube 114 as is shown in the embodiment of FIGS. 1B–1BA. Additionally, as shown in FIG. 1BA, a recess 116 could be machined into the vibration member to match the cross section of the substrate to be processed.

Good physical contact does not in and of itself ensure good energy coupling between the substrate and the vibration member. One effective way to obtain optimal energy coupling when the substrate is in intimate contact with the vibration member, is to have the sum of the thickness of the vibration member and of the substrate, equal to an odd multiple one-quarter wavelength ($n\lambda/4$, where $n=1, 3, 5, 7 \ldots$) of the megasonic energy wave. The speed of sound in each material must be taken into account to determine the corresponding thickness for that material. The greater the deviation from this optimal thickness, the poorer the coupling and less energy that is transferred, even with substantial physical contact. In many embodiments, transmission of megasonic energy having a wavelength that is within +/−30% of this desired substrate thickness may be sufficient to transfer adequate energy to the substrate.

In theory, the thickness of a vibration member, or a combination of a vibration member and contacting substrate, should equal an odd multiple of one-quarter of the wavelength of incident radiation, when the piezoelectric crystal is of the correct thickness and operating at its natural resonant frequency. In practice, however, the piezoelectric crystal can act partly like a vibration-generating element and partly like a vibration member.

This result changes the preferred thickness of the vibration member slightly from the theoretical value, especially when the crystal is not operated at its natural resonant frequency. For purposes of the present invention, slight differences between theoretical and actual thickness are not quantified for each possible embodiment. These thickness differences, however, are often relatively small and generally fall within the specification ranges listed above.

For purposes of the instant patent application, a "vibration member" is defined as a member such as a tank wall, flat plate, or wedge face, to which a vibrating element such as a piezoelectric crystal or mechanical actuator is attached, or the combination of the member and the vibrating element. Thus the thickness of the vibration member can refer only to the thickness of the member bearing vibrating element, or may refer to the combined thickness of that member plus the vibrating element.

The substrate may be wetted by the processing fluid by total or partial immersion, or from having the fluid being sprayed directly onto the substrate, or from the condensation of a volatile gas or vapor as the temperature changes within the process vessel. Especially for the immersion approach, when megasonic energy emanates from a vibration member into a liquid, or from a combination of substrate and vibration member in intimate contact with each other into a liquid, at a distance into the liquid from the surface of the substrate, the energy field may not be uniform. Standing waves can be established within this distance due to localized reinforcement and cancellation of the energy wave. These standing waves can lead to spots of non-uniformity. This region of non-uniform field intensity is often referred to as the near field, and generally extends to a distance on the order of ten wavelengths away from the vibrating surface, depending upon frequency and intensity of the incident energy. For water, ten wavelengths at a frequency of 800 KHz translates into a distance of approximately 1.85 cm. Many conventional batch processing systems are designed to keep substrates separated from vibration members (or tank walls) by more than this amount in order to avoid the nonuniform nature of the near field.

In another embodiment where the substrate and the vibration member are in intimate contact, a reflecting surface is provided to cause emanated energy to be reflected back into the near field and make it more uniform. Various examples of reflecting devices are shown in FIGS. 2A, 2B, 2C and 2D. Some of the devices are static, such as the air-liquid interface 202 of FIG. 2A, or the randomly pitted reflecting surface 204 facing the substrate of FIG. 2B.

As used herein, the term "static" does not necessarily imply stationary. It is meant to imply a situation where the member is not subjected to active mechanical agitation or repetitive motion.

In the case of the air-liquid interface 202 of FIG. 2A, the energy is reflected back at this interface relatively randomly as the surface of the liquid moves during operation. This interface can occur at the top of the fluid level within the process vessel, or could occur as bubbles are generated or introduced into the processing fluid within the energy path.

In other cases, the reflecting devices are dynamic or moving, such as the vibrating reflective plate 206 of FIG. 2C or the rotating reflective plate 208 of FIG. 2D. The dynamic devices reflect energy back to cancel out the spots of non-uniformity within the field. While repetitive, these moving reflecting devices tend to sweep points of constructive and destructive interference of sonic energy across the surface of the substrates through the near field. While not truly random reflections, over time they tend to make the energy patterns in the near field and those contacting the substrate more uniform.

Whether moving or stationary, the reflecting member should be constructed to reflect, rather than transmit, the megasonic waves. When separated from a vibration member, an effective reflecting member may be constructed of solid material with a thickness equal to approximately an odd multiple one-quarter wavelength of the energy wave, the same combined thickness that would afford strong energy coupling if the reflecting member were in intimate contact with the vibration member. Regardless of the thickness of the reflecting member, embodiments featuring a gas or vacuum on the other side of the reflecting member will produce effective reflection, much as with the case at the gas-liquid interface.

FIGS. 3A and 3B show embodiments in accordance with the present invention where fluid introduction is coupled with reflection of megasonic energy. The combination of reflection with fluid introduction not only tends to make the energy field more uniform, but also may increase uniformity of the processing chemistry near the surface of the substrate. Uniform concentrations and temperatures at the substrate surface become more important when it is desired that controlled chemical reactions take place at a substrate surface.

FIGS. 3C and 3D show embodiments in accordance with the present invention where fluid introduction is coupled not only with reflection of megasonic energy, but also with fluid removal. Like the embodiment of FIGS. 3A–B, fluid is introduced through conduits 302. In the embodiment of FIGS. 3C–D, however, fluid is simultaneously or subsequently removed through local conduits 304. Processing can thus be accomplished where fluids are both introduced and removed locally.

Thus far, the above description has focused upon the use of reflected sonic energy to enhance the quality of processing in near field regions. However, embodiments in accordance with the present invention may also utilize reflected sonic energy to achieve processing of substrate regions that would otherwise be shadowed from receiving that energy, for example by an intervening substrate support member.

A discussion of such alternative embodiments utilizing reflected sonic energy is provided below in Section A. A discussion of other approaches for avoiding sonic shadowing of substrate regions is provided below in Section B.

And while the above description has focused upon the use of reflected sonic energy to enhance processing in near field regions, alternative embodiments in accordance with the present invention may utilize other techniques. One such alternative approach is to vary the character of the sonic energy applied, and is discussed in detail below in Section C.

Two applications of particular interest in accordance with embodiments of the present invention are brush scrubbing and chemical mechanical polishing (CMP) processing. FIGS. 4A and 4B show embodiments for brush scrubbing and CMP respectively, wherein megasonic energy is transmitted across the substrate and directly into the brush 402 or pad 404. In this manner the mechanical energy and megasonic energy are focused simultaneously at a single spot or region of the substrate.

One benefit of the approach shown in FIGS. 4A and 4B may be that as the brush 402 is removing macroscopic particles from a smooth substrate surface portion, the megasonic energy is simultaneously lifting particles out of recesses such as trenches and vias. By contrast, conventional systems are limited to applying megasonic energy to the side or periphery of mechanical members such as brushes or CMP pads, as those mechanical members are generally not conducive to the transfer of energy. Thus those conventional systems can only apply the mechanical and megasonic energies to a substrate sequentially rather than simultaneously.

A further embodiment in accordance with the present invention could incorporate a localized liquid feed, with liquid removal via suction. Such an embodiment could aid in the removal of unwanted materials from recessed regions of a substrate such as trenches and vias. Further discussion of simultaneous addition/removal of processing liquid is set forth below.

Embodiments in accordance with the present invention do not require the substrate to be completely submerged in a liquid. In another embodiment shown in FIG. 5A, where the substrate 500 and the vibration member 502 are in intimate contact as a spray of liquid 504 processing fluid may wet the exposed surface.

While FIG. 5A depicts the substrate and vibration member positioned vertically, they could alternatively be positioned horizontally as shown in FIG. 5B. The continuing spray 504 replenishes the film of processing fluid on the surface of the substrate 500, so that energy can interact with the chemistry at the substrate surface. This embodiment could be utilized in designing single wafer processing equipment.

Figure 6A:
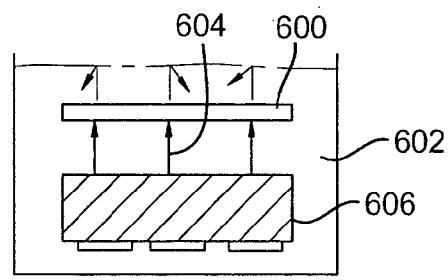
FIG. 6A shows a simplified cross-sectional view of an embodiment of an apparatus in accordance with the present invention wherein applied megasonic energy is incident perpendicular to a substrate bounded on both sides by liquid

In an alternative embodiment energy may be transferred across a substrate 600 bounded on both sides by liquid 602 with incidence of megasonic energy 604 normal to the substrate surface. FIG. 6A shows such an embodiment, wherein the substrate thickness should match an even multiple of one-quarter wavelengths ($n\lambda/4$, $n=2, 4, 6, 8 \ldots$) of the applied megasonic energy. Conventional megasonic cleaning systems have not been very successful in transferring energy across or through silicon wafers because they use megasonic frequencies/wavelengths that would require wafers to be much thicker than is practicable.

Figure 6B:
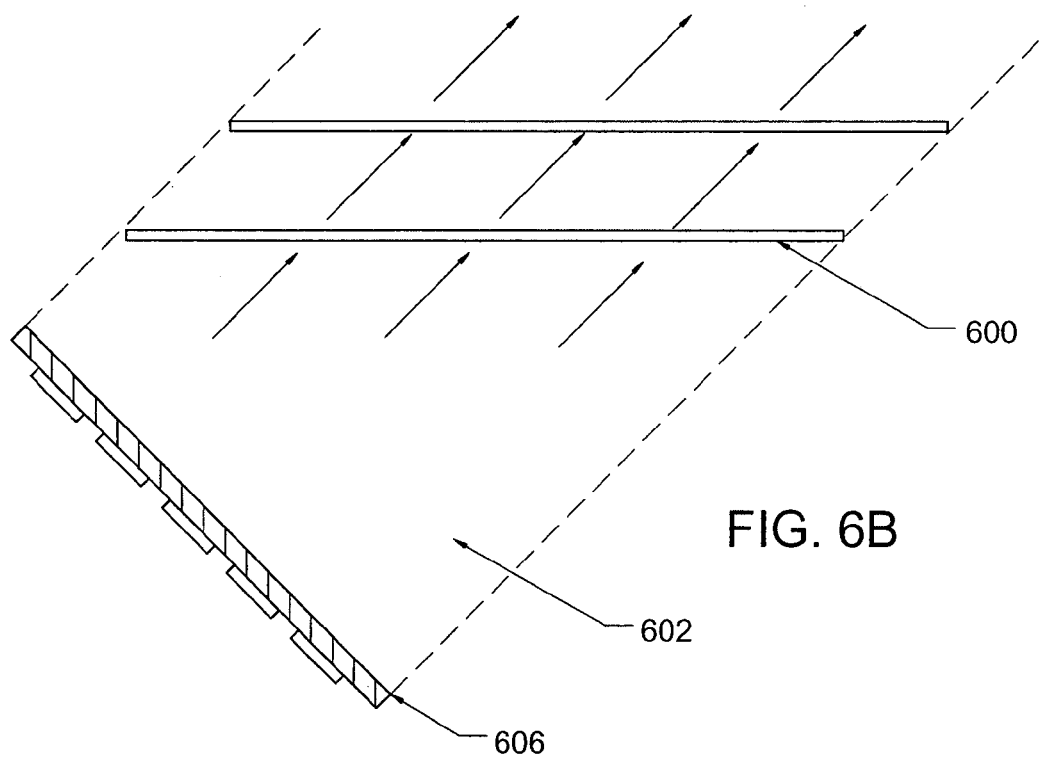
FIG. 6B shows a simplified cross-sectional view of an alternative embodiment of an apparatus in accordance with the present invention, wherein substrates are positioned at a proper angle to the incidence megasonic waves to maximize cross substrate energy transfer.

In another embodiment, energy may effectively be transferred across relatively thin substrates submerged in a liquid, even if the substrate thickness does not approximate the even multiple of one-quarter wavelengths just described. As shown in FIG. 6B, this may be accomplished when the substrates 600 are positioned at a proper angle to the incidence megasonic waves. This incidence angle should lie between first and second critical angles for the fluid/substrate/fluid arrangement.

In sonic theory for non-destructive testing, the terms first and second critical angles may have well defined meanings. For example, when an incident dilatational wave traveling in one medium strikes the surface of a second material having a higher impedance, the incident wave can form both a dilatational wave and a shear wave in the second material.

As the angle of the incident wave to the surface of the second material is increased, so do the angles of the refracted dilatational and shear waves created. The angle when the dilatational wave is refracted to 90° (parallel with the surface of the second material) is termed the first critical angle. The second critical angle occurs when the refracted shear wave lies 90° to the surface.

For purposes of the instant patent application, however, the first critical angle is defined as the incident angle at which a significant fraction of incident energy is transferred across a substrate when that substrate is submerged in a liquid and not positioned perpendicular to energy incidence. The second critical angle is defined as the angle of incidence which marks the halt of significant energy transfer.

The optimal range of critical incidence angles may differ under different conditions. Where sonic energy is applied to a member surrounded by a liquid, the critical angle will range between about 18–58°, more preferably between about 25–50°, and most preferably between about 30–45°. At such incident angles, a significant amount of energy is transferred across the substrates, while less energy would be expected to be transferred if the megasonic waves impinged upon the substrate at angles outside these ranges.

For example as the angle becomes larger or smaller, less energy would be transferred and more reflected, especially for angles approaching 90° (0° deviation from the normal to the substrate surface), where little coupling occurs with substrates of thickness not conforming to the rule set forth above of an even multiple one-quarter wavelength.

Figure 6C:
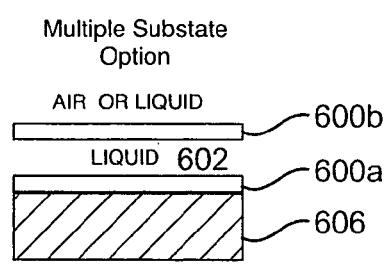
FIG. 6C shows a simplified cross-sectional view of an alternative embodiment of an apparatus in accordance with the present invention, wherein one substrate has a surface in contact with the vibration member and another substrate does not.

A further advantage with across-wafer transfer of energy in accordance with the present invention is that multiple substrates can be processed simultaneously. This is true for the embodiment of FIG. 6B where the liquid contacts both surfaces of the substrate. This is also true for the embodiment shown in FIG. 6C, where one substrate 600a has one surface in contact with the vibration member and another substrate 600b does not.

The number of substrates that a single wave can penetrate is not limitless. Some attenuation of signal occurs due to the thickness of each of the substrates, and fluid conditions between substrates.

Another potential advantage in accordance with the present invention is that the wave mechanics and interaction at the surface are different than occur with traditional designs. These new and different interactions may result in different forces at the substrate surface on contaminant particles.

Without wanting to be bound by any particular theory, across-substrate energy transfer may be visualized as follows. As the propagating dilatational megasonic wave in the liquid strikes the substrate surface at the proper angle, it is converted into a shear wave in/on the solid substrate. The shear wave in the substrate is then converted back into a dilatational or pressure wave as it emanates from the opposite side of the substrate. Where a gas or vacuum rather than liquid is present on the other side of the substrate, the shear wave could continue along the substrate as a shear or surface wave, or be partially or totally reflected.

The concepts of wave mechanics, including incidence, reflection, refraction and mode conversion are well known in classical acoustic and elasticity theory. These concepts describe that dilatational waves involve particle motion in the same direction as wave propagation. With shear waves, which occur only in solids, particle motion is at right angles to the direction of propagation. For a free surface on a solid half-space, particle motion is complicated and decays rapidly away from the surface. Surface waves can also form in thin substrates, often in substrates comprised of multiple thin layers.

In another embodiment showing energy transfer across a substrate whose thickness is not approximately an even multiple one-quarter wavelength of the applied megasonic energy, the megasonic energy may be directed perpendicular to the surface of the substrate. Simultaneously, a bulk fluid movement may create a fluid velocity parallel to the substrate surface. The fluid velocity is adjusted so that the resultant angle at which the megasonic energy hits the substrate surface is within the range of angles conducive to across substrate-energy transfer. For example, where megasonic energy is at a frequency of approximately one megahertz, it is estimated that a water fluid velocity of approximately six meters per second could be chosen to produce an acceptable resultant angle. Because a range of resultant angles is acceptable for across substrate energy transfer, a range of fluid velocities at each frequency can be utilized. As is discussed in more detail below, a steady flow of processing fluid without significant mixing is preferred to maintain integrity of transport of sonic energy within the liquid.

The bulk fluid movement could be produced in various ways, including but not limited to pumping, gravity feed, and the introduction of a second megasonic wave at an appropriate angle. It is desirable to have the resultant angle of the energy pattern created by the intersection of two separate waves fall within the range of acceptable angles for acceptable cross substrate energy transfer. When the frequency of the first megasonic wave and second megasonic wave are similar, the intersection of the two waves could be at near right angles. Since acoustic streaming velocity is a function of frequency and intensity, dissimilar frequencies and intensities could result in other angles.

Alternatively, relative motion between the substrates and the vibration members could be established to produce a relative velocity on the order of the fluid velocity mentioned above. The relative motion could be linear, or angular as in the case of rotation. Either of these approaches could lead to enhanced energy transfer across the substrate, where the thickness of the substrate does not conform to the approximate even multiple of ¼λ of the applied megasonic energy previously described.

In another embodiment, a first substrate positioned at an angle to the incidence of the megasonic energy coming from a vibration member may be moved or vibrated. This movement can occur along both the x- and the y-axes. This movement could be represented in FIG. 6D where the angle of the first substrate 600a relative to the vibration member is changed or "wobbled" relative to the angle of the second substrate 600b to the same vibration member 606. As a consequence of this "wobbling" the resulting energy field transferring across this first substrate and contacting the second substrate varies.

This variation in field can include variation in intensity as well as orientation. When the first substrate has a thickness of approximately an even multiple of one-quarter wavelength of the megasonic energy, the resulting change in field can be particularly evident. The varying field essentially causes a continual sweeping of energy across the surface of the second substrate. The second substrate can be any thickness or even be positioned parallel to the vibration member. Energy field non-uniformity can thus be moved around over time, essentially making the resulting time-averaged field more uniform, which may in turn lead to more uniform processing under certain conditions.

Figure 6D:
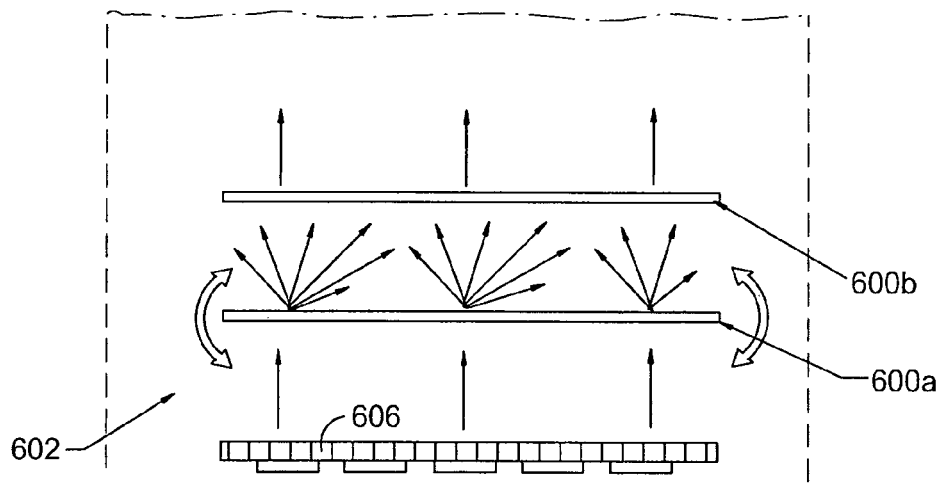
FIG. 6D shows a simplified cross-sectional view of an alternative embodiment of an apparatus in accordance with the present invention where the angle of the first substrate relative to the vibration member is changed or "wobbled" relative to the angle of the second substrate to the same vibration member.

While the vibrating substrate is shown as a flat plate-like object of uniform thickness in FIG. 6D, the vibrating substrate may have a varying thickness. It may be shaped as either a concave or a convex lens-like structure. Additionally, while shown as being held parallel to the vibration member, the first substrate could be positioned at some selected angle, or allowed oscillate over some range of angles.

Another benefit of direct contact between the substrate and the vibration member requires only that the sum of the thickness of the substrate and the vibration member be approximately equal to an odd multiple one-quarter wavelength of the megasonic energy. Thus as the substrate thickness changes, the thickness of the vibration member can easily be adjusted to compensate. This avoids requiring new generation frequencies, which may be difficult or impossible to do cost effectively today.

Figure 7A:
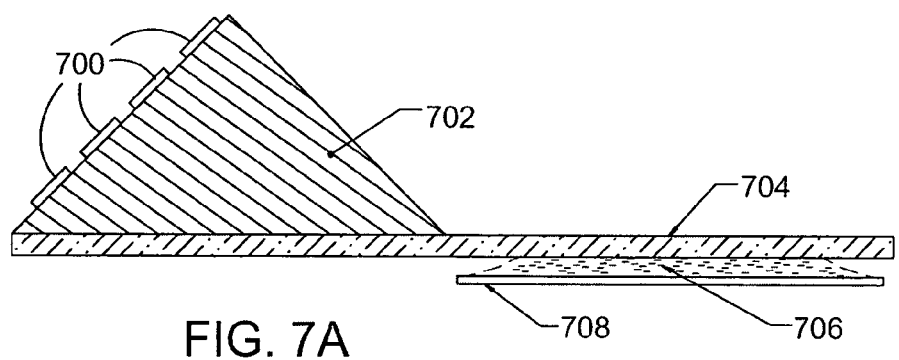
FIG. 7A shows a simplified cross-sectional view of an alternative embodiment of an apparatus in accordance with the present invention where energy is transferred from piezoelectric crystals through a solid wedge into a thin flat plate.

In another embodiment shown in FIG. 7A, energy is transferred from piezoelectric crystals 700 through a solid wedge 702 into a thin flat plate 704. At the proper angle, the dilatational or longitudinal pressure wave created by the piezoelectric crystals mounted on the vibration member is transferred through the solid wedge and converted into a shear or surface wave in the thin solid plate. When the thickness of the contacting plate is on the order of one wavelength or less, the surface/shear wave is sometimes known as a Lamb wave. For thicker plates, these surface waves may be called Rayleigh waves. For multiple layer plates with one layer thinner than another, the resulting surface waves may be called Love waves. The wave mechanics may be different in each case.

Additionally there are torsion and flexural waves that transfer down the length of the plate. Each type of wave has its own distinctive surface movement, which can translate into different forces being applied to a surface particle. While other lengths and thicknesses can be effective for processing, in order to maximize the transfer of energy along the flat plate for different applications, its thickness and length generally should be controlled to certain multiple one-quarter wavelength values.

With the wedge/flat plate embodiment depicted in FIG. 7A, the substrate 708 to be cleaned or processed is kept parallel to the vibrating plate member and maintained at a separation distance forming a gap. The gap between the substrate and the vibration member is filled with processing liquid. Energy is transferred from the vibration member through the liquid 706 into the substrate. Ideally the gap should be on the order of an even multiple of $\frac{1}{4}\lambda$ of the applied megasonic energy. In practice, since the gap is filled with a relatively incompressible liquid, its thickness can vary widely. Alternatively, the substrate could be in direct contact with the plate vibration member.

Figure 7B:
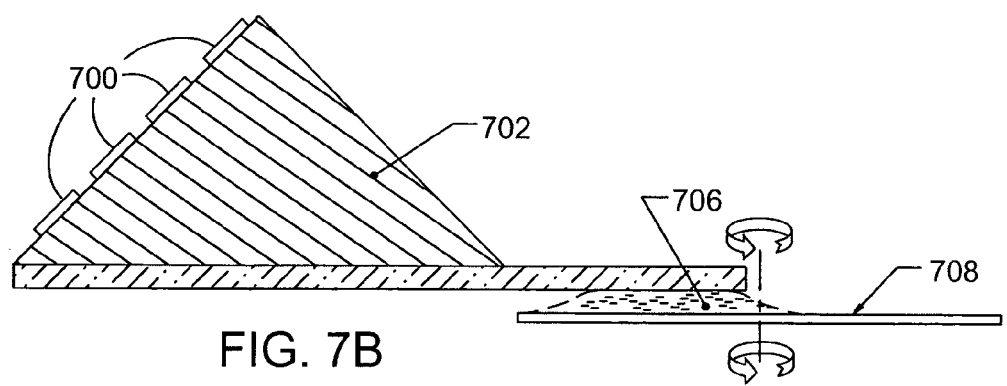
FIG. 7B shows a simplified cross-sectional view of an alternative embodiment of an apparatus in accordance with the present invention where the substrate can be rotated.
Figure 7C:
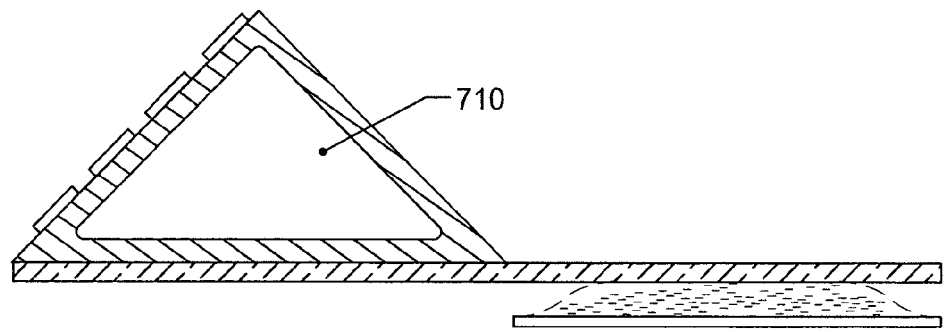
FIG. 7C shows a simplified cross-sectional view of an alternative embodiment of an apparatus in accordance with the present invention where the wedge is hollowed with a passage and flushed with a cooling fluid.

A further advantage of such a wedge arrangement occurs when the wedge is hollowed with a passage 710 and flushed with a cooling fluid, as is shown in the embodiment of FIG. 7C. Piezoelectric crystals tend to heat up during operation. The less efficient the energy coupling, the higher the operating temperatures. Also, higher applied power density tends to develop higher crystal operating temperatures. Higher operating temperatures make it more difficult to keep piezoelectric crystals attached to a vibrating member because of differential expansion between various glue materials and the piezoelectric crystals and the vibration member. At excessively high temperatures, the crystals can even loose their ability to function. Therefore an efficient way to cool them during operation is important.

As an alternative to cooling channels within the wedge, another type of cooling structure could be attached to one of the surfaces. Such an alternative cooling structure could include a Peltier (thermoelectric) cooler or some other non-liquid device.

A further advantage of a wedge arrangement with an extended vibration plate is that it allows the entire substrate surface, or a major portion of it be covered and processed with megasonic energy at the same time.

Figure 7D:
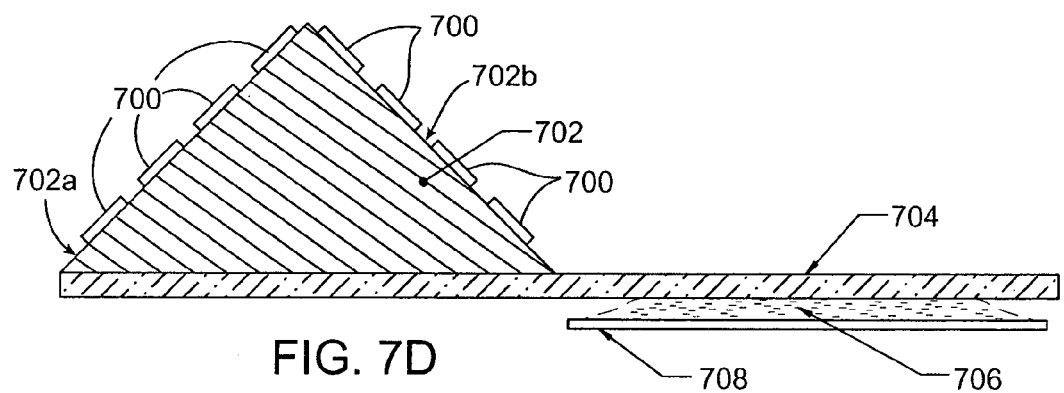
FIG. 7D shows a simplified cross-sectional view of an alternative embodiment of an apparatus in accordance with the present invention, where energy is transferred from multiple piezoelectric crystals present on more than one face, through a solid wedge, into a thin flat plate.

A further embodiment in accordance with the present invention is shown in the simplified cross-sectional view of FIG. 7D, where piezoelectric crystals 700 are placed on multiple sides 702a–b of a wedge design 702. The crystals may operate at the same or at different frequencies. Variation of the operating frequencies of these crystals can lead to enhance energy field uniformity over time.

Figure 7E:
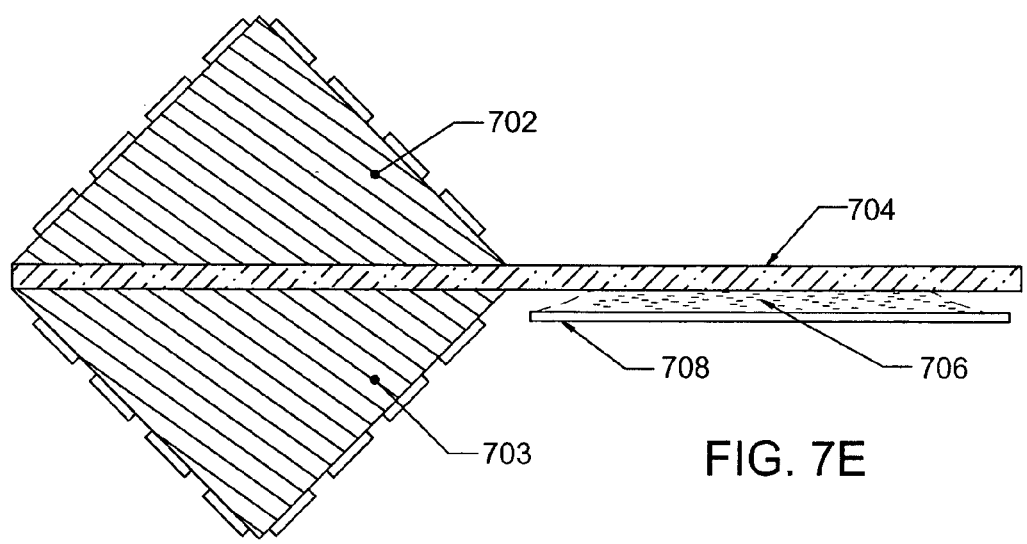
FIG. 7E shows a simplified cross-sectional view of an alternative embodiment of an apparatus in accordance with the present invention, where energy is transferred from piezoelectric crystals through multiple solid wedge devices into a thin flat plate.
Figure 7F:
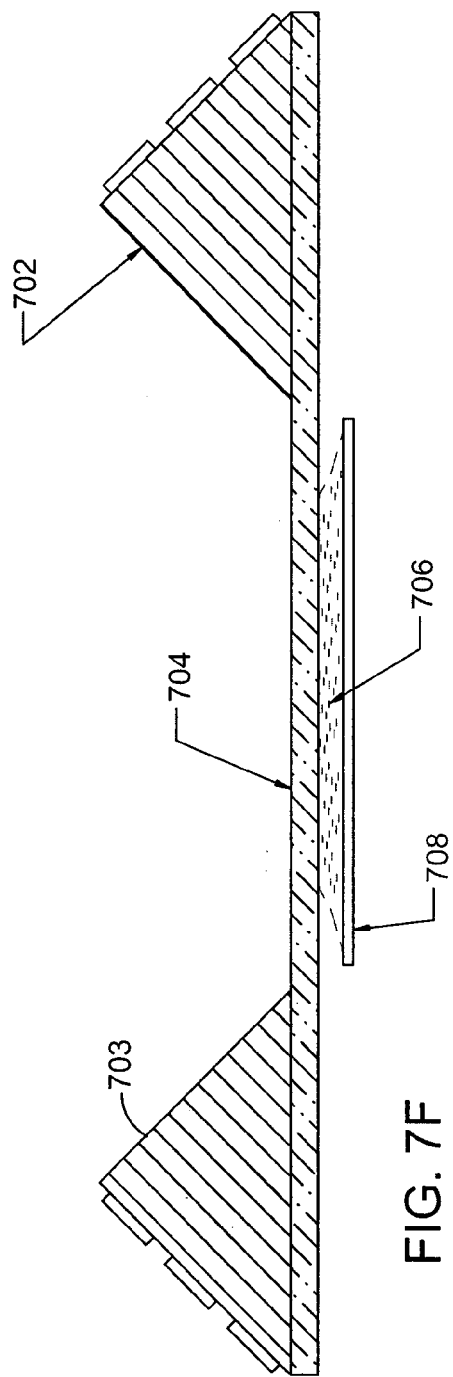
FIG. 7F shows a simplified cross-sectional view of an alternative embodiment of an apparatus in accordance with the present invention, where energy is transferred from piezoelectric crystals through multiple solid wedge devices placed at opposite ends of a thin flat plate.

While the embodiments of FIGS. 7A through 7D show a single wedge device, this is not required by the present invention. A second device 703 could be present, as illustrated in the simplified cross-sectional views of FIGS. 7E–F. In FIG. 7E, a second wedge device 703 is added directly under a first wedge device 702 and transfer plate 704. In FIG. 7F, a second wedge device 703 could be placed on the opposite end of the transfer plate 704 with the substrate situated between them.

Alternatively, one could combine a wedge device with a flat plate vibration member. Such a combination of wedge device and flat plate vibration member may produce unconventional sonic energy patterns when used for substrate processing. These patterns may include both surface and pressure waves simultaneously leading to complex waveforms, and complex interactions between the waveforms and the contaminant particles.

While the cross-sectional shape of the wedge device of the embodiments of FIGS. 7A–F is shown as a right triangle, this is also not required by the present invention. For example, in accordance with one alternative embodiment, the cross-sectional profile of the wedge device could exhibit two angles of 30°, and another of 120°.

Moreover, while the cross-sectional profile of the wedge device of the embodiments of FIGS. 7A–F is shown as a triangle, that is also not required by the present invention. Other shapes may be favored with energy waves exiting a crystal which act through a surface at some non-zero angle. Not only can angles of less than 30° or greater than 60° be used, but as shown in FIGS. 8F–H, even an angle of 90° can be used under certain conditions.

Such wedge-like devices may exhibit several useful characteristics not realized by conventional flat plate vibration members. First, the energy intensity of individual crystals can be combined into a single larger energy output on the face utilized for energy transfer.

Second, the energy from the individual crystals may be spread out relatively uniformly over the target face. While generally larger than the area of an individual crystal, it could also be smaller. Thus the energy intensity (energy density) on the active face can be greatly different from the energy density on an individual crystal. This is in contrast with a conventional flat plate vibration member where the sonic energy at megasonic frequencies is well collimated, and falls off rapidly outside the edged of the energy projection (crystal outline) through the plate.

Third, it is possible to operate individual crystals at either similar or different frequencies, resulting in a combined waveform for substrate processing. Conventional piezoelectric crystal act like a large number of separated and distinct vibration point sources when excited, leading to various wave interference interactions in the near and far fields. When the output wave from individual or multiple crystals goes through mode conversion across the appropriate angles, such as in a wedge-like structure, it is speculated that perhaps the resulting activated surface from which the sonic energy is emitted, may actually act a little bit more like a uniform set of point sources acting at the conditions dictated by the combined waveform.

Also, the rod offers only a small cross-sectional area for contact with a vibration element in order to transfer energy down its length. Such a small energy-transfer cross section requires that the vibration element operate at high energy density or intensity in order to transfer sufficient energy down the rod to accomplish the processing.

The wedge design of the instant invention stands in contrast with that of U.S. Pat. No. 6,463,938 ("the '938 patent"), where dilatational waves from a piezoelectric crystal attached to the end of an elongated rod are transferred down the length of the rod. Being only a rod and not a plate, just a small interaction area between rod and substrate can occur at any one time. In order to process or cover the entire substrate surface in the '938 patent, the substrate must be rotated.

With embodiments of the current invention, however, substrate rotation is not required. FIG. 7B shows a simplified cross-sectional view an embodiment employing such optional rotation.

With the wedge design producing a shear or surface wave, not only is a different waveform used to transfer energy, but also a large area of contact between substrate and vibration member can exist. While rotation or movement of the substrate, or rotation or movement of the vibration member is also possible to enhance processing, it is not required.

Alternative embodiments in accordance with the present invention may utilize a relatively large surface area for contact with a vibration element, a much larger vibration element, or even several vibration elements operating at relatively low energy intensity or density, or a combination of these aspects. Lower energy density operation of the vibration elements generally translates into lower operating temperatures requiring less cooling.

The '938 patent describes transferring energy from a piezoelectric crystal to a substrate surface utilizing rods of various shapes. In accordance with embodiments of the present invention, however, a wide variety of other shapes can be used, including various elongated transfer members.

Figure 7G:
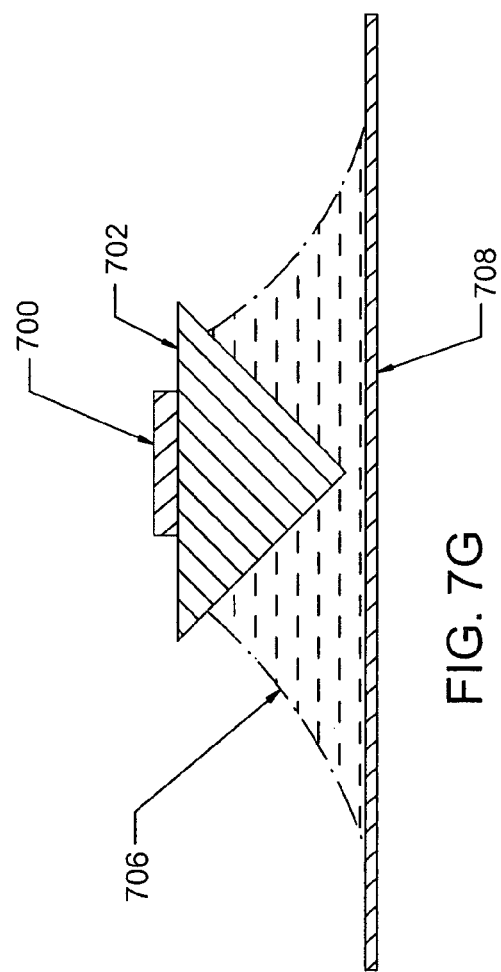
FIG. 7G shows a simplified cross-sectional view of an alternative embodiment of an apparatus in accordance with the present invention, where energy is transferred from piezoelectric crystals through a solid wedge device into a flat substrate across a gap filled with liquid.
Figure 7I:
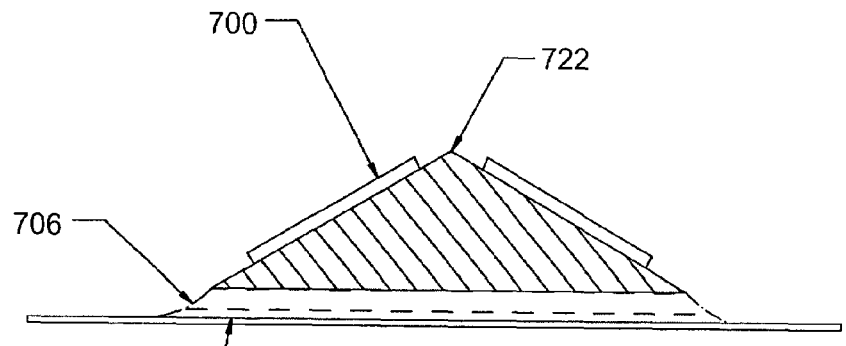
FIG. 7I shows a simplified cross-sectional view of an alternative embodiment of an apparatus in accordance with the present invention, where energy is transferred from piezoelectric crystals through multiple edges of a triangular solid wedge device, across a fluid filled gap and into a substrate.

For example, in FIGS. 7G, 7H, 7I, and 7K, the cross section of the transfer member is triangular. In FIG. 7G, each of the two angled sides (angled with respect to the substrate surface) are positioned at an angle that may actually enhance transfer of applied sonic energy across the thickness of the substrate 708. The angled incidence of energy may result in either better cleaning or reduced damage, under certain processing conditions.

In the embodiment of FIG. 7H, rather than attaching the crystals directly to the top of the triangle as in the embodiment of FIG. 7G, a wedge device 702 is brought into contact with the top surface of the triangular member 720. The transfer member 722 illustrated in FIG. 7I has similar cross sectional shape to that shown in FIG. 7G, except crystals 700 are attached to one or both of the slanted sides, and the third side is rotated 180° and kept parallel with the substrate surface 708. The flat side that was parallel to the substrate surface but spaced away from it in the embodiment of FIG. 7G, is instead positioned near the substrate surface.

Figure 7J:
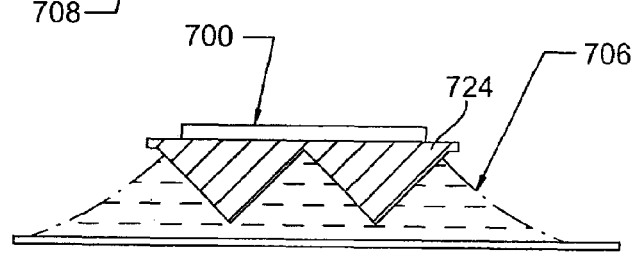
FIG. 7JA–D show simplified cross-sectional views of an alternative embodiment of an apparatus in accordance with the present invention, where energy is transferred from an elongated transfer member having various shapes, across a fluid filled gap and into a substrate.
Figure 7J:
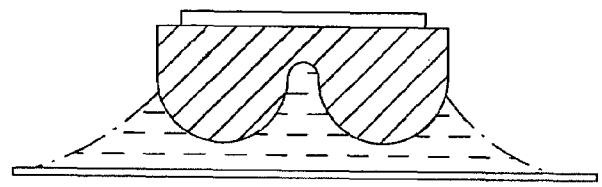
Figure 7J:
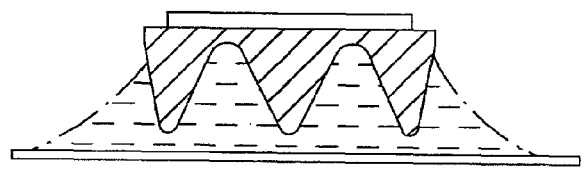
Figure 7J:
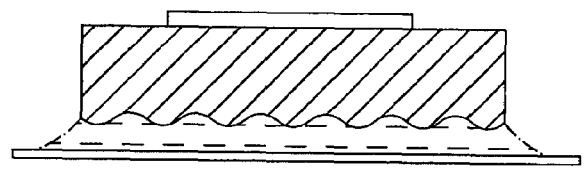

In the embodiment of FIG. 7J, a transfer member 724 exhibiting a "w" shape is used. In accordance with this embodiment, the crystals 700 can either be attached directly to the member 724, or attached to a wedge that is attached to the member.

While the embodiments of FIGS. 7G through 7J have shown energy transfer members exhibiting triangular cross-sections, this is not required by the present invention. Other shapes may also be useful. Such other shapes could include triangular shapes having one corner rounded or flattened (FIG. 7JC), or could include cross-sections having either concave and/or convex portions as illustrated in FIGS. 7JB and 7JD.

Most conventional batch type megasonic systems utilize a flat plate vibration member, having piezoelectric crystals attached to a flat plate of the appropriate thickness, or attached to a tank wall of the appropriate thickness. Traditionally the surfaces of these vibrating members that contact processing fluids have been smooth and flat. Non-flat plate designs may be desirable for some applications when cross substrate energy transfer is desired. In such cases, the surface of the vibration member contacting the processing fluid (flat plate or inside tank wall), can have a contoured cross section.

For example, the cross sections shown in 7JB and 7JD could be extended to much wider structures. Many other contours are acceptable.

In such cases, the resulting vibration plate surface might appear to have a sawtooth or washboard (corrugated) cross section. The repetitive "undulating" surface can cause fluid to be pushed away from the vibration plate surface at various angles. Such contoured cross sections can also be applied to wedge type devices, not just flat plate vibration members.

At first glance, constructing vibration members that intentionally create energy and fluid flow field interference patterns may seem counterintuitive. Specifically, the prior art has generally emphasized designs minimizing energy interference. In certain embodiments in accordance with the present invention, designs purposely creating interference patterns are acceptable and even preferred. As such various fluid and sonic interference patterns are established, however, variation in the frequency and intensity of applied sonic energy can be utilized to render the "effective" energy fields more uniform for substrate processing. Use of such variation in applied sonic energy is discussed below in Section C.

In accordance with additional embodiments of the present invention, the transfer member could be constructed with a hole or channel to allow expulsion of processing fluid simultaneous with application of sonic energy from either a single or multiple nozzles or jets. Such an embodiment is illustrated in simplified cross-section as structure 754 of FIG. 7K. The fluid exiting holes 750 as these jets 752 would be ultrasonically activated. Designs for sonic nozzles are discussed in detail below, including sonic nozzles utilizing wedge structures.

Various other shapes for energy transfer members are possible, as long as energy can readily be transferred to the members without forcing the energy to be transferred solely along the length of the rod through only the rod's cross section, as with the '938 patent.

In another embodiment, processing fluid is applied to a substrate through a megasonic nozzle that is set to deliver megasonic energy to the substrate surface at a selected angle. When selected from a proper range of angles, significant energy transfer across the substrate can occur when the substrate is at least partially submerged in a processing fluid. Alternatively, when the substrate is not submerged, or is in contact with a support member, the application of megasonic energy from a megasonic nozzle at a proper angle can result in the wave mode conversion. The dilatational or pressure waves exiting the megasonic nozzle can be converted to surface waves in the substrate. Depending on frequency and substrate and/or support thickness, these surface waves can take the form of Rayleigh, Lamb, or Love waves, the last waveform type being described below in connection with FIG. 8A.

Figure 4C:
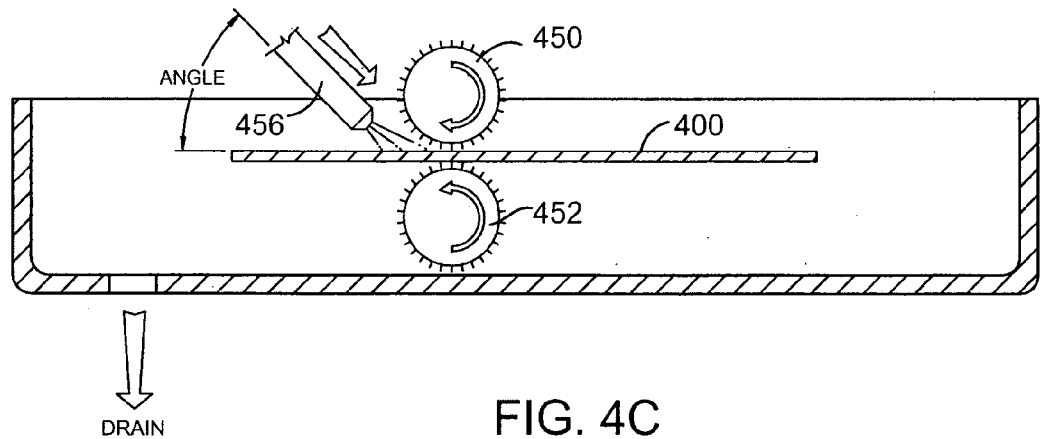
FIG. 4C shows a simplified cross-sectional view of an embodiment of an apparatus in accordance with the present invention for performing dual brush scrubbing combined with a megasonic nozzle.

One application that can benefit from this mode conversion of megasonic energy is dual brush scrubbing, where two brushes 450 and 452 are directly opposed to each other across a substrate as shown in the simplified cross-sectional view of FIG. 4C. In the earlier mentioned application with a single brush embodiment shown in FIG. 4A, megasonic energy was transferred directly across the substrate into the brush/substrate contact area as well as on both sides of that area simultaneously. With the dual brush example, across-substrate energy transfer in the same way may not occur.

Therefore to get megasonic energy delivered to the brush/substrate/brush contact areas simultaneously, a megasonic nozzle 456 is utilized. The nozzle 456 is directed to the surface of the substrate 400 at an angle between a first and second critical angle, where the pressure waves in the liquid stream exiting the nozzle are converted to shear or surface waves in the substrate. These shear or surface waves then travel into the brush/substrate/brush contact areas. This allows the simultaneous localized introduction of sonic energy and the scrubbing action of dual brushes onto a single substrate or substrate area.

Figure 4D:
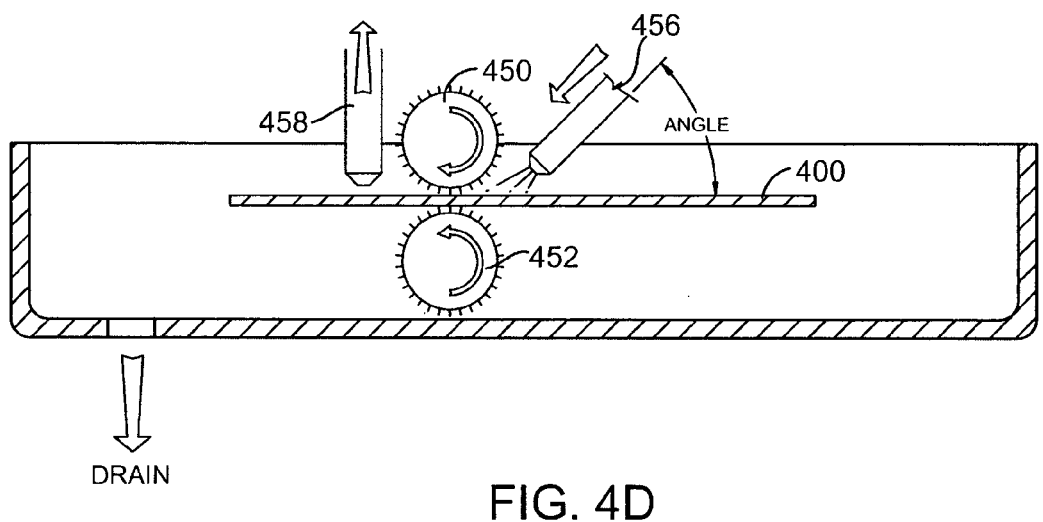
FIG. 4D shows a simplified cross-sectional view of an embodiment of an apparatus in accordance with the present invention similar to FIG. 4C, but having the capability to remove fluid via suction during processing.

To cover the entire contact area, the nozzle could be moved back and forth adjacent to one of the brushes, or multiple nozzles could be used. The nozzle could face either the top or bottom surfaces of the substrate, or multiple nozzles could be directed at both surfaces at the same time. FIG. 4D shows a simplified cross-sectional view of an alternative embodiment of a processing apparatus, wherein fluid applied by nozzle 456 is removed by suction through outlet 458.

Figure 87:
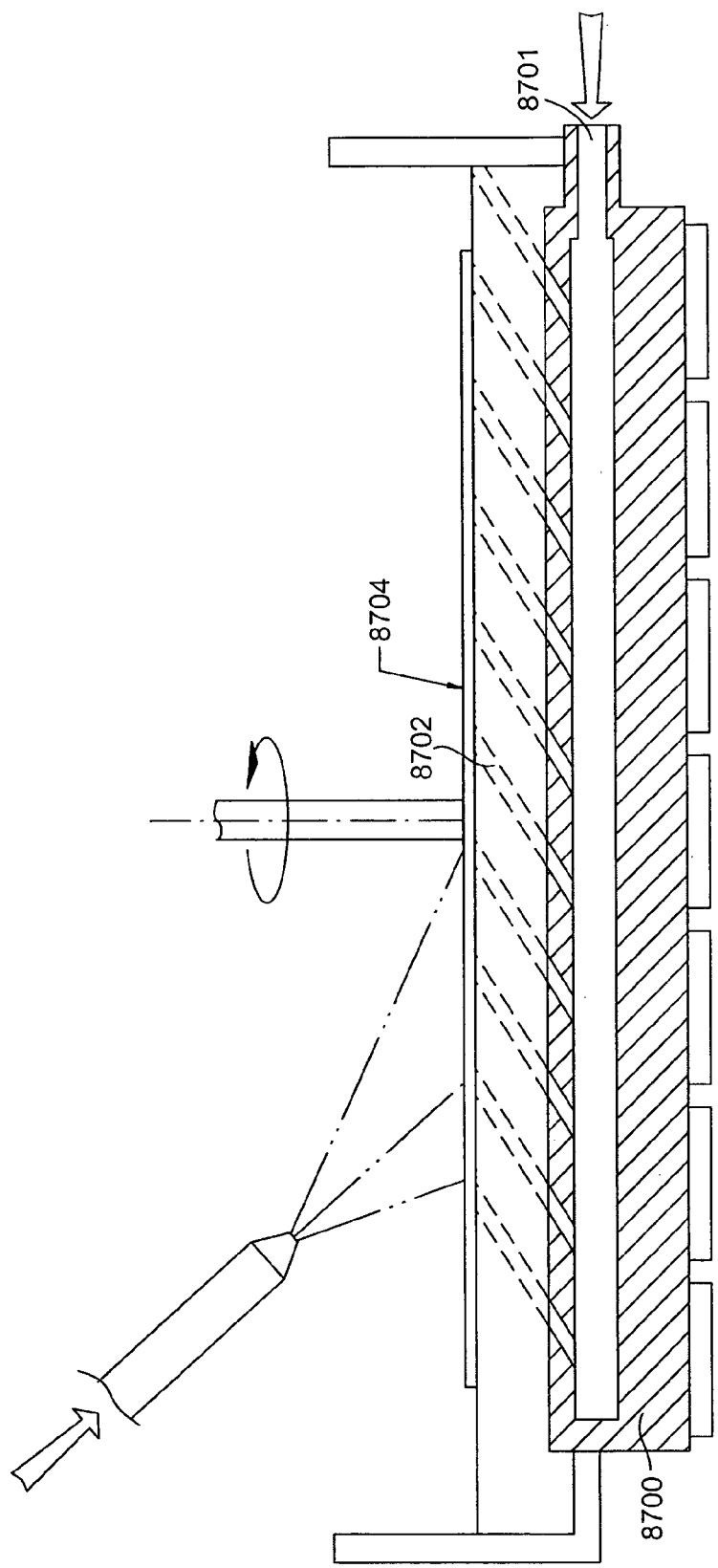

An alternative embodiment of an ultrasonic nozzle is shown in FIG. 4E, which depicts a wide active area with liquid 401 exiting a porous or liquid permeable transducer plate 460. In this embodiment, liquid is pumped into hollowed section 462 of vibration member plate 460 and forced out through multiple small holes or openings 464 simultaneously. The thickness of the outer surface of the plate 460 is selected to be an even multiple of one-quarter wavelength of the sonic energy, to ensure substantial transfer of energy from the surface of the vibration member submerged in a liquid. When not fully submerged, or when high velocity jets of fluid exit the surface of the vibration member, the fluid is sonically energized locally as it exits the cavity. The fluid can exit perpendicular to the vibration member surface or at some angle to enhance cross substrate energy transfer or to accomplish more effective processing, as shown in FIG. 87.

In accordance with embodiments of the present invention, it is not necessary to select the liquid gap thickness within the vibration member to be an even multiple one-quarter wavelength. However, such a design in conjunction with the use of flat plate vibration members may enhance transfer of energy across the internal liquid layer when the gap is relatively narrow (i.e. few wavelengths thickness).

Holes in the vibration member can be of any shape, with shapes leading to a maximized steady flow of exiting fluid often preferred. Shaping the hole to aerodynamically enhance fluid flow and minimize mixing and turbulence or the generation of eddy currents within the fluid flow, may also be preferred. Additionally, various ports for sucking liquid off the substrate surface during processing could also be employed.

While the vibration member has been illustrated so far as a flat plate structure, this is not required by the present invention. A wedge having a triangular or multi-edged polygonal cross-sectional profile could also be utilized, as illustrated in the alternative embodiment of FIG. 4F.

And while the cavity within the vibration member has generally been depicted as being rectangular in shape, this is also not required by the present invention. Other shapes of various sizes can be utilized.

Moreover, with non-flat plate-like vibration member structures such as a wedge device where energy waves intersect a surface at an angle other than perpendicular, the thickness of the top of the fluid cavity need not be of an even multiple one-quarter wavelength thickness as suggested for a flat plate vibration member.

FIG. 4G illustrates the simplified cross-section of a narrow area ultrasonic nozzle 480 based on a wedge-like device. The fluid is maintained in a steady flow condition as its direction is changed in the nozzle, leading to sonic activation of the exiting spray. A wide area nozzle arrangement could be made with an analogous design as well.

And while the face or side from which energy applied by the megasonic sources exits the wedge device ("the activated face") has generally been portrayed as flat, this is not required. Various contours are possible. For example, in either a large or small area sonic nozzle, the third face of a wedge device could be curved instead of flat (straight). Such a curved face may help to promote steady flow. Thus the activated face could be totally or partially flat, concave or convex with constant or variable radius of curvature.

Figure 8A:
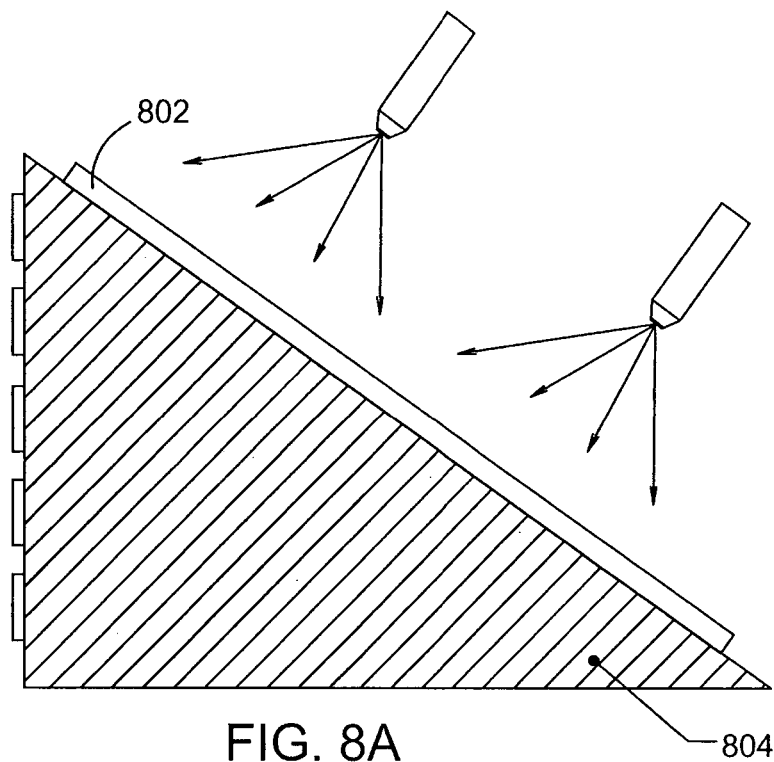
FIG. 8A shows a simplified cross-sectional view of an alternative embodiment of an apparatus in accordance with the present invention, where a wedge or device is used to convert megasonic pressure waves into surface waves for processing with substrate in direct contact with one face of the wedge and liquid sprays.
Figure 8B:
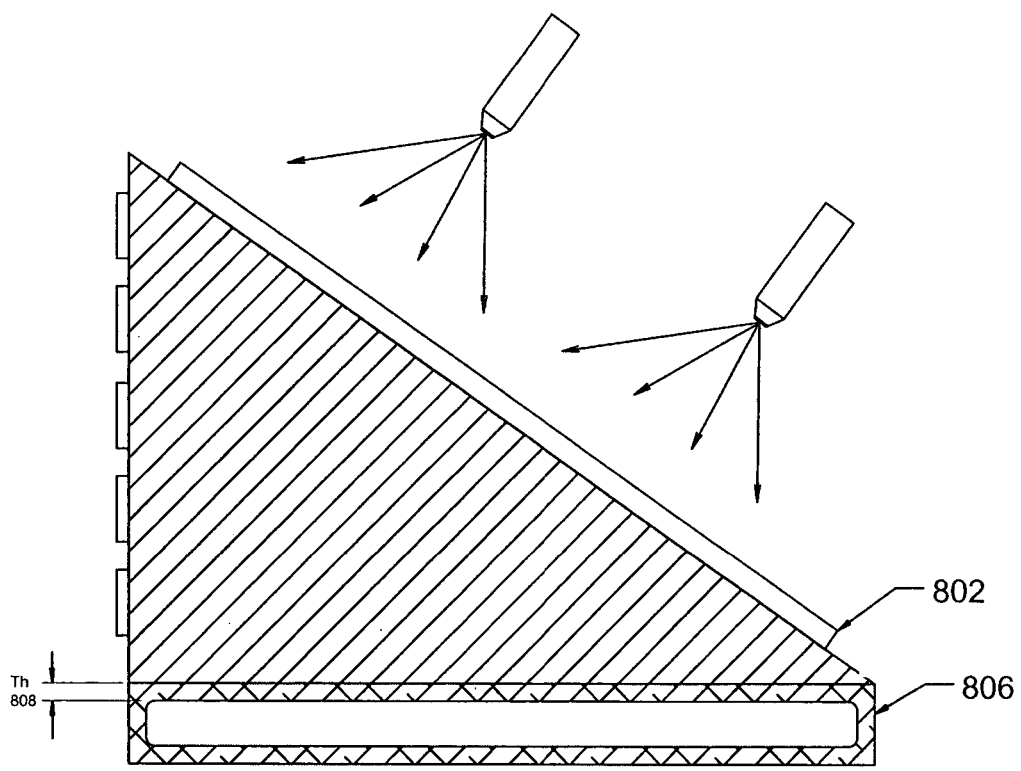
FIG. 8B shows a simplified cross-sectional view of an alternative embodiment of an apparatus in accordance with the present invention, where a distinct cooling member is adjacent to the wedge.
Figure 8C:
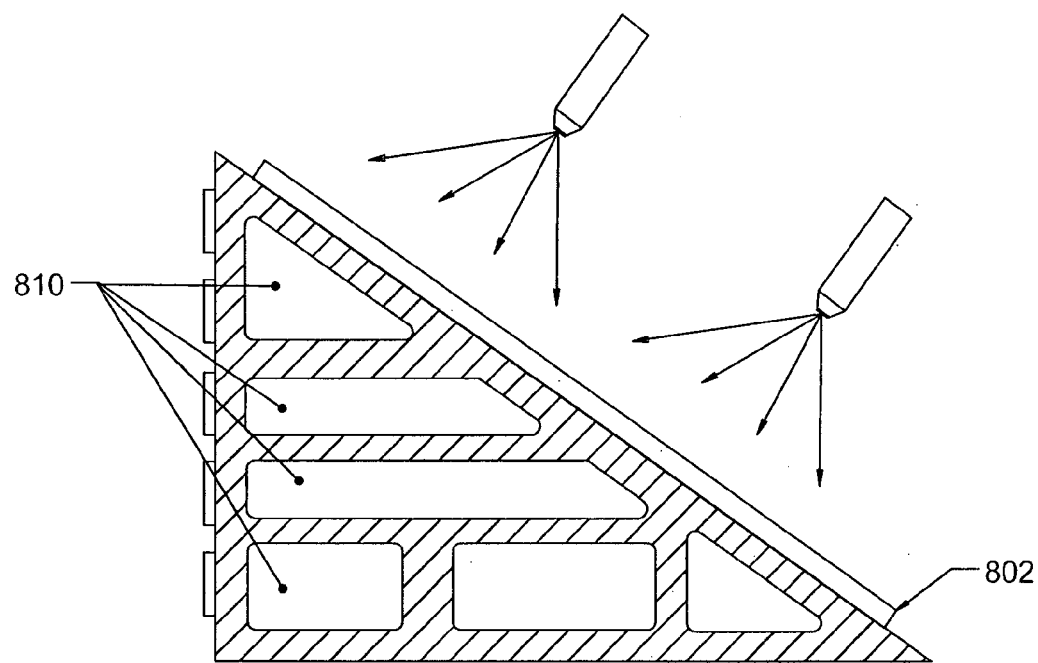
FIG. 8C shows a simplified cross-sectional view of an alternative embodiment of an apparatus in accordance with the present invention, where the wedge is designed to include hollow or fluid-filled passages for cooling.

Another embodiment utilizing the concept of a wedge or device to adjust the incident angle of megasonic energy onto a plate is illustrated in FIG. 8A. The substrate 802 and vibration plate 804 is in intimate contact and at the proper angle to gain mode conversion from longitudinal to shear wave. When a shear wave is formed in a multi-layer vibration member comprised of a thin and a thick section, it is concentrated in the thin layer and is termed a Love wave. Processing liquid is sprayed onto the substrate surface allowing unique surface energy patterns to be formed and interact with contaminant particles. Alternative embodiments include a distinct cooling member 806 adjacent to the wedge (FIG. 8B), and designing the wedge to include hollow or fluid-filled passages 810 for cooling (FIG. 8C). Additionally, a vacuum chuck arrangement (complex of vacuum holes) could be constructed to keep the substrate in good mechanical contact with the vibration member.

Figure 8D:
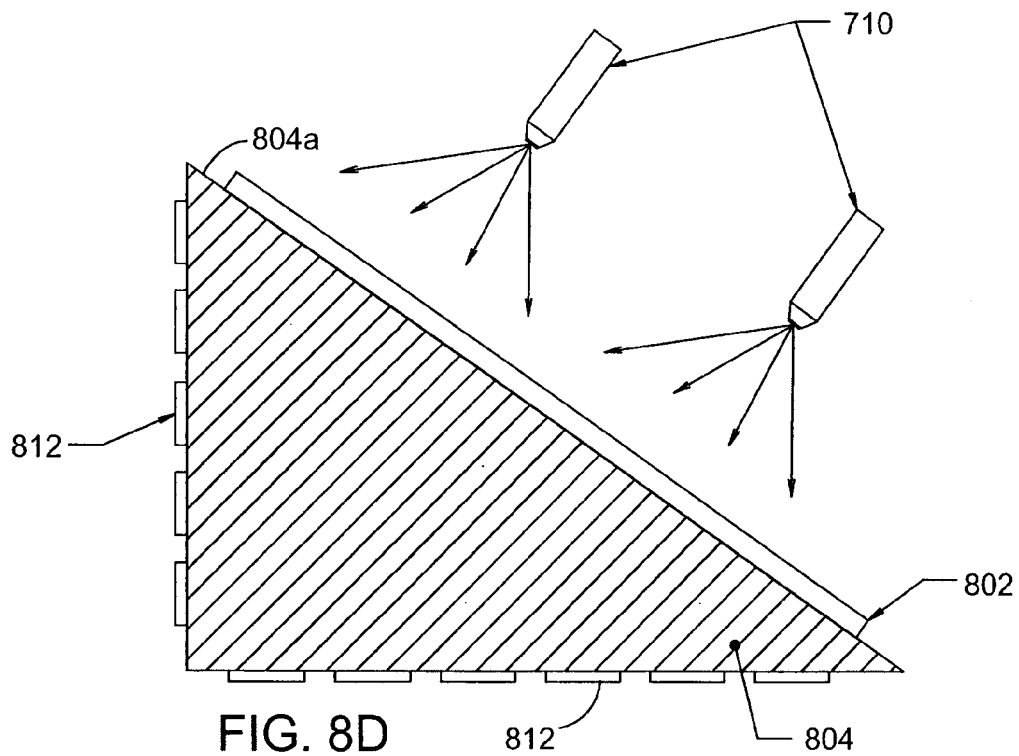
FIG. 8D shows a simplified cross-sectional view of an alternative embodiment of an apparatus in accordance with the present invention, where piezoelectric crystals are located on two faces of a wedge structure, and a substrate contacts the third face.

Still another embodiment utilizing the concept of a wedge device is illustrated in FIG. 8D, where piezoelectric crystals 812 are attached to more than one side of a wedge 8xx simultaneously. The substrate 802 is brought into close contact with the third face (hypotenuse) 804a of the triangular wedge device 804. The dilatational waves produced by the crystals are likely converted to surface waves that perform the substrate processing. Complex waveforms can be generated from multiple crystals operating at different frequencies on each of the adjacent sides. Processing fluid can be applied to the processing face by at least a spray, mist or immersion.

Figure 8E:
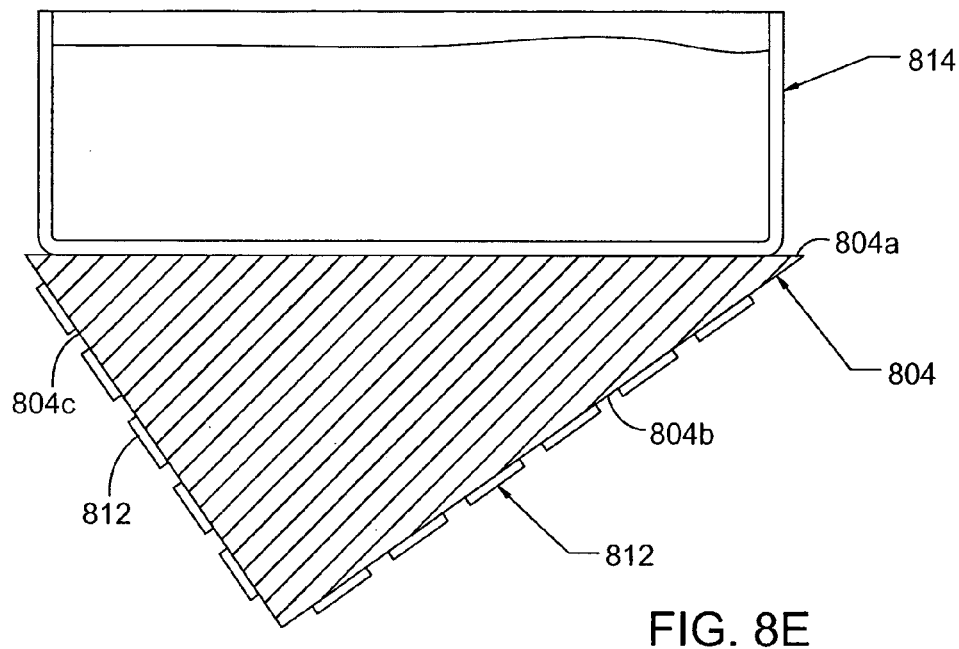
FIG. 8E shows a simplified cross-sectional view of an alternative embodiment of an apparatus in accordance with the present invention, where piezoelectric crystals are located on two faces of a wedge structure, and the third face contacts the wall of a processing vessel.
Figure 8F:
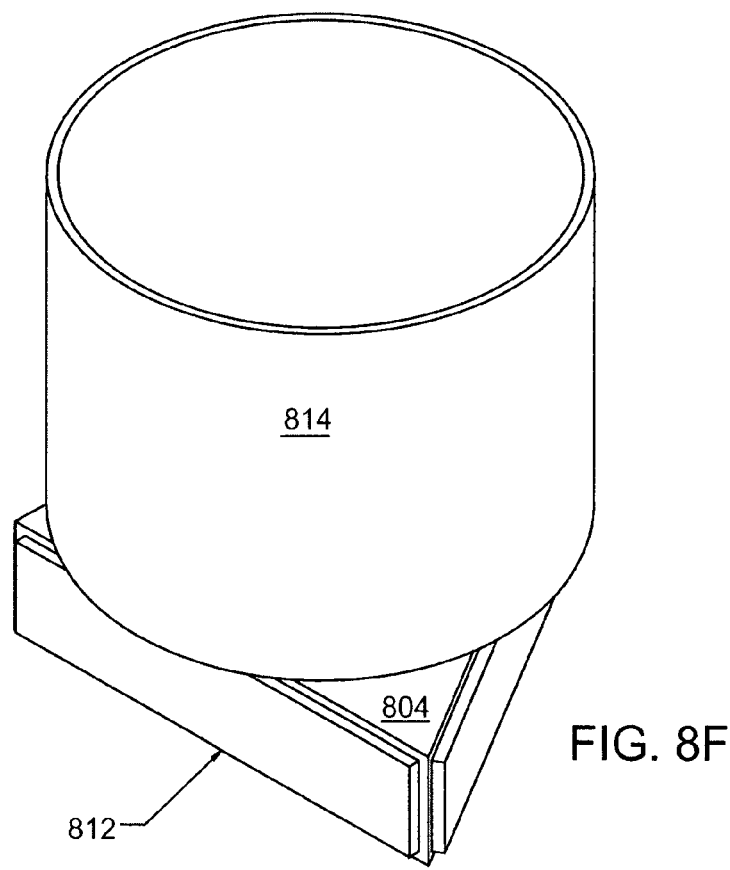
FIG. 8F shows a simplified cross-sectional view of an alternative embodiment of an apparatus in accordance with the present invention, where piezoelectric crystals are located on two faces of a wedge structure, with a processing vessel in contact with a top side of the wedge
Figure 8G:
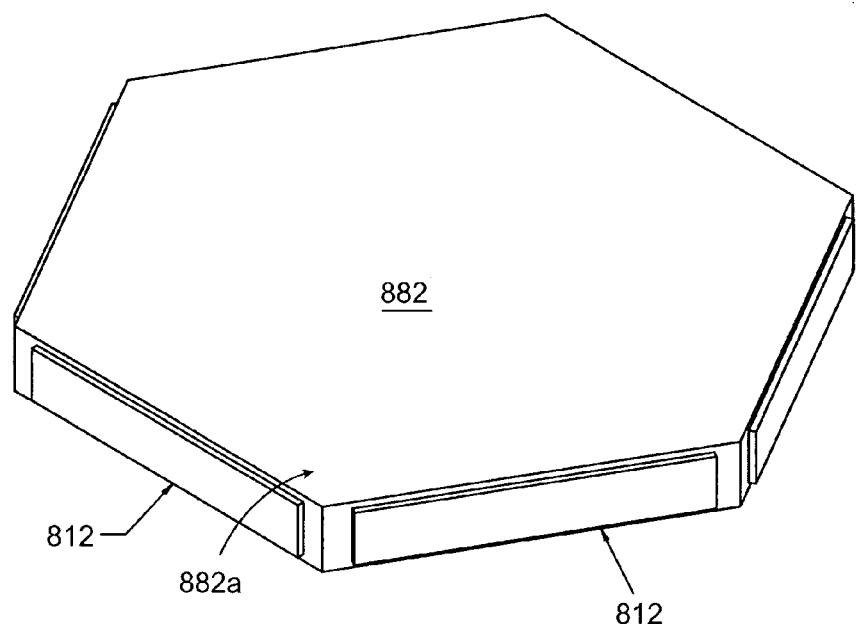
FIG. 8G shows a simplified cross-sectional view of an alternative embodiment of an apparatus in accordance with the present invention where piezoelectric crystals are located on multiple faces of a polygonal structure with sides forming a right angle with the top side and a process vessel in contact with a portion of that top side.
Figure 8H:
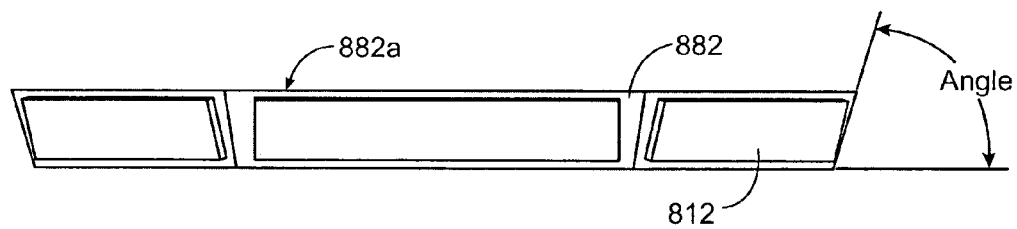
FIG. 8H shows a simplified cross-sectional view of an alternative embodiment of an apparatus in accordance with the present invention, where piezoelectric crystals are located on multiple faces of a polygonal structure whose sides form an angle with the top side, a portion of the top side in contact with a process vessel.

A further embodiment utilizing a wedge device is illustrated in FIG. 8E, with crystals on two surfaces 804b–c and the third face (hypotenuse) 804 in direct contact with a tank 814. The sonic energy is readily transferred from the wedge device into the processing tank. As shown in FIG. 8E, any number of crystals may be used by making the wedge "thicker" or deeper. Crystals having almost any aspect ratio can be oriented in any direction on any of the wedge faces.

One of the advantages of having the tank wall or even the substrate in direct contact with the vibration as stated previously, is that the thickness of the substrate can be easily compensated for to produce maximum energy transfer either across the substrate or into the processing vessel or tank.

In accordance with another embodiment of the present invention shown in simplified cross-section in FIG. 8F, a tank or vessel may contact either (top or bottom) sides of the wedge device, rather than the third face as in the embodiment of FIG. 8E. In such an embodiment, crystals 812 may be arranged on multiple faces or sides of a wedge 804. In the embodiment of FIG. 8F, energy unexpectedly flows perpendicular to the plane of the dilatational or pressure waves emanating from the crystals into the wedge and then into the overlying tank 814. Spray, immersion or contact with a tank may be utilized for processing.

While the embodiment of FIG. 8F shows crystals on two sides, this is not required by the present invention. In alternative embodiments in accordance with the present invention, crystals could be present on only one side, or on three or more sides as desired.

Figure 8I:
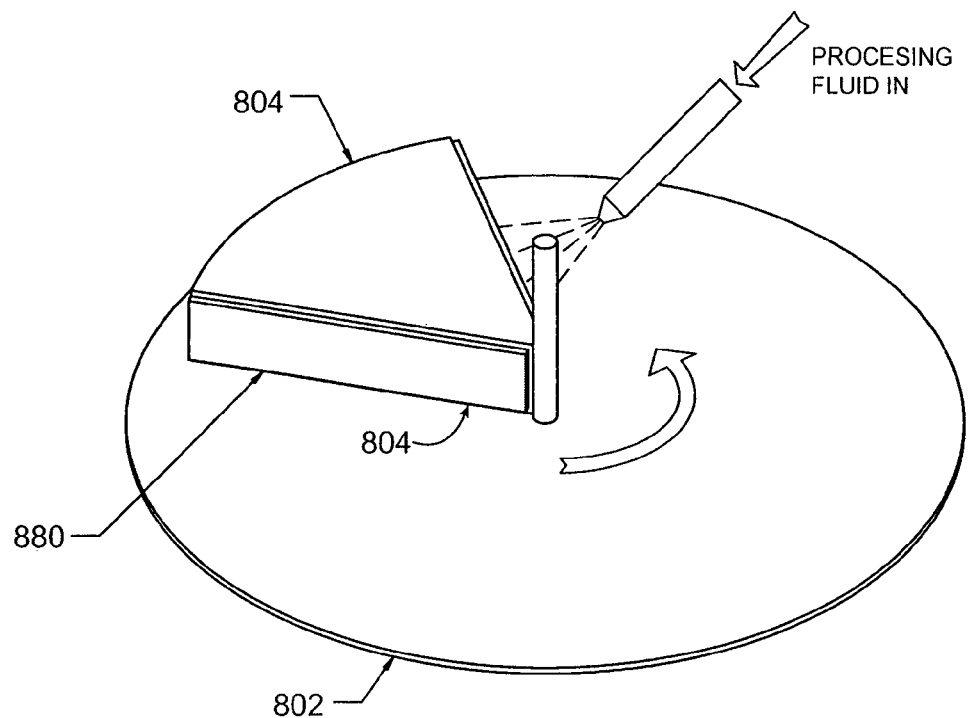
FIG. 8I shows a simplified perspective view of wedge structure with piezoelectric crystals on two faces at right angle with the top and bottom sides and contact with a substrate is made through a bottom side though a thin liquid layer or meniscus.

In accordance with another embodiment of the present invention, the bottom surface 804d of a modified wedge device 804 illustrated in FIG. 8I is placed parallel to the top or bottom surface of a rotating substrate 802. The sides of the wedge where the crystals are mounted are at right angles (90°) with the bottom surface. Bottom surface 804d and substrate 802 are brought into relatively close proximity to each other with the gap being filled with a thin film 880 of processing liquid.

Figure 8J:
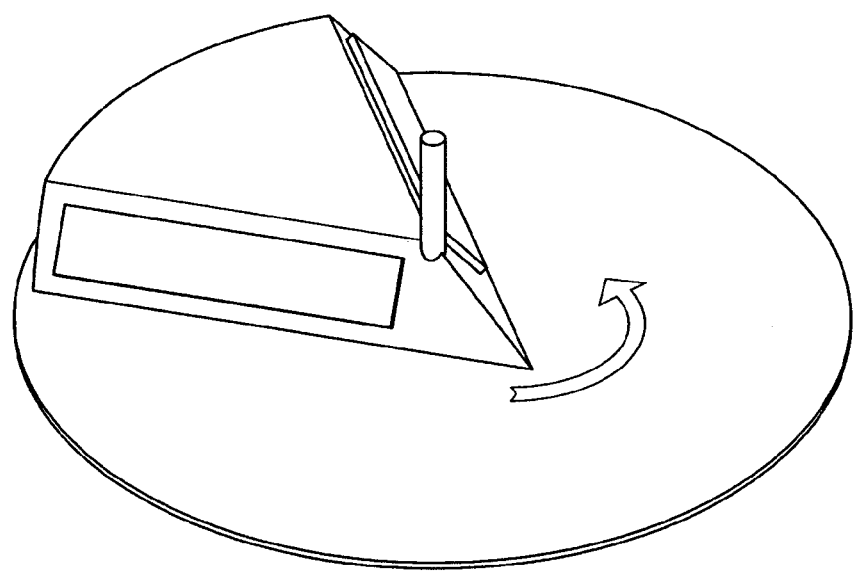
FIG. 8J shows a simplified perspective view of an alternative embodiment of a processing apparatus in accordance with the present invention similar to that shown in FIG. 8I, except the sides of the wedge form an angle with the top and bottom sides of the wedge.

In accordance with yet another embodiment of the present invention shown in FIG. 8J, the bottom surface of a wedge structure that has crystals attached to sidewalls angled at other than the 90° shown in the embodiment of FIG. 8I, is positioned above a substrate. The sonic energy emanating from the crystals impinges the bottom of the wedge at an angle. The angled incidence likely converts the dilatational waves from the crystals into surface waves on the bottom of the wedge. The surface wave then interacts with the substrate through a thin liquid layer or meniscus.

In accordance with still other embodiments of the present invention, shapes other than a wedge of triangular cross section can be used in the transfer device design. FIG. 8G illustrates a polygonal shape 882 fitted with multiple crystals 812. Energy may be transferred as shown, from the side of the device directly into a tank.

While the embodiment of FIG. 8G shows the crystals mounted on edges at right angles to the surfaces to which sonic energy is applied, this is not required by the present invention. Instead, the edges could be constructed at an angle with the side, as shown in the embodiment of FIG. 8H, thereby possibly allowing the transfer of even more energy to the top side 882b of the device 882.

Figure 8K:
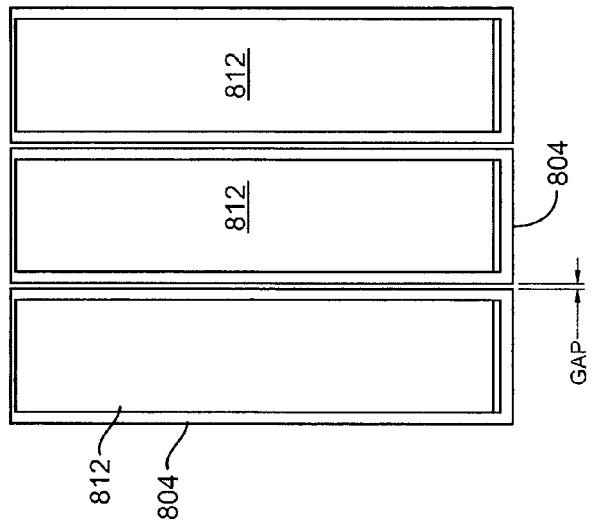
FIGS. 8KA–C show simplified perspective views of an embodiment of a wedge structure in accordance with the present invention.
Figure 8K:
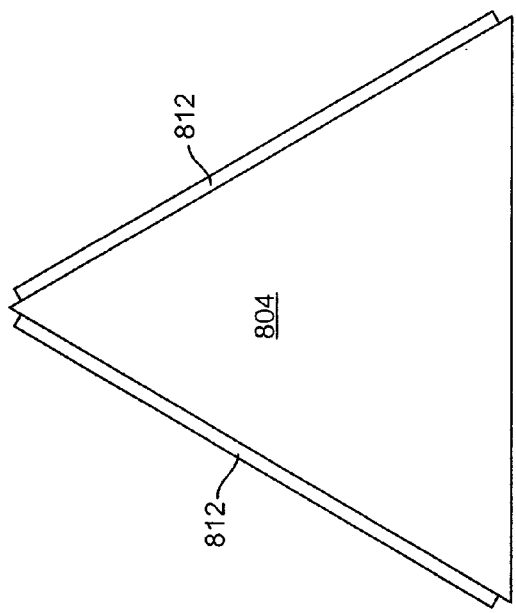
Figure 8K:
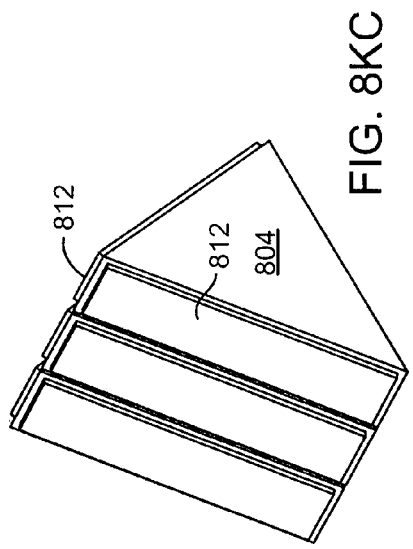
Figure 8L:
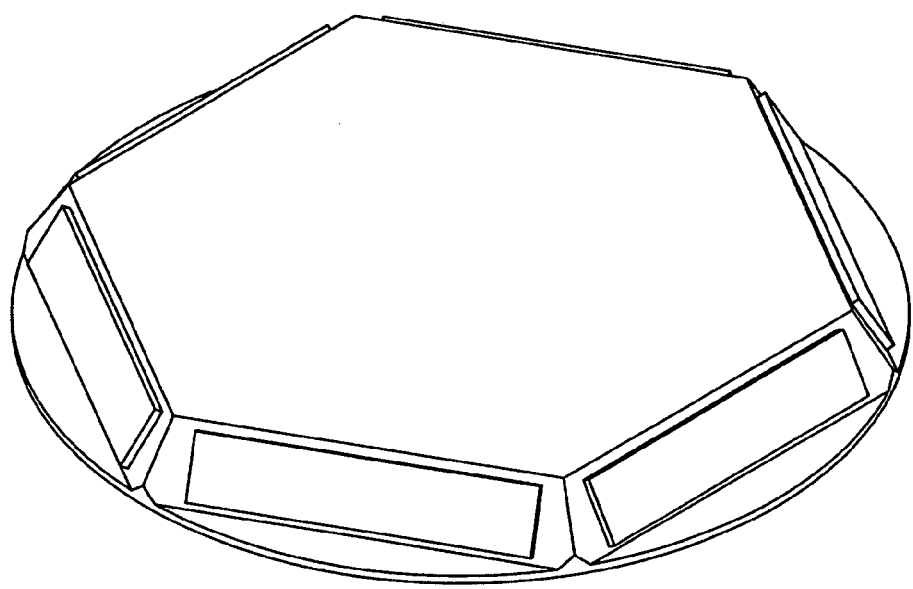
FIGS. 8LA–B show simplified perspective and edge views, respectively, of another embodiment of a wedge structure in accordance with the present invention.
Figure 8L:
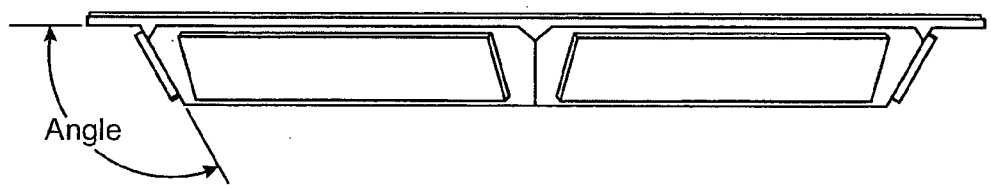

FIGS. 8LA–B show perspective and edge views, respectively, of an alternative embodiment of a vibration member in accordance with the present invention. FIGS. 8LA–B show that the energy-transferring surface can extend out past the sides of the polygonal structure on which the vibrating elements are attached. Further, the polygonal structures need not be regular. Each side could have a different length.

In a further refinement of this and other embodiments disclosed where a thin liquid film or meniscus is formed on the surface of the substrate, the gas atmosphere can be charged with various species to enhance processing. For example, to remove organic particles, ozone gas could be introduced into the gas space. The ozone molecules could then easily diffuse across the fluid layer on the surface of the substrate and react with the surface or contaminates on the surface.

To enhance the rate of ozone transfer, the gas phase could be pressurized. Such an approach would contrast with conventional industry processes, which operate at atmospheric pressure.

Instead of ozone, hydrogen peroxide could be added to the processing liquid or sprayed onto the thin liquid film on the substrate surface. Other processing chemicals could also be chosen, such as organic acids, inorganic acids, bases, oxidants, reducing agents. They could be in the form of solids, liquids or gases.

When combined with the introduction of megasonic energy, the liquid film layer can be broken up and mixed rapidly, increasing transfer of a gas species from the atmosphere to the surface of the substrate, whether operated at either elevated or even atmospheric pressure. The megasonic energy could also aid in removing loosened material from the substrate surface. Such a processing mechanism could be helpful when applied to a number of processing steps, but could be especially advantageous when applied to processes such as photoresist stripping. Additionally, the application of megasonic energy can lead to the formation of desirable chemical species in the processing fluid or on the surface of the substrate.

The thickness of the vibration member and the substrate may be dictated or set by other constraints. If the combination of their individual thickness do not add up to the desired thickness for good energy coupling at a given frequency, it may be desirable to adjust the frequency. Conventionally, this can only be accomplished over a relatively narrow range around various harmonic frequencies of the piezoelectric crystals to produce the desired odd multiple one-quarter wavelength of the megasonic energy. With megasonic generators manufactured by PCT Systems Inc. of Fremont, Calif., in accordance with embodiments of the present invention, however, some degree of frequency adjustment of individual crystals to accommodate minor thickness differences or changes is possible. With many conventional fixed frequency systems using generators with RF outputs that cannot be changed for individual crystals, this type of adjustment may not possible.

In some applications, less than optimal energy transfer may be acceptable, and only partial energy transfer may be adequate to perform the processing. For example, in the case of optimal energy transfer, no gap(s) or voids are present between the vibration member and the substrate. Practically, however, some gaps or voids may exist due to machine tolerances, or machine designs requiring separation. In such applications, it may be especially important that the gaps or voids not be filled with compressible fluids, such as gases.

When unavoidable gaps or voids between the vibration member and the substrate are filled with relatively incompressible fluids such as water, acceptable energy transfer can often occur. In applications using relatively incompressible fluids, the gaps can become quite large (>1 m) and still demonstrate significant energy transfer, especially with fluids containing relatively low levels of dissolved gases. FIG. 6A is a representation of such an embodiment.

In practice, the gap between the vibration member and the substrate may be filled with a solution containing a significant amount of dissolved gas. Some of that gas is liberated in the form of bubbles as the megasonic energy is applied because of the reduced pressure region on the trailing edge of the pressure wave.

These liberated bubbles may interfere with optimal energy transfer through the solution. However, with the high intensity energy surges occurring with multiplexed crystal operation, bubbles may effectively be "pushed" out of the sonic pathway, so that little problem is encountered with such solutions.

Historically, high fluid velocities have been used in an attempt to sweep the bubbles out of the active energy field in order to enhance energy transfer. However, such designs based on forced high fluid velocities have only met with limited success. A very large fluid velocity may be utilized to dislodge some bubbles from energized/vibrating surfaces. If the fluid velocities become too large, or if large turbulence or eddy currents are generated in the fluid, the transfer of energy through the fluid may be adversely affected.

Thus in another embodiment, the system is operated at increased pressure to overcome these limitations. The increased operating pressure acts to both reduce the volume of any bubbles formed, and to increase the concentration of gas that may be dissolved in the liquid at a given temperature. Therefore, any bubbles formed by the megasonic energy tend to be smaller and are forced back into solution more quickly. This leads to better energy transfer, and can lead to more uniform processing as well, especially when active gas species are dissolved in the liquid.

As a consequence, solutions with high dissolved gas content may now be utilized effectively. These high gas concentrations can enhance chemical reactivity. Additionally, they can promote increased microcavitation that may aid in substrate cleaning. Further, increased pressure can force solutions into smaller crevices than surface tension of the fluids alone would allow at atmospheric pressure.

In another embodiment, where the substrate is in intimate contact with the vibration member, an electrochemical reaction may be carried out simultaneously or intermittently with the application of megasonic energy. And where the substrate is separated from the vibration member and submerged in a fluid with the megasonic incident angle allowing across-substrate or across-electrode transfer of energy, an electrochemical reaction may be carried out simultaneously or intermittently during the application of megasonic energy. In either case, transfer of energy across the substrate and/or across the electrode can be important to maximize fluid exchange in small diameter holes, vias, and narrow trenches, to produce more uniform processing.

Section D below presents a detailed discussion of the application of ultrasonic energy to perform electrochemical processing of a substrate, in accordance with embodiments of the present invention.

In certain of the various embodiments described above, it may be preferable that the substrate front side, rather than back side, contact the vibration member. Moreover, either the substrate front side or the back side may face away from the vibration member when the substrate is fully submerged. These configurations could be important where the cross-substrate energy transfer aids in cleaning out surface voids such as vias and trenches. The cross-substrate energy transfer may help push contaminants out the front side of the substrate when energy enters from the backside of the substrate. By contrast, for conventional processing where energy is parallel to the substrate surface, little or no cleaning action within recesses or voids results, as these features are positioned at right angles to the flow of energy. Moreover, with conventional processing where the energy is directed perpendicular to the substrate surface, much of the applied energy may be reflected back toward the vibration member, possibly pushing contaminants even deeper into voids and crevices.

As mentioned above, suction can be applied sequentially or simultaneously with megasonic substrate processing. When liquid is both directed towards the substrate surface (multiple feed nozzles) and removed via suction (single or multiple suction nozzles), there is a greater likelihood that liquid within high aspect ratio trenches and vias can be exchanged more easily or more frequently. Both effects could result in enhanced processing.

In accordance with an alternative embodiment in accordance with the present invention, megasonic energy may first be transferred across the substrate in one direction, and then transferred across the substrate in another direction, thus treating both sides of the substrate with energy and momentum. For example, U.S. Pat. No. 6,098,643 ("the '643 patent") is hereby incorporated by reference for all purposes.

The '643 patent describes a tank that may be modified to produce cross-substrate energy transfer. Substrates positioned within the tank may have their orientation rotated 90° in a horizontal plane from the orientation shown in the '643 patent. Megasonic energy would thus impinge the surface of the wafers at a proper angle for cross wafer energy transfer from the end of the substrate carrier, instead of the energy being directed parallel to the substrate surface along the length of the substrate carrier.

As the piezoelectric crystals are fired sequentially first from one side of the side of the V-bottom tank and then from the other, megasonic energy goes through the wafers first from one end of the carrier and then from the other. Thus both sides of the substrates may be treated equally by megasonic energy bursts. This can be utilized for both single wafer as well as batch processing of multiple wafers simultaneously.

As described above, there can be some attenuation of energy as it crosses each substrate and the space separating the substrates. Therefore the energy density is not necessarily constant from one end of a cassette to the other.

In an arrangement wherein both sides of the substrates are treated with bursts of megasonic energy, substrates at each end of the cassette would receive a high energy density burst from one direction and a low energy density burst from the other. This would tend to even out the total applied sonic energy. For most effective processing, it may be desirable to use a carrier holding fewer that 50 or even 25 substrates.

Embodiments in accordance with the present invention are not limited to using any one type of megasonic generator or mode of operation. For example, the megasonic generators could be of the type in which the piezoelectric crystals are fired singly, or several are fired simultaneously or in repeating sequence. The megasonic generators could generate either at a fixed frequency, a programmed variable frequency, or a randomly fluctuating frequency. Thus while the above embodiment describing operation in a V-bottom tank specifically refers to sequentially firing one transducer on one side of a tank and then a transducer from the other side of the tank, other modes of operation are possible as well.

In certain applications, process fluids may be maintained at high temperatures that could damage either the megasonic transducers or their method of attachment, or could lead to poor megasonic performance. In such applications, direct cooling of the piezoelectric crystal(s) can be employed. Such direct cooling of the piezoelectric crystal(s) may also be useful in cases when high megasonic energy density is required which would cause high operating transducer temperatures, again leading to possible damage or poor performance.

Figure 9A:
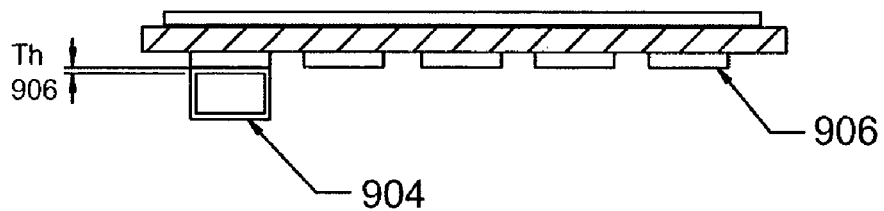
FIGS. 9A–B show simplified cross-sectional views of alternative embodiments of apparatuses in accordance with the present invention which utilize direct cooling of transducers.
Figure 9B:
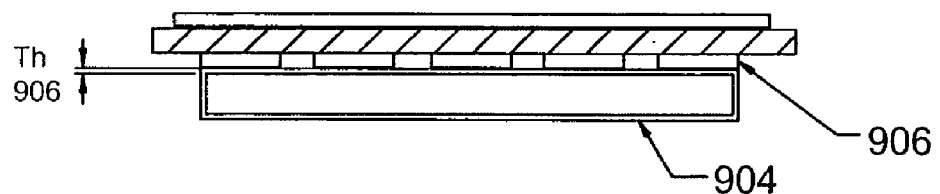

FIGS. 9A and 9B illustrate two embodiments of direct cooling of transducers, where a fluid filled cooling member 904 is attached to the backside of the piezoelectric crystal(s) 906 with adhesive or other bonding means, or clamping and other holding means. In order to minimize the amount of megasonic energy transferred into the cooling member (and perhaps lost in the cooling fluid), thickness of the sheath of the cooling member is chosen to be approximately an even multiple one-quarter wavelength of the ultrasound energy.

In practice, potentially some loss could occur should the thickness of the sheath be closer to an odd multiple one-quarter wavelength, promoting transfer of energy into the cooling member. Even so, some fraction of the energy transferred into the cooling member would likely be reflected back into the vibration member from the air-sheath interface on the backside of the cooling member, minimizing actual loss of megasonic energy.

The sheath material can be comprised of a number of materials, including but not limited to metals, plastics and composites and combinations thereof. Generally a metal may be preferred when good electrical insulation can be ensured between the cooling member and the transducer body because of the generally higher thermal conductivity of many metals. Non-electrically conductive sheath materials can often be placed into direct physical contact with the transducers without any additional electrically insulating layers or films separating them.

The cooling or heat transfer fluids in the cooling members can also be comprised of a number of materials including, but not limited to both electrically conductive and non-conductive fluids. These fluids could be introduced as gases, liquids or solids. They may remain in their initial state or they may go through a phase change as they absorb heat from the transducers. Further, they could also include processing and rinsing fluids commercially used in semiconductor processing and other industries. Perfluorinated fluids such as Galden manufactured by 3M can be used either as fluids circulating through the cooling member, or could be sprayed directly onto the back of the exposed transducer body causing rapid cooling of the transducers. When dealing with structures exhibiting an angle relative to incident energy (i.e. other than flat plate vibration members), limitations in thickness are changed when conditions promoting significant cross substrate energy transfer are used.

In the embodiment of FIGS. 9A–B, as well as with many others already disclosed, a more rigorous discussion of this subject matter could include impedance terms rather than mere thickness criteria, taking into account physical parameters like Yong's modulus, density and speed of sound in differing materials.

Processing in accordance with embodiments of the present invention can occur in a single chamber with a single processing step, or could comprise multiple processing steps with various chemistries. Alternatively, processing may be carried out in multiple chambers sequentially. Processing could include wet processing, dry processing, or a combination of both wet and dry processing.

Coupled with megasonic energy, a variety of radiation types may be useful for different applications. Types of applied radiation include, but are not limited to: microwave, ultraviolet, infrared, and electromagnetic induction. In another embodiment of the invention, the radiation may heat the substrate or processing liquid on the substrate surface, thus promoting more rapid reaction without necessitating heating of the entire process chamber. Microwave, infrared, and electromagnetic induction could be useful in heating a processing liquid or substrate.

In another embodiment, the radiation could promote a particular reaction at a surface of the substrate. In such an approach, the application of ultraviolet radiation can offer particular advantages. An oxidant could be utilized in combination with the radiation to enhance degradation of the residual contaminants or to modify surfaces. Examples of useful oxidants include but are not limited to ozone, hydrogen peroxide, and oxides of nitrogen.

In another embodiment, residual processing liquid on the surface of a substrate can be vaporized off the surface by the addition of megasonic energy. As with many of the other embodiments, the residual processing liquid could be in the form of droplets or even a film covering the substrate surface. In some cases, very small cavities within the substrate may be filled with processing liquid as well. It has been discovered that thin films or droplets of liquid can be quickly vaporized, leaving substrate surfaces dry by applying megasonic energy directly to, or through, a substrate. A detailed description of the application, of sonic energy in accordance with embodiments of the present invention to accomplish substrate drying is provided below in Section E.

A detailed description of the application of sonic energy in accordance with embodiments of the present invention to accomplish other processing applications is provided below in Section F. A detailed description of the use of different types of fluids in megasonic processing is provided below in Section G.

For purposes of this patent application, the term "wedge device" can be defined to include devices with various cross sections. For example, a wedge device could be comprised of a triangular cross section with three faces and two sides (top/bottom), or could be comprised of a polygonal structure with a larger number of faces.

In the case of wedge devices in particular, the face or side from which energy emanates may demonstrate a more uniform vibration pattern resembling a row of point sources firing sequentially, rather than a number of randomly firing point sources as is more typical in a flat plate vibration member. This characteristic could translate into more uniform processing for some substrates within various vessel and holder configurations.

The energy in a wedge device tends to be spread over the entire surface. Therefore, sequential firing of multiple crystals on one or more sides of the device would result in energy waves covering essentially the entire wedge/face of interest. Such an arrangement would result in a multiplexing generator design in which the crystals are fired sequentially, appearing as if a generator of the same total wattage output were used having all crystals continuously energized at a reduced energy density. Instead of producing a continuous energy output, such an arrangement would result in continuous pulses of energy having a duration equal to the length of time each crystal is fired, before being switched to the next crystal.

With megasonic energy transmitted through a fluid, when the crystal is first energized, the initial magnitude of the pressure wave increases to a maximum and then decreases over the remainder of the energy pulse dependent upon pulse duration. The pulsating, "always on" characteristic described above for a crystal multiplexing of the wedge device could thus be beneficial for substrate processing, with both continuous power and peak surges during each on duration for each crystal.

To prevent the spreading of the energy from a single crystal over the entire bottom of a tank or process vessel, the wedge device could be constructed of multiple narrower wedge device elements 804 rather than a single larger device, as illustrated in the side and perspective views of FIG. 8KA–C. With a minute air gap between neighboring wedge devices 804, or less than optimal coupling between them, transfer of energy from one device element to the next could be minimized, thus maintaining a higher energy density on each individual section with multiplexing systems. With some appropriate limited transfer between adjacent sections (energy overlap), there would not be totally dead areas (areas of non-uniformity) between the elements, which could adversely impact localized substrate processing.

Generally, sonic nozzles are used to direct a small, energized liquid stream at a non-submerged surface. This approach is successful where the nozzle is relatively close to the surface, and a continuous liquid column or stream between the nozzle and surface can be achieved. Separation distances larger than several centimeters, however, generally results in inefficient energy transfer.

In accordance with an alternative embodiment of the present invention, the nozzle may be incorporated in a fully submerged processor. Thus, not only is megasonic energy transferred from the vibration member to the substrate, but significant high fluid velocity profiles are developed between the two. In some cases, the megasonic energy follows the fluid pulses from the jet as with a megasonic nozzle. This combination of megasonic energy and high localized fluid velocities, may great enhance processing under some conditions, especially those in which mass transfer is an important issue. Examples of the enhanced processing as a consequence of high fluid velocities, absent even the addition of megasonic energy, are evident from the enhanced rates of photoresist stripping of co-pending U.S. patent application Ser. No. 10/150,748.

The speed of sound in a material may differ according to wave type. For example, dilatational or pressure waves often exhibit nearly twice the speed of sound in many materials relative to a shear or surface wave in the same material. Thus, with mode conversion or diffraction of an incident dilatational wave, the speed of the resulting waveform could be significantly different, perhaps leading to different processing performance.

With wedge devices, the dilatational or pressure waves generated by the piezoelectric and other crystal types can be converted into various waveforms depending not only upon the angles the wave encounters, but also upon the environments through which the wave(s) must travel. In the embodiment of FIG. 7C, for example, even with a fluid-filled region the dilatational waves are converted to shear or surface waves on the activated face or in the attached plate.

By contrast, in a somewhat similar wedge device shape of the embodiment of FIG. 8E, the energy waves leave the activated surface at an orientation normal to that surface and enter the process tank. This mode conversion can occur over a broad range of angles.

Such mode conversion over a broad range of angles, may be contrasted with the ability of dilatational or pressure waves to transfer across a submerged substrate over a much narrower range of incident angles. For example, if the fluid filled wedge of the embodiment of FIG. 7C were separated from the extending plate, and liquid were placed on the face of the wedge that had been in direct contact with the plate, it could be difficult to predict the resulting transfer of energy types and patterns across the activated face if the shell of the wedge were thin.

Depending on the angle of incidence of the dilatational waves transmitted through the fluid inside the wedge, upon striking the shell of the activated face, both mode conversion and transfer could occur. At one range of incidence angles, energy transfer across the thin shell could predominate. At another range of incidence angles, mode conversion to surface waves may occur. At still other incidence angle ranges, varying degrees of internal reflection could occur. Testing may reveal with greater precision the results of applying sonic energy at various angles with such a complex structure design.

Figure 81:
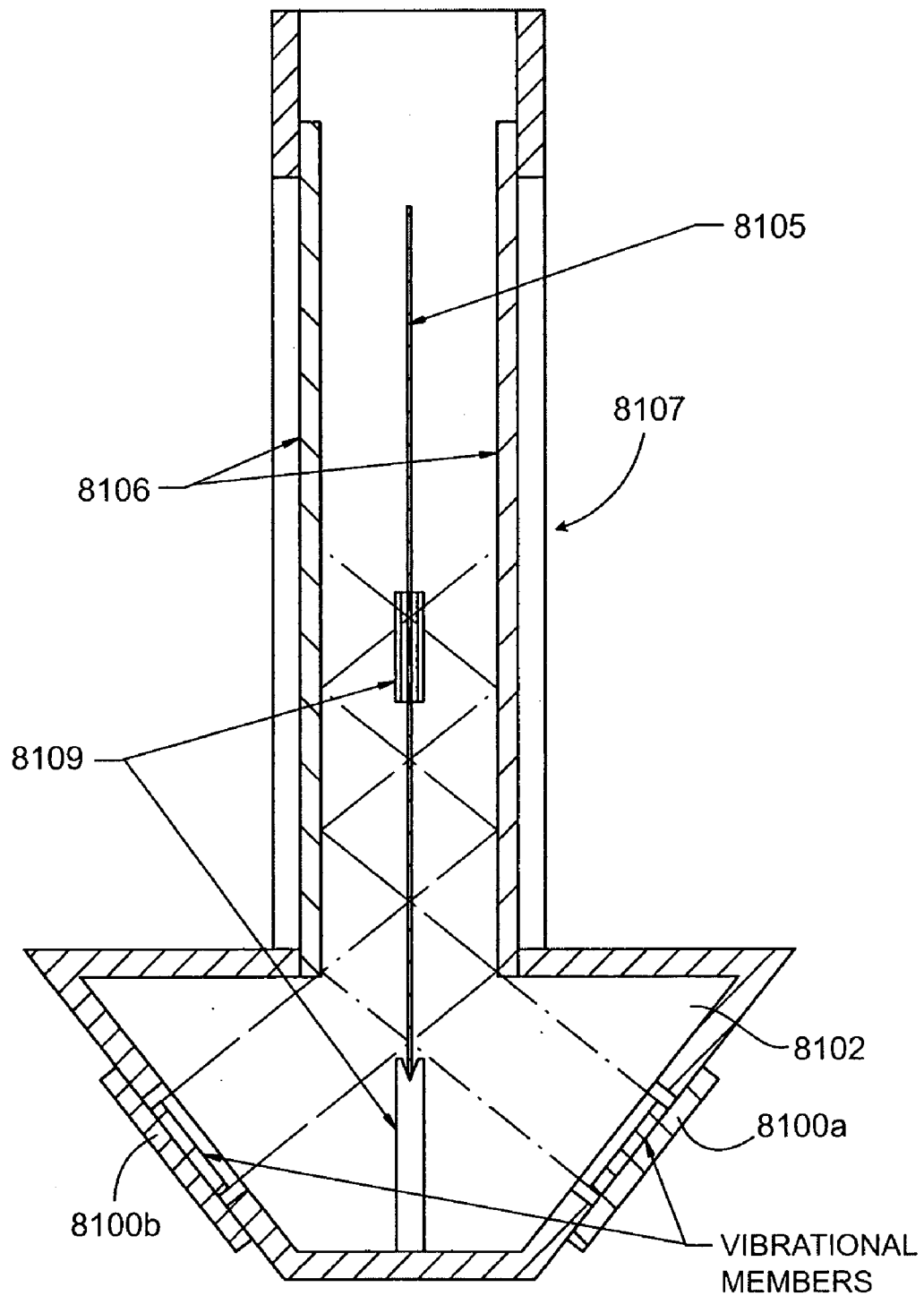
FIG. 81 shows a simplified cross-sectional view of an alternative embodiment of a substrate processing apparatus in accordance with the present invention, having vibration members oriented for cross-substrate energy transfer.

FIG. 81 illustrates a simplified cross-sectional view of another embodiment in accordance with the present invention comprising a single wafer processor having vibration members oriented for cross-substrate energy transfer. Vibration members 8100a and 8100b positioned on opposing sides are energized sequentially, not simultaneously. Substrate 8105 is supported within tank 8107 by supports 8109. Energy from each vibration member travels through the liquid 8102 and impinges the surface of the substrate 8104 at an angle proper for reasonable transfer of energy thereacross.

Energy that transfers across the substrate continues on in the liquid on the other side in a relatively straight line until it impinges one of the two reflecting sidewalls 8106. The transferred energy is then reflected back towards the substrate. The energy again impinges the surface of the substrate at a correct angle for significant cross substrate energy transfer, and passes again through the substrate at a higher point. The energy continues on to reflect off the other sidewall and back through the substrate yet again at a point higher in the tank.

Some attenuation occurs each time the energy crosses the substrate, the further it travels in the liquid and each time it reflects off a sidewall. The character of substrate processing could thus change as the energy travels from the bottom to the top of the tank.

Figure 82:
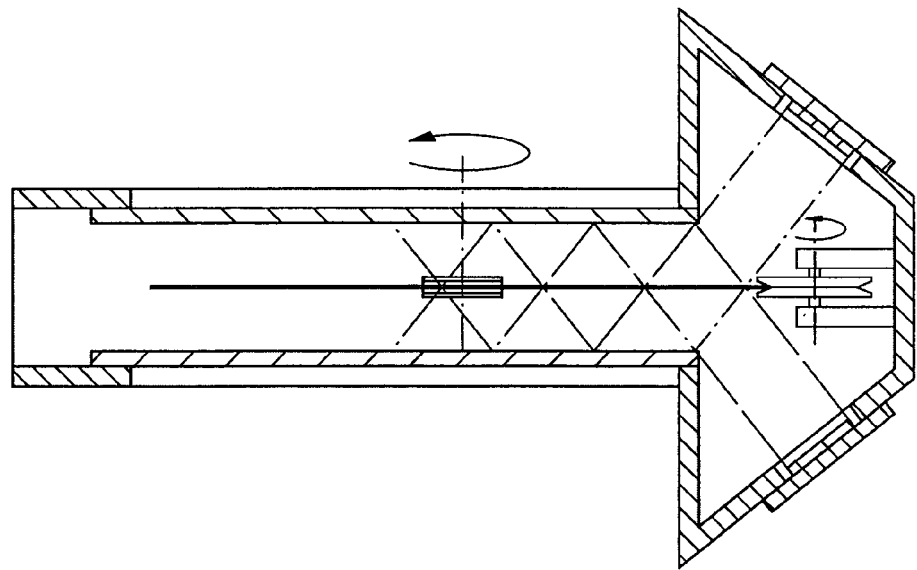

To enhance overall uniformity of processing, a substrate could be rotated during processing so that all areas of the substrate are exposed to similar energy impingement. Such an apparatus is illustrated in simplified cross-section in FIG. 82.

While the vibration members of the embodiment shown in FIG. 81 are described as being fired sequentially, this is not required by the present invention. Alternatively, both vibration members could be fired simultaneously. Any resulting interference patterns generated from such simultaneous firing could be moved around with proper frequency and power variation, thus allowing uniform processing of a substrate.

Figure 83:
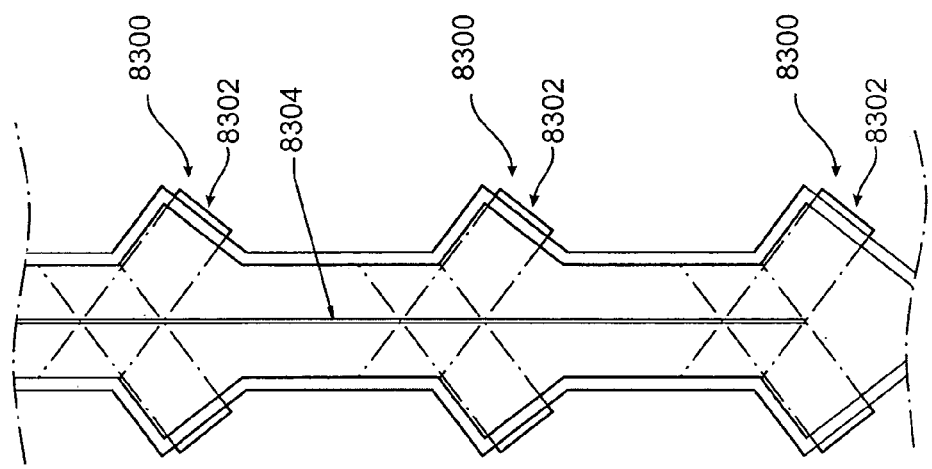

While the above embodiment is shown with only two vibration members, this is not required by the present invention. Multiple vibration members could be spaced about the height of the tank. A section of such a design is illustrated in simplified cross-section in FIG. 83. Use of such multiple levels 8300 of vibration members 8302 reduces the need to rotate the wafer 8304 in order to effect more uniform processing.

Figure 84:
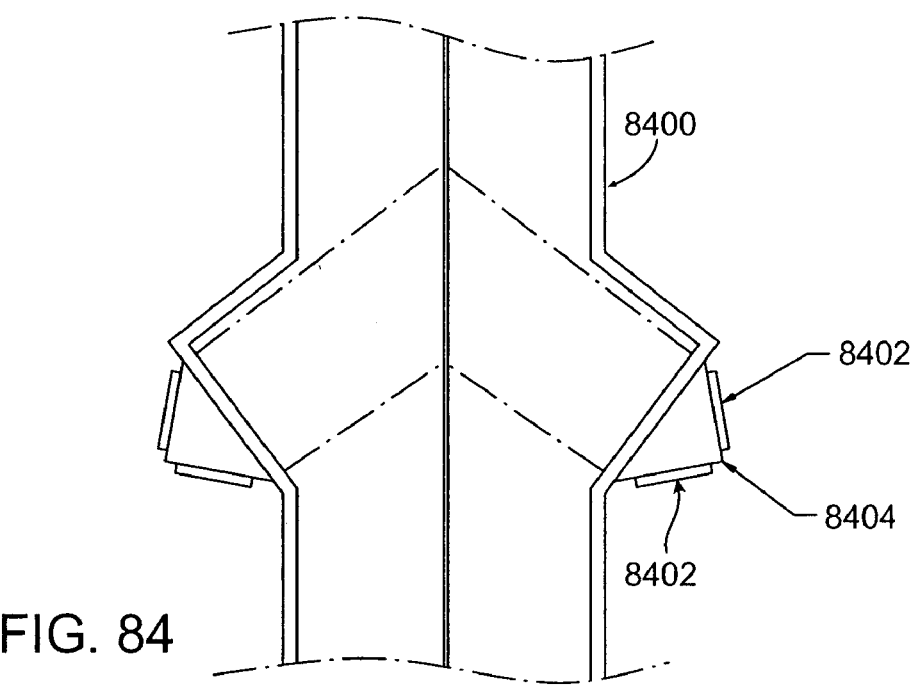
Figure 85:
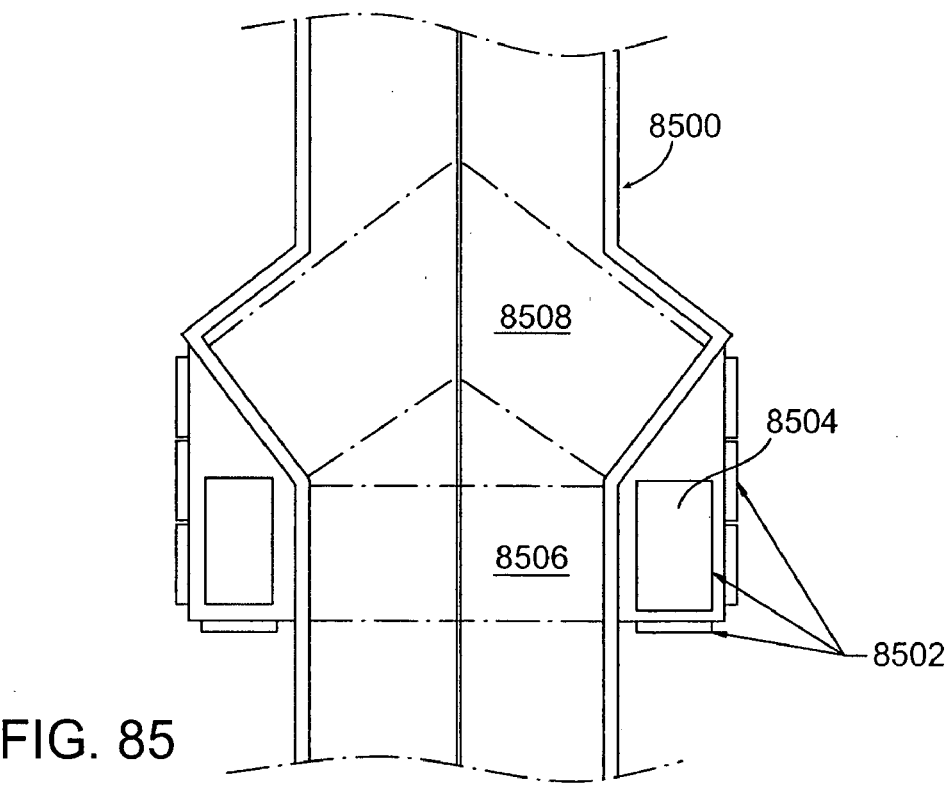

FIGS. 84 and 85 illustrate simplified and enlarged cross-sectional views of a portion of an additional embodiment of processing apparatuses in accordance with the present invention. Apparatus 8400 of FIG. 84 is similar to that shown in FIG. 83, except that the simple flat plate transducer has been replaced with a pair of transducers 8402 in contact with wedge structure 8404 having a triangular cross-section. Apparatus 8500 of FIG. 85 is similar to that shown in FIG. 83, except that the simple transducer has been replaced with multiple transducers 8502 in contact with a wedge structure 8504 having a cross-sectional profile. The embodiment of FIG. 85 produces two paths of incident sonic energy 8506 and 8508, respectively. While the sonic energy paths 8508 may occur at any depth in the process vessel, it can also occur at the gas/liquid interface at the top of the tank. Thus, the substrate could be receiving sonic energy while it is being withdrawn from the processing liquid.

Figure 86:
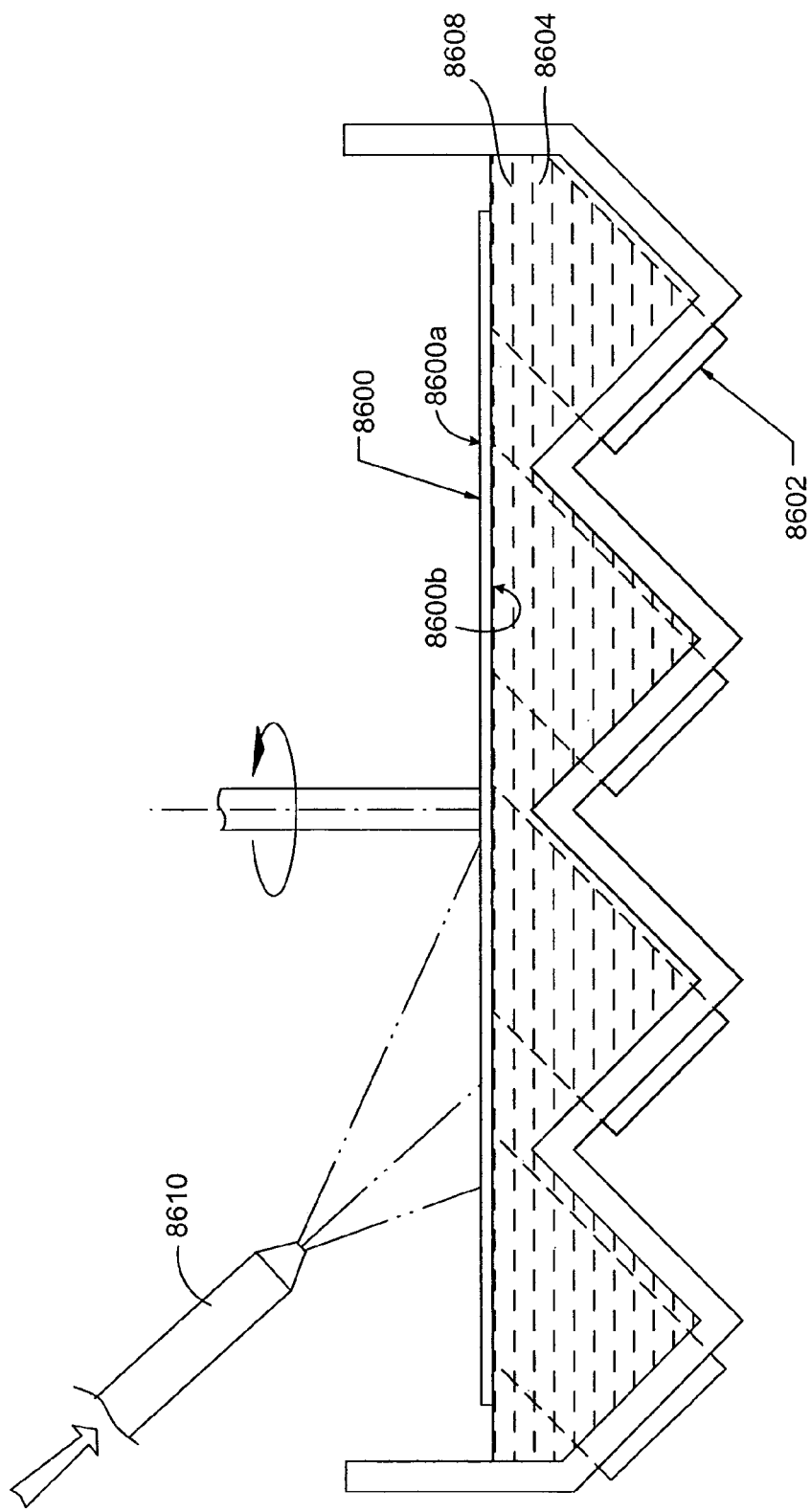

Another embodiment of an apparatus in accordance with the present invention for performing horizontal processing is illustrated in FIG. 86. In the embodiment of FIG. 86, substrate 8600 is positioned in relatively close proximity to the multiple vibration members 8602, which are oriented at appropriate angles to obtain efficient cross-substrate energy transfer. Gap 8604 between vibration members 8602 and substrate 8600 is filled with liquid 8608. Top surface 8600a of substrate 8600 can bear a thin liquid layer, or be exposed to the ambient within the processor, or could be wetted with a liquid spray from nozzle 8610.

The substrate 8600 can optionally be rotated. Either the frontside 8600a or the backside 8600b of the substrate 8600 can face the vibration members 8602. Both the frontside 8600a and the backside 8600b of the substrate 8600 may be processed simultaneously. While nozzle 8610 is shown as producing a liquid spray of processing liquid, the nozzle could also comprise a megasonic nozzle configured to sonically energize the exiting liquid. The nozzle could even be oriented to operate within a range of angles promoting transfer of energy across a substrate.

Another embodiment of and apparatus for horizontal single substrate processing is illustrated in simplified cross-section in the embodiment of FIG. 87. Specifically, the vibration members of FIG. 86 are replaced with a single wide area sonic nozzle 8700 having liquid inlet 8701 such that jets 8702 directed at an appropriate angle for some transfer of energy across substrate 8704. Optionally, the substrate could be rotated, submerged, exposed to the atmosphere or wet with a liquid spray. Processing of both the frontside and the backside of the substrate can occur simultaneously.

When the gap between the wide area sonic nozzle and the substrate is not completely filled with liquid, energy may be transferred through the various fluid jets. The energy travels through the liquid in the jet stream as long as the jet stream is comprised of a continuous liquid stream between the vibration member and the substrate. When the gap is completely filled with liquid, energy transfer can occur by a combination of both energy transfer with the jet and direct transfer from the surface of the vibration member through the filling liquid to the substrate.

Physical fluid flow collimating devices added to the near field may modify the processing performance of megasonic systems. One type of such a collimating device could resemble a grating having relatively small openings for the transmission of fluid and energy. In some embodiments openings on the order of one wavelength or less may preferred. In other embodiments, openings larger than one wavelength may be preferred. The thickness of the grating could vary from less than one wavelength, to tens of wavelengths or more.

Depending upon the characteristics of the fluid, including but not limited to the degree of gas saturation, smaller openings of a grating may undesirably become "blinded" by gas bubbles generated in the megasonic energy field during operation. In certain embodiments, this could be avoided by utilizing gases having different surface tension characteristics, or utilizing higher pressure differentials to force fluid flow though the opening. As frequency or intensity of ultrasonic energy applied is varied, bubbles that form could be redissolved.

The diffraction of energy waves through narrow slots or openings in a grating may seem counterintuitive when attempting to form a uniform energy field. When employed, however, in conjunction with proper frequency or power variation, points of non uniformity can be moved around through the confined liquid space effectively making the sonic processing better or more uniform. Generally, it would be desirable to consider both fluid flow/velocity profile with energy uniformity.

FIG. 88A shows a simplified cross-sectional view of an embodiment of an apparatus 8800 in accordance with the present invention featuring a diffraction grating 8802 between the substrate 8804 and a vibration member 8806 in contact with multiple transducers 8808. FIG. 88B shows a plan view of one example of a diffraction grating for use in accordance with embodiments of the present invention, comprising a screen 8810 defining openings 8812 much larger than one wavelength of the incident sonic energy.

Alternatively, the grating could comprise thin-plates having relatively large aspect ratios arranged parallel to each other are separated by a distance on the order of less than about 6 mm. As the sonic energy moves up between the plate elements, the energy field in this near field region changes and becomes more collimated. As frequencies or power levels are varied, points of field non uniformity are moved around may make the effective substrate processing more desirable. Substrates to be processed could be positioned on the top edge of these plates in a generally parallel or some other arrangement.

FIG. 88C shows a plan view of another example of a diffraction grating 8814 for use in accordance with embodiments of the present invention, comprising openings defining various shapes and sizes. FIG. 88D shows an enlarged view of a portion of the diffraction grating of FIG. 88C.

While the embodiment of FIG. 88A shows the diffraction grating as separated from the vibration member by a distance, this is not required by the present invention. FIG. 88E shows a simplified cross-sectional view of an alternative embodiment of an apparatus in accordance with the present invention utilizing a diffraction grating 8816 in direct physical contact with the vibration member.

A. Reflected Energy

In many megasonic cleaning and processing applications, non-uniform distribution of sonic energy within a processing tank may result from the presence of various obstructions therein, for example built-in supports for substrate carriers, or the structural members of the substrate carriers themselves. Portions of a processed substrate behind such obstructions may be "sonically shadowed" from receiving the full impact of ultrasound energy transmitted into the tank.

Over the years, a variety of designs of processing tanks and substrate carriers have been proposed to lessen such nonuniform energy distribution attributable to sonic shadowing. One conventional approach taught elimination of shadowing by imparting relative motion between the substrates and the sonic energy sources, for example by moving the energy sources, moving the substrates, or both. Such processing equipment designs however, can be mechanically complex, offering the disadvantage of higher maintenance costs. Other disadvantages of designs involving numerous moving parts include additional space requirements, the unwanted generation of particles, and the non-uniform flow of fluid within the bath.

Another conventional approach to reducing ultrasound shadowing involves designing the tank to promote reflection of ultrasonic energy to process areas otherwise shadowed behind various obstructions, including carrier supports. One such approach is shown and described in U.S. patent no. U.S. Pat. No. 6,523,557, incorporated by reference herein for all purposes.

That patent illustrates a design where sidewalls of the processing tank include a convex portion, with sonic energy reflected off the convex portion into regions that would otherwise be sonically shadowed. This specific design required that the incidence angle of the sonic energy impinging the curved wall be less than a critical angle for that material. For quartz, this critical angle was 26°.

One limitation of such a design, is that the curved areas must be relatively large, owing to the limitation of maintaining a small angle of incidence (e.g. less than ~26° for quartz). This forces the processing tanks to become larger, and hence more difficult and costly to fabricate. For example with quartz, fabricating large curves into a tank wall are much more difficult and expensive than fabricating tanks from flat plates.

The relatively small angle of incidence described in this patent also forces reflecting surfaces within a bath to be relatively large, which may interfere with fluid flow and efficient utilization of space within the tank volume.

A further limitation with conventional reflecting-type ultrasonic processing systems becomes apparent when applied ultrasound beams are relatively wide, or multiple piezoelectric crystals are fired simultaneously. In such cases, the reflected portion of the beam can interfere with the unreflected portion of the beam. This can result in localized constructive and destructive interference, generating points of high- and low-energy intensity. Such non-uniformity in the energy field can correspondingly result in processing of substrates in a non-uniform manner. As described below, embodiments in accordance with the present invention may resolve such non-uniform processing by altering the position of such high- and low-energy intensity points over time.

One approach to overcoming this constructive and destructive interference, is to design the tank such that energy reflected off of the carrier and tank walls is directed towards the liquid surface within in the tank. One such a design is disclosed in U.S. Pat. No. 6,098,643, incorporated by reference herein for all purposes.

Another conventional approach to reducing sonic shadowing of conventional ultrasonic/megasonic processing systems, places the piezoelectric crystals on more than one wall or location of a processing tank or vessel, thereby ensuring areas shadowed from receiving energy from one transducer would not also be shadowed from receiving energy from another transducer. Tank designs providing such features are disclosed in U.S. Pat. Nos. 5,279,316, 6,098,643 and 6,595,224, each of which is incorporated by reference herein for all purposes.

Still another conventional approach to eliminating sonic shadowing in ultrasonic/megasonic processing systems reduces the size, shape, and/or number of supporting members of the substrate carrier. For example, U.S. Pat. No. 6,209,555 teaches that substrate carrier structural members be constructed out of flat plate material having a thickness equal to a precise multiple of a fractional wavelength of the sonic energy traveling through the bath. This design promotes the transfer of energy across the carrier structural supports of the carrier, rather than absorption or reflection of incident ultrasound energy by the supports.

However, different systems utilize different frequencies of applied ultrasound energy. Thus, one disadvantage of this conventional approach is that the thickness of the plate components would need to be matched with the particular frequency of the applied ultrasonic energy, or vice-versa, reducing flexibility in operation of the device.

Moreover, the speed of sound through a particular material depends upon its composition. Thus another disadvantage of this conventional approach is that the thickness of the plate components would also need to be matched to the composition of the plate components, or vice-versa, also reducing flexibility in construction and operation of the device.

Therefore, a need exists for both tank designs and cassette designs that overcome limitations inherent with current designs to ensure uniform substrate processing with various frequencies of ultrasonic energy.

A tank and a substrate carrier in accordance with an embodiment of the present invention, for supporting either single or multiple substrates in a megasonic processing bath, allow ultrasonic energy introduced into the bath to be reflected from a surface in order to process a substrate portion located behind a sonically obstructing member. In accordance with one embodiment of the present invention, the other side of the reflecting surface may be in contact with a gas such as air, thereby ensuring reflection of sonic energy incident at a wide range of angles. In accordance with another embodiment of the present invention, where the other side of the reflecting surface is in contact with a liquid, reflection of the sonic energy will be achieved where the angle of incidence is either less than the first critical angle or greater than the second critical angle. The reflecting surface can be flat, or partially or entirely curved (convex or concave) with a constant or variable radius of curvature. Direction of reflected ultrasonic energy to shadowed regions may be enhanced by controlling the direction of flow of fluid within the tank.

A tool for processing substrates with ultrasonic energy in a liquid bath in accordance with an embodiment of the present invention, allows some amount of ultrasonic energy introduced into the bath to be reflected off a reflecting surface to process a part of the substrate located behind a sonically obstructing member. In accordance with certain embodiments, the angle of incidence of the sonic energy relative to the reflecting surface is less than a first critical angle or greater than a second critical angle. In other embodiments, a gas is present on the side of the reflecting surface opposite to the incident ultrasound energy, such that reflection takes place regardless of the angle of incidence.

Figure 10:
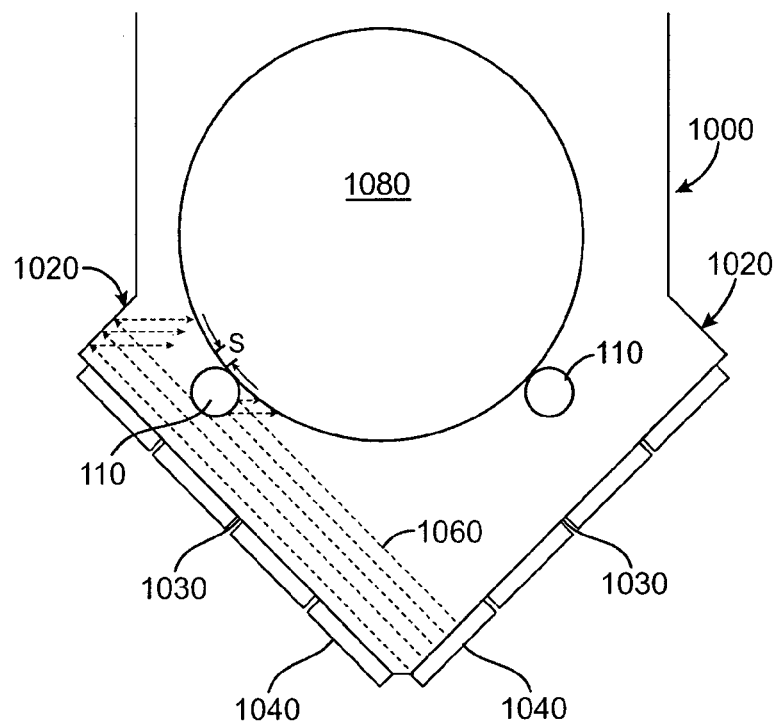
FIG. 10 shows a simplified cross-sectional view of one embodiment of a ultrasonic processing apparatus in accordance with the present invention utilizing reflection of sonic energy to perform processing behind an obstruction.

FIG. 10 shows a simplified cross-sectional view of one embodiment of a ultrasonic processing apparatus in accordance with the present invention. Tank 1000 comprises walls 1020 in contact with sidewalls 1030 that are angled with respect to one another. Ultrasonic transducers 1040 are in contact with sidewalls 1030.

Ultrasound energy 1060 is emitted from transducers 1040 toward substrate 1080 supported by members 110. Energy 1060 is reflected from walls 1020 toward formerly shadowed portions S of the substrate 1080 that would otherwise be shadowed by the presence of the intervening support member 110.

Figure 11:
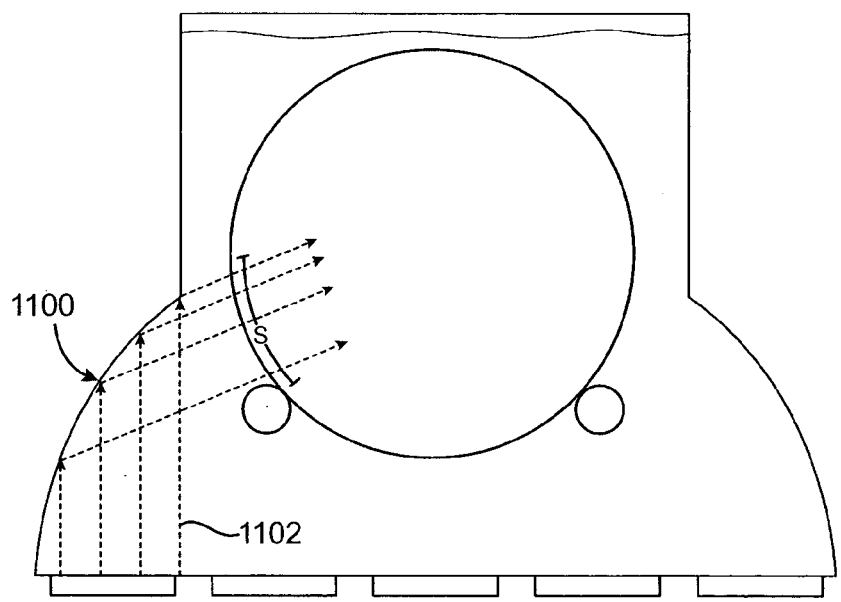
FIG. 11 depicts a simplified cross-sectional view of another embodiment of an ultrasonic processing apparatus in accordance with the present invention wherein a curved tank wall provides the reflecting surface for incident ultrasonic energy.

While the specific embodiment illustrated in FIG. 10 depicts the reflecting surface of the tank as flat, this is not required by the present invention. FIG. 11 depicts a simplified cross-sectional view of another embodiment in accordance with the present invention, wherein tank wall 1100, providing the reflecting surface for incident ultrasonic energy 1102, is curved.

And while the embodiment of FIG. 11 shows the application of ultrasonic energy to a reflecting surface that is concave and continuous, this is also not required by the present invention. Alternative embodiments could employ a reflecting surface that this only partially curved, and which may exhibit a convex or concave shape with a constant or variable radius of curvature.

Embodiments in accordance with the present invention overcome many limitations of known designs for substrate processing apparatuses. Specifically, embodiments in accordance with the present invention may advantageously utilize angles larger than the first critical angle and less than the second critical angle under certain conditions. For example, when one side of the reflecting surface is in contact with a gas (i.e. air surrounding the tank), while the side of the reflecting surface receiving the incident ultrasound energy is in contact with a liquid (i.e. inside the processing bath), essentially all of the incident sonic energy is reflected back into the liquid.

Figure 12:
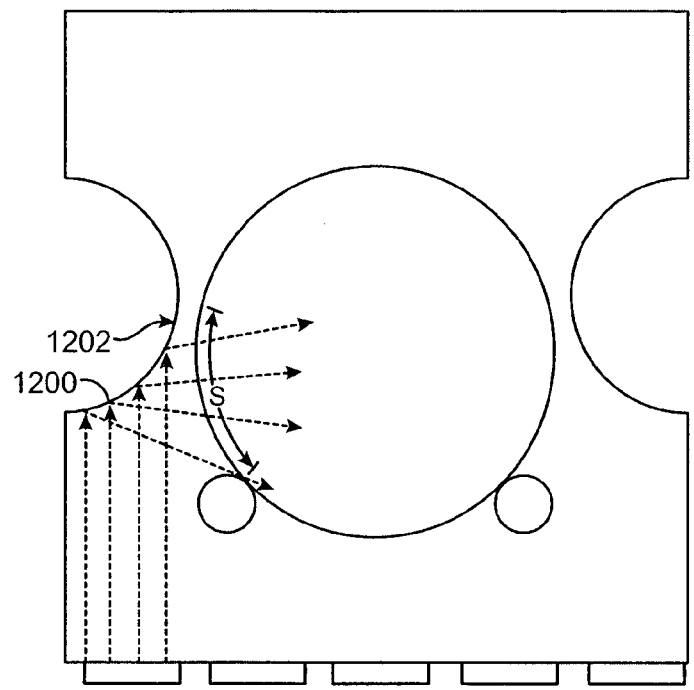
FIG. 12 shows a simplified cross-sectional view of an alternative embodiment of an apparatus in accordance with the present invention where reflection of incident sonic energy occurs at the curved wall of a tank surrounded by gas.

Such an embodiment is shown in simplified cross-section in FIG. 12, where reflection of incident sonic energy occurs at the curved wall 1200 of tank 1202 that is surrounded by gas. Unlike conventional approaches, for example where the curved tank wall comprises quartz and the incidence angle of sonic energy impinging the wall is less than ~26°, if a gas is present on the opposite side of the reflecting surface, the ultrasound energy need not be applied incident at any particular angle or range of angles.

In accordance with still other embodiments of the present invention, incident sonic energy could be reflected by walls of a pipe-like structure that is filled with a gas, such that internal reflectance is exhibited. In such embodiments, surfaces receiving ultrasonic energy incident at angles larger than the first critical angle and less than the second critical angle, could readily reflect significant amounts of energy back into the liquid.

As described previously, depending on the material composition of the solid reflecting surface, various amounts of incident ultrasound energy may be directly absorbed by that material and hence unavailable for reflection. Under almost all conditions, polymer amorphous materials such as PTFE absorb energy without significant reflection or transmission. By contrast, solid crystalline materials such as quartz, or metals such as stainless steel, either reflect or transmit sonic energy depending upon incidence angles and whether only one side or both sides of the reflecting/transmitting surface are in contact with a liquid. Many construction materials, such as crystalline polymeric materials, exhibit partial absorbency and partial reflection or transmission.

Thus one factor for selecting the correct range of incidence angles for applied ultrasonic energy is whether the reflecting surface is in contact with liquid on one or both sides. If the surface of the solid member has liquid on both sides, sonic energy directed toward one of those sides could actually be transferred across the member when the incident angle is larger than a first critical angle and smaller than a second critical angle. Where the applied ultrasound energy is incident at an angle of less than the first critical angle or larger than the second critical angle, reflection of the sonic energy predominates.

Conventional approaches for ultrasonic/megasonic processing teach the presence of large, gently sloping convex surfaces receiving energy within a narrow range of angles, or the presence of flat planar surfaces designed to reflect energy to the surface of the liquid to prevent interference. Embodiments in accordance with the present invention, however, utilize surfaces of various shapes. These shapes can include convex, concave, and planar or even be comprised of composite designs. The radius of curvature can remain constant or may vary.

Further, embodiments in accordance with the present invention describe embodiments where energy may impinge surfaces at different than the "critical angle or range of angles" described by conventional approaches, and still readily reflect back into the liquid. In accordance with alternative embodiments of the present invention, a structure having a predetermined thickness may be oriented to receive incident sonic energy outside of range of critical angles. For quartz, those critical angles range between about 26° and 60°. At angles less than about 26° or greater than about 60°, most sonic energy impinging the surface will be reflected from quartz surfaces. At angles between about 26–60° with liquid on both sides of the reflecting member, significant energy can be transferred directly across the member. When liquid only contacts one surface and gas contacts the other, most sonic energy is reflected, regardless of incident angle.

And while some prior art designs feature a water boundary layer between the transducer and the bottom of the tank, this is not required by embodiments in accordance with the present invention, but may be employed when useful. For example, transducer plates or individual piezoelectric crystals can be either directly bonded to the wall of the tank or processing vessel, or fabricated with a water boundary layer, without deviating from the spirit and teachings in accordance with embodiments of the present invention.

Further, different embodiments in accordance with the present invention also envision utilizing of megasonic systems that energize individual piezoelectric crystals within a transducer or transducer array either simultaneously, or sequentially.

In accordance with another embodiment of the present invention, supports for the wafer carrier may be constructed integral to the tank wall from materials and designs promoting transfer of significant amounts of sonic energy across those structures.

Figure 15:
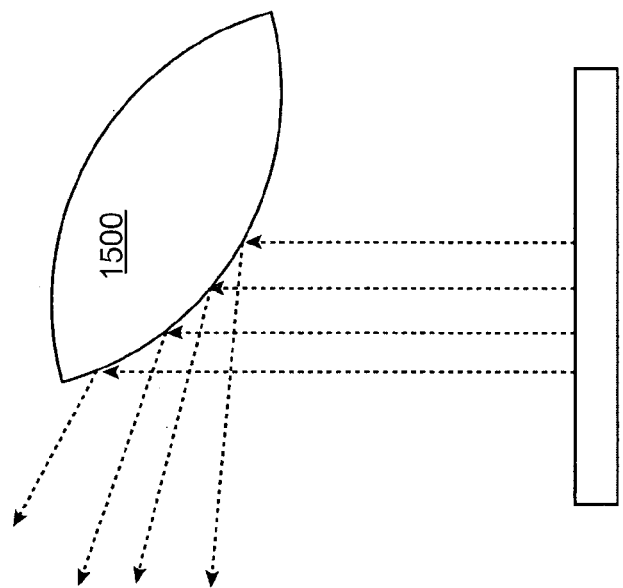
FIG. 15 shows a simplified cross-sectional view of a member exhibiting an oval cross-section, where sonic energy is incident outside of the preferred range of angles for energy transfer and is reflected off of the member.

For example, rather than using round solid rod stock to construct the wafer carrier support, or relying upon a separate reflecting surface within a tank, support stock exhibiting an oval cross section may instead be used. Such an embodiment is shown in simplified cross-section in FIG. 15.

A substrate holder member or substrate holder support 1500 having such an oval cross section may be oriented to ensure that a significant amount of the surface area of the rod lies within a range of angles between a first and a second critical angle, thereby maximizing transfer of sonic energy directly across the rod. Conversely, if the member or support is oriented such that a significant amount of surface area of the rod lies at less than the first critical angle or at greater than the second critical angle, energy reflection is maximized.

Still other embodiments in accordance with the present invention may utilize designs that reflect or re-direct fluid flow smoothly in another direction. The reflector structures can be planar, curved either convex or concave, oval, or otherwise aerodynamic in shape to promote smooth fluid flow either past, or off of, the surface of the structure.

By maintaining steady flow with smooth streamlines and pathlines where the re-direction of fluid flow does not cause turbulence or mixing, sonic energy follows along those lines. The fluid flow can result from acoustic streaming, or from forced fluid flow such as results from pumping.

Alternatively, if instead of being solid, the rod is hollow and gas filled, the orientation of the oval could be such that the incident sonic energy strikes the surface at greater than the first but less than the second critical angle and still reflect the majority of the energy. Other embodiments in accordance with the present invention may thus utilize a hollow, gas-filled pipe or other structure readily able to reflect sonic energy.

Figure 13:
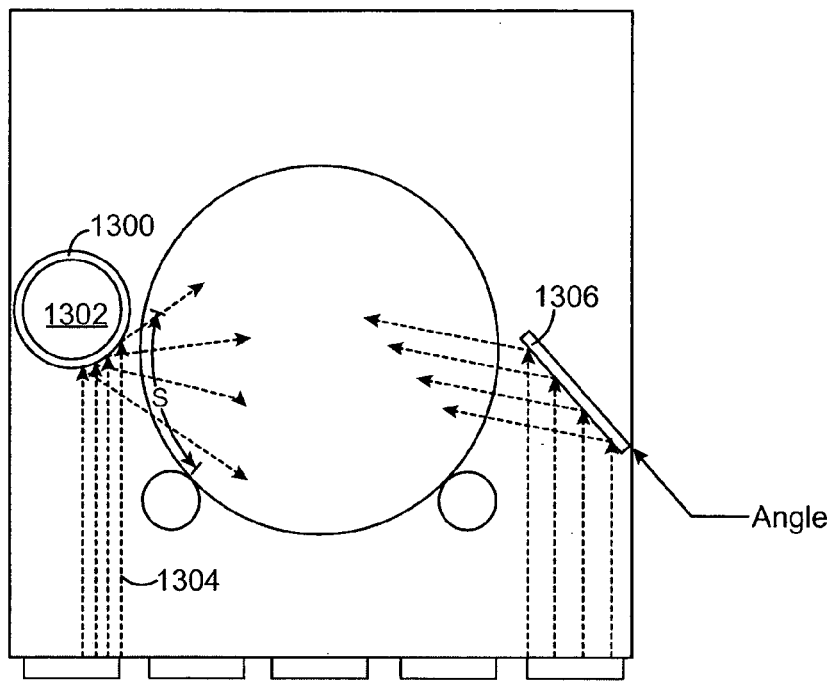
FIG. 13 shows a simplified cross-sectional view of a member comprising a hollow, gas-filled pipe or plate that is readily able to reflect sonic energy.

Such an embodiment is shown in simplified cross-section in FIG. 13. Such a reflecting structure 1300 containing a gas 1302 in accordance with embodiments of the present invention, allows for significant reflection, rather than absorption or transmission, of incident sonic energy 1304 impinging the surface of the structure, regardless of whether the incident sonic energy lies within the correct range of angles.

FIG. 13 shows the contrast in behavior between the hollow reflecting structure 1300 and a solid reflecting surface 1306 that is surrounded by liquid. Specifically, solid reflecting surface 1306 would tend to transmit ultrasonic energy incident at angles within a critical range (for example 26–60°), reflecting ultrasonic energy incident at angles outside that critical range.

Figure 14:
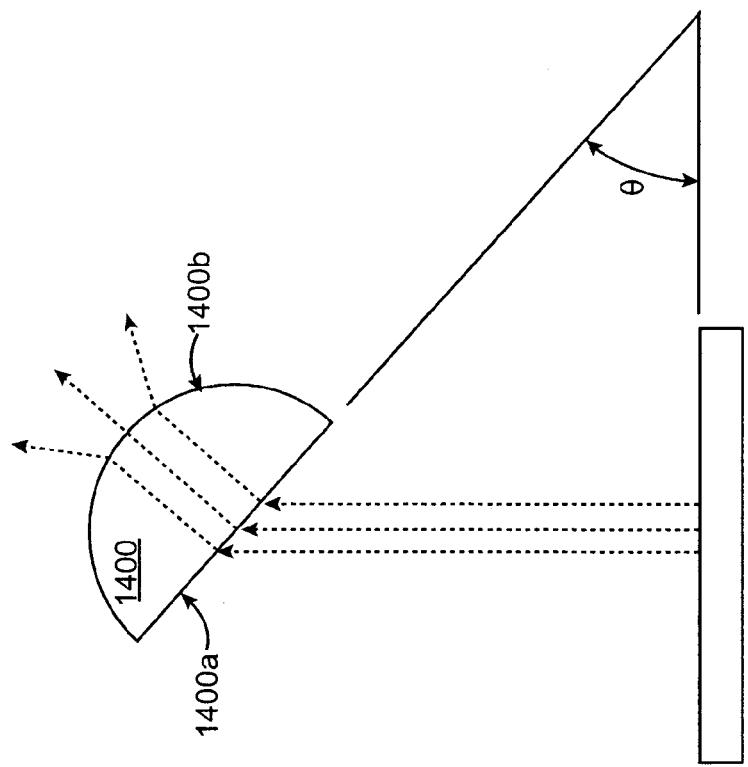
FIG. 14 shows a simplified cross-sectional view of a member exhibiting a semicircular cross-section, where sonic energy is incident within the preferred range of angles for energy transfer.

In accordance with further embodiments of the present invention, composite shapes may be employed to construct the wafer carrier. For example, a rod with a semicircular cross section may be used. Such an embodiment is shown in simplified cross-section in FIG. 14.

In this embodiment, semi-circular rod 1400 may be oriented such that the sonic energy 1402 impinges the flat planar surface 1400a at an angle between the first and second critical angles. Energy will be transferred across the cross-section of the rod, emanating from the curved rod surface 1400b. Other cross-sectional profiles could exhibit surfaces having concave or convex shapes.

B. Transfer of Sonic Energy Across Member

In a number of industries, ultrasonic energy may be applied to a liquid bath in order to enhance substrate processing. The use of the ultrasound energy has become especially common in the manufacture of electronic components. As structures on the substrates have become smaller and more delicate and easily damaged, higher ultrasonic frequencies have been employed to remove smaller contaminant particles without harming the underlying structures.

Figure 16:
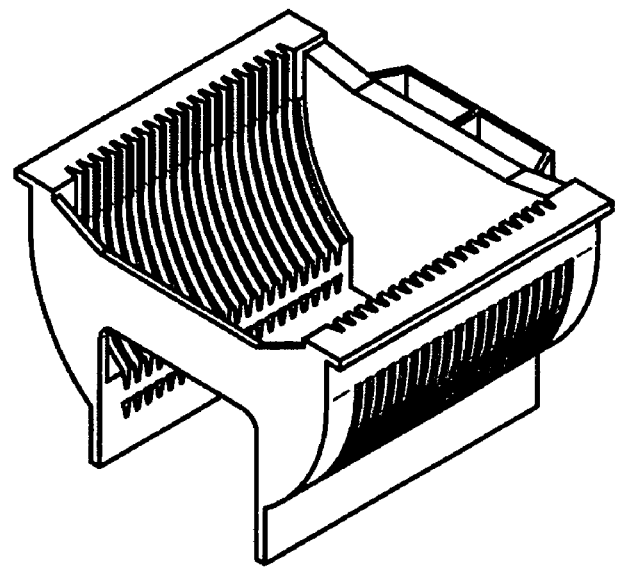
FIG. 16 shows a simplified perspective view of a conventional cassette design.

Historically, multiple substrates (often as many as 25 to 50) have been held in a partially closed single cassette or carrier in a generally parallel orientation, with uniform separation between adjacent substrates. FIG. 16 shows a perspective view of one such conventional cassette design.

During processing, this loaded cassette was lowered into a liquid bath fitted with a means to introduce ultrasonic energy. Many early tank designs featured the ultrasonic transducers located generally in the bottom or sides of a rectangular tank. Since at relatively low ultrasonic frequencies the energy pattern was almost omni-directional within the tank, energy to interact with the surfaces of the substrates was readily obtained, even when the substrates were held in a partially closed cassette structure.

However, as the frequency of applied ultrasonic energy has increased to near the megahertz range to remove smaller particles and cause less substrate damage, the resulting energy waves have become more collimated and travel through the bath in a generally straight path. This allows the megasonic waves to rise up through the bath between the substrates within the cassette at an orientation that is generally parallel to the substrate surfaces.

As the ultrasonic waves encounter obstructions such as structural members of the cassette, the waves may typically either be absorbed or reflected, resulting in an area behind the obstructions to be shadowed from the ultrasonic energy. This shadowing can in turn practice non-uniform processing across the substrate surfaces, as some surface regions receive different amounts of energy from other surfaces.

Previously, several approaches have been adopted to enhance uniformity of the ultrasonic energy reaching the surface of the substrates. One approach was to physically rotate the wafers. However, this resulted in larger and much more complicated cassette structures which were often expensive and cumbersome. The cassettes were also potential sources of particle generation, as the substrate edge rubbed against the structural members of the cassette.

Figure 17:
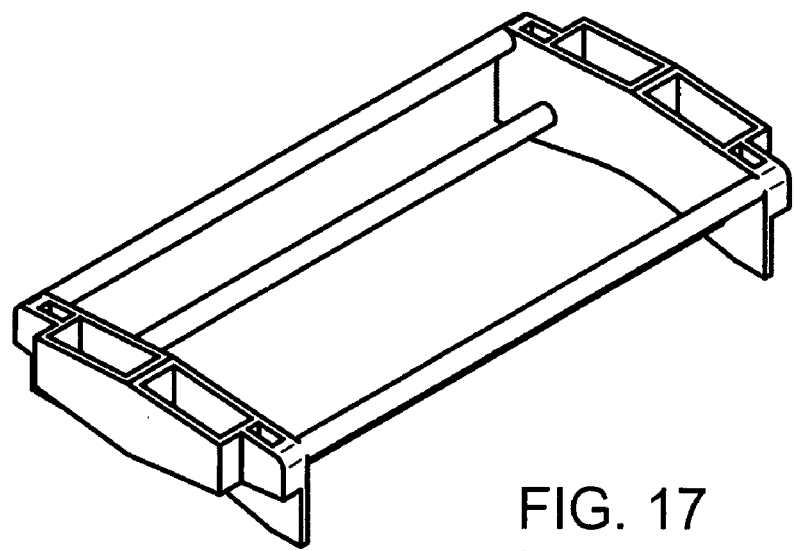
FIG. 17 shows a simplified perspective view of another conventional cassette design.

Another conventional approach to ensuring uniform application of ultrasonic energy opens up the cassette by using just three or four spaced-apart rods to support the substrates. Such designs omit the conventional sidewall, plate and finger members of earlier cassette designs. FIG. 17 shows a conventional low profile cassette having four support rods.

While such cassette designs allowed more uniform energy coverage, there remained shadowed areas located directly behind the support rods. Additionally, reduced contact between the substrates and the cassette resulted in the substrates being more easily knocked out of proper orientation by bursts of fluid or bubbles. Other conventional cassette designs open and close the holder slightly (thereby increasing and decreasing the separation between adjacent supports), so that substrates were constrained from popping out of their desired resting slots within the carriers during processing, yet were easily removable when processing was completed. Examples of such a compliant cassette design are presented in U.S. Pat. Nos. 6,041,938 and 6,153,533, incorporated herein by reference for all purposes.

Still another conventional approach to cassette design was to construct supports from materials of critical thickness to match a multiple partial wavelength of the applied ultrasonic energy. More specifically, physical theory teaches that thickness of the cassette member should be equal to an even multiple of one-quarter wavelength ($n\frac{1}{4}\lambda$, n=even integer$\geq 2$) of the applied megasonic energy. It was hoped that a significant amount of energy would be transmitted across support members having this particular thickness, thereby partially eliminating sonic shadowing behind them. These cassette designs and the underlying theory required applied ultrasonic energy to encounter the support members at approximately a right angle (90°) to the surface of the cassette support member.

However, because frequencies varied between ultrasonic systems, different thickness of supports were required. This resulted in specific, unique holders for each ultrasonic processing system. Thus a cassette constructed for one system operating at a particular frequency could not be used in another system operating at a different frequency. Additionally, flexibility in choosing materials for cassette construction was reduced by the precise material thickness as required. This translated into a more costly and less flexible cassette.

In yet another conventional approach, a tank with slanted sidewalls was specially designed and constructed, so that ultrasonic energy encountered the substrate from two directions nearly orthogonal to one another to eliminate any shadowed areas behind obstructions. Such a design is disclosed in U.S. Pat. No. 6,098,643, incorporated by reference herein for all purposes.

However, a need still exists for a cassette that overcomes limitations inherent with current designs to ensure uniform substrate processing with various frequencies of ultrasonic energy.

In accordance with one embodiment of the present invention, a cassette or wafer carrier for supporting single or multiple substrates in a megasonic processing bath allows a significant amount of incident ultrasonic energy directed towards the supported substrates to be transmitted across cassette structural supports in the path of the sonic energy, thereby reducing sonic shadowing on substrate surfaces lying directly behind the supports. An embodiment of a carrier in accordance with the present invention includes a side or bottom support connecting an end panel forming a structure to maintain substrates in a desired orientation during processing. At least one of the side and/or bottom support(s) of the carrier is formed from plate components. A surface of the plate components is maintained between first and second critical angles relative to the surface of the megasonic transducer. The angle is chosen to allow the maximum amount of projected megasonic energy to be transmitted across the plate components. By not absorbing or reflecting all of the incident ultrasonic energy, the plate components do not create a total shadowing of supported substrates.

The side and bottom supports of the cassette are formed of relatively narrow plates of any convenient thickness, and may be constructed of a single material or of a composite of multiple materials. When positioned at the proper critical angle, a significant portion of incident megasonic energy at any frequency can be transmitted across the supports. The narrow plates can also feature holes and cutouts to minimize disruption to uniform fluid flow within the cassette and around the substrates held therein.

Embodiments in accordance with the present invention comprise substrate cassette or carrier for supporting either single or multiple substrates in an ultrasonic or megasonic processing bath. A cassette design in accordance with embodiments of the present invention allows a significant amount of incident applied ultrasonic energy to be transmitted across those structural supports of the cassette in the path of the sonic energy, thus reducing sonic shadowing on substrate surfaces directly behind such supports is reduced over designs utilized by the prior art.

In accordance with embodiments of the present invention, sonic energy applied incident to a planar surface of a supporting member over a range of critical angles can result in significant transfer of energy across the supporting member. Such supporting members featuring an incident planar surface facing the ultrasonic/megasonic transducer are referred to herein as "plate components". Transfer of energy across plate components in accordance with the present invention was observed even when the thickness of the support components varied over a wide range.

The ability to transfer applied sonic energy across a member is highly dependent upon the material comprising the member. For example, members comprising the fluoropolymers PFA (perfluoroalkoxy) and PTFE (polytetrafluoroethylene) likely would not allow transfer of as much incident angled energy as a member comprising quartz. With some materials, energy incident perpendicular to the surface of a member having a thickness of an even multiple one-quarter wavelength, could result in the transfer of greater energy than if incident within the range of critical angles. This is particularly possible if conversion between pressure and surface waves occurs with energy applied at critical angles.

By failing to absorb or reflect all of the incident ultrasonic energy, the plate components avoid total sound shadowing of portions of substrates supported within the carrier. This result is unexpected and in stark contrast with prior art designs requiring the ultrasonic energy to impinge the surface of a plate support member at approximately right angles or normal to the support surface, and also requiring the cassette support members to be of a very precise thickness specific to each applied ultrasonic frequency.

Figure 18A:
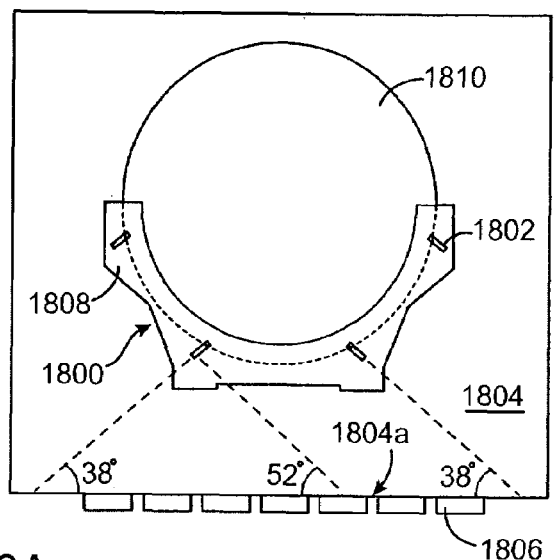
FIG. 18A shows a simplified end view of one embodiment of a cassette in accordance with the present invention.
Figure 18B:
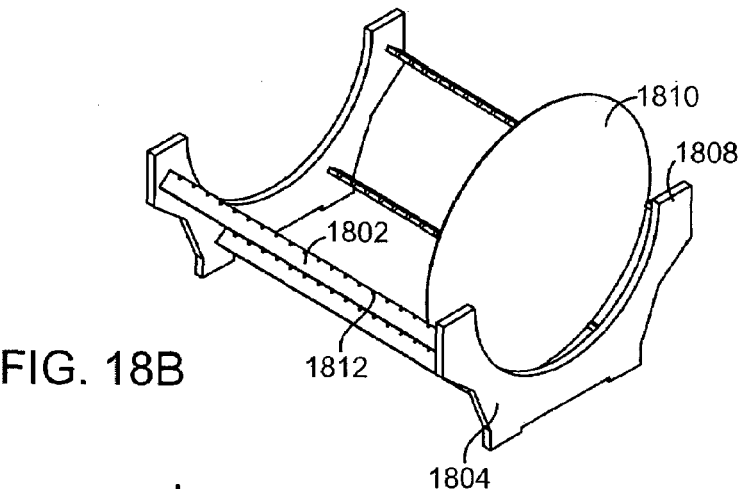
FIG. 18B shows a simplified isometric view of the cassette shown in FIG. 18A.

FIG. 18A shows an end view of one embodiment of a cassette 1800 with the present invention having four support members 1802 for a flat bottom tank 1804 with megasonic transducer elements 1806 located on the tank bottom 1804a. FIG. 18B shows an isometric view of the cassette shown in FIG. 18A.

Cassette or carrier 1800 includes at least a single side or bottom support 1802 connecting to at least a single end panel 1808 forming a structure to maintain substrates 1810 in a desired orientation during processing. Generally, two, three, or in some cases more side/bottom supports will be used to provide adequate structural strength for the cassette.

Figure 18C:
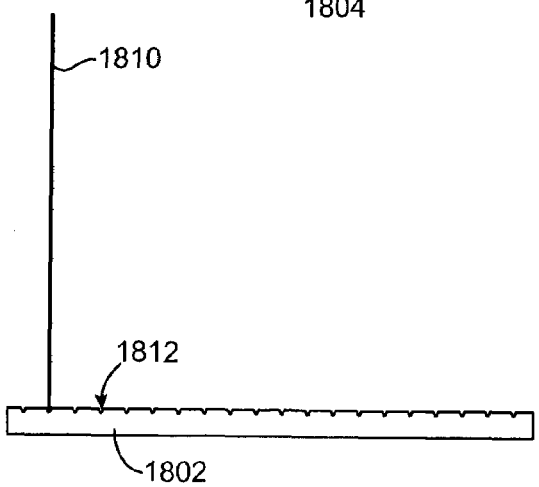
FIG. 18C shows a simplified expanded side view of a rectangular plate component support member having periodic slots to contain edges of multiple substrates.

At least one of the side/bottom supports 1802 of the carrier 1800 is formed of plate components. A plate component comprises a member having a planar surface incident to the applied sonic energy. FIG. 18C shows an expanded side view of a rectangular plate component support member 1802 having periodic slots 1812 to contain the edges of multiple substrates 1810.

In order to effectively transmit sonic energy across plate components of moderate thickness, the surface of the plate components are maintained within a correct range of angles with respect to the surface of the megasonic transducer. In accordance with embodiments of the present invention, the normal to the incident planar surface of the plate component is maintained at an angle between a first and second critical angles relative to the normal to the surface of the megasonic transducer.

With structures such as wafers comprising silicon, these first and second critical angles are typically between about 18° and 58°, respectively. Other materials may exhibit different ranges of critical angles.

This orientation is shown in FIG. 18A, wherein the incident surfaces of supporting plate components 1800 are oriented at an angle of 38° with respect to the megasonic transducer elements 1802 present at the bottom of processing tank 1804. The normal of the incident surface of the plate components is thus orientated at an angle of 52° with respect to the megasonic transducer elements.

Figure 19:
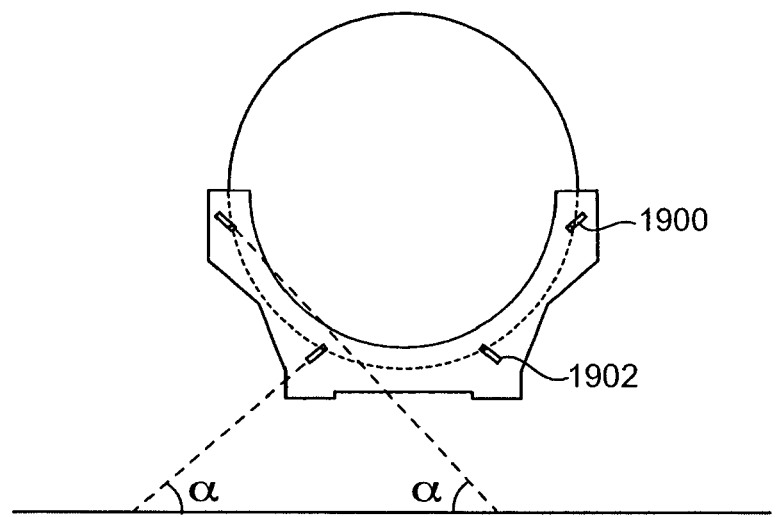
FIG. 19 shows a simplified end view of an alternative embodiment of a cassette in accordance with the present invention.

FIG. 19 shows an end view of an alternative embodiment of a cassette in accordance with the present invention. The cassette of FIG. 19 is similar to that of FIG. 18a except that the relative orientations of two of the supporting plate component members 1900 and 1902 is reversed. However, the incident surfaces of all the plate components remain inclined within the critical angle range of about a relative to the plane of megasonic transducers located in the bottom of the processing tank.

While FIGS. 18A–19 show cassette structures formed from plate components comprising single flat surfaces, this is not required by embodiments in accordance with the present invention. FIG. 20 shows a cross-sectional view of a three-support arrangement, with bottom support 2000 comprising an inverted V-shaped member for a flat bottom tank with megasonic transducer 2002 positioned on the bottom.

Figure 20A:
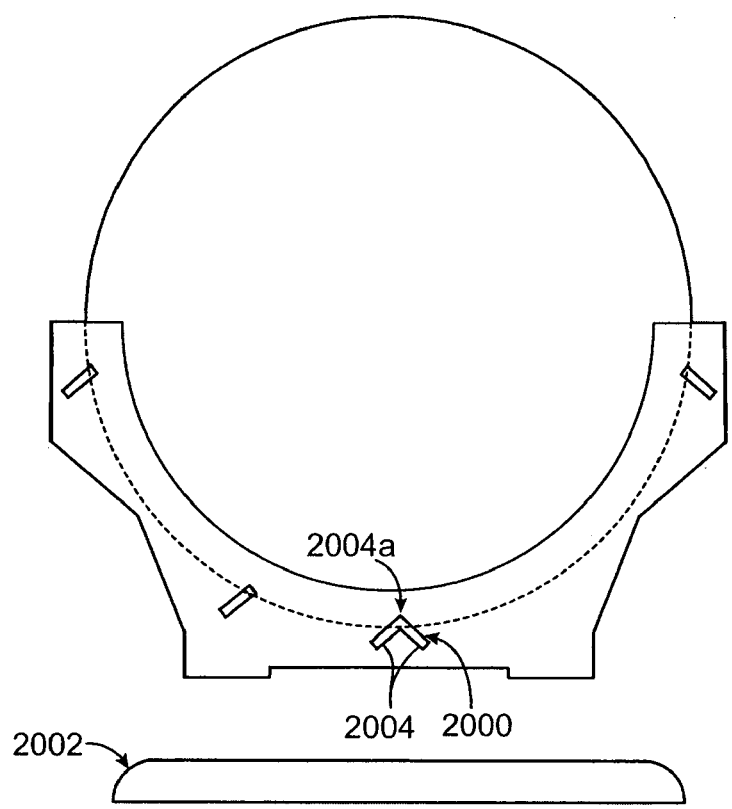
FIG. 20A shows a simplified cross-sectional view of a three-support arrangement.

As shown in FIG. 20A, two plate components 2004 having rectangular cross sections are bonded together along one lateral surface, forming a V shaped cross section allowing the use of thin plate components not otherwise exhibiting adequate strength. In order to function as a cassette support, the normal to one of the surfaces of each individual piece would form an appropriate angle with the normal to the surface of the megasonic transducer.

Figure 20B:
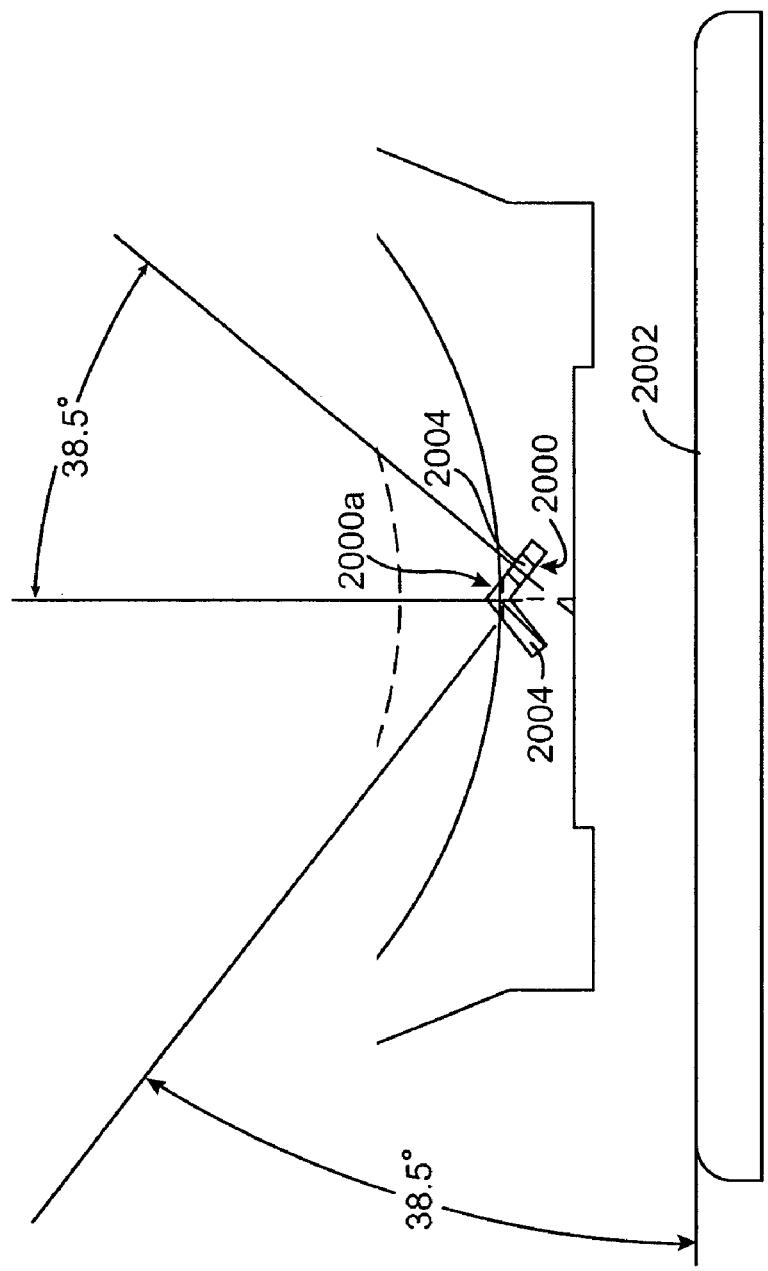
FIG. 20B shows a simplified enlarged cross sectional view of the V shaped support of the cassette of FIG. 20A.

FIG. 20B shows an enlarged cross sectional view of the V shaped support of the cassette of FIG. 20A illustrating a correct angle with respect to the normal of both the support and transducer surfaces. Apex 2000a of V shaped support structure 2000 could point either toward or away from the plane defined by the surfaces of the ultrasonic/megasonic transducers.

And while FIGS. 18A–B and 19 show the support plates as having a rectangular cross section that leads to the incident ultrasonic energy exiting the back surface of the plate at the same angle, this is not required by the present invention. In accordance with other embodiments, one surface of the plate could be flat while the opposite surface could be curved, either concave or convex or in another more complex shape.

Figure 21:
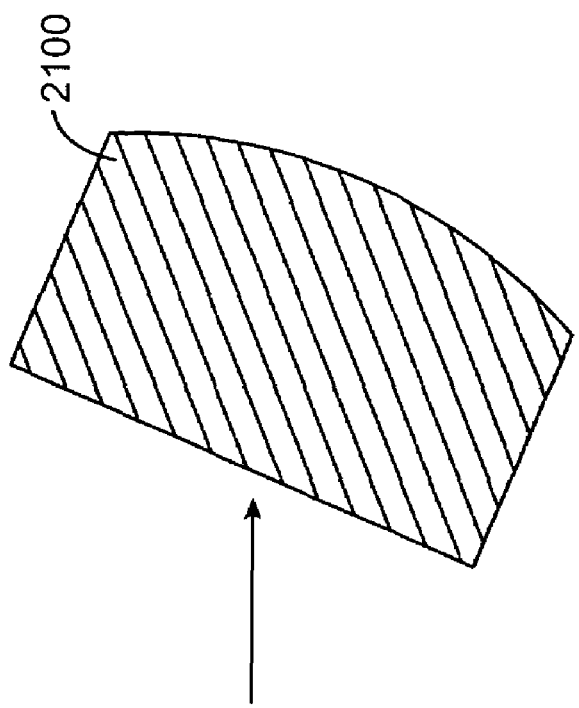
FIG. 21 shows a simplified expanded cross sectional view of a non-rectangular support member.

FIG. 21 shows an expanded cross sectional view of a non-rectangular support member 2100. In the case of FIG. 21, the angle at which the energy leaves the plate could be different from the angle of incidence.

Many types of materials could be used to form the plate component supports in accordance with embodiments of the present invention. Selection of material type may be based upon its desired physical characteristics such as strength and flexibility. In general, more sonic energy can be transmitted across thicker members exhibiting lower energy attenuation, than members exhibiting higher energy attenuation.

For example, greater sonic energy may be transmitted across metallic or highly crystalline materials of the same thickness exhibiting relatively low energy attenuation, than can be transmitted across amorphous polymer materials of the same thickness exhibiting relatively large energy attenuation. Relatively stiff materials such as quartz allow greater transfer of energy as compared with more flexible materials such as polytetrafluoroethylene (PTFE). A discussion of the attenuation of sonic energy by various materials is presented by Buckin and O'Driscoll, "Ultrasonic Waves and Material Analysis: Recent Advances and Future Trends", LabPlus International (June 2002), and also by McClements, "Ultrasonic Measurement in Particle Size Analysis", from Encyclopedia of Anayltical Chemistry, Robert A. Meyers, Ed. (John Wiley & Sons), both of which are incorporated by reference herein for all purposes.

Moreover, support plate components in accordance with embodiments of the present invention need not be created from a single material. Composite structures fabricated from multiple materials can be used, keeping in mind considerations regarding physical properties and energy attenuation just discussed. Thus in accordance with certain embodiments of the present invention, one material exhibiting desired structural properties with low energy attenuation could be combined with another material exhibiting excellent chemical resistance and relatively high energy attenuation, to produce a support element exhibiting acceptable structural strength and energy transfer properties.

Figure 22:
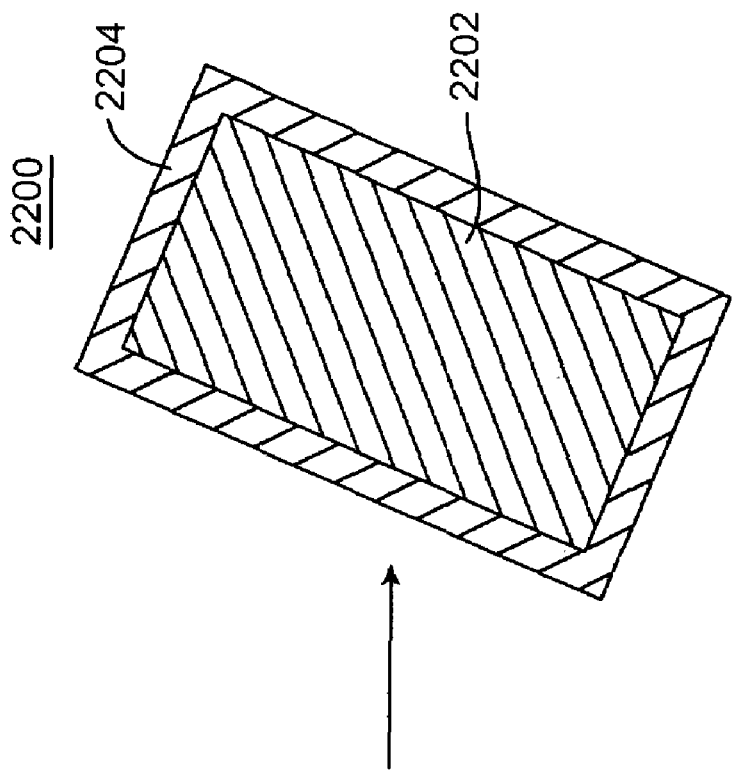
FIG. 22 illustrates a simplified expanded cross sectional view of a typical rectangular support member comprising a composite of first inner material and second outer material.

Such an alternative embodiment is shown in FIG. 22. FIG. 22 illustrates an expanded cross sectional view of a typical rectangular support member 2200 comprising a composite of first inner material 2202 and second outer material 2204. While the composite support structure of FIG. 22 is depicted as being comprised of solid materials, this is not required by the present invention. In accordance with alternative embodiments, the support could comprise a solid outer shell filled with fluid. In this manner, hollow tubes exhibiting various cross-sectional profiles could be utilized.

In accordance with other alternative embodiments in accordance with the present invention, the plate components can contain holes and cutouts to minimize disruption of uniform fluid flow within the cassette and about the substrates being treated. With substrate processing, non uniform localized fluid velocities and energy densities can lead to nonuniform substrate processing, whether that processing be cleaning, etching or other substrate surface modification. Thus for certain applications it will be preferred that the substrate support feature holes or cutouts.

The sizes of such openings or cutouts can vary. In some circumstances, the openings can be relatively large, or substantially greater than one wavelength of the applied energy. For processing with gas saturated solutions, depending upon the surface tension of the processing fluid, gas bubbles generated during processing may lodge in small-sized openings, interfering with the effective transmission of sonic energy through the apparatus to the substrate.

Figure 23A:
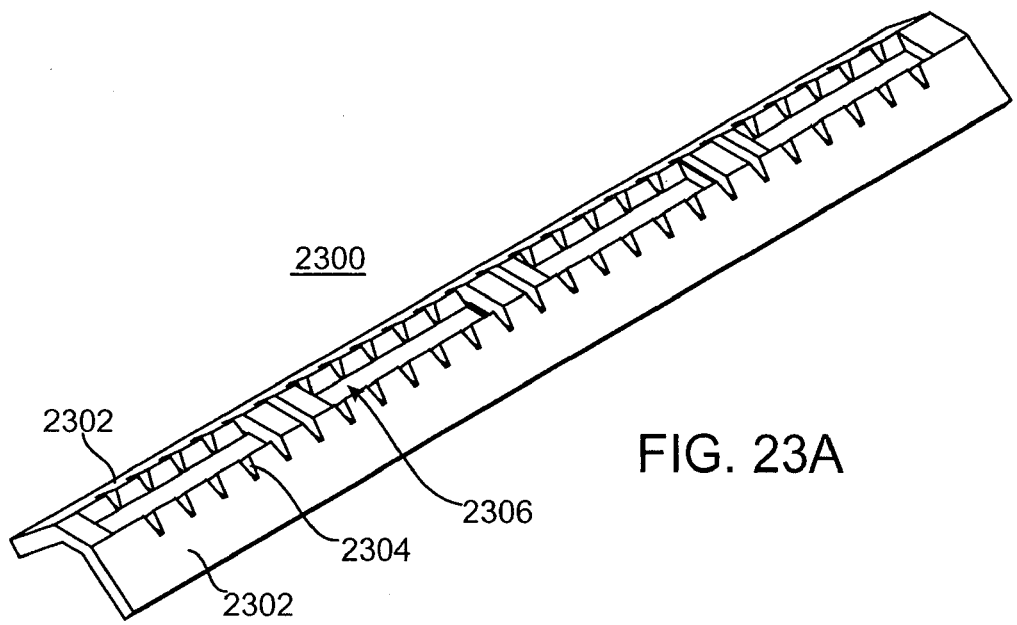
FIGS. 23A and 23B show simplified perspective and cross sectional views, respectively, of an inverted V-shaped support member comprising plate components having slots for supporting the edges of wafers and allowing fluid flow.
Figure 23B:
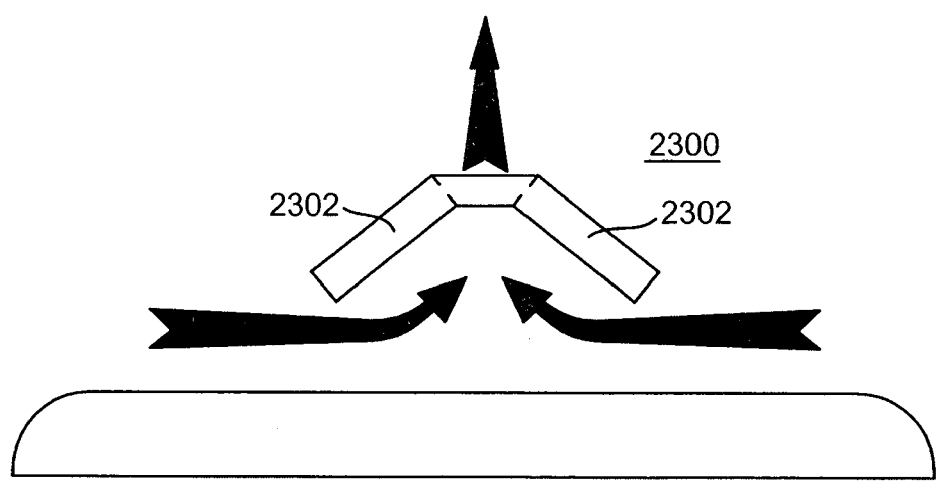

Accordingly, FIGS. 23A and 23B show perspective and cross sectional views, respectively, of an inverted V-shaped support member 2300 comprising plate components 2302 having slots 2304 for supporting the edges of wafers. Support member 2300 further defines cut-outs 2306 between plate components 2302. Cut-outs 2306 promote circulation of processing fluid between the supporting plate components during use.

In other embodiments, it may be desirable for the cutouts or openings to be sized approximately equal to or less than the wavelength of the applied sonic energy. In such a configurations, incident ultrasound energy encountering the cassette may be diffracted. Such diffraction can potentially have beneficial results, enhancing the uniformity or effectiveness of ultrasonic processing.

Figure 24:
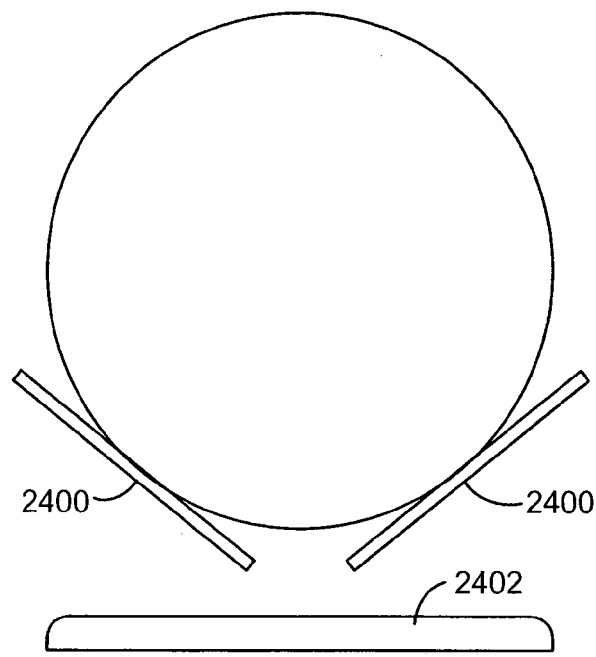
FIG. 24, which show a simplified cross-sectional view of a wide rectangular support member for a flat bottom tank having a bottom mounted transducer.

Certain of the embodiments previously shown and described depict a wafer support structure comprising side and bottom supports are formed of relatively narrow plate components, this is not required by the present invention. While in certain embodiments relatively narrow plate components may be preferred to minimize localized disruption in fluid flow, in other applications much wider plates could alternatively be used when different fluid flow was desired. Such an alternative embodiment is depicted in FIG. 24, which shows a cross sectional view of a wide rectangular support member 2400 for a flat bottom tank having a bottom mounted transducer 2402.

Figure 25:
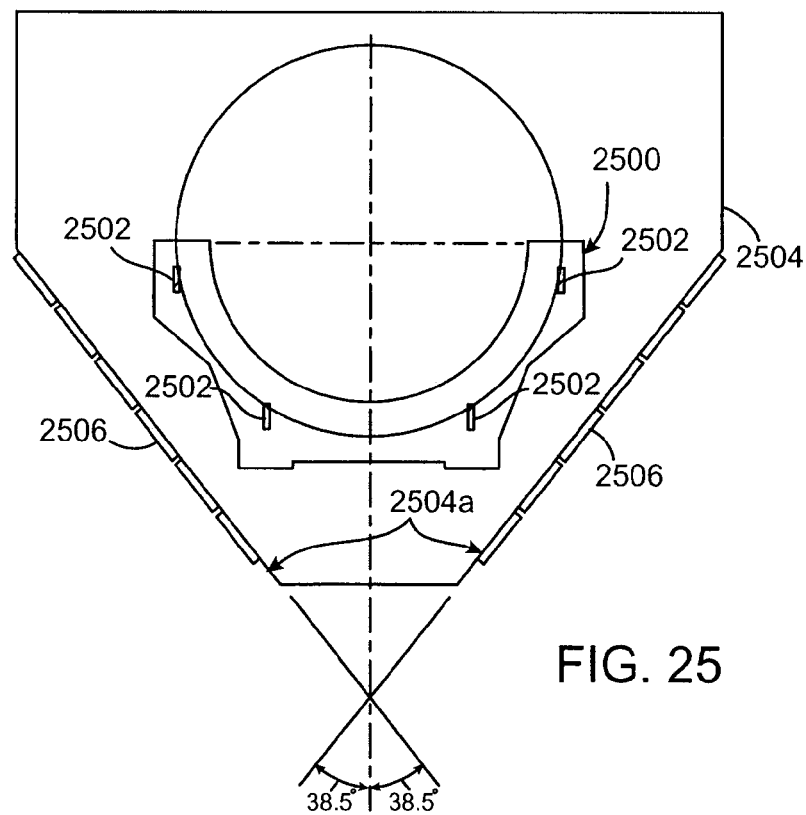
FIG. 25 illustrates an alternative embodiment in accordance with the present invention, wherein a cassette comprises a plurality of vertically-oriented support plate components.

And while the embodiments of FIGS. 18A–19 illustrate a wafer support structure featuring plate components oriented relative to sonic transducers positioned in a common plane at the bottom of a processing tank, this configuration is not required by the present invention. FIG. 25 illustrates an alternative embodiment in accordance with the present invention, wherein cassette 25000 comprises a plurality of vertically-oriented support plate components 25002. Processing tank 25004 features V-shaped bottom, with transducers 25006 mounted on sides 25004a of tank bottom. The sides of the processing tank are inclined at the critical angle relative to the vertically-oriented support plate components comprising the cassette.

Embodiments in accordance with the present invention offer a number of possible advantages over conventional approaches. For example, unlike conventional substrate support designs, the thickness of the plate component support member in accordance with the present invention need not be any specific multiple of applied ultrasonic wavelength. Thus as frequency changes, the thickness of supports for the new invention need not be changed.

In accordance with alternative embodiments of the present invention, support members may be designed to produce steady flow with smooth streamlines (pathlines) in fluid flowing past them. Such smooth fluid streamlines around support structures allow applied sonic energy to flow around the structures, instead of being transferred directly across or through them. The cross-sections of support members may be hydrodynamically designed to offer minimum drag, allowing fluid streamlines to be smoothly split at the leading edge, and then smoothly rejoined at the trailing edge, without the formation of eddies or turbulence. In this manner, members in accordance with embodiments of the present invention can be shaped to allow significant amounts of sonic energy to essentially "bend" around them.

The flow of sonic energy in a fluid causes movement of fluid referred to herein as "acoustic streaming". This acoustic streaming is comprised of macroscale streaming involving bulk fluid flow and movement, as well as microscale streaming (localized streaming of several types). When fluid streamlines (pathlines) containing acoustic streaming of sonic energy are smoothly split and then smoothly recombined, much of the energy remains with the fluid flow, effectively allowing transfer of sonic energy around appropriately-shaped structures.

Figure 26:
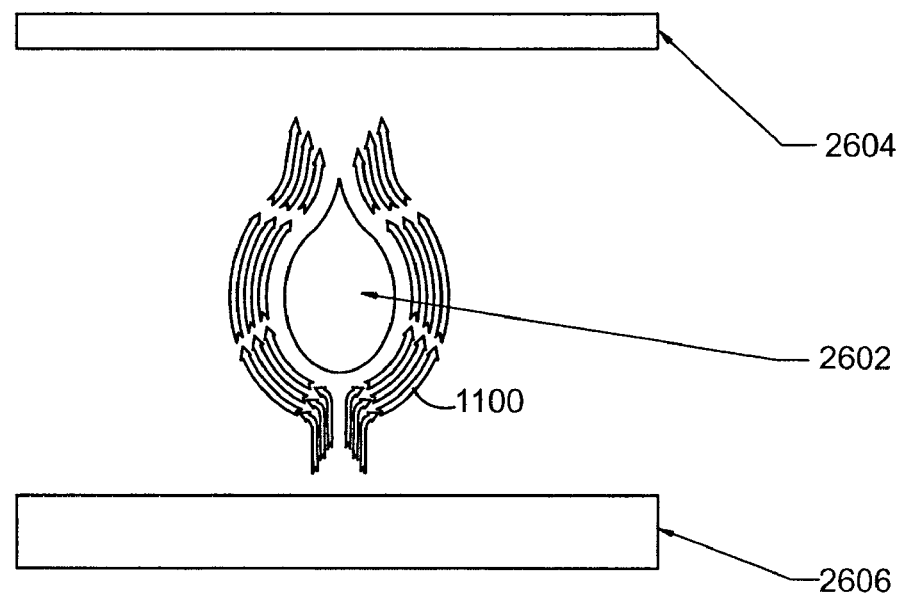
FIG. 26 shows a simplified cross-sectional view of an alternative embodiment of the present invention employing such a hydrodynamic support member to move sound waves around the member.

An alternative embodiment of the present invention employing such a hydrodynamic support member is shown in simplified cross-section in FIG. 26. Support member 2602 is positioned within the tank between vibration member 2606 and substrate 2604 that is to be processed. Support member 2602 exhibits a teardrop shape that promotes hydrodynamic fluid flow such that illustrated streamlines 2600 are split and recombined around support member 2602 without turbulence and mixing. Shaped support member 2602 need not be oriented at some critical angle, but is shaped so that it smoothly separates and recombines streamlines/pathlines.

The particular support member 2602 shown in FIG. 26 represents a portion of a substrate support structure that is not in direct physical contact with the supported wafer 2604. In accordance with alternative embodiments, however, the hydrodynamically-shaped support member could be in direct contact with the wafer, for example supporting the wafer on the tip of the teardrop-shaped member 2602.

And while support 2602 is shown as being solid, this is not required. The support could optionally be comprised of a hollow tube. The tube could then be either empty or fluid filled. The fluid could either be a gas or a liquid. As long as the cross-sectional profile of the member did not lead to disruption of streamlines resulting in mixing, significant transfer of sonic energy around the support member could occur.

Hydrodynamic structures may be oriented relative to the direction of acoustic streaming flow, so that turbulence is not created at their trailing edge. Orientation of the hydrodynamic structures should also take into account any substantial fluid velocity components not caused by the sonic energy, for example a flow of fluid caused by pumping action. Care should accordingly be employed in designing the processing tank to minimize the adverse effects of the hydrodynamic flow on the acoustic streaming, and vice-a-versa.

Figure 27:
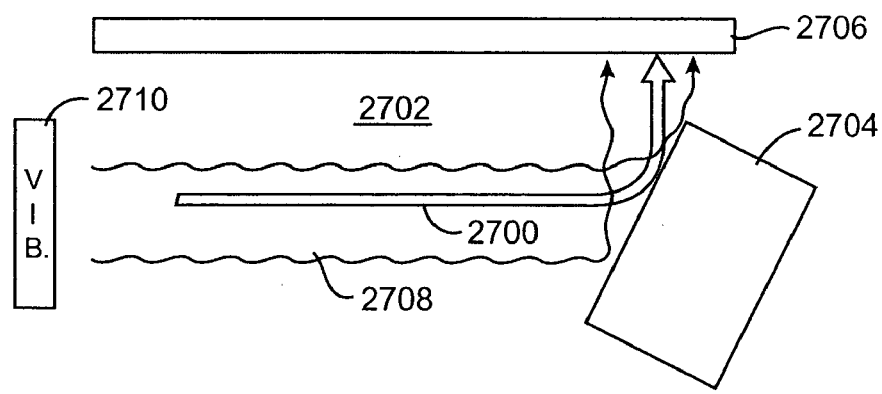
FIG. 27 shows a simplified cross-sectional view of an alternative embodiment of an apparatus in accordance with the present invention, wherein the flow of processing fluid is diverted against the substrate that is to be processed, and the sonic energy follows the fluid path.

Acoustic streaming in accordance with embodiments of the present invention may not be limited to transmission of ultrasound energy in a direction across a supporting substrate. FIG. 27 shows a simplified cross-sectional view of an alternative embodiment in accordance with the present invention, wherein the flow 2700 of processing fluid 2702 encountering structure 2704 is diverted against substrate 2706 that is to be processed. This deflection of fluid flow 2700 by structure 2704 may be accompanied by a similar deflection of sonic energy 2708 emitted by vibration member 2710 against substrate 2706, according to an acoustic streaming mechanism.

To summarize, sonic energy applied perpendicular to a surface of a member having a thickness of an even multiple of one-quarter the wavelength of applied energy, results in energy being transferred across the member. If the sonic energy is applied between first and second critical angles relative to the surface of the member, energy can be transferred across a member if there is liquid on both sides. If there is gas present on both sides of the member, mode conversion can arise. If there is liquid on one side of a member and gas on the other side of the member, energy will be reflected from the member regardless of the angle of incidence on the liquid side.

C. Improved Near Field Uniformity

Figure 28:
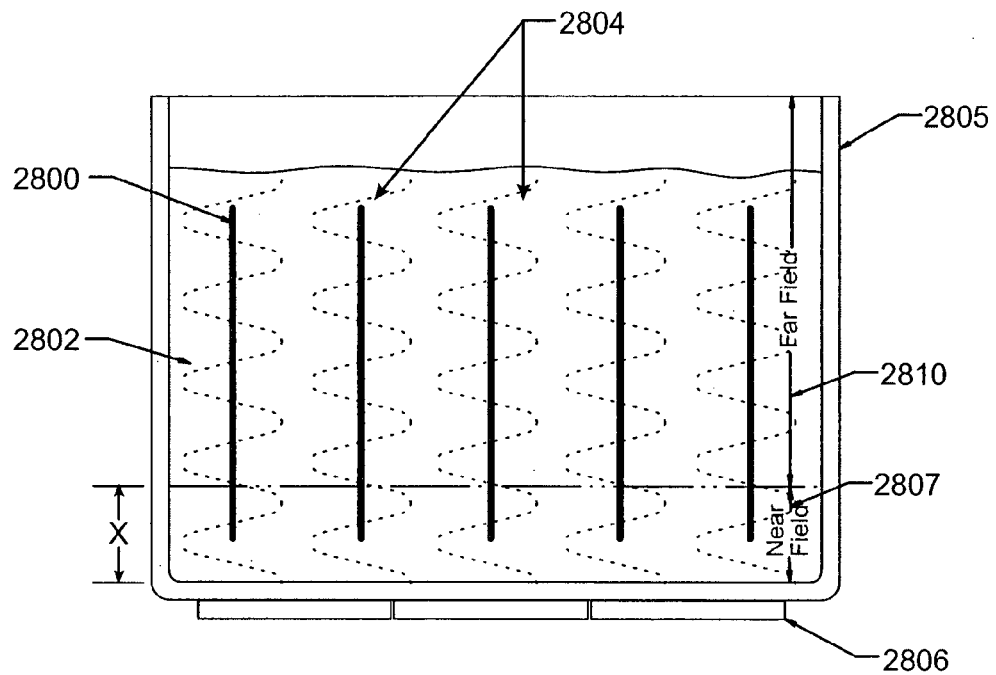
FIG. 28 shows a simplified cross-sectional view of a member to be processed, immersed in a surrounding liquid in a conventional process tank.

In a number of industries, ultrasonic energy may be applied to a liquid bath in order to enhance processing of substrates positioned therein. The use of the sonic energy has become especially common in the manufacture of electronic components. FIG. 28 shows a simplified cross-sectional view of member 2800 to be processed, immersed in a surrounding liquid 2802 in a conventional process tank 2805. Beam(s) 2804 of ultrasonic energy is applied from vibration source 2806 to liquid 2802, which in turn transmits the energy to member 2800. The interface between liquid 2802 and the surface of member 2800 in turn vibrates in response to the ultrasonic energy received. Cavitation, microcavitation, acoustic streaming, and microstreaming of various types can all occur at or near this interface and can be useful in promoting cleaning and processing of member 2800.

The near field 2807 is a region extending a distance X from the vibration source 2806 into the surrounding bath. The near field 2807 is characterized by nonuniformity of the resulting energy field, as shown in FIGS. 29A and 29B. The distance that the energy field extends into the liquid and degree of non-uniformity that it exhibits is a function of frequency, intensity, and vibration member design. Specifically, as standing waves and various interference patterns between interacting waves develop in the near field region 2807, locations of high and low energy intensity develop and are dispersed throughout the near field region 2807.

While not wishing to be bound by any particular theory of operation, the following examples and explanation are discussed for reasons of understanding only. It is thought that these points of high and low energy intensity are generally created by standing wave and interference patterns leading to cancellation or reinforcement of energy waves. These interference patterns can arise because there can be slight localized material variation or non-uniformity from point to point within a single vibration member piezoelectric crystal. This localized nonuniformity can lead to not all points on the face of the vibration member resonating at identical frequency. Instead of the entire piezoelectric crystal vibrating as a single uniform vibrating point source, it can vibrate as a collection of many individual point sources. Thus, at a given generator frequency, not all of the points will vibrate with the same intensity, as some will be excited at other than their resonance frequency. There can even be slight phase shifts of the applied or driving voltage between points on an individual crystal introduced by the crystal's non-uniformity.

Even if all of the point sources on a vibration member crystal did vibrate at the same resonance frequency, with the same amplitude, and were energized completely in phase with each other, the distance from each point source to a selected point on the surface of member 2800 within the bulk liquid 2802 can be different. The waves emanating from each point source into the liquid tend to spread out as they travel away from the vibrating member to varying degrees based on a number of factors, including frequency, intensity and shape of the vibration member.

At a given frequency, a vibrating member will generate a pressure wave in the liquid with a well-defined wavelength. If distances from two closely-spaced point sources on a single crystal to a given position within the bath are different, even if the waves are generated in phase with each other, they would reach the given point at slightly different times. Therefore the waves from the individual point sources can arrive at selected points near the surface of member 2800 in varying degrees of phase alignment or agreement.

At a certain distance from the vibrating element (the dividing line between the near field and the far field shown in FIG. 28, the intensity of the resulting energy field becomes relatively uniform. The region outside of the near field 2806 is known as the far field 2810. The far field 2810 is characterized by field uniformity and field attenuation with distance from the vibrating member 2806. Specifically, the intensity of the energy field drops off at a fairly uniform rate, depending upon localized fluid properties as distances from the surface of the vibration element increase. The length of the near field, or distance that it extends into the liquid from the vibration member, increases with increasing frequency and increasing applied intensity.

The quality of interaction between a substrate and a surrounding processing bath is partly dependent upon the energy field at the substrate/bath interface. Thus where ultrasonic energy is applied to a substrate within a processing bath within the near field region, non-uniform energy in the near field may result in non-uniform cleaning and processing of substrates or parts of substrates.

Accordingly, there is a need in the art for methods and apparatuses for applying ultrasound energy to substrates which ensures uniformity of substrate processing.

The frequency, power, phase between simultaneously fired crystal elements, and/or pulse width of ultrasonic energy applied to a substrate within a processing bath, may be varied over time in an attempt to make the near field more uniform. This variation over time causes movement of the location of points of constructive and destructive interference, or localized points of high and low energy intensity in the near field. As a result of the changing character of the applied ultrasonic energy, the overall or effective intensity of energy in the near field, and hence processing of the substrate in near field regions, is rendered more uniform.

Figure 30:
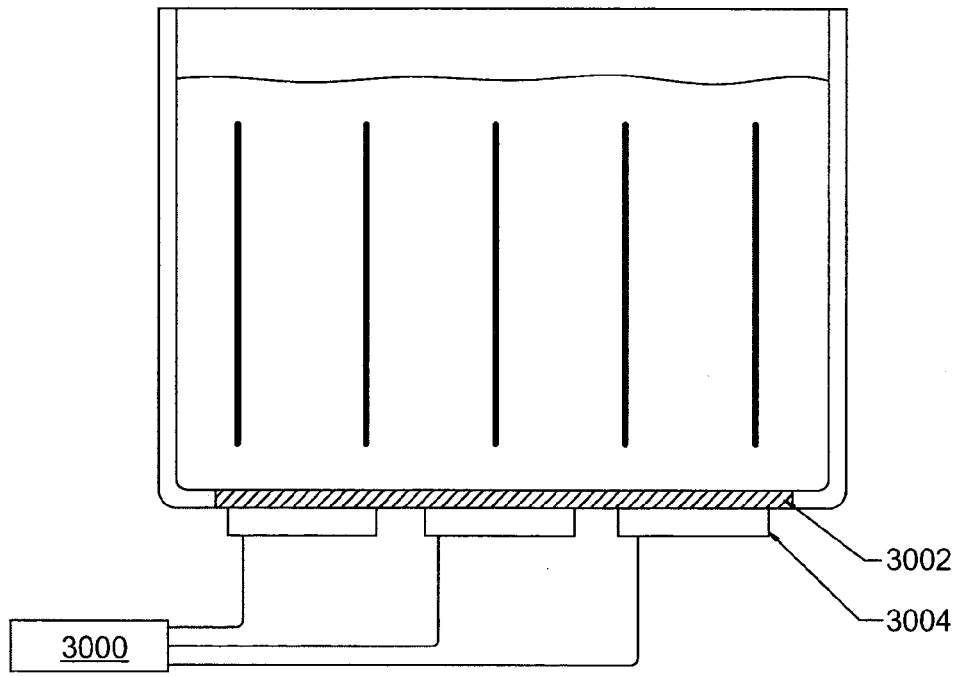
FIG. 30 shows a simplified cross-sectional view of a megasonic energy source comprising a transducer including multiple individual piezoelectric crystals.

As shown in FIG. 30, megasonic energy source 3000 comprises transducer 3002 including multiple individual piezoelectric crystals 3004. In accordance with embodiments of the present invention, megasonic energy source 3000 is operated to sequentially fire these individual piezoelectric crystals 3004. Specifically, voltage at a selected or resonance frequency and magnitude is applied to individual piezoelectric crystals 3004 is varied in a uniform or predetermined manner about this resonance frequency and selected magnitude. Typically, a different frequency is chosen for each piezoelectric crystal in an array in an attempt to match that crystal's resonance frequency that will maximize that crystal's performance. The magnitude of the applied voltage determines the vibration intensity generated by each crystal.

As a result of varying the frequency and magnitude of the voltage applied to the piezoelectric crystals, the frequency and intensity of oscillation produced within the bath by of the piezoelectric crystals 3004 also varies.

Like phased array radar with its multiple transmitter points, each piezoelectric crystal is comprised of multiple vibration point sources. When the frequency/phase between the various emitters in the phased array is varied, the direction of the energy beam sent out from each emitter changes slightly.

If the frequency were cycled, the emanating beams would tend to move or "flicker" analogous to the flame of a burning candle. Where this "flickering" occurs with the ultrasonic waves in a process bath, it would have the effect of moving the various nodes (points of high energy intensity) and nulls (points of low energy intensity) from position to position within the near field region. Historically, megasonic processing has emanated energy waves out parallel to the surface of a substrate. For embodiments with significant energy transfer directly across the thickness of a substrate member, varying the vibrational frequency also modifies the ultrasonic/megasonic near field emanating from the exiting side or surface of the substrate that is to be processed.

Absent such frequency variation, the non-uniform energy field known as the near field would be established off of the front side of the vibration member, or exiting side of a substrate, extending for up to several inches into the bulk liquid in the tank. This non-uniform field would result in non-uniform cleaning and processing of substrates or parts of a substrate situated within the non-uniform field area.

When a standing wave is generated, points of maximum reinforcement (nodes), can have intensity twice as large as the intensity seen in a single free wave (amplitude of first wave adds to amplitude of second wave). At points of maximum cancellation (nulls), the wave intensity goes to zero (first wave cancels the second wave). At constant frequency, these points of cancellation and reinforcement do not move within the bath. It is only when the frequency/phase/power etc. are varied, that the location of these points move. Various methods and apparatus for measuring field intensity and even localized field intensity are commonly know in industry and academia and are readily available. For measuring gross values of intensity, hydrophones are often used.

As the frequency varies slightly, the intensity, direction, and wavelength of the wave of ultrasonic energy also varies slightly. This slight variation in direction, intensity, and wavelength can result in changes in the position of points of positive and negative reinforcement in the near field, but there may also even be conditions that prevent the formation of standing waves altogether. As these locations of high and low energy intensity change, or the magnitude of differences between them are minimized, the entire surface of a substrate is more likely to experience similar processing. By exposure to both high and low intensity points, as these points move about the substrate surface, the resulting processing is likely to be more uniform than if those points were stationary within the bath.

In a sense, this movement of high- and low-energy points generates a near field region exhibiting more energy uniformity or smoothness over a period of time. This time period is a function of the rate at which the frequency and magnitude of the applied voltage is varied. For example, some piezoelectric crystals may be excited adequately with a constant applied voltage of 500 VAC operating at a frequency of 750 kHz. Points of high and low energy intensity will be generated in the near field region and perhaps even in the far field region depending upon tank characteristics.

For example, instead of being held constant, the frequency of the applied voltage may be cycled between values. If cycled between 748 and 752 kHz once per second, the points of high and low intensity established in the liquid when the frequency is 748 kHz, will switch every second to the new positions associated with 752 kHz. If the rate of change of the frequency of the applied voltage is now raised to one hundred thousand cycles per second, rapid switching back and forth, or movement between node positions associated with 748 kHz to node positions associated with 752 kHz, will occur.

Alternatively switching could occur between five discrete frequencies, for example of 748, 749, 750, 751 and 752 kHz. The location of nodes and nulls formed at each of these five discrete frequencies will differ. As the frequency is changed from one value to another, the nodes and nulls will move accordingly. The more rapidly the switching of frequency from one value to another, the faster the nodes and nulls will change position.

Further alternatively, frequencies could be altered continuously and be swept over a range, with nodes and nulls in the near field continuously moving from one position to another. In such a continuously varying approach, standing waves would not be established in the far field even for very poorly designed tanks, since standing waves in the far field could not even form under such varying conditions.

The position of nodes and nulls within the near field is also a function of field intensity, which is determined by the magnitude of the applied voltage to each piezoelectric crystal. Therefore, varying the magnitude of the applied voltage can also result in movement of the nodes and nulls generated. If such a change in intensity occurred continuously, the nodes and nulls may appear to effectively disappear.

In accordance with one embodiment of the present invention, the backside of the wafer being treated may be placed in direct contact with a modified transducer, thereby forming a single vibration element. The megasonic generator is a sequenced firing generator that sequentially fires the individual piezoelectric crystals comprising the modified transducer. Such an embodiment of a modified transducer is shown in FIG. 31.

Figure 31:
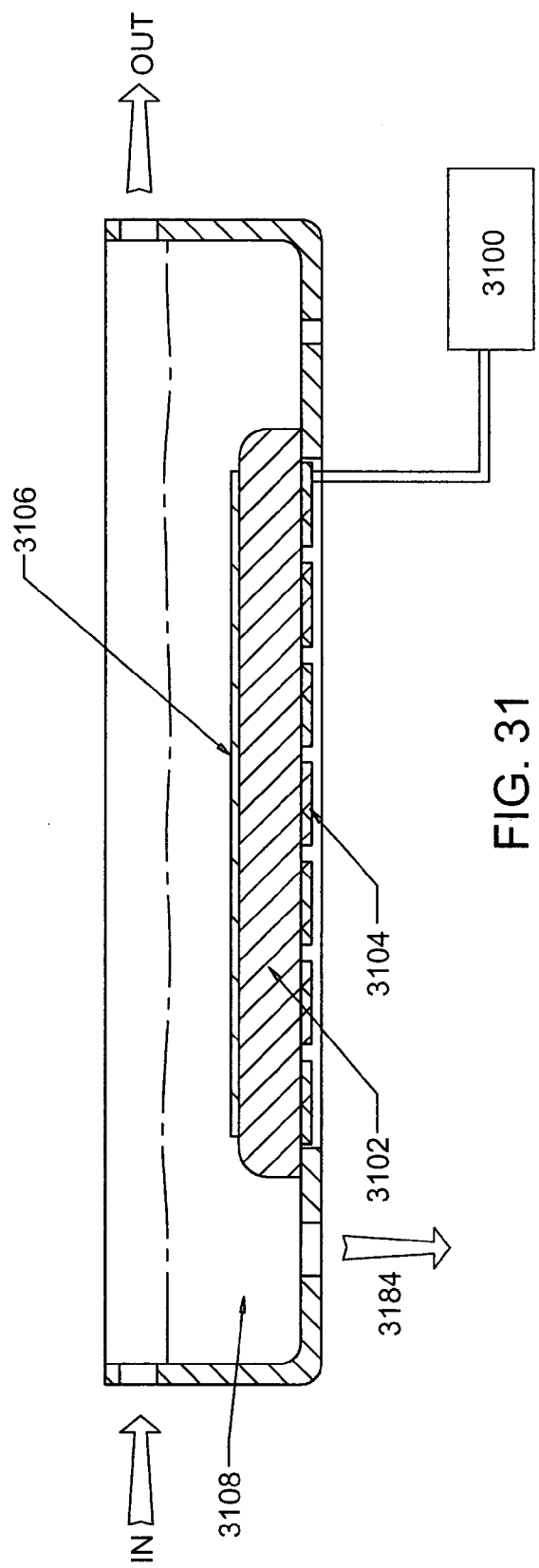
FIG. 31 shows a simplified cross-sectional view of a megasonic generator featuring a modified transducer in communication with a sequenced firing generator that sequentially fires the individual piezoelectric crystals.

In the embodiment of FIG. 31, the voltage frequency applied to each crystal 3104 by the generator 3100 is varied, either randomly or in predetermined stepwise or other manner. This voltage frequency variation by a predetermined amount not only increases the uniformity of the near field emanating from the front side of the wafer 3106, but also increases the likelihood that each portion of each crystal is operating about its resonance frequency for at least part of the time. The frequency of this variation in frequency of the applied voltage could range from just a few cycles per second to the megahertz range. It could vary both above and below a set point frequency by an equal amount in a smooth sinusoidal or other manner, or could vary randomly within some preset range.

Alternatively, it could vary stepwise in a cyclic manner. For example, the frequency of the applied voltage could be bumped up above a set point frequency by a certain number of kilohertz in a single step. The frequency could then be dropped back to the original set point frequency in smaller increments over 10 or more steps. These steps could occur at a rate of just a few per second to a rate of over a megahertz.

Piezoelectric crystals often can be excited at more than a single frequency. These various frequencies at which the crystals can be excited are often referred to as resonance harmonic frequencies. As such it is possible to have the frequency variation of the applied voltage occur between different harmonic frequencies and not merely cycle about a single resonance frequency.

In addition to varying the frequency of vibration of the piezoelectric crystals of the transducer by varying the frequency of the applied voltage supplied by the generator, the pulse width of the energy beam can be varied. This can be accomplished by rapidly switching the generator output voltage on and off in either a random or in a predetermined stepwise or other manner. Pulse widths can vary from being continuously on to switching on and off at a frequency in the megahertz range. This switching frequency need not be constant and can also vary in a stepwise or other manner.

It is possible to vary the intensity and the uniformity of the ultrasonic energy in the near field by varying the magnitude of the applied voltage. As with the variation in frequency of the applied voltage, this variation in the magnitude of the applied voltage can take any number of the forms of continuous or discreet variation as described above.

It is further possible to vary simultaneously the frequency and power or magnitude of the applied energy, or even the frequency, intensity and pulse width. Varying both the frequency and the magnitude of the applied voltage either randomly or in predetermined stepwise or other manner, or additionally varying the pulse width as described above accomplishes this.

Frequency, power and pulse width variation is not limited to sequenced firing of individual piezoelectric crystals. For systems designed for continuous firing of multiple crystals simultaneously at a single frequency, frequency variation could also be advantageously applied. In such an embodiment, at a single frequency not all crystals are firing at their individual resonance frequency. As frequency varies, the likelihood of all of the crystals and perhaps all points of all crystals being fired at their individual resonance frequency for at least part of the time, is increased. And, similar to embodiments employing sequenced firing of piezoelectric crystals, the near field will also experience an averaging or smoothing out as points of high and low energy intensity change location.

Further, if multiple crystals are fired simultaneously, it is possible to vary the phase between the waves generated by each of the crystals. Varying the phase angle between these multiple crystals fired simultaneously in a random fashion, or varying according to some predetermined stepwise or other manner, can result in enhanced uniformity as nodes and nulls move about or are perhaps even prevented from forming.

Figure 32:
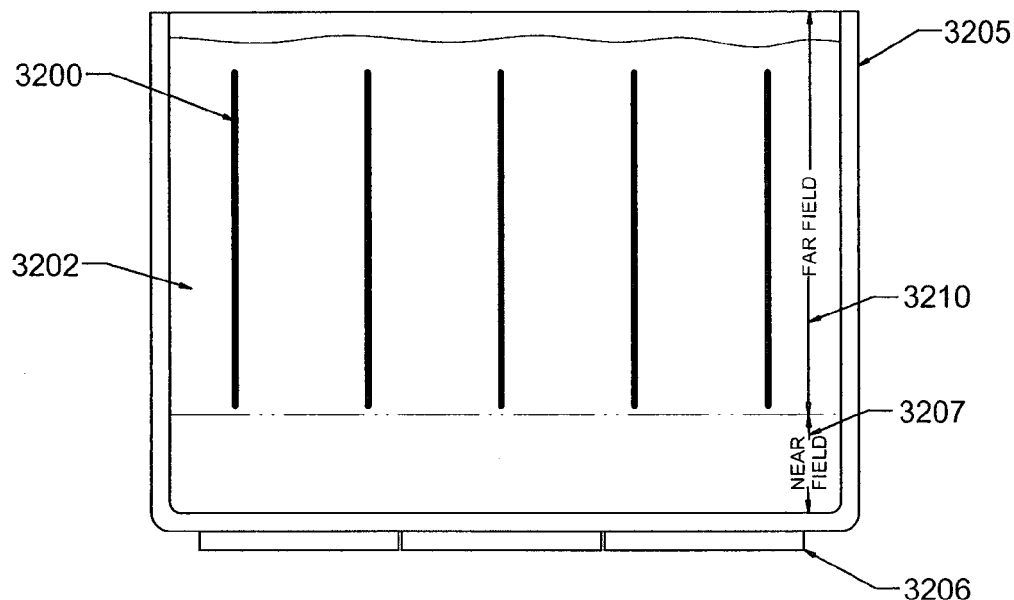
FIG. 32 shows a simplified cross-sectional view of a conventional megasonic cleaning system configured to apply energy to a member in a tank, with energy projected parallel to the surface of a substrate.

Use of frequency, power, and pulse width variation to smooth non-uniformity of the near field is not limited to having the substrate contact, or become part of the transducer vibration member. Traditional megasonic cleaning systems apply the energy to a member in a tank, with energy projected parallel to the surface of a substrate, as shown in FIG. 32. In such systems, the substrates 3200 are not positioned too closely to the vibration surfaces 3206 because of the non-uniform cleaning experienced in this region. This distancing from vibration surfaces increases the size of the processing tanks, consuming more chemicals than architectures allowing close proximity of the substrate to the vibration surface. By varying the frequency, intensity, and pulse width of the megasonic beam, "effective" field uniformity is improved in this region.

In accordance with another alternative embodiment of the present invention, using a sequenced firing of the vibration elements, a second element could be positioned at a distance from the near field region of the first element. This second element would send megasonic energy into the near field region of the first element when the first element is inactive. The second element would thus provide megasonic energy in its far field, to clean and process substrates present in the original near-field of the first element.

Figure 33:
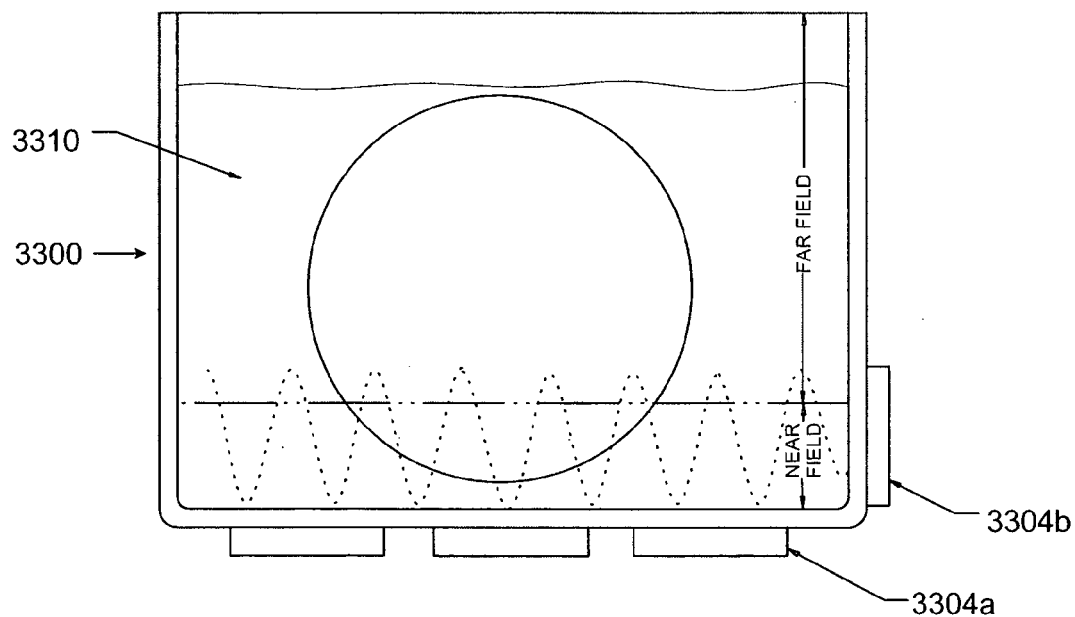
FIG. 33 shows a simplified cross-sectional view of an embodiment of an apparatus in accordance with the present invention featuring second transducer elements included on a vertical wall at or near a 90° angle relative to the first transducer element(s) located on the bottom of the tank.
Figure 34:
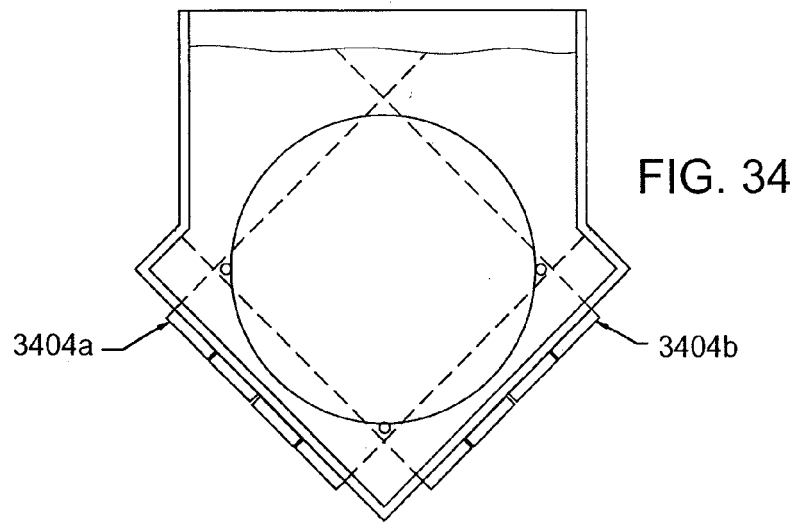
FIG. 34 shows a simplified cross-sectional view of another embodiment of an apparatus in accordance with the present invention featuring first transducer elements located on one angled bottom wall while the second transducer elements are located on the other.

Such a combination of first and second vibrating elements could be arranged in either a flat-bottomed or V-bottomed tank. In the case of a flat-bottomed tank of FIG. 33, the second elements 3304b could be included on a vertical wall at or near a 90° angle relative to the first transducer element(s) 3304a located on the bottom of the tank 3300. Such an embodiment is shown in FIG. 34. An acceptable tank design for this embodiment is disclosed in U.S. Pat. No. 6,595,224, incorporated by reference herein for all purposes.

Figure 35:
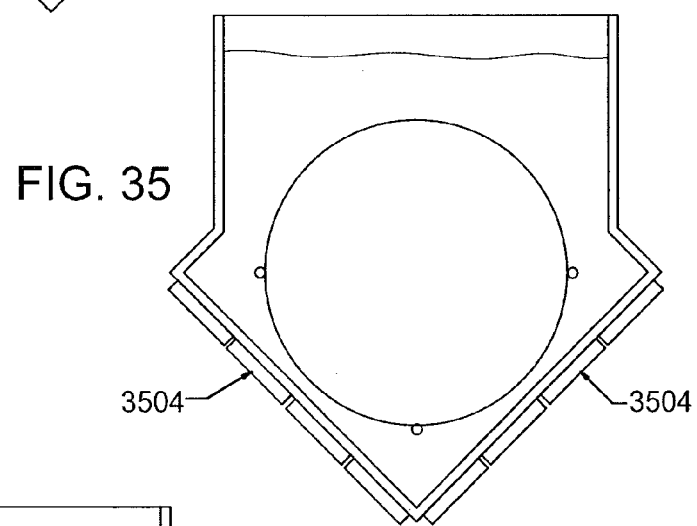
FIG. 35 shows a simplified cross-sectional view of another embodiment of an apparatus in accordance with the present invention.
Figure 36:
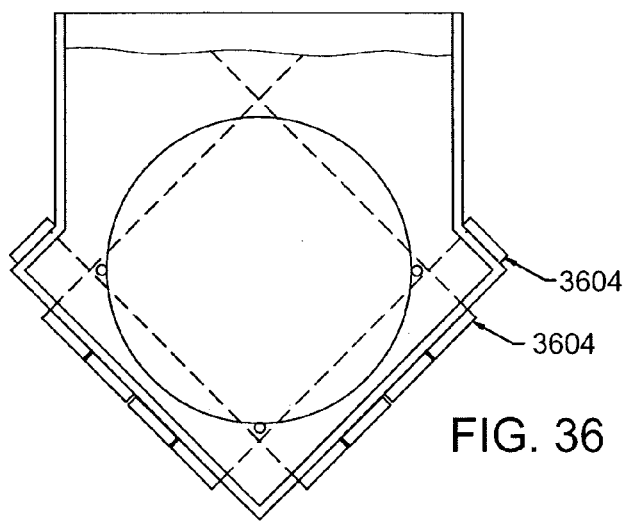
FIG. 36 shows a simplified cross-sectional view of another embodiment of an apparatus in accordance with the present invention featuring additional elements added to the overhang above the V-shape to allow energy to be projected across the face of the sloped side walls of the tank.

In the case of a V-bottom tank, the first transducer elements 3404a can be located on one angled bottom wall while the second transducer elements 3404b can be located on the other as shown in FIG. 34. Such a tank design is disclosed in U.S. Pat. No. 6,098,643 and is herein incorporated by way of reference for all purposes. Additionally, the transducer plates shown in FIG. 34 could be widened, or additional elements could be added to the overhang above the V-shape to allow energy to be projected across the face of the sloped side walls of the tank. Such alternative embodiments are shown in FIGS. 35 and 36, respectively.

The design approach shown in FIGS. 33–36 could also be applied to a megasonic unit firing all vibration elements simultaneously. Historically, when beams were directed from multiple angles simultaneously, some beam interference and resulting cancellation and reinforcement was expected. However, by varying the frequency, power, phase angle, or pulse width of the applied ultrasonic energy, points of high and low intensity could be moved within the bath, effectively rendering the overall bath more uniform for purposes of processing or cleaning.

In accordance with still another embodiment of the present invention, a single substrate is oriented such that its surface is held parallel to the surface of a vibration member. While either partially or fully submerged in the processing fluid, the substrate may be brought into close proximity to, but not in direct contact with, the vibration member. The distance separating the vibration member and the substrate could range from between about 1 µm to about several inches or more. Such an arrangement is shown in FIG. 37.

In FIG. 6A, a similar concept is shown, except that substrate thickness should approximate an even multiple of one-quarter the wavelength of the applied megasonic energy in order to accomplish significant transfer of energy across the substrate. In general, the thickness of semiconductor wafers would not promote transfer of energy at frequencies conventionally employed in single wafer megasonic processors. With primarily reflection of megasonic energy occurring off the wafer surface back towards the vibration member, a very strong and pronounced standing wave can be established. Because the wafer is held parallel to the vibration member, this standing wave is comprised of a fixed array of points of constructive and destructive interference, leading to less than optimal wafer processing.

To overcome the disadvantages of such non uniform energy exposure during processing, embodiments of the present invention disclose techniques for eliminating points of constructive and destructive interference, minimizing the energy difference between them, or changing over time the physical location of their location. One approach to enhance uniformity in such a situation is to vary frequency or intensity of applied megasonic energy in an appropriate manner. Another approach to enhancing uniformity is to change a position of the wafer relative to an energy source, for example by wobbling or rocking. Both approaches are described in detail in earlier sections of this application.

FIG. 38 shows an embodiment in accordance with the present invention including two vibration members 3802a and 3802b, aligned parallel to each other and spaced apart with a substrate 3800 inserted between them. The gap between the vibration members is completely filled with processing fluid 3802. The processing fluid can either be flowed from one end of the vibration members to the other past the substrate, or may enter into the gap between the vibration members through slots in one or both vibration members positioned between adjacent piezoelectric crystals 3804.

Varying the frequency and/or power level can act to even out the negative effects of the non-uniform near field region, which results in non-uniform processing of the substrate. And serendipitously, the variation of some combination of frequency, power, phase angle, and pulse width can also reduce damage to sensitive structures on the surface of the substrate both in the near and far fields.

In yet another embodiment in accordance with the present invention, the substrate may be positioned non-parallel to the vibration member, and separated from a vibration member by a distance. When the angle between a substrate surface and the surface of a vibration element lies within a certain range, a significant portion of impinging ultrasonic energy is transferred across the thickness of the substrate. However, at angles outside this critical range, the majority of the energy is reflected off the surface of the substrate. In either case, embodiments in accordance with the present invention may help to minimize adverse affects of near field non-uniformity where frequency, power, phase angle, and pulse width are varied appropriately.

In any of the embodiments in accordance with the present invention, the substrates could exhibit motion relative to the surface of the vibration element. This relative motion could take the form of rotation, lateral movement, moving closer to or farther away, or a combination of rotation, lateral, and other movement. Motion of the substrate relative to the vibration element can be uniform or variable, depending upon the stage of processing.

For example rapid rotation of a single wafer not submerged in a tank, but instead wetted by spray nozzles, may be desired for a resist strip processing step. The rapid rotation tends to reduce the thickness of the liquid layer on the substrate surface. A thinner liquid layer could allow faster diffusion of a gas component, such as ozone gas, from the surrounding atmosphere to the surface of the wafer where it may participate in a desired reaction.

Conversely, in a later step it may be desirable to clean a wafer in an SC 1 solution and rinse the wafer in DI water by fully submerging the wafer in a liquid in a tank. A much slower rotation or even back and forth motion may be preferable for these two steps. In a processing step wherein the substrate is submerged, any components desired for reaction at the surface of the wafer would need to be dissolved in the liquid. Rotation of the submerged wafer would not appreciably reduce the hydrodynamic boundary layer on the surface of the wafer over the thickness of the acoustic boundary layer formed by the use of ultrasonic energy, either alone or in combination with the rotation, unless the rotation speed was very high. Therefore, rotation would not appreciably increase the diffusion rate of a dissolved species in the bulk fluid to the substrate surface.

Additionally, various chemicals could contact the substrate surface before, following, or during the application of ultrasonic energy of varying frequency, power, or pulse width. For example, a fine mist or spray of a liquid comprised essentially of DI water could be applied to the substrate surface simultaneously with the application of ultrasonic energy, while an oxidizing gas is introduced into the atmosphere surrounding the substrate. Alternatively, the liquid could be comprised of an organic acid or an inorganic base dissolved in DI water.

While the preceding embodiments and examples have dealt with the application of ultrasound at frequencies commonly used in the manufacture of electronic component substrates, the invention is not limited to these frequencies or components. For example, frequencies outside the traditional ultrasonic and megasonic processing ranges may also be used advantageously. Historically, frequencies in the range from a few kilohertz to several hundred kilohertz have often been referred to as ultrasonic processing frequencies and those from a few hundred kilohertz to several thousand kilohertz have been referred to as megasonic processing frequencies. For purposes of the present invention, the terms ultrasonic and megasonic frequency can refer to any frequency range. Frequencies much higher than these, even in the conventional microwave processing range, can also be used without departing from the spirit and intent of this invention.

An example of microwave processing of various substrates is disclosed in U.S. patent application Ser. No. 10/150,748 and is hereby incorporated by way of reference for all purposes. Various embodiments of this incorporated application disclose the processing of substrates even when they are not fully or even partially submerged in a liquid. With microwave processing, various standing wave patterns can be established in the processing chamber. By varying the frequency, power, phase angle of multiple sources, and/or the pulse width of the applied energy, the negative impact of these standing waves with their attendant points of high energy and low energy can be minimized or even eliminated.

Additionally, processing can occur at pressures above atmospheric pressure and include the application of megasonic energy. Such processing is disclosed in U.S. patent application Ser. No. 10/456,995, herein incorporated by way of reference for all purposes. Also, various processing chemistries and processing sequences are disclosed which can be advantageously used with the instant invention of this current application.

Further, substrates other than electronic components can also be advantageously treated with sonic energy in accordance with embodiments of the present invention. Such substrates could come a wide variety of industries, such as from the disk drive, optics, flat panel, medical, microbiological and pharmaceutical industries just to name a few.

In addition, embodiments in accordance with the present invention are not limited to changing the character of sonic energy in the manner described to achieve more uniform processing in the near field. In accordance with alternative embodiments of the present invention, the character of other forms of applied radiation, such as microwave radiation, may also be varied in the manner described to achieve more uniform processing of a substrate receiving the applied radiation. Moreover, multiple forms of radiation could be applied simultaneously or in sequence to accomplish the desired processing.

While the most common vibration elements used in electronic component substrate processing are comprised of piezoelectric crystals bonded to a plate-like structure, other types of crystals, materials, and structures, may also be used without departing from the spirit and teachings of this instant invention. Many of these alternative transducer element materials are well known in industry.

Moreover, other methods of applying pressure pulses to the processing fluid and processing fluid/substrate interface may also be used to advantage in accordance with embodiments of the present invention, including but not limited to pulsed high pressure jets and vibrating surfaces moved by mechanical agitation.

And while the above description has focused upon improving uniformity of processing in near field regions proximate to a vibration member, embodiments in accordance with the present invention are not limited to this application. For example, in alternative embodiments of the present invention, megasonic energy could be applied from a vibration member to a substrate located in far field regions, thereby generating regions of constructive and destructive interference. Subsequently, utilizing techniques such as at least 1) energy reflection, 2) the use of multiple energy sources, or 3) variation in the character of energy emitted from the megasonic energy sources, the location of points of constructive and destructive interference could be altered over time, thereby enhancing the uniformity of processing in far field regions outside of the vibration member near field.

D. Mechanical and Electrochemical Processing

With most conventional chemical mechanical polishing or planarization (CMP)-type processing, substrates are gripped in a device and then set in rotational motion adjacent to a large rotating abrasive pad. Both the substrate and the abrasive pad may be in motion with respect to the machine as well as with respect to each other).

As the substrate is brought into contact with the abrasive pad, various processing slurries are introduced onto the surface of the pad to aid in uniform grinding and removal of unwanted material from the substrate surface. Various pressure profiles are established across the diameter (or length, not thickness) of the substrate due to the relative velocity between the substrate and the abrasive pad.

Typically, the established pressure profiles are not uniform across the entire substrate. Sometimes the first part of the substrate to contact the pad dips towards the abrasive pad, while the last part of the substrate to contact the pad lifts further away from the pad. In other applications, the leading surface of the substrate may lift or hydroplane while the lagging surface dips.

The pressure profiles are often nonlinear across the entire diameter or length of the substrate, taking the form of a curved surface containing minimums and/or maximums. Localized pressure can increase or build leaving the leading edge of the surface of the substrate, and then fall away when approaching the other end or trailing edge. Alternatively, the localized pressure may first decrease, and then increase, from one side of the substrate to the other.

Conventional approaches have attempted to apply ultrasonic energy to clean accumulated grit from the surface of abrasive pads. Since these pads are generally constructed of flexible polymeric materials that readily absorb vibrational energy, it is generally difficult to transfer vibrational or sonic energy across them.

This transfer of sonic energy during an abrasive polishing or planarization process is further complicated when the pads and/or substrates are moving or spinning. One conventional design for a polishing unit utilizes a belt/loop design for the abrasive pad. The belt continually loops around drive pulleys, in a manner analogous to a belt sander. The substrate is held stationary and allowed to come into contact with the abrasive belt.

Ultrasonic energy may be applied to the top side of the belt during this operation, with the intent of having some small portion of the energy transfer across the polymeric belt to the interface between the belt and substrate, aiding in processing or cleaning accumulated grit from the belt. Because of the poor energy transfer across flexible polymeric materials, such conventional designs have only met with limited success.

Accordingly, a need exists in the art for methods and apparatuses for applying sonic or vibrational energy to enhance a semiconductor fabrication process.

In accordance with embodiments of the present invention vibrational energy is applied to a substrate or workpiece being subjected to chemical mechanical planarization or some other form of processing. In accordance with one embodiment, the vibrational energy may be imparted to the workpiece from an energy source through contact with a stationary energy-transfer member. In accordance with an alternative embodiment of the present invention, the vibrational energy may be imparted to the workpiece through an energy-transfer member featuring a rotating element such as a bearing. Application of vibrational energy in accordance with the present invention may alter a pressure profile experienced by a substrate in contact with an abrading member, thereby affecting a quality of the resulting processing.

Embodiments in accordance with the present invention generally relate to modification of surfaces of workpieces by processing in conjunction with the application of vibrational energy. The applied vibrational energy may take various forms, and may be produced from various sources.

In accordance with one embodiment, of the present invention, vibrational energy in the form of mechanical vibrations, sonic/ultrasonic waves, or microwaves, may be applied to a substrate prior to, during, or after processing of the substrate to improve the uniformity of local or global substrate processing. One specific application in accordance with the present invention involves planarization of a semiconductor workpiece, either generally over an entire wafer, or over individual features present on that surface.

Other more common forms of planarization and surface modification include mechanical polishing, lapping, grinding (removal of material by abrasion), and electrochemical machining processes involving removal of material/planarization due to electrochemical reactions on a surface. Alternatively, embodiments in accordance with the present invention can apply vibrational energy to a substrate in the course of adding, as well as removing, material to a workpiece. Such additive sonic-assisted processes include but are not limited to electroplating and various forms of coating.

In the specific field of CMP processing, introducing vibrational energy into and/or through a substrate during planarization/processing may render more uniform the localized pressure profile developed between the substrate and the contacting abrasive pad. This more uniform pressure profile may in turn lead to more uniform removal of material from the substrate surface.

In the field of electrochemical machining, introduction of vibrational energy may lead to more uniform concentration and temperature profiles near the surface of the substrate. More uniform profiles may lead to more uniform and rapid removal of material from substrate surfaces or more uniform and rapid reactions.

The applied vibrational energy may also reduce the thickness of fluid boundary layers, referred to as the acoustic boundary layers in the case of applied ultrasonic energy, or as the hydrodynamic boundary layers in the case of forced fluid flow. Such thinned fluid/hydrodynamic/acoustic boundary layers may lead to faster mass transfer across the layers to the substrate and correspondingly accelerated processing when mass transfer limiting steps are involved. This effect can occur generally over an entire surface, or be limited to specific local areas only, or act differently in different local areas.

For example, during processing the concentration of a specific ionic species of interest can be depleted in the fluid boundary layer next to an active surface. The individual ions cannot diffuse or move as rapidly into and through the fluid boundary layer under the applied potential, as they can in the bulk fluid by means of the bulk fluid flow. The resulting depletion of specific ions in the fluid boundary layer is often referred to as concentration polarization, and results in slower and non-uniform processing.

By reducing the thickness of the fluid boundary layer through the application of vibrational or sonic energy in accordance with embodiments of the present invention, the rate at which the desired ionic species becomes available at the reacting surface, is increased.

For substrate processing involving planarization, the inverse effect can be observed. Specifically, a boundary layer having thickness reduced by the application of vibrational energy in accordance with the present invention, allows species removed from the substrate surface to more rapidly enter the bulk fluid. This results in both faster and more uniform processing.

Vibrational energy applied to enhance processing in accordance with embodiments of the present invention can be produced by any convenient mechanical/electrical source. Examples range from a piston/eccentric arrangement exhibiting relatively low frequency, to electronic excitation of ultrasonic piezoelectric crystals exhibiting moderate frequency, to generation and application of higher frequency microwave energy. These generated vibrations may be communicated to the interface between the substrate and the processing entity (i.e. the abrasive pad and/or the processing chemistry) in various ways.

As previously described, polymeric pads which may be employed in abrasive processing may absorb vibrational energy. Therefore, instead of attempting to transfer significant amounts of energy across such a flexible energy absorbing element, embodiments in accordance with the present invention transfer significant amounts of vibrational energy directly across a relatively rigid substrate and/or substrate holder, where little of the energy is absorbed and lost.

One specific design for accomplishing this application of vibrational energy is described above. Specifically, by transferring large amounts of energy directly across the substrate instead of only transferring small amounts across the abrasive pad, much more energy is available at the interface between the pad and the substrate to modify the localized pressure profile initially developed.

While not wishing to be bound by any particular theory, the applied vibrational energy may disrupt or modify localized pressure profiles arising during substrate processing. For application of moderate frequency vibrational energy, the full pressure profile across the entire substrate resulting from a conventional processing apparatus machine/unit may be prevented from fully forming, because the time between vibration pulses is too short to allow full development of a non uniform pressure profile.

An analogous situation may be described for conventional megasonic processing of substrates in a liquid bath. As fluid flows past a stationary substrate, a hydrodynamic boundary layer is formed above the substrate where the fluid velocity ranges from zero at the substrate surface to the bulk fluid velocity at some distance removed from the substrate surface. This profile grows in thickness or develops the further the fluid flows along the plate. Therefore, the profile of "reduced" fluid velocity in the resulting fluid boundary layer is thinner near the nose of the substrate and thicker near the tail.

By applying megasonic energy during processing, however, the full localized profile is never allowed to fully develop. As a result, the acoustic-determined boundary layer may be less than 1/1000 the thickness of the hydrodynamic-determined boundary layer. In this manner, application of megasonic energy can promote cleaning or processing operations in which mass must be transferred across the fluid boundary layer.

One issue addressed by embodiments in accordance with the present invention is the difficulty in transferring vibrational energy across the substrate while the substrate is rotating or moving. Several embodiments in accordance with the present invention accomplish this goal without also requiring the source of the vibrational energy to also move. Such movement of the vibrational energy source would add complexity to the apparatus by requiring moveable power connections.

Figure 39:
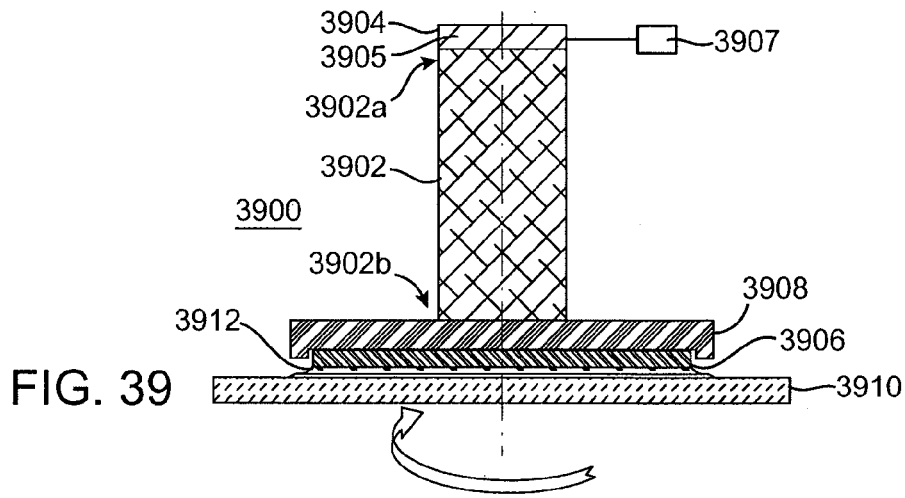
FIG. 39 shows a simplified cross-sectional view of one embodiment of an apparatus for employing vibrational energy to enhance processing of a substrate.

FIG. 39 shows a cross-sectional view of one embodiment of an apparatus for employing vibrational energy to enhance processing of a substrate. Processing apparatus 3900 of FIG. 39 shows solid member 3902 having one end 3902*a* fitted with source of vibrational energy, for example an ultrasonic transducer 3904 including piezoelectric crystals 3905 in electrical communication with a power source 3907. Second end 3002*b* of solid member 3902 is in contact with the substrate 3906 through substrate support plate 3908. Energy is transmitted through the solid energy transfer member, the substrate, and into interface 3910 between substrate 3906 and abrasive pad 3910 in the presence of slurry 3912. Solid member 3902 is stationary and does not rotate or move while abrasive pad 3910 rotates in contact with the substrate.

Figure 40:
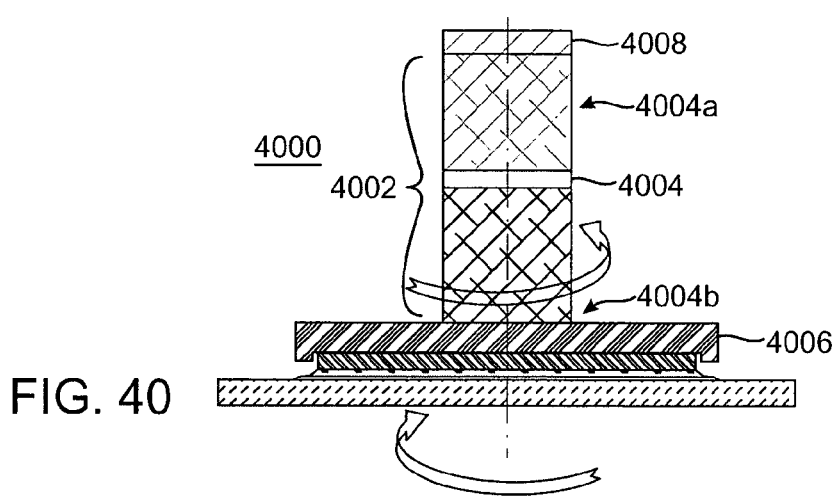
FIG. 40 shows a simplified cross-sectional view of an alternative embodiment of an apparatus in accordance with the present invention for employing vibrational energy to enhance processing of a substrate.

FIG. 40 shows a cross-sectional view of an alternative embodiment of an apparatus in accordance with the present invention for employing vibrational energy to enhance processing of a substrate. Apparatus 4000 of FIG. 40 is similar to that of the first embodiment of FIG. 39, except that transmission member 4002 includes rotatable bearing 4004. Bearing 4004 allows top portion 4002a of solid member 4002 in contact with vibration source 4008 to remain stationary, while bottom portion 4002b in contact with substrate support 4006 is free to turn.

Various bearing designs are known that could allow transfer of vibrational energy simultaneous with rotation of the substrate holder. Examples of such bearing designs include but are not limited to mechanical bearings and low friction slip surfaces.

While FIG. 40 does not explicitly illustrate how the substrate holder can be rotated, many methods are well known in the industry that could be employed to accomplish this movement. Examples of such mechanisms for inducing rotation include but are not limited to belts/pulleys, gears, and friction with other moving members.

Figure 41:
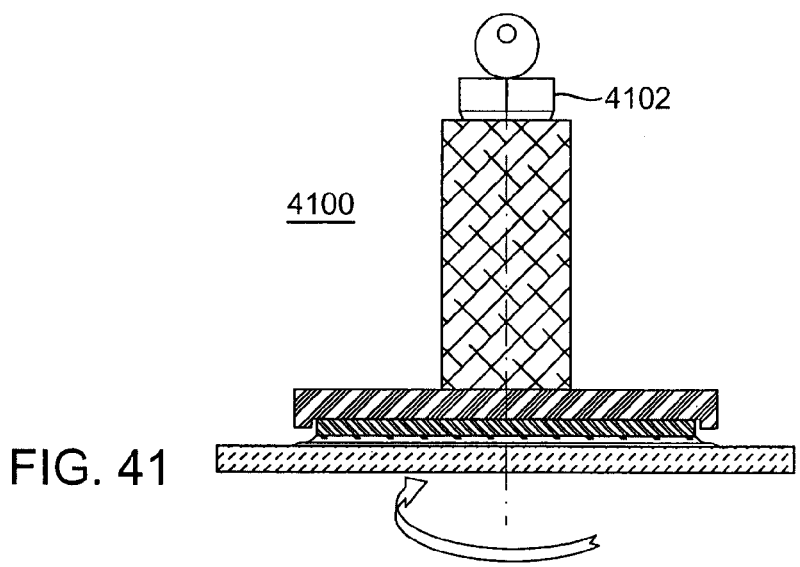
FIG. 41 shows a simplified cross-sectional view of another alternative embodiment of an apparatus in accordance with the present invention employing vibrational energy to enhance processing of a substrate.

FIG. 41 shows a cross-sectional view of another alternative embodiment of an apparatus in accordance with the present invention for employing vibrational energy to enhance processing of a substrate. Apparatus 4100 shown in FIG. 41 is similar to that shown in FIG. 40, except that a mechanical vibrator 4002 is used as the vibration element.

While the substrate holder is shown as static in FIG. 41, this is not required by the present invention. In accordance with other embodiments, the vibration transfer element could be rotated as the mechanical vibrator operates.

Figure 42:
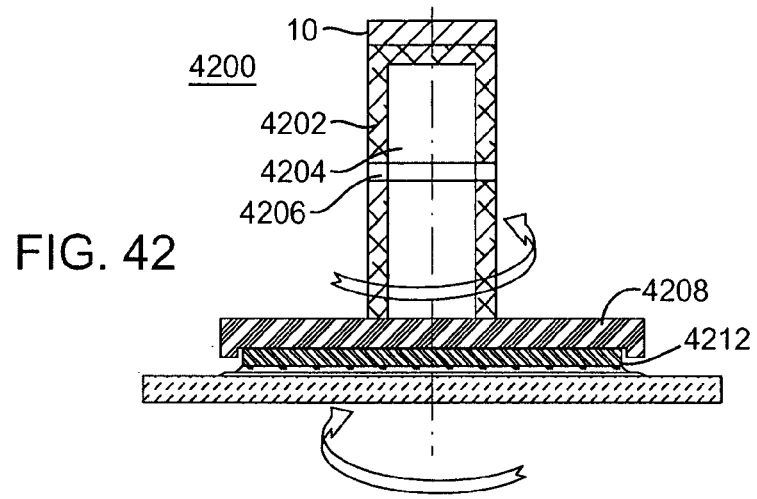
FIG. 42 shows a simplified cross-sectional view of yet another alternative embodiment of an apparatus in accordance with the present invention for the application of vibrational energy to enhance processing of a substrate.

Liquid is well known as a medium for the transmission of vibrational and sonic energy. Accordingly, FIG. 42 shows a cross-sectional view of yet another alternative embodiment of an apparatus in accordance with the present invention for application of vibrational energy. Apparatus 4200 utilizes a hollow vibrational energy transmission member 4202 filled with liquid 404 in conjunction with a bearing/seal structure 4206 to facilitate transfer of vibrational energy to substrate support 4208 during processing. One example of such a bearing/seal structure for use in accordance with the present invention is the ferrofluidic seal structure.

In the specific embodiment shown in FIG. 42, it may be preferable to employ a degassed liquid to limit bubble formation, which would reduce the transfer of sonic energy from source 4210 to the substrate 4212.

Figure 43:
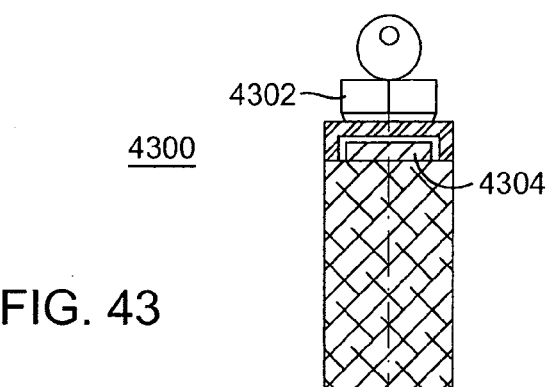
FIG. 43 shows a simplified cross-sectional view of still another alternative embodiment of a processing apparatus in accordance with the present invention, incorporating a mechanical structure for generating vibrations.

FIG. 43 shows a cross-sectional view of still another alternative embodiment of a processing apparatus in accordance with the present invention. Apparatus 4300 of FIG. 43 employs vibrational energy from mechanical vibrator 4302 actuated at a relatively low frequency (e.g. ~1–1000 Hz or ~1–10 kHz), in combination with vibrational energy from a megasonic unit 4304 having crystals stimulated at a moderate frequency (e.g. ~0.7–1 MHz). In accordance with still other embodiments, microwave or other higher frequency energy pulses may also be applied, either in conjunction with the low and moderate frequency energy, or in place of these other energy frequencies.

Figure 44:
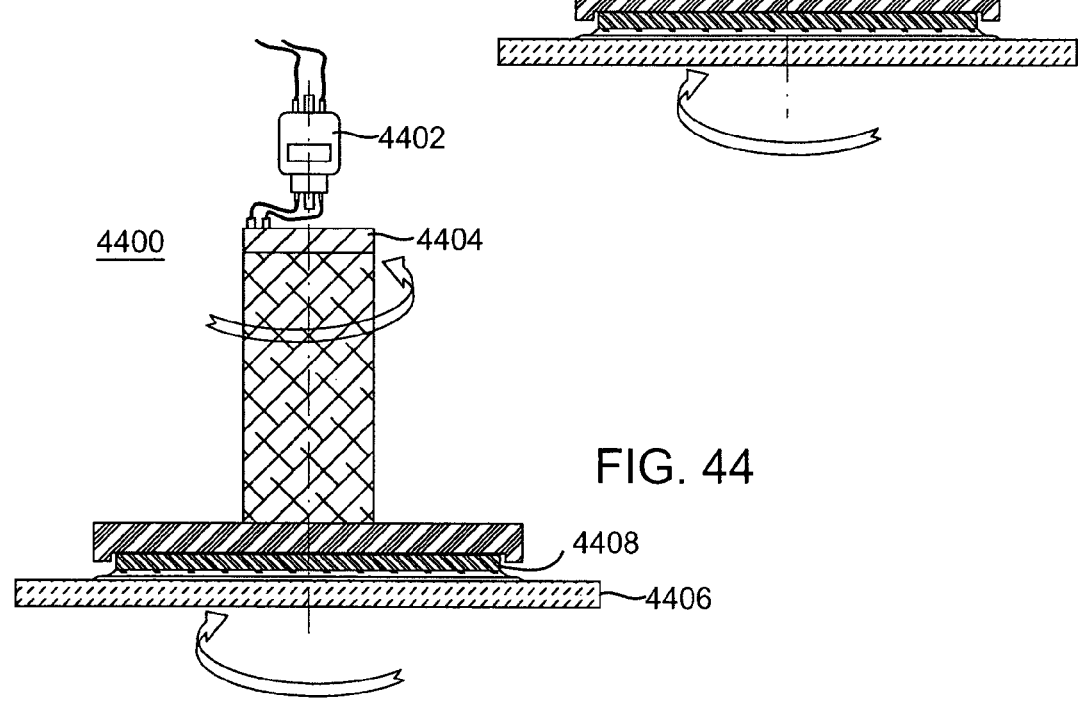
FIG. 44 shows a simplified cross-sectional view of another alternative embodiment of a processing apparatus in accordance with the present invention.

FIG. 44 shows a cross-sectional view of another alternative embodiment of a processing apparatus in accordance with the present invention. Apparatus 4400 of FIG. 44 utilizes slip ring structure 4402 to allow transfer of electrical energy from a stationary source of power (not shown) to a rotating moving vibrational element 4404 (e.g. a piezoelectric crystal). Slip ring 4402 may feature contacts comprised of an electrically conducting liquid such as mercury, or formed from a solid conductor such as copper metal. Such an arrangement as shown in FIG. 44 allows the rotation of both the abrasive pad 4406 as well as substrate 4408 itself, without requiring a bearing or bearing surface through which vibrational energy must be transferred.

Figure 45:
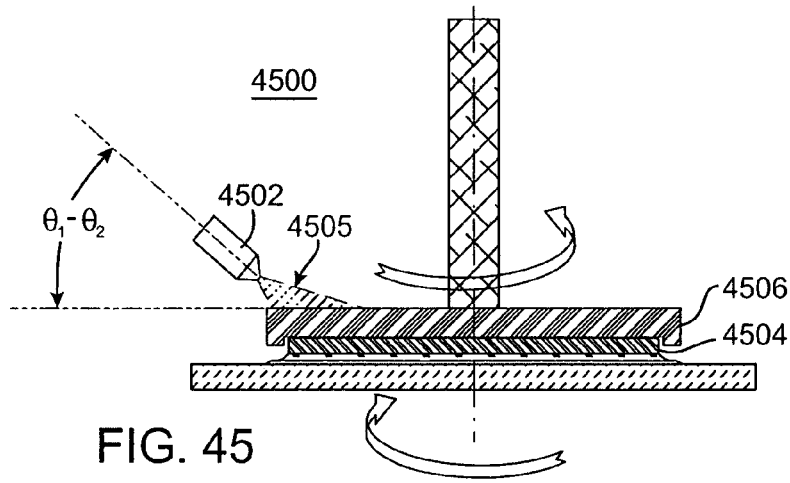
FIG. 45 shows a simplified cross-sectional view of another alternative embodiment of a processing apparatus in accordance with the present invention, incorporating a sonic nozzle configured to operate within a correct range of angles to generate vibrations.

FIG. 45 shows a cross-sectional view of another alternative embodiment of a processing apparatus in accordance with the present invention. Apparatus 4500 of FIG. 45 includes megasonic nozzle 4502 positioned within a specific range of angles ($\theta_1$–$\theta_2$) with respect to the front or back surface of substrate 4504, or the surface of the holding or support plate 4506. Within the specific range of angles ($\theta_1$–$\theta_2$), mode conversion occurs where dilatational pressure waves 4505 exiting megasonic nozzle 4502 are converted into surface waves in the substrate, substrate holder, or substrate support.

Figure 46:
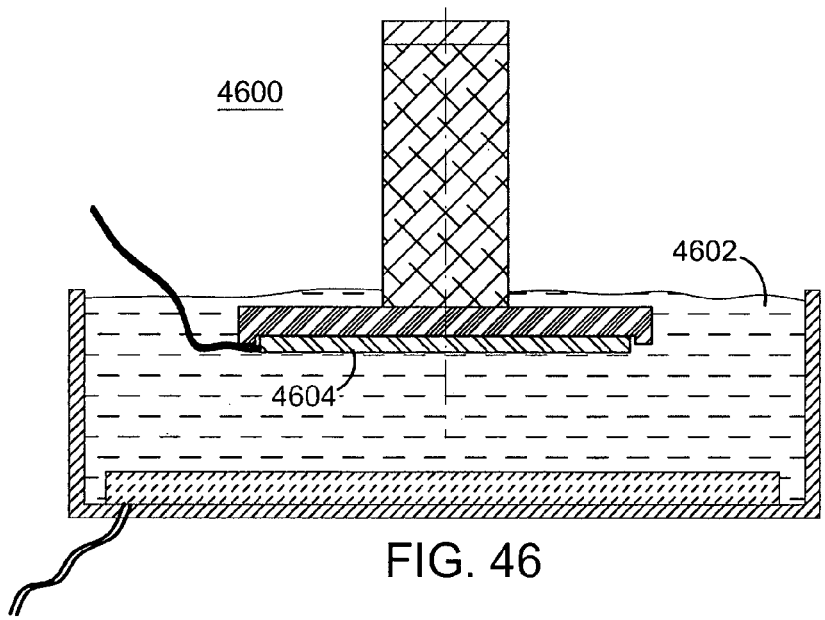
FIG. 46 shows a simplified cross-sectional view of one embodiment of a processing apparatus for electrochemical processing in accordance with the present invention.

FIG. 46 shows a cross-sectional view of yet another embodiment of a processing apparatus in accordance with the present invention. Apparatus 4600 is configured to perform electrochemical polishing or machining. Rather than utilizing an abrasive pad to perform substrate planarization, in apparatus 4600 electrolyte liquid 4602 acts as a medium to transfer various ionic species to and from the surface of substrate 4604. Electrochemical processes utilizing either constant current or constant voltage operational modes are particularly suited to take advantage of benefits offered by embodiments in accordance with the present invention.

While the embodiment of FIG. 46 shows vibrational energy being transferred across the thickness of the substrate, this is not required by the present invention. In accordance with alternative embodiments, vibrational energy can be directed parallel to the substrate surface in order to reduce the thickness of any associated fluid boundary layers.

And while the embodiment of FIG. 46 shows a large electrode positioned parallel to the substrate surface, this is not required by the present invention. Because of the electrical conductivity of the electrolyte solution, in accordance with alternative embodiments the electrode may be positioned some distance from the substrate surface, and/or in a non-parallel orientation relative thereto.

While electrochemical processing is generally conducted in a tank with the substrate either partially or completely submerged, this is also not required by the present invention. In accordance with still other alternative embodiments of the present invention, it may be preferable to employ only a thin fluid layer between an electrode closely spaced from the substrate. Such an arrangement could be particularly useful in applying microwave energy when the electrode is relatively transparent to microwave energy.

For example, many semiconductor substrate materials are relatively transparent to microwave energy. Such substrate materials may also posses sufficient electrical conductivity, or may contain conducting traces or other sufficiently conductive features, to allow the substrate to act as an electrode. Thus in accordance with alternative embodiments of the present invention, high frequency microwaves may be applied in order to enhance electrochemical processing.

Figure 47:
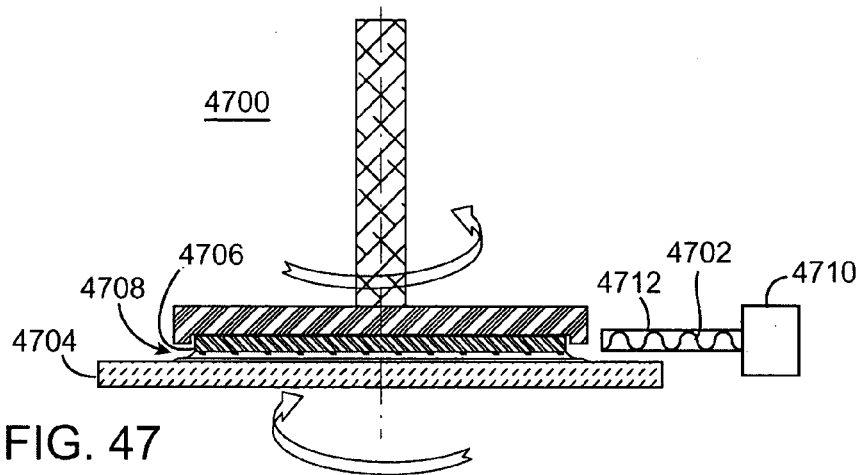
FIG. 47 shows a simplified cross-sectional view of another alternative embodiment of a processing apparatus in accordance with the present invention.

FIG. 47 shows a cross-sectional view of another alternative embodiment of a processing apparatus in accordance with the present invention. Apparatus 4700 of FIG. 47 shows delivery of microwave energy 4702 from microwave source 4710 to interface 4708 between abrasive pad 4704 and substrate 4706, utilizing wave-guide 4712. A wave-guide delivers the microwave energy to the desired point of application to maximize energy transfer directly to the substrate/pad interface. In the particular embodiment shown in FIG. 47, a thin liquid layer at interface 908 and/or on the surface of the substrate holder could be advantageously used to absorb the microwave energy applied from the source.

While FIG. 47 shows the microwave radiation as being directed by the waveguide parallel to the substrate surface and the substrate/pad interface defined thereby, this is not required by the present invention. In accordance with alternative embodiments, a waveguide could be disposed at an angle relative to the substrate surface to maximize efficient transfer of energy to the substrate/pad interface. Mode conversion of the waveform could occur under the proper conditions.

While the previously-described embodiments have depicted the processed substrate as being positioned above a processing member, this is not required by the present invention. In accordance with alternative embodiments, the substrate could be disposed beneath or beside a processing member.

Before, during, or after performance of a sonic-assisted processing step in accordance with the present invention, a second processing step may be commenced. This second processing step may include electrochemical processing including electroplating, electropolishing and electromachining. The incorporation of vibrational energy of any frequency, but especially ultrasonic and microwave frequency energy into the interface between the substrate and any contacting liquid, can be of great benefit in reducing the thickness of any associated fluid boundary layers formed on the surface of the substrate.

Reduction of such fluid boundary layers in accordance with the present invention can lead to more rapid and/or uniform processing, especially for processing involving a mass-transfer-limiting step. Additionally, reduction of the thickness of fluid boundary layers renders more uniform the fluid concentration and temperature contacting the substrate surface. This in turn leads to more uniform processing, and can prove especially effective for processing uneven surfaces of substrates.

It is further noted that the steps of processing described in the various above embodiments can be performed in any order, and still remain within the scope of the present invention. For example, vibrational energy may be applied before, during, or after processing to enhance results.

Electrochemical processing is finding increasing use in the fabrication of semiconductor devices. One prevalent use is in the formation of copper metallization of interconnect structures. In such damascene applications, copper is deposited by electroplating within recesses formed in dielectric material.

In such electrochemical processing, it may be difficult to obtain/maintain uniform addition or removal of materials from a substrate surface exhibiting complex topography. One difficulty encountered with conventional electrochemical processing is that the concentration of various ionic and other active chemical species, and fluid flow velocity profiles, change across the hydrodynamic boundary layer at the surface of the substrate or within recessed features present thereon. Thus, with the electroplating of metal layers over substrates, it may be difficult to form layers of a uniform thickness over lower portions of trench features exhibiting high aspect ratios, or to insure that such features are filled uniformly without the inclusion or creation of voids.

In particular, as electrolyte fluids flow over the recessed features, the fluids form a hydrodynamic boundary layer on the substrate surface and the fluid-filled trenches may become stagnant. Liquid in the trenches may thus fail to rapidly transfer via fluid convection or be regularly replaced with fresh bulk fluid overlying the boundary layer. In some cases, a vortex within the trench may be formed, causing localized fluid circulation within the trench but otherwise preventing fluid contained therein from mixing with the surrounding bulk fluid. In such circumstances, the mechanism of transporting various ionic and other chemical species across stagnant regions may be limited to diffusion, which is generally quite slow.

Alternatively or in conjunction with diffusive transport, chemical species may move across stagnant regions under the influence of an applied potential. Under such conditions, concentration polarization arising in these stagnant regions can be amplified. Such concentration polarization may lead to slow and non-uniform processing, especially around sharp edges or in corners within structures.

In an attempt to render electrochemical processing more uniform, various additives are conventionally introduced in the electrolyte baths. Some additives may enhance or speed up deposition or removal of material in selected areas, such as in fluid stagnant areas where ionic concentrations have dropped significantly. Other additives may retard or slow down deposition or removal in areas where fluid velocities and ionic concentrations are elevated. Combinations of additives may be used to make the final deposited material layers or surfaces more level, especially across various non-planar substrates with high aspect ratio features.

While processing uniformity often improves in the presence of additives, processing may still exhibit significant non-uniformity. Such nonuniformity can necessitate additional processing steps to remove or add material in some locations, and to compensate for voids formed in other locations. Such additional steps decrease throughput and increase expense.

Introduction of additives such as enhancers, retarders and levelers, can also serve as another source of contamination that must be removed from the substrate before further processing steps can be implemented. Such contamination removal steps can also decrease throughput and increase expense.

It is known that the introduction of sonic energy may reduce the thickness of the hydrodynamic boundary layer. In certain cases, the acoustic boundary layer resulting from introduction of sonic energy at near 1 MHz, may only be ~1/1000 the thickness of the original hydrodynamic boundary layer. This reduction in the effective thickness of fluid boundary layers can be especially important in processing of trenches, vias, or other structures on the substrate surface that exhibit high aspect ratios.

Introduction of sonic energy of the correct frequency can diminish the effective thickness of fluid boundary layers, thereby increasing the rate of fluid flow/chemical transport in these areas. Where fluid flow is essentially nonexistent, or circulates only locally, fluid transfer out of the feature to the surrounding bulk fluid is prevented. Sonic energy can be utilized to disrupt such localized vortices, and thereby enhance fluid transfer between stagnant areas and the bulk fluid.

However, conventional attempts to use sonic energy to reduce the thickness of the fluid boundary layers during electrochemical processing have typically met with only limited success. In certain cases, these conventional approaches proved unable to effectively transfer energy across an electrode positioned parallel to the surface of the substrate. For designs where the electrode was not positioned parallel to the surface of the substrate, and not positioned between the substrate and the vibration member, non-uniform processing often resulted.

Accordingly, a need exists in the art for methods and apparatuses for improved electrochemical processing of semiconductor substrates.

Electrochemical processing of a semiconductor workpiece in accordance with embodiments of the present invention may be enhanced by application of various forms of energy, including sonic energy, across the thickness of the electrode, especially an electrode positioned between the substrate and a vibrating sonic energy source and pulsed fluid flow. In accordance with embodiments of the present invention, sonic energy may be transferred across electrodes having solid, composite, open (i.e., mesh), or porous structures. Electrochemical processing in accordance with embodiments of the present invention may also be accomplished by or be accompanied by pulsed fluid flow to further reduce the thickness and impact of hydrodynamic boundary layers on processing effectiveness and uniformity.

Embodiments in accordance with the present invention disclose methods and apparatuses for transferring energy to the substrate surface across solid, as well as composite, open, or porous electrode structures, alone or in combination with pulsed fluid flow. Embodiments in accordance with the present invention reduce the thickness of fluid boundary layers, and enhance the uniformity of those layers, and prevent fluid stagnation in high aspect ratio structures. Embodiments in accordance with the present invention thus result in faster and more uniform processing, while eliminating or reducing the need for additives.

Figure 48:
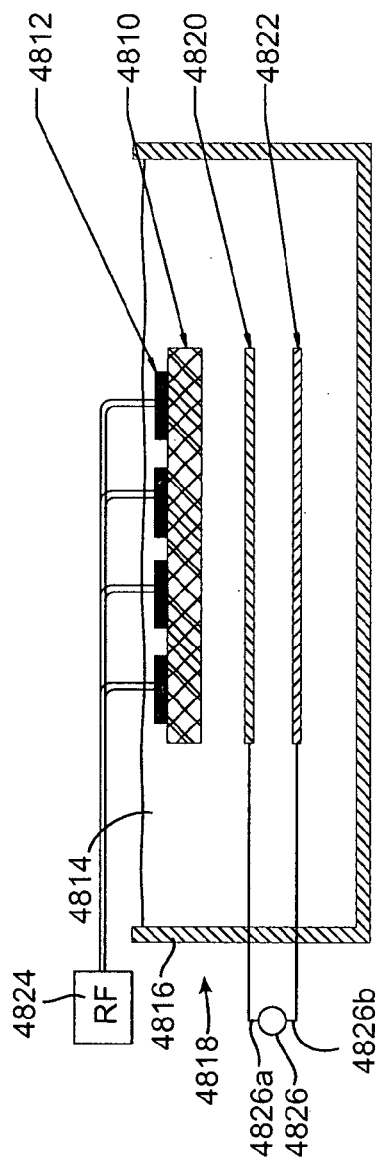
FIG. 48 shows a simplified cross-sectional view of another embodiment of an apparatus for performing electrochemical processing in accordance with the present invention.

FIG. 48 shows a simplified cross-sectional view of one embodiment of an apparatus for performing electrochemical processing in accordance with the present invention. Vibration member 4810 in direct physical contact with piezoelectric crystals 4812 is partly or fully immersed in electrochemical processing bath 4814 contained within walls 4816 of processing vessel 4818. Electrode 4820 is positioned in bath 4814 spaced apart from vibration member 4810. Substrate 4822 is positioned in bath 4814 spaced apart from, and on the opposite side of, electrode 4820.

Piezoelectric crystals 4812 are in electrical communication with RF power source 4824. Electrode 4820 and substrate 4822 are in electrical communication with opposite poles 4826a and 4826b of voltage source 4826, respectively.

During processing, a potential difference is applied across substrate 482 and electrode 4820 by power source 4826. This potential difference creates an electric field that activates the chemical species of bath 4814 to process the substrate surface. This potential difference can be held constant, allowed to change magnitude, or even alternate between positive and negative values, depending upon the specific processing desired to be accomplished. Electrochemical processing modes utilizing either constant or variable current operation are possible in accordance with embodiments of the present invention.

Prior to or during application of the potential difference, piezoelectric crystals 4812 receive voltage from RF source 4824, and commence vibrating. The vibrational energy of piezoelectric crystals 4812 is in turn imparted to the adjoining vibrating member 4810. Vibrating member 4810 in turn communicates the vibrational energy to electrochemical bath 4814.

As a result of the application of vibrational energy to bath 4814, the hydrodynamic boundary layer on both the surface of the substrate and the electrode are substantially lessened. This promotes transfer of chemical species to and from the surface of both the substrate and the electrode.

Processing apparatuses in accordance with embodiments of the present invention may feature electrodes specifically designed to promote their conduction of ultrasonic energy. For example, a solid electrode may be designed to have a thickness of an even multiple of one-quarter of the wavelength of the applied sonic energy (i.e. thickness=$n\lambda/4$, n=2, 4, 6 . . . ).

Figure 49:
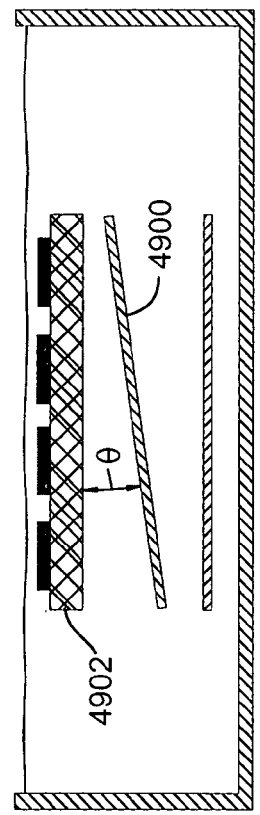
FIG. 49 shows a simplified cross-sectional view of an alternative embodiment of an apparatus in accordance with the present invention, wherein an electrode is disposed at an angle lying between a range of critical angles relative to the direction of sonic energy incident from a vibrating member.

While FIG. 48 shows the electrode disposed orthogonal to sonic energy incident from the vibrating member, this is not required by the present invention. FIG. 49 shows an alternative embodiment, wherein electrode 4900 is disposed at an angle $\theta$ lying between a range of critical angles $\theta_1$–$\theta_2$ relative to the direction of sonic energy incident from vibrating member 4902. Positioning the electrode at an angle in the manner shown in FIG. 49 allows vibrational energy to be transmitted across the electrode without requiring that the thickness of the electrode be approximately equal to an even multiple one-quarter wavelength, as is the case shown in FIG. 48.

In the embodiment of FIG. 49, there is no limitation on the electrode thickness, and cross electrode transfer of energy will occur as long as the surface of the electrode is at a proper angle with respect to the surface of the vibration member. While FIG. 49 depicts an angle between the electrode and the substrate, as well as between the electrode and the vibration member, this is not required. The substrate may be parallel to the electrode, or oriented at any angle to it. Further, an angle between the electrode and the substrate may be held constant or may change during processing. An angle between the electrode and the vibration member may also be held constant or may change during processing.

Figure 50:
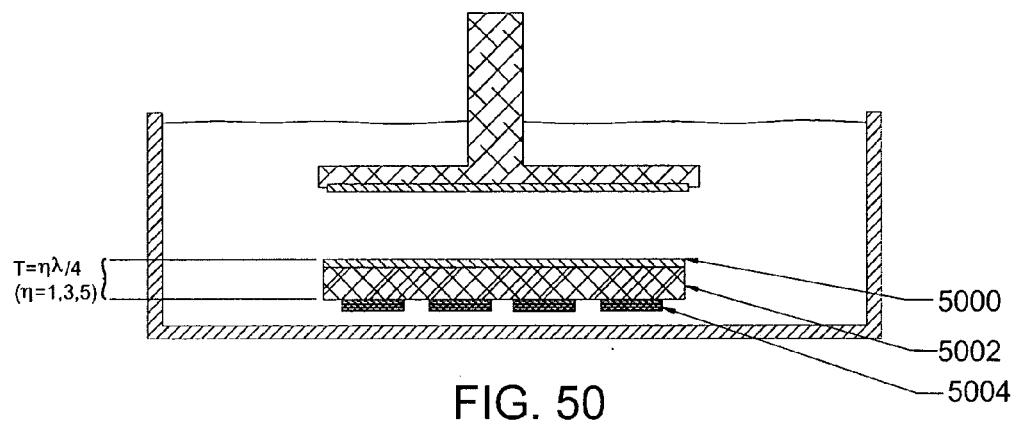
FIG. 50 shows a simplified cross-sectional view of another embodiment of an electrochemical processing apparatus in accordance with the present invention.

FIG. 50 shows a simplified cross-sectional view of another embodiment of an electrochemical processing apparatus in accordance with the present invention. Specifically, the apparatus of FIG. 50 is similar to that shown in FIGS. 48 and 49, except that electrode 5000 is in direct physical contact with vibrating member 5002 including piezoelectric crystals 5004. The combined electrode/vibration member structure 5000/5002 can be designed in a number of ways to optimize the transfer of vibrational energy from member 5002 across electrode 5000.

For example, while electrode 5000 need not exhibit any particular thickness, the thickness of the resulting electrode vibration member combination should be approximately an odd multiple of one-quarter the wavelength of the applied vibrational energy (thickness=$n\lambda/4$, n=1, 3, 5 . . . ). This odd multiple one-quarter wavelength thickness is desirable for effective coupling of sonic energy from a vibration member into a fluid.

In certain electrochemical processes, portions of the electrode material may be consumed, thereby altering the overall thickness of the electrode over time. In such applications, where the thickness of the electrode element does not comprise a significant % of the overall thickness of the combination of the electrode/vibrating member, changes in the electrode thickness will not greatly effect package operation. For example, if the thickness of the vibration member is four times the thickness of the electrode, a reduction of 50% in the electrode thickness will reduce the overall thickness of the electrode/vibration member by only 10%. While overall thickness variation of the combination of as much as +/−50% may be acceptable under some conditions, variation of less than +/−30% is generally preferred.

Moreover, certain generators of sonic energy allow adjustment in the firing frequency of the piezoelectric crystals. Over time, the firing frequency of the piezoelectric crystals could be adjusted, thereby compensating for changes in electrode material thickness.

In accordance with still other embodiments of the present invention, the vibrating member may comprise the electrode itself. Specifically, the vibrating member could be fabricated from the appropriate electrically conducting material, such that application of a potential difference produces the desired electric field and resulting electrochemical processing. In embodiments where vibration results from application of current to a piezoelectric crystal in contact with the vibration member, the piezoelectric crystal could be electrically, but not mechanically, insulated from the vibration member.

Figure 51:
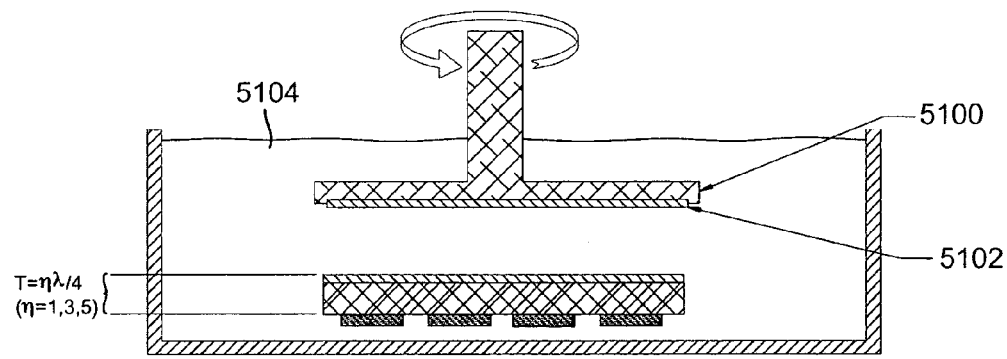
FIG. 51 shows a simplified cross-sectional view of an embodiment of an electrochemical processing apparatus in accordance with the present invention, wherein the substrate holder supporting the substrate Within a chemical bath, is rotated.

Sonic-assisted electrochemical processing in accordance with embodiments of the present invention may be enhanced utilizing relative motion between one or more elements and the surrounding electrochemical bath. FIG. 51 shows a simplified cross-sectional view of one such embodiment, wherein substrate holder 5100 supporting substrate 5102 within chemical bath 5104, is rotated. This relative motion serves to further reduce the thickness of the hydrodynamic boundary layer between the substrate and the surrounding bulk fluid, thereby enhancing transport of ions and other chemical species to and from the substrate surface during processing.

Perhaps more importantly, relative motion can also increase the uniformity of processing, especially when the substrate and electrode are positioned relatively close to one another. This increase in processing uniformity can result from the relative motion of the various equipment elements through non-uniform energy fields. In this manner, nodes of high and low energy intensity created in the non-uniform fields are not concentrated onto fixed points on the substrate during the entire processing sequence.

For example, if the applied potential field contains localized non-uniformity, movement of the substrate/electrode/vibration member can minimize the negative impact on processing. Without relative motion, points on the substrate surface located in a high energy intensity node could experience an increased rate of material addition, while a point in a low energy intensity node could experience a reduced rate of material addition. Relative motion would tend to smooth out the impact of these high and low intensity nodes on processing uniformity.

Similarly, relative motion may also tend to minimize negative impact of a non-uniform sonic field, which may be created as sonic energy departs a vibrating surface. The region near a vibrating surface is often termed the near field and is characterized by field non-uniformity. This non-uniformity may extend up to several inches from the vibrating surface depending upon constraints imposed by frequency, intensity, and geometry.

While FIG. 51 shows imparting relative movement between the substrate and the surrounding bath, this is not required by the present invention. In accordance with other embodiments, one or both of the electrode or vibrating member could experience motion within the bath, alone or in combination with movement of the substrate. Such relative motion would tend to minimize adverse effects on processing of non-uniformity either in the applied potential field, or in the generated sonic field emanating from a vibrating surface.

And while FIG. 51 shows imparting relative rotational movement between the substrate and the surrounding bath, this is also not required. Forms of relative motion other than rotational motion may be employed, for example, lateral movement or vibrational movement.

The specific embodiments described above have focused upon the use of a solid electrode structure. In accordance with alternative embodiments, however, other than solid electrodes may be employed to enhance electrochemical processing in accordance with the present invention.

Figure 52:
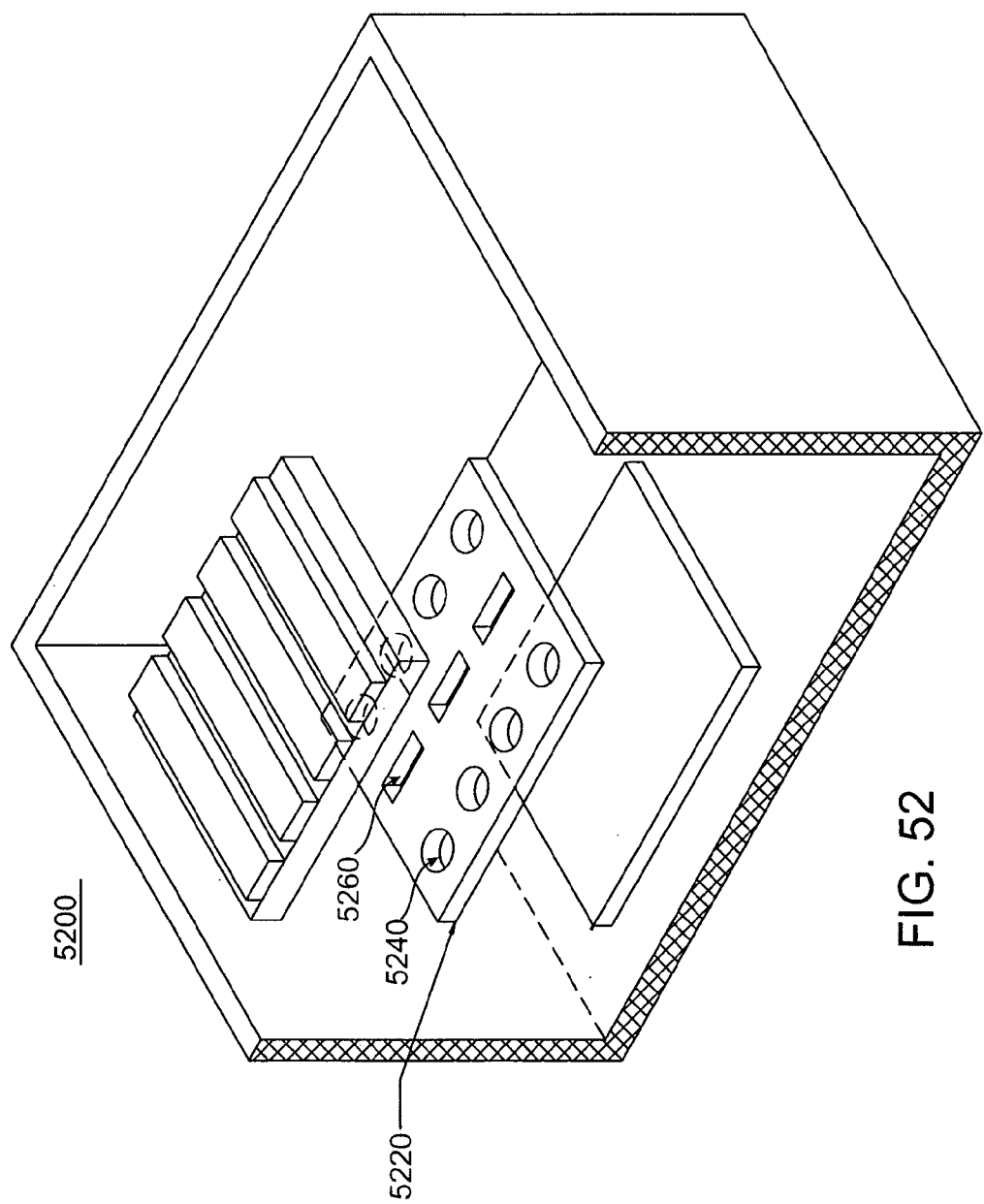
FIG. 52 shows a simplified perspective view of an embodiment of an electrochemical processing apparatus in accordance with the present invention utilizing an open electrode structure.

For example, FIG. 52 shows a simplified perspective view of an embodiment of a processing apparatus in accordance with the present invention utilizing an open electrode structure. Electrochemical processing apparatus 5200 is similar to that shown in FIG. 48, except that electrode 5202 features a pattern of openings 5204 and 5206. Openings 5204 and 5206 allow and direct the flow of fluid of the electrochemical processing bath through the electrode, thereby promoting uniform distribution of chemical and ionic species in the bulk fluid. The overall thickness or orientation of the electrode plate 5202 remains within the desirable ranges described above, so that vibrational energy is transferred across the electrode 5202.

The size and number of openings 5204 and 5206 in electrode 5202 are designed to minimize any nonuniformity in sonic energy received at the substrate surface. In certain embodiments, the width of the openings could be greater than or equal to one wavelength (or multiple wavelengths) of the incident sonic energy, in order to allow passage of the energy wave.

In other embodiments, the width of the openings in the electrode can be designed to be less than one full wavelength. Such an electrode structure could result in diffraction of the incident wave of sonic or other energy types, creating various diffraction interference patterns. By varying frequency, power level, and phase angle of the incident sonic energy, such interference patterns can be caused to change over time, producing different processing effects.

Figure 53:
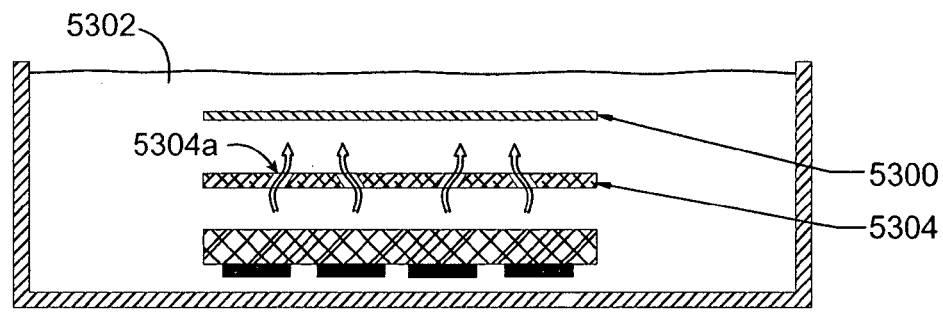
FIG. 53 shows a simplified cross-sectional view of an alternative embodiment of a processing apparatus similar to that shown in FIG. 48, but featuring the substrate supported within the bath over the electrode which is open for fluid flow.

FIG. 53 shows a simplified cross-sectional view of an alternative embodiment of a processing apparatus similar to that shown in FIG. 52, but featuring substrate 5300 supported within bath 5302 over electrode 5304. The cross-sectional view illustrated in FIG. 53 also shows the circulation of electrochemical processing fluid through openings 5304a in electrode 5304.

Unlike FIG. 52, which suggests the flow of fluid straight through the electrode, FIG. 53 depicts an electrode that imposes a change in the direction of fluid flow during operation. This change of the direction of the flowed fluid could range from a single shift of only a few degrees, to repeated changes as might result from operation of a static mixer.

Figure 54:
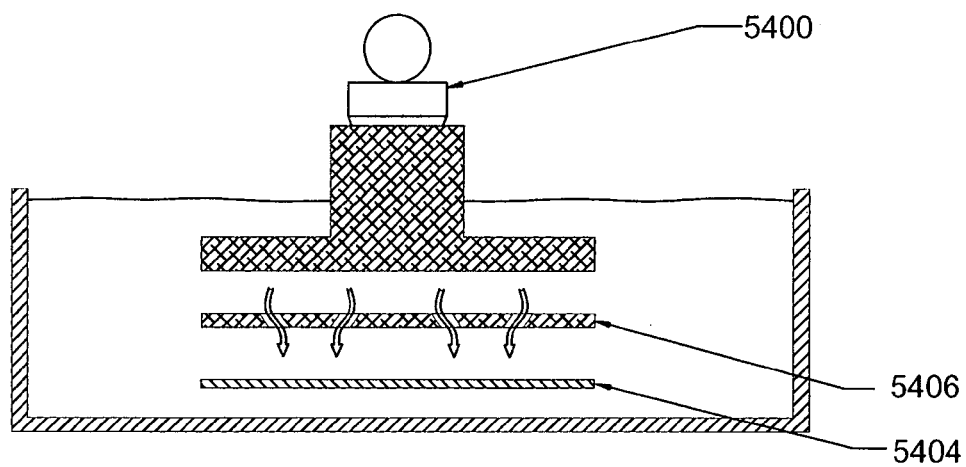
FIG. 54 shows a simplified cross-sectional view of another alternative embodiment of a processing apparatus in accordance with the present invention, which is inverted relative to that shown in FIG. 53, but further features a mechanical vibrator rather than piezoelectric crystals.

FIG. 54 shows a simplified cross-sectional view of another alternative embodiment of a processing apparatus in accordance with the present invention, which is similar to that shown in FIG. 52 but features a mechanical vibrator 5400, rather than piezoelectric crystals, in contact with vibrating member 5400. In this embodiment, bulk electrochemical processing fluid 5402 flows to substrate 5404 through openings in electrode 5406. Such a mechanical vibrator design could be particularly effective when a relatively low frequency of vibration is desired, especially if such vibration is to be accompanied by a large amplitude or displacement of the vibration member.

Figure 55:
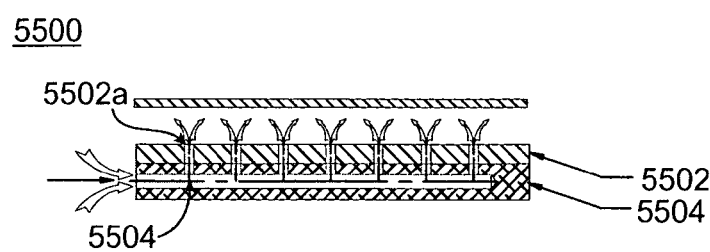
FIG. 55 shows a simplified cross-sectional view of yet another alternative embodiment of a processing apparatus in accordance with the present invention.

FIG. 55 shows a simplified cross-sectional view of yet another alternative embodiment of a processing apparatus in accordance with the present invention. Apparatus 5500 FIG. 55 is similar to that shown in FIG. 53, but features electrode 5502 direct contact with 5504a in manifold 5504, such that jets of fluid flowing out of the electrode are created.

In a further refinement of the embodiment shown in FIG. 55, the flow of fluid can be pulsed on and off. A pump (not shown) can be used to generate the pulsed fluid flow. The generated fluid pulsation may roughly simulate the pressure pulses present in the previous examples, which were caused by either the movement of piezoelectric crystals, or by a mechanical vibrator coupled to the vibration member.

The pulsed fluid flow can be effective not only in reducing the thickness of a hydrodynamic boundary layer present on the surface of one or more elements of the system, but may also be particularly effective in disrupting vortices that have arisen in stagnant fluids present within recessed features on the substrate surface.

Embodiments in accordance with the present invention may match the frequency of fluid pulsation with dimensions of a recessed feature, in order to maximize mixing and fluid transfer between the recess and the bulk fluid. For example, if the frequency of pulsation is either too high or too low, sub-optimal fluid transfer may occur between a recessed feature and the surrounding fluid.

Figure 58:
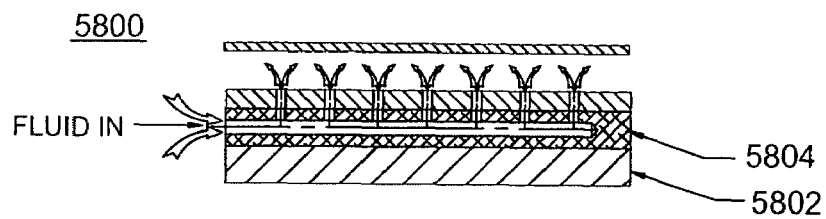
FIG. 58 shows a simplified cross-sectional view of yet another alternative embodiment of a processing apparatus in accordance with the present invention.

FIG. 58 shows a simplified cross-sectional view of yet another alternative embodiment of a processing apparatus in accordance with the present invention. Apparatus 5800 of FIG. 58 is similar to that shown in FIG. 55, but features vibration member 5802 in direct physical contact with manifold 5804. Thus, fluid pulses generated from a pump source (not shown) can be augmented with pressure pulses from either piezoelectric crystals (not shown) or a mechanical vibrator (not shown) coupled to vibration member 5802. Such an arrangement could result in multi-mode vibration frequency. Thus it would be possible to simultaneously produce vibrations at a high, medium and low frequency, each vibrational frequency having a different intensity.

Embodiments of apparatuses in accordance with the present invention described above have focused upon utilization of an electrode member that is solid or has openings. In accordance with alternative embodiments, however, an electrode made out of other than solid material may be utilized. For example, porous, electrically conducting materials are used as electrodes in fuel cells. Such electrodes are often combined with various ion exchange membranes and separators. Embodiments in accordance with the present invention could also utilize electrodes, membranes, and separators formed from such materials. The porosity exhibited by such an electrode structure would enhance the flow of bulk electrochemical processing fluid through the electrode, in a manner similar to that described above in connection with the open electrode structure.

Further, incorporation of ion exchange membranes and separators could actually prevent or inhibit transfer of undesirable chemical species contained in the bulk fluid, to the surface of the substrate, while promoting transfer of desirable species. Thus different reactions could occur simultaneously within the electrochemical processing cell.

Still further alternatively, the electrode structure utilized in connection with embodiments of the present invention may be formed from a composite of materials. For example, the electrode may be hollow or fluid-filled to enhance the transmission of sonic energy. Alternatively, the electrode may be filled or coated, partially or completely, with a polymer material, also to enhance its ability to transfer applied sonic energy, while producing desirable electrochemical reactions.

While the previous figures have depicted the electrode as planar member, this is not required by the present invention. In accordance with alternative embodiments, the electrode could exhibit different shapes. For example, where the surface of the processed substrate exhibits a curved shape, the electrode could be similarly shaped to conform thereto.

Figure 56:
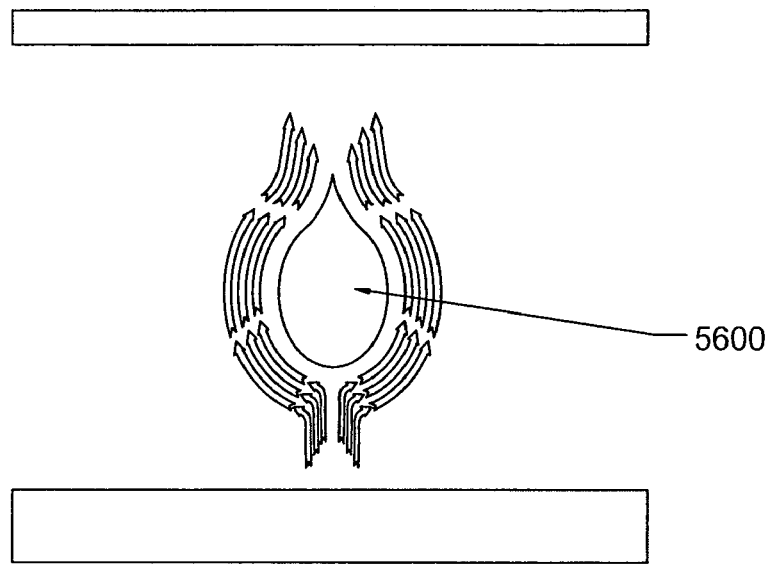
FIG. 56 shows a simplified cross-sectional view of an alternative embodiment of a structure in accordance with the present invention, where a shaped electrode exhibits a tear-drop or airfoil profile in order to promote circulation of bath fluid with smooth or steady streamlines characteristic of laminar, rather than turbulent, flow.

In accordance with still other embodiments, the electrode may be shaped to promote the smooth flow of fluid. Accordingly, FIG. 56 shows an alternative embodiment of a structure in accordance with the present invention, where shaped electrode 5600 exhibits and tear-drop or airfoil profile in order to promote circulation of bath fluid with smooth streamlines characteristic of laminar, rather than turbulent, flow. The shape of the electrode may further promote transmission of sonic energy along a path conforming to these fluid streamlines. Such an electrode shape would promote the propagation of sonic energy around obstructions in the electrochemical bath such as the electrode or supporting members, thereby preventing sonic shadowing resulting in nonuniform processing. While shown as a single large electrode in FIG. 56, the active electrode surface could actually comprise multiple smaller hydrodynamically-shaped elements.

Figure 57:
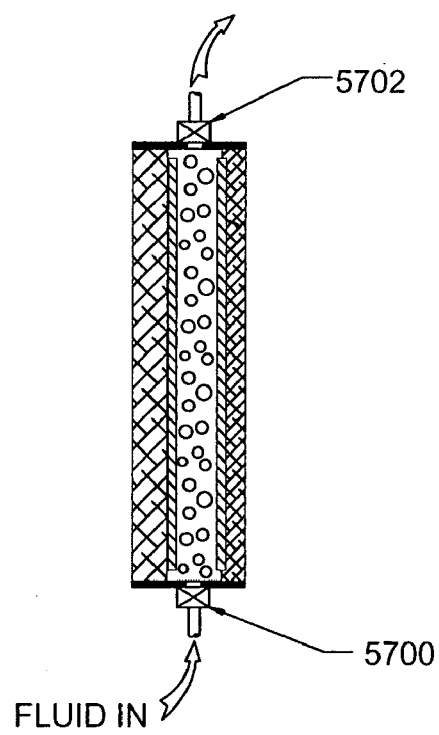
FIG. 57 shows a simplified cross-sectional view of one embodiment of an apparatus in accordance with the present invention utilizing induced pressure drops.

As described more fully in U.S. nonprovisional patent application Ser. No. 10/150,748, performing electrochemical processing performed at elevated pressures may involve the pulsed flow of fluid. The pressure pulsed operation could also include pressure/release operation, where dissolved gas at higher pressure is released as bubbles when the system or localized pressure is reduced. This could include the inclusion of a pressure drop as a result of high velocity fluid flow within the tank. FIG. 57 shows one embodiment utilizing such induced pressure drops. Opening/closure of the two valves 5700 and 5702 can be sequenced to develop various pressure and flow pulsed operation within the tank. The generation of bubbles can also contribute to fluid uniformity within the tank.

Figure 59:
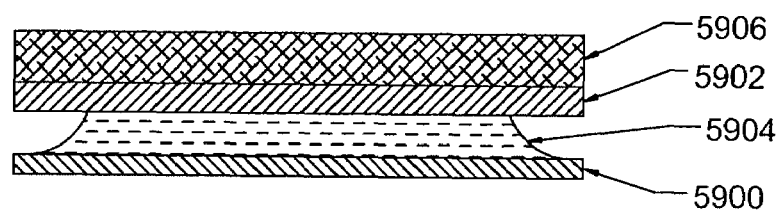
FIG. 59 depicts a simplified cross-sectional view of an embodiment where the substrate and the electrode are separated by a thin fluid layer, but are not fully submerged within a liquid bath.

Embodiments in accordance with the present invention are not limited to the transmission of sonic energy across an electrode submerged in an electrochemical processing bath. FIG. 59 depicts an embodiment where substrate 5900 and electrode 5902 are separated by a thin fluid layer 5904, but are not fully submerged within a liquid bath. This thin fluid layer 5904 allows the electrochemical reaction to take place. The specific apparatus for introducing fresh fluid to the interface between electrode 5902 and substrate 5900 could include forced fluid flow from either a narrow or wide area nozzle or jet, gravity flow from vertical operation or the introduction from a porous electrode and/or vibration member. Electrode 5902 could be of solid, open or porous design. Vibration member 5906 could be fitted with piezoelectric crystals or with a mechanical vibrator.

Figure 60:
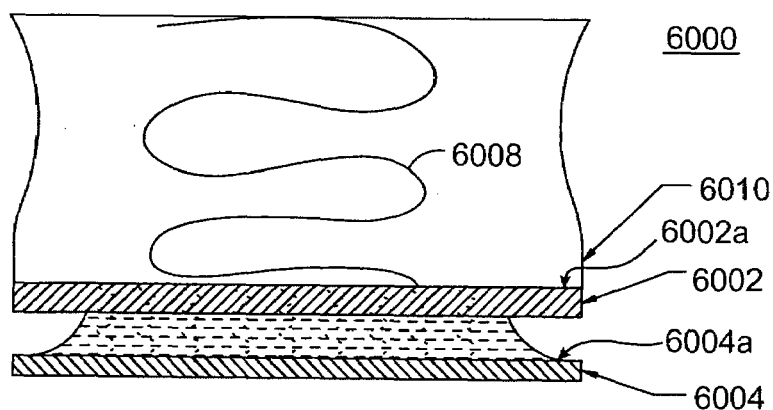
FIG. 60 shows a simplified cross-sectional view of another embodiment of an apparatus in accordance with the present invention utilizing microwave energy.

FIG. 60 shows another embodiment of an apparatus in accordance with the present invention. Specifically, apparatus 6000 of FIG. 60 includes electrode 6002 oriented proximate and parallel to surface 6004a of substrate 6004. Rather than being totally submerged in electrolyte liquid, a thin layer 6006 of liquid is provided between electrode 6002 and substrate 6004.

During processing, a potential difference is applied between electrode 6002 and substrate 6004 to promote electrochemical processing. Also during this process, microwave energy 6008 from a source (not shown) is transmitted through microwave conduit 6010 to backside 6002a of electrode 6002. This microwave energy 6008 is transmitted across electrode 6002 and impinges the surface of substrate 6004. Application of microwave energy across an electrode to a substrate surface during electrochemical processing can be effective to enhance the speed or uniformity of the resulting electrochemical processing. Such application of microwave energy may or may not be accompanied by the application of sonic energy.

While FIG. 60 shows introduction of microwave energy solely through the electrode, this is not required. In accordance with alternative embodiments of the present invention, microwave energy can be introduced through the substrate or at some angle relative to the electrode or substrate. These angles could include the introduction of the energy parallel to, perpendicular to, or orientated at some angle relative to either the electrode or the substrate.

While much of the electrochemical processing discussion has dealt with transfer of energy across an electrode, it should be understood that this is not required. Energy could also be reflected off of electrode structures and still fall within the spirit of this invention. And, rather than utilizing energy transferred across electrodes in the manner shown, these embodiments could be modified to illustrate the transfer of energy across substrates or substrate holders.

E. Substrate Drying

Drying of semiconductor substrates after various wet-processing steps has become even more important as feature sizes shrink. Incomplete or ineffective drying can leave watermarks, which lead to device defects and reduced manufacturing yields. Some early dryers were based on the use of hot gases to evaporate water and other processing liquids directly from substrate surfaces. Others were based on the use of organic solvents to displace residual water or processing liquids. The residual solvent films were then removed by evaporation with heated gas flow.

This solvent-based drying technology was eventually supplanted by surface tension gradient (STG) dryer technology, sometimes referred to as marangoni drying. While more effective than earlier dryer designs, current STG designs suffer from slow processing speed, fugitive alcohol and solvent emission, and potential fire hazards.

Accordingly, there is a need in the art for methods and apparatuses for rapidly and effectively drying processed substrates.

In accordance with embodiments of the present invention, drying of substrates exposed to liquid processing solutions may be enhanced utilizing a number of techniques, alone or in combination. In accordance with one embodiment, the substrate drying process occurs at elevated pressure to increase concentration of a surface-tension reducing component. In accordance with another embodiment, radiation applied during the drying process, and in particular applied at the meniscus, may reduce surface tension. In accordance with still another embodiment, ultrasonic energy may be applied during the drying process to vaporize residual liquid from the substrate surface.

The present invention addresses the limitations mentioned for these various earlier dryer designs. The multiple embodiments of this invention provide flexibility in overcoming those limitations. An embodiment of a pressurized STG dryer is disclosed in copending U.S. nonprovisional patent application Ser. No. 10/150,748 ("the '748 application"). The use of rapid, effective and efficient heating of substrates during processing is disclosed in US non-provisional patent application Ser. No. 10/456,995, also incorporated by reference herein for all purposes.

In accordance with one embodiment of the instant invention, a pressure-based STG dryer may incorporate radiation heating and modification of substrate surfaces. By operating under pressure, a surface tension lowering component may be forced into solution at the gas-liquid interface at a faster rate. Increasing the rate of dissolution can lead to an increased amount of component being dissolved in the liquid at the gas-liquid interface in a limited time. Increasing the amount of the component dissolved in the processing fluid at this interface can result in a lower localized surface tension. A lower localized surface tension in the fluid, especially in the meniscus area, can lead to a larger surface tension gradient or differential between that surface tension and the surface tension of the bulk processing fluid. This larger surface tension gradient can lead to faster and more effective and efficient drying.

One problem sometimes encountered in conventional STG drying, is condensation of gases and vapors on the substrate surface as the substrate is raised out of the processing liquid. Thus in accordance with another embodiment in accordance with the present invention, the STG gas may be heated while the processing liquid is not, or while the processing liquid is actually cooled.

In such an alternative embodiment, the heated STG gas heats the substrate as the substrate exits the processing liquid, which prevents condensation of water vapor or STG gas components on the exposed substrate surface. Since the heat capacity of the STG gas is small compared to the heat capacity of the processing liquid, even though the gas is heated, it does not appreciably raise the temperature of the processing liquid. Keeping the temperature of the processing liquid low insures that the solubility of the STG gas in the processing liquid remains relatively unchanged, or increased in the case of cooling of the processing liquid.

Embodiments in accordance with the present invention may operate at elevated pressures of between about 1 and 10 ATM, although operation at pressures higher than 10 ATM and as high as 100 ATM or higher are possible. Operation at elevated pressures may be accomplished by flowing a gas, a processing fluid, and/or a rinsing fluid into a closed or substantially closed processing vessel, as described generally in the '748 application.

Suitable surface tension lowering agents can exist as solids, liquids, vapors, and gases, and in combinations thereof. The surface tension lowering gases can be either locally applied at the gas-liquid interface, or they can be generally applied within a vapor space. In some cases the agents might be applied to the bulk liquid phase itself to reduce the surface tension of all of the processing fluid. Some of these agents exhibit the lower vapor pressures common with some liquids and solids, while other agents can exhibit high vapor pressures associated with extremely volatile gases. By processing in a closed chamber or system, little volatile surface tension lowering agent can escape into the atmosphere. It is also easy to recover and reuse these agents if desirable. When it is necessary to treat or destroy used or excess STG agents, they can be treated at a point of maximum concentration, avoiding the need for installation and use of expensive treatment systems required to treat an entire air-handling system.

In another embodiment, surface tension lowering components with limited solubility in the processing liquid can be utilized. For example, carbon dioxide and ozone gas show limited solubility in most common aqueous based solutions. As the operating pressure is increased, not only the rate, but also the amount of these partially soluble surface tension lowering components entering the processing solution is increased. Higher solubility resulting from the increased pressure can lead both to reduced localized surface tensions, and increased surface tension differentials or gradients between liquids at the gas-liquid interface and those of the bulk fluid.

In accordance with still another embodiment of the present invention, STG gas can be dissolved in a carrier liquid. The carrier liquid can then be added to the surface of the processing liquid without mixing to maintain a separate and distinct layer of the STG rich carrier liquid on top of the processing liquid. The substrate is then raised through the carrier liquid layer.

In various embodiments, the carrier liquid and the processing liquid may be the same or different materials. An STG gas is not required. A carrier liquid with a surface tension different than the processing liquid can be used without the addition of a separate STG gas component. The carrier liquid can be of the same or a different temperature than the processing liquid. While either the processing liquid or the carrier liquid may be water based or miscible in aqueous solution, this is not required. Further, one of the carrier liquid and the processing liquid may be water miscible, while the other liquid is not miscible. Differences in physical properties such as density may also be used to help keep the layers separated.

In accordance with still other embodiments, radiation may be applied locally to the substrate and/or processing liquid, particularly in the area of the meniscus, in order to enhance the surface tension gradient. This applied radiation can result in the localized heating of the substrate or of the processing liquid in this meniscus region. With many processing fluids, an increase in temperature lowers surface tension. For example, microwave radiation can heat both aqueous solutions and silicon substrates.

As a silicon substrate emerges from an aqueous solution, applied microwave energy heats both the substrate and the solution. The portion of the substrate not immersed in the aqueous solution heats up much more rapidly than the bulk solution, or the portion of the substrate still immersed in the bulk solution. This heating differential is due to the smaller heat capacity of the exposed substrate as compared to the heat capacity of the bulk solution. Therefore, even with poorer coupling of microwave energy with the silicon substrate than with the solution, a given radiation flux can cause much faster heating of the exposed substrate.

In addition, the liquid in the meniscus region also heats faster than the bulk solution. Not only is the solution volume in the meniscus areas very small (surface area/volume larger in meniscus than bulk solution), the solution in this area also receives energy from the hot exposed substrate. Therefore the solution in the meniscus heats more rapidly and its surface tension is reduced. In another embodiment, the bulk solution itself may be heated prior to removal of an immersed substrate.

Temperature changes can affect the solubility of a number of suitable agents. In accordance with still another embodiment, with some partially soluble surface tension lowering gases, as the liquid temperatures increase, their solubility in those liquids decrease. By increasing the process pressure, more of the surface tension lowering gas is forced into solution. This increased solubility resulting from an increased pressure can act to offset or compensate for the reduced solubility at higher temperatures. This increased solubility also allows for the generation of higher surface tension gradients, leading to enhanced drying. This increased solubility further also allows the use of some previously unavailable surface tension lowering components.

Additionally, the chemical reactivity of many processing fluids is a function of process temperature. As such, it may be desirable to change the temperature or pressure during the processing to take advantage of the characteristics of different components when several are used in combination. In some embodiments, it may be desirable to perform processing with one agent, followed by a second. In another embodiment, it might be desirable to perform processing in a single vessel. In still another embodiment, processing may take place in multiple vessels in a sequential process.

A variety of radiation types may be useful for different applications. These could include, but are not limited to microwave, ultraviolet, infrared, and electromagnetic induction. In another embodiment of the invention, the radiation may heat the substrate or processing liquid on the substrate surface, thus promoting faster evaporation. For example microwave, infrared and electromagnetic induction could be useful as various types of energy useful in heating.

In another embodiment, the radiation could promote decomposition of an organic drying liquid present on the surface of the substrate. The residual drying liquid could be oxidized, either partially or fully, thus increasing the rate of clearing of the liquids from the substrate. In such an embodiment, application of ultraviolet radiation can offer certain advantages. Further, an oxidant could also be utilized in combination with the radiation to enhance degradation of the residual liquids. Examples of useful oxidants include, but are not limited to, ozone, hydrogen peroxide, and oxides of nitrogen.

In still other embodiments, the residual processing liquid on the surface of a substrate can be vaporized off the surface by the application of ultrasonic energy. As with many of the other embodiments, the residual processing liquid could be in the form of droplets or even a film covering the substrate surface. In some cases very small cavities within the substrate may contain processing liquid as well. It has been discovered that thin films or droplets of liquid can be quickly vaporized by applying ultrasonic energy directly to a substrate, thereby leaving substrate surfaces dry.

In order to effectively and efficiently transfer energy from a vibration member to a substrate, an effective sonic coupling between the vibration member and the substrate should occur. The energy should then be coupled between the substrate and the residual liquid. The energy then causes the liquid to vaporize or form a mist, which comes off the substrate surface.

One effective way to ensure optimal coupling is to cause the substrate to be in intimate contact with the vibration member, and have the sum of their individual thickness' equal to an odd multiple one-quarter wavelength (substrate plus vibration member thickness $=n\lambda/4$, $n=1, 3, 5, 7\ldots$) of the ultrasonic energy wave. The speed of sound in each material must be taken into account. The more deviation from this thickness, the poorer the coupling and less energy is transferred. In the horizontally- and vertically-oriented embodiments shown in FIGS. 61B and 61A, respectively, the ultrasonic energy is transferred directly from the vibration member 6100 through the substrate 6108 into residual liquid on another surface.

Figure 62:
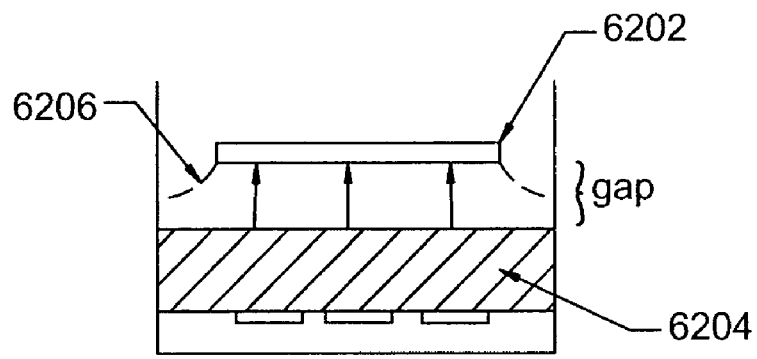
FIG. 62 shows a simplified cross-sectional view of an embodiment of an apparatus in accordance with the present invention using relatively incompressible fluids, where the gaps can become quite large and still have significant energy transfer occur.

In some applications, it may not be essential to have optimal energy transfer, and only partial energy transfer may be adequate to perform the drying acceptably. For example, in the optimal case there would be no gap(s) between the vibration member and the substrate. In many practical applications, because of machine tolerances or machine designs requiring separation, some gaps occur. In those cases, it may generally be important that the gaps not be filled with compressible fluids such as gases. When those gaps are filled with relatively incompressible fluids such as water, acceptable energy transfer can occur. FIG. 62 represents an embodiment using relatively incompressible fluids

6206, where the gaps can become quite large (>1 m) and still have significant energy transfer occur.

Figure 63:
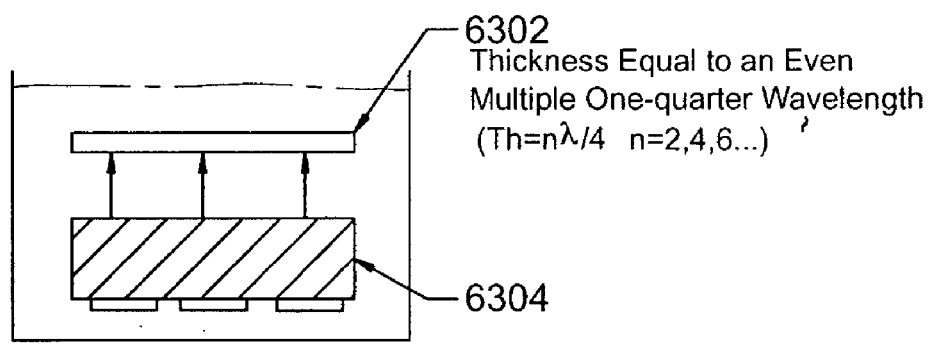
FIG. 63 shows a simplified cross-sectional view of yet another embodiment of a processing apparatus in accordance with the present invention, where energy is transferred across a substrate bounded on both sides by liquid, such that the thickness of the substrate should match an even multiple of one quarter wavelength.

In still another alternative embodiment, when transferring energy across a substrate bounded on both sides by liquid, the substrates thickness should match an even multiple of one quarter wavelengths (substrate thickness=$n\lambda/4$, n=2, 4, 6, 8 . . . ). FIG. 63 illustrates such an embodiment. Because wafers 6302 would be required to be much thicker for the megasonic frequencies generally employed today, this is likely one reason that conventional megasonic cleaning systems have had limited success transferring energy across or through silicon wafers. When in direct contact with the vibration member, it is only required that the sum of the thickness of the substrate and the vibration member approximately equal an odd multiple one quarter wavelength.

Moreover, the thickness of the vibration member and the substrate may be dictated by other constraints. If the combination of their individual thickness do not add up to the desired thickness for favorable energy coupling at a given frequency, it may be desirable to adjust the frequency to produce an odd multiple one-quarter wavelength of the ultrasonic energy equal to the sum of their combined thicknesses. While preferred megasonic systems in accordance with embodiments of the present invention, some degree of frequency adjustment of individual crystals to accommodate thickness differences or changes is desirable, it is not required. Such frequency adjustment is generally not available for many conventional fixed frequency systems, yet they can be made to operate satisfactorily.

While these embodiments are useful for processing and drying substrates, energy transfer through the substrate resulting from contact with a vibration member of the correct thickness can also be useful in substrate cleaning and processing applications. Single wafer processing equipment is especially well suited to advantageously employ embodiments of this invention. These and other embodiments could be particularly useful in chemical mechanical polishing (CMP), wafer cleaning by brush scrubbing, and electrochemical processing as well.

Other concepts of acoustics can be used to advantage with new embodiments of the invention by applying the principles of reflection, transmission, refraction and mode conversion to the generated ultrasonic wave. Of particular interest are designs that utilize mode conversion to transform longitudinal or dilatational waves into surface waves. These surface waves can include Rayleigh, Lamb and Love waves. Each of these waves produces a different wave pattern on the surface of the vibrating article. These differing wave patterns can have unique interactions with substrates and contaminants on substrates. As device feature sizes shrink, it is becoming even more important to find "gentler" ways of applying ultrasonic energy without causing device damage. Additionally, mode conversion can play a big role in effectively transferring energy across silicon wafers immersed in an aqueous bath at commercially available frequencies.

While embodiments in accordance with the present invention may relate to chemical processing of substrates utilized during the manufacture of semiconductor devices, for example substrates comprising silicon, SiGe, GaAs, Si, GaAs, GaInP, and GaN to name a few. However, the present invention is not limited to processing of semiconductor substrates, and other materials may be subjected to microwave heating during processing. Examples of other candidates for chemical processing utilizing the present invention include, but are not limited to, hard disks and hard disk substrates, optical devices such as mirrors, lenses, or waveguides, and substrates utilized in the fabrication of micro-electrical mechanical systems (MEMS), liquid crystal display devices, bio-medical slides, optical devices, mirrors, lenses, waveguides, substrates for DNA or genetic markers, liquid crystal displays, and other media.

F. Other Megasonic Processing Applications

Processing a substrate utilizing a directed force (i.e., a flow of energy or matter), or utilizing a supercritical fluid, may be enhanced by the simultaneous application of sonic energy, which causes vibration displacement of the substrate or contacting fluid. Other forms of energy including mechanical vibration and microwave, can also be applied, either in conjunction with or in place of the sonic energy. In accordance with one embodiment of the present invention, coupling sonic or vibration energy to the substrate with greater effectiveness and uniformity may enhance the processing of a substrate with supercritical carbon dioxide.

Different types of substrate processing that might be accomplished in accordance with the present invention, include but are not limited to, cleaning or removing particles and contaminants, coating or depositing materials, etching or removing materials and chemically or electrically modifying various substrate surfaces, structures and layers.

Embodiments in accordance with the present invention may also be useful to enhance the effect of processing substrates utilizing a number of different techniques. One such processing technique is the application of a jet of gas, liquid, solid, or mixtures thereof, to a substrate surface.

Figure 64:
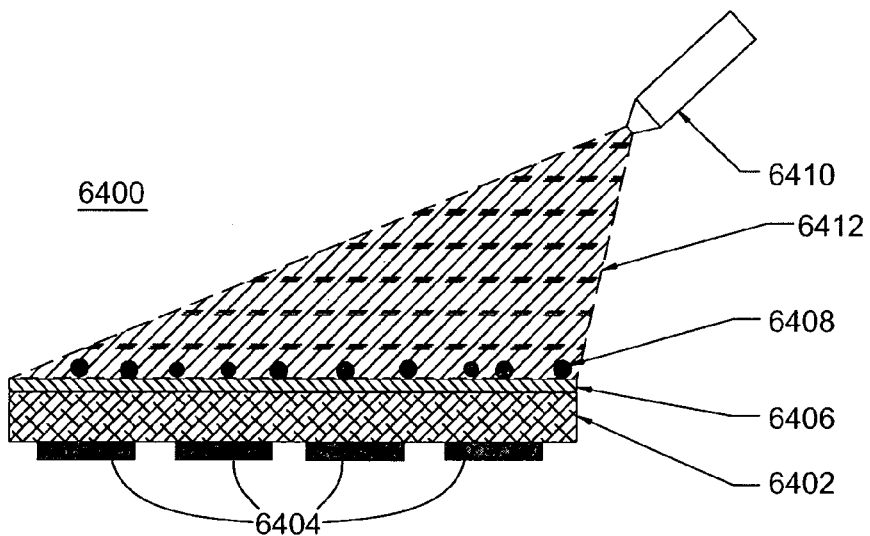
FIG. 64 shows a simplified cross-sectional view of one embodiment of an apparatus for performing cleaning of a substrate with a jet of carbon dioxide snow (dry ice), and/or cryogenic argon aerosol.

In accordance with one embodiment, the present invention is useful to enhance cleaning of a substrate with a jet of carbon dioxide snow (dry ice), and/or cryogenic argon aerosol. FIG. 64 shows a simplified cross-sectional view of one embodiment of an apparatus 6400 for performing such processing. Vibration member 6402 is in mechanical communication with piezoelectric crystals 6404. Substrate 6406 bearing contaminant particles 6408 on its surface, rests on vibration member 6402. Nozzle 6410 ejects jet 6412 of a cryogenic aerosol at the substrate surface, thereby physically displacing particles 6408 therefrom.

For cleaning a substrate with dry ice or snow, a gaseous or liquid carbon dioxide is allowed to expand (e.g. at constant enthalpy) in nozzle 6410, thereby cooling the gas and liquid to the point that solid carbon dioxide particles are formed in the gas stream/jet 6412. These particles of frozen carbon dioxide are directed towards a substrate surface and knock off contaminant particles from the substrate surface.

It has been suggested that some of the solid carbon dioxide particles melt due to deformation resulting from collision with contaminant particles or the substrate surface. The resulting "liquid" carbon dioxide provides a good solvent for dissolving or dislodging contaminants from a substrate surface. The melted dry ice particle then may re-solidify as it rebounds back off the substrate, carrying the contaminant with it.

Impingement of the cold stream/jet also can lead to substantial cooling of the substrate surface as processing proceeds. Energy could be introduced to the substrate to prevent the usual cooling, and minimize condensation of moisture or other vapors. Such processing is generally carried out at atmospheric pressure, although this is not required.

For cryogenic aerosol cleaning with argon, the gaseous argon is generally allowed to expand in a nozzle (e.g. adiabatic expansion/cooling) into a chamber maintained at substantially less than atmospheric pressure, thereby causing some of the argon gas to be converted into small frozen argon particles. These frozen particles propelled in the gaseous argon stream/jet are similarly directed towards a substrate surface to knock off particulate and other contaminants. Again, substantial substrate cooling can occur during processing.

While not wishing to be bound by any particular theory, it is possible that processing in accordance with embodiments of the present invention may be enhanced by the following mechanism. As the surface of the substrate vibrates, and its position in space is repeatedly changed, the dynamics of various processing events occurring with different technologies are modified.

For example, where a cryogenic aerosol jet comprised of cold argon gas and frozen argon particles is applied against a substrate surface, the nature of the interaction between those frozen argon particles and the contaminant particle on the substrate surface is changed. Where the substrate surface is stationary, a particular collision dynamic is present between the frozen argon particle and the contaminant particle, resulting in a particular momentum exchange and particle deformation and rebound.

When vibration or rapid movement of the substrate surface/particle occurs, the dynamics of the collision may be modified. Thus depending upon the frequency of vibration, during one portion of the collision event (i.e. the duration of particle-to-particle interaction) the surface and contaminant borne thereon may be accelerated towards the incoming frozen argon particle. However, during another portion of the collision event, the surface/contaminant may be accelerated away from the incoming frozen argon particle. The interaction energy/force is increased with acceleration toward the incoming particle, and decreased during acceleration away from the incoming particle.

Moreover, with high frequency vibration, several changes in the direction of acceleration of the surface/contaminant may occur during a single collision event. Thus instead of involving a single collision and corresponding momentum transfer, high frequency vibration may actually provide for repeated increase and decrease in the force applied to the particle during the collision time period. The resulting momentum transfer may exhibit a pulsed nature, in a manner analogous to a jackhammer.

Several of the processing techniques and technologies discussed herein may cause substrates/surfaces to vibrate during operation. Historically, there have not been convenient ways to change the resulting frequency, intensity, and uniformity of such processing-induced vibration to more desirable frequencies, intensity or uniformities that can be used to enhance processing. Therefore, convenient ways to adjust or modify frequency, intensity and uniformity of vibration of various substrates are needed.

One approach to adjusting the character of substrate vibration during processing is to effectively couple sonic and other vibration-causing energy with the substrate. Several methods and apparatuses demonstrating increased coupling of sonic energy with various substrates have been disclosed above. Enhanced sonic coupling with the substrates can occur with the front side, back side, or edge of the substrate. In the latter case, the application of sonic energy is parallel to the substrate surface.

Another approach to adjusting the character of the substrate vibration during processing is to enhance the uniformity of energy emanating from vibrating surfaces. Methods and apparatuses demonstrating increased uniformity of the energy field emanating from a vibrating surface are also disclosed above. Such increased field uniformity can correspondingly lead to increased uniformity of processing of a substrate surface.

Other types of applied energy, exhibiting a wide range of frequencies, intensities, and uniformity, may enhance processing. Such alternative forms of energy include, but are not limited to, thermal, microwave, mechanical vibration, IR, UV, hydrodynamic or fluid flow.

The application of thermal energy can cause a change in substrate temperature. Energy can be added, resulting in substrate heating. Alternatively, energy can be removed, resulting in substrate cooling. The characteristics of adhesion of various particles and contaminants to the substrate surface can be modified as the temperature changes.

With some substrates, microwaves and infrared radiation can be used to increase substrate temperature, while other substrates may require direct contact between the substrate and a heated element. Cooling can be accomplished effectively by bringing the substrate into intimate contact with a cooling member containing channels able to accept liquid nitrogen.

Processing at elevated or reduced pressure may be beneficial, especially at conditions above the critical point for various processing fluids including carbon dioxide. The substrates may be caused to vibrate at various frequencies utilizing different techniques. These approaches include, but are not limited to: sonic coupling through direct contact with a vibrating member or indirectly through an intervening fluid layer; contact with a flowing or pulsating fluid and presence within an oscillating or pulsed electrical, RF or magnetic field. The energy can be coupled to, or impinged upon, any side or surface of the substrate, or at any angle with respect thereto.

In accordance with some embodiments, at some angles, the applied energy may reflect from a substrate surface, while at other angles the energy might be transferred across the substrate. At still other applied angles, one form of energy wave, (such as a dilatational pressure wave) can be transformed into another (such as a surface or shear wave) depending upon the environment around the substrate.

Figure 1B:
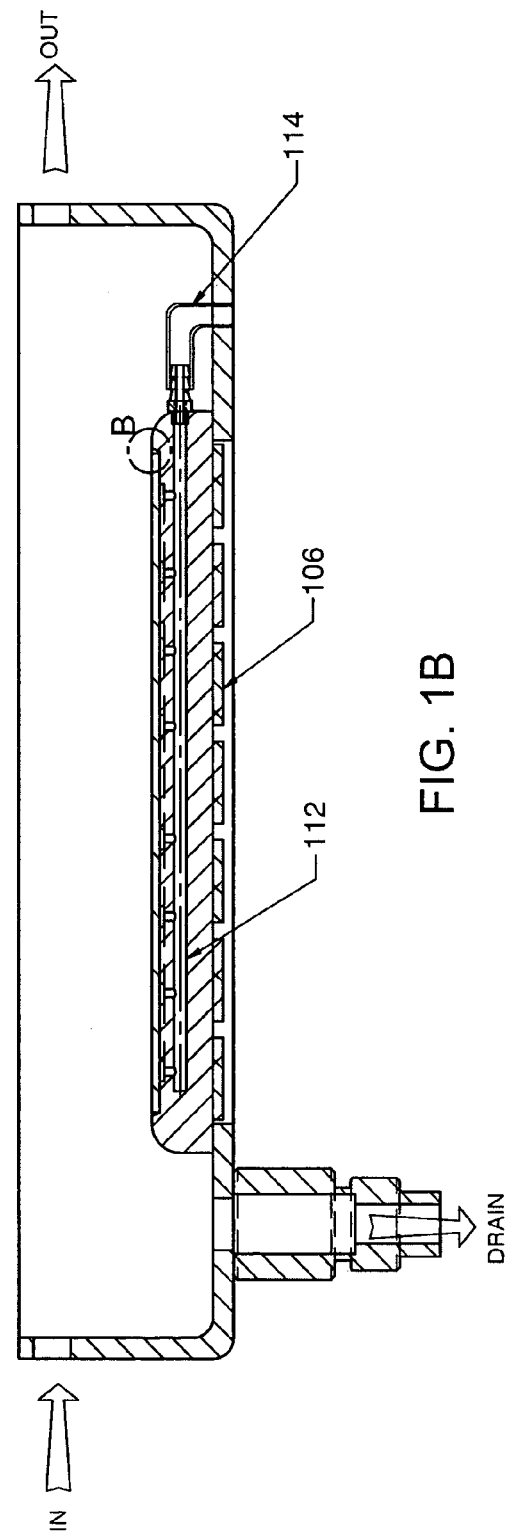

By way of further example, the substrate surface/contaminant can be made to vibrate by coupling sonic energy to the backside of the substrate as also shown in FIG. 1. This is accomplished by bringing the substrate into direct contact with one lateral surface of a vibration member. This vibration member can be comprised of a plate with piezoelectric crystals attached to the opposite lateral surface. The plate can be constructed of various materials including but not limited to such widely differing materials as aluminum, stainless steel, quartz and ceramics. The piezoelectric crystals can be energized with an applied potential alternating at a frequency of near 1 MHz. Once vibrating, a jet of carbon dioxide snow can be directed towards the substrate surface bearing contaminant particles.

There is no upper or lower limit to the range of acceptable frequency of vibration. In practice, however, usable frequencies will likely lie within the range of from 1 Hz to 1 GHz. Other types of energy having even higher operating frequencies, such as conventional microwaves, could also be used under certain conditions.

Alternatively, instead of having direct contact between the substrate and the vibration member, a coupling fluid may be used when the vibration member is separated from the substrate. Various methods of coupling and energy transfer include the use of sonic nozzles. Some methods allow coupling with the front surface of the substrate, while others allow coupling with the back surface of the substrate. Other methods allow energy to be transferred across the thickness of the substrate, and still other methods lead to reflection of energy. Some methods completely immerse the substrate in a processing fluid, while others call for the application of only a thin liquid film.

Figure 69:
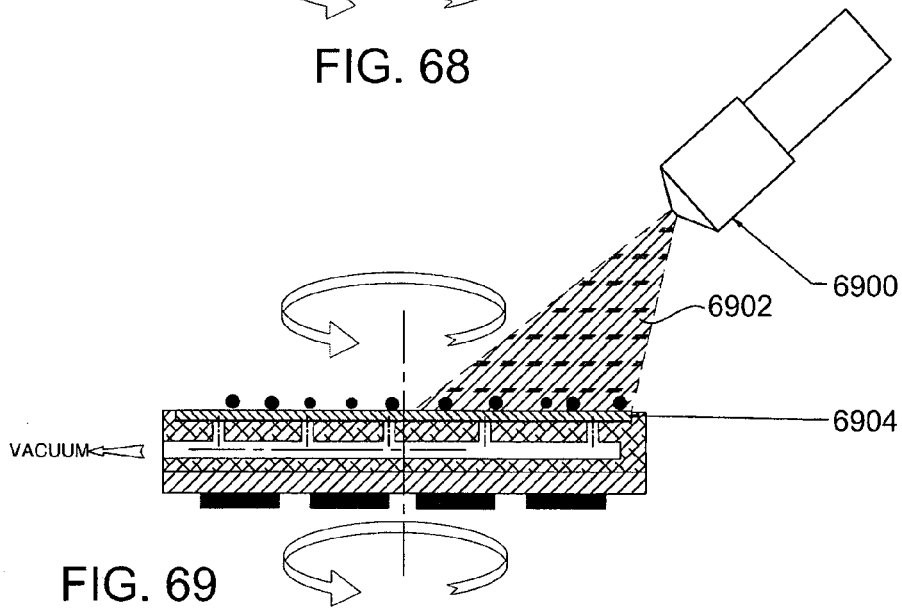
FIG. 69 shows a simplified cross-sectional view of another embodiment of an apparatus in accordance with the present invention featuring an ultrasonic nozzle for the gas/liquid/solid jet utilized to form pressure pulses in the gas/liquid/solid jet prior to the jet striking the surface of the substrate.

In another embodiment shown in FIG. 69, an ultrasonic nozzle 6900 for the gas/liquid/solid jet 6902 is utilized to form pressure pulses in the gas/liquid/solid jet prior to the jet striking the surface of the substrate 6904. In this embodiment, piezoelectric crystals are incorporated into the expansion nozzle 6900 used in cryogenic aerosol cleaning with argon. While this application is generally carried out at below atmospheric pressure, this is not required by other types of jet cleaning. In some cases, pressures above atmospheric may be desirable.

Figure 70:
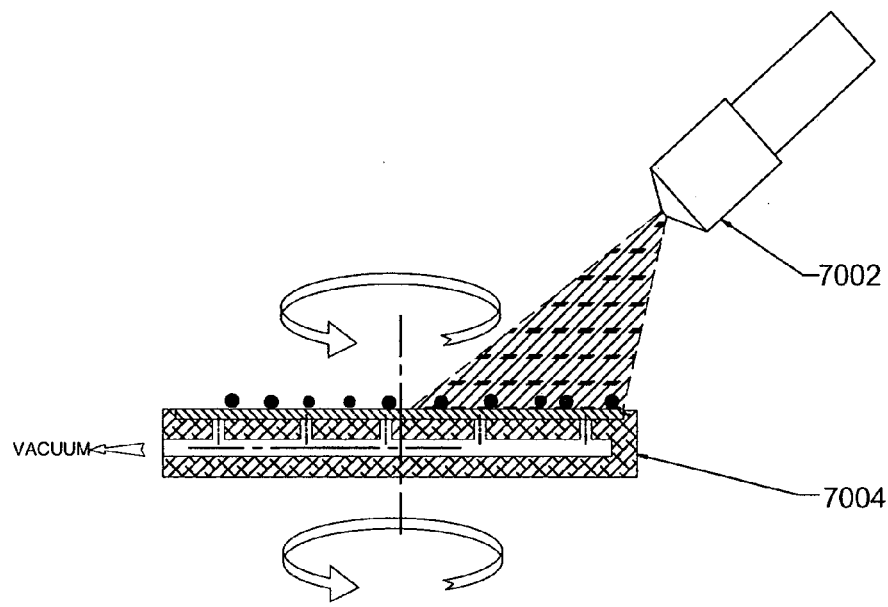
FIG. 70 shows a simplified cross-sectional view of another embodiment of an apparatus in accordance with the present invention, featuring a megasonic nozzle used in conjunction with a vibration member.

In an alternative embodiment, shown in FIG. 70, a megasonic nozzle 7002 can be used in conjunction with a vibration member 7004. In another alternative embodiment, shown in FIG. 71, a megasonic nozzle 7112 can be used in conjunction with the application of microwave energy. In either of the embodiments shown in FIGS. 70–71, relative movement between the substrate and the nozzle is possible.

In accordance with another embodiment, the substrate may be cooled prior to, during, and/or after introduction of the jet of energy or matter. While the jet can be comprised of the typical mixtures of gas and frozen particles described above, in certain embodiments the jet may be comprised of a gas, a liquid, or a combination of the two. Sonic energy or substrate surface vibration may be used, but is not required.

Figure 72:
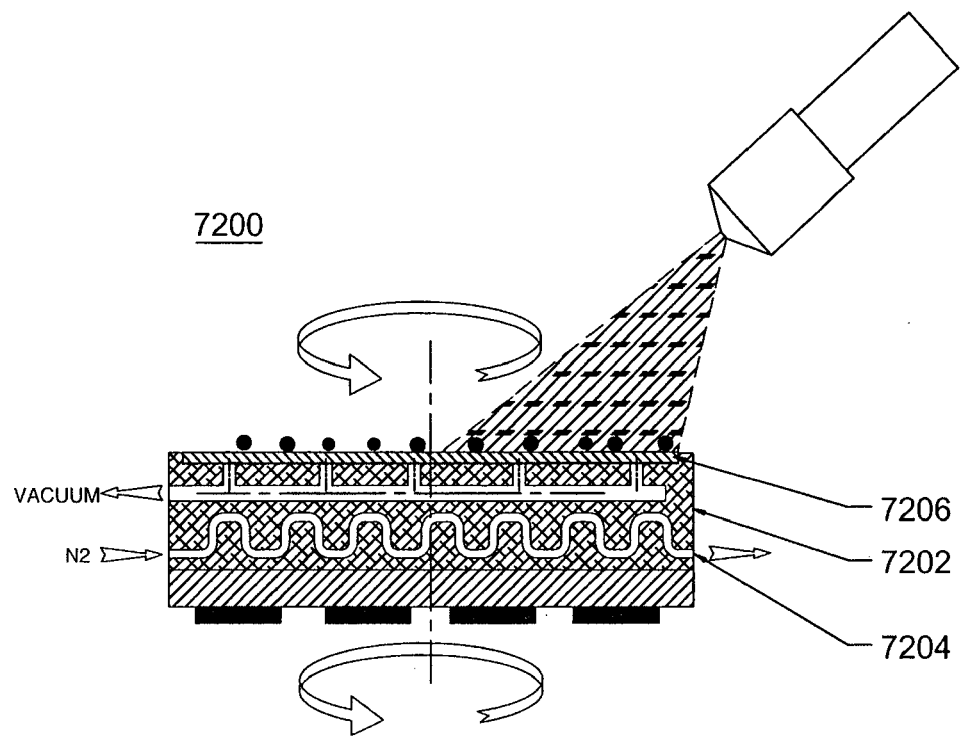
FIG. 72 shows a simplified cross-sectional view of one embodiment of a processing apparatus in accordance with the present invention including a substrate holder cooler or heater.

This cooling can be accomplished in a number of ways and performed at various rates and to different temperatures depending upon the individual characteristics of the substrate and the contaminant particle. FIG. 72 shows a simplified cross-sectional view of one embodiment of a processing apparatus 7200 in accordance with the present invention. Substrate holder 7202 features maze 7204 of cooling channels. Liquid or gaseous nitrogen could be introduced into channels 7204 to rapidly reduce the temperature of substrate 7206 to a cryogenic range. Rapid cooling may lead to a reduction in the force of adhesion exhibited between the substrate surface and a contaminant particle, facilitating particle removal.

Figure 80:
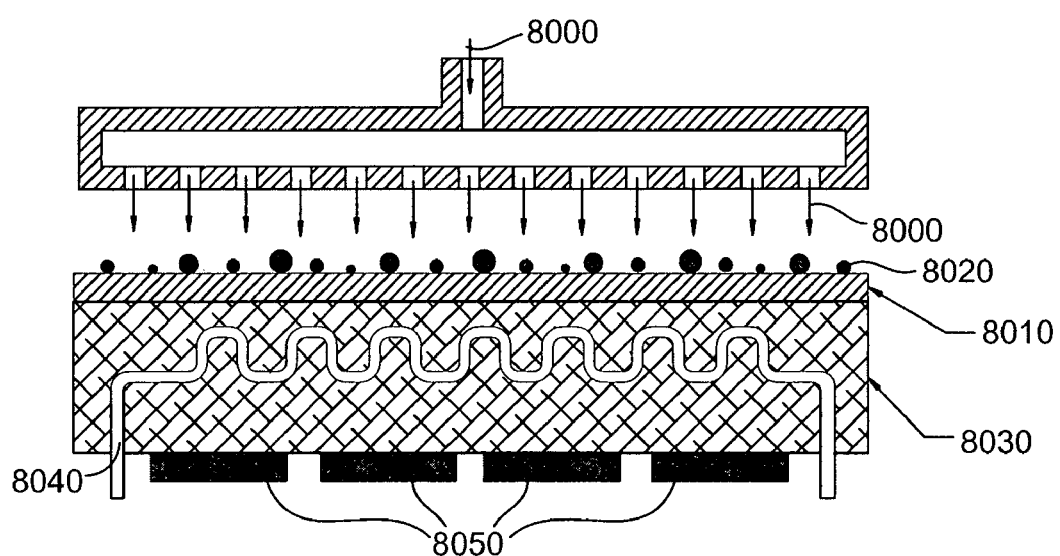
FIG. 80 shows a simplified cross-sectional view of an alternative embodiment of a processing apparatus in accordance with the present invention, wherein a uniform low velocity of a partially condensable gas is flooded over the face of the substrate.

In another embodiment as shown in FIG. 80, a uniform low velocity of a partially condensable gas 8000 is flooded over the face of the substrate 8010 with contaminant particles 8020 thereon. Cold chuck 8030 is rapidly cooled. As some of the gas 8000 condenses and freezes between the substrate surface 8010 and contaminant particles 8020, the bond between substrate 8010 and particle 8020 is broken. An optional high velocity fluid jet (not shown) blows the dislodged contaminant particles 8020 off substrate surface 8010 while piezoelectric crystals 8050 provide high frequency vibration to substrate 8010.

Less energy is typically required to break the bond between ice and a substrate than is required to melt a covering ice layer. Thus in accordance with still another embodiment of the present invention, after the condensable gas has formed an ice layer over the particles and surface of the substrate, sufficient energy may be applied to heat the substrate and break the bond between the ice and substrate, but not sufficient to completely melt the ice layer. Once the substrate-ice bond is broken, ice and contaminants can be blown off or removed more easily, hopefully as a sheet or chunks containing the contaminant particles.

In accordance with yet another embodiment, the substrate may be heated prior to introduction of a jet of energy or matter comprising at least one of a gas, a liquid, a solid, or combinations thereof. Microwave energy can be an effective means of heating a substrate rapidly for those substrates that are able to accept microwave energy.

Additionally, microwave energy will heat some substrates while not heating certain gases and solids. This can allow the substrate to be maintained at a desired temperature without heating the incoming jet of material prior to contact with the substrate.

Figure 71:
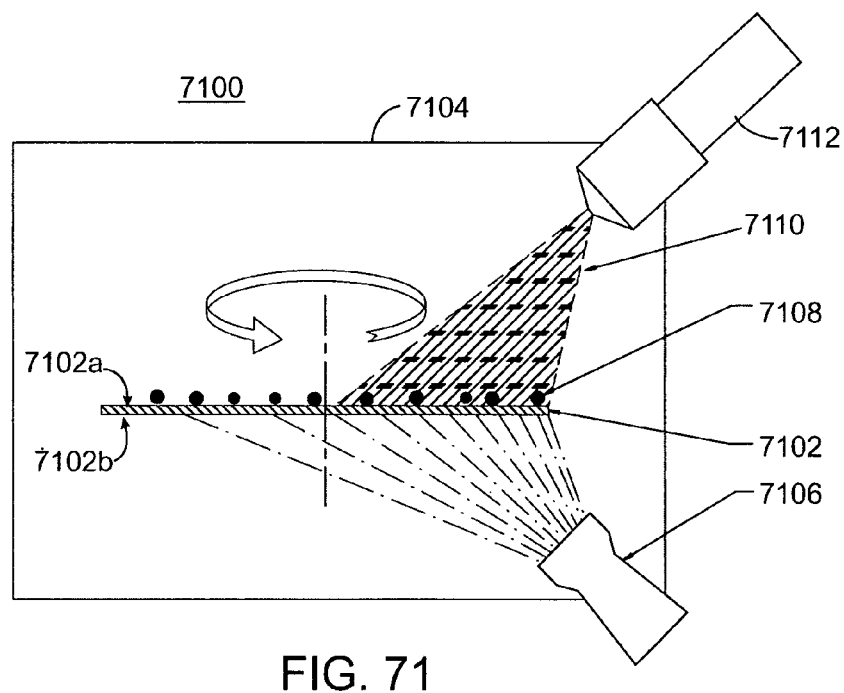
FIG. 71 shows a simplified cross-sectional view of an embodiment of a processing apparatus in accordance with the present invention incorporating microwave energy.

FIG. 71 shows a simplified cross-sectional view of an embodiment of a processing apparatus 7100 in accordance with the present invention. Substrate 7102 is supported within processing chamber 7104. Backside 7102*b* of substrate 7102 is exposed to microwave energy from source 7106, and is heated thereby. Front side 7102*a* of substrate 7102 bearing contaminant particles 7108, is exposed to jet 7110 of cryogenic aerosol from nozzle 7112.

The addition of vibration or other forms of energy is optional. Additionally, a liquid jet could also be included along with, or in place of a cryogenic aerosol cleaning jet to further extend the range of possible processing.

In order to maximize displacement of the substrate surface during vibration, it may be beneficial to physically hold the substrate into contact with the vibration element. This could be accomplished in a number of ways including use of a vacuum chuck or other holding fixture. Various holding and clamping designs not relying upon vacuum could also be employed.

Figure 66:
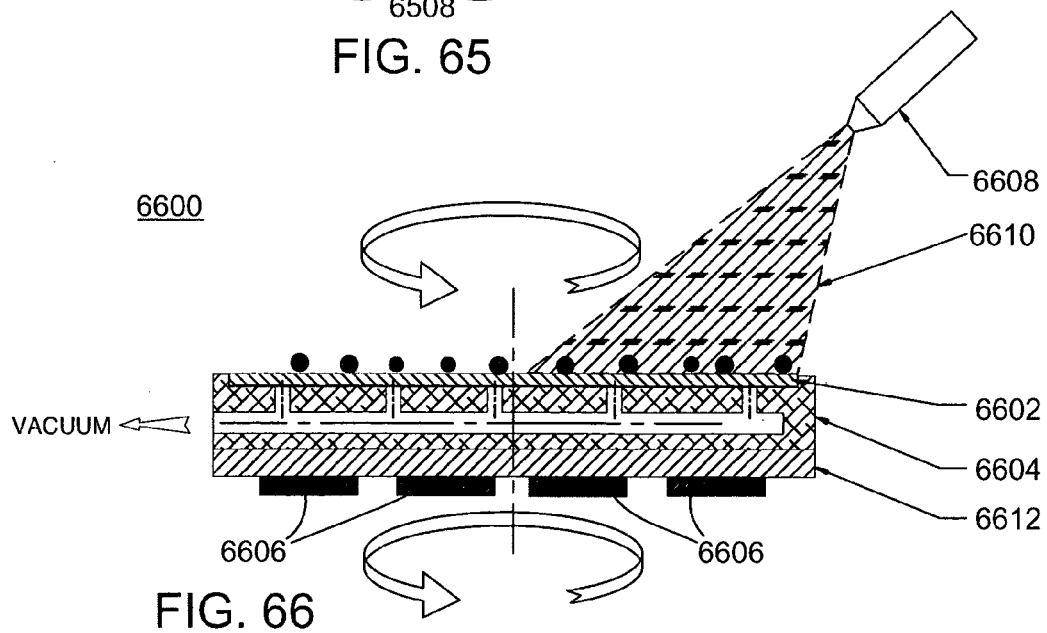
FIG. 66 shows a simplified cross-sectional view of an alternative embodiment of a processing apparatus in accordance with the present invention, wherein the substrate is clamped on substrate holder by vacuum suction.

FIG. 66 shows a simplified cross-sectional view of an alternative embodiment of a processing apparatus 6600 in accordance with the present invention, wherein substrate 6602 is clamped on substrate holder 6604 by vacuum suction. Piezoelectric crystals 6606 are attached to the back of vibration member 6612 that is in turn in contact with the back of holder 6604. Crystals 6606 are energized with a high frequency 6602 while holder 6604 is rotated to introduce relative motion between the aerosol jet and the substrate surface. Alternatively, the jet could be moved while the substrate and holder remains stationary.

Figure 67:
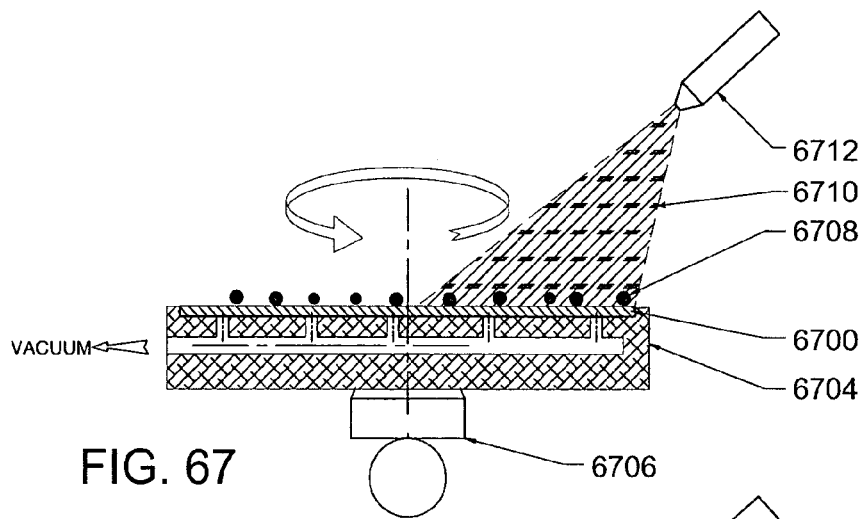
FIG. 67 shows a simplified cross-sectional view of another embodiment of an apparatus in accordance with the present invention, wherein the substrate is positioned in substrate holder utilizing mechanical vibration.

Mechanical vibration can be utilized either in place of or in combination with, sonic energy. In another embodiment of the present invention shown in the simplified cross-sectional view of FIG. 67, substrate 6700 is positioned in substrate holder 6702. Mechanical vibrator 6706 is coupled to the back of the substrate holder that also serves as vibration member 6704 to allow transfer of vibrational energy from vibrator 6706 to substrate 6700 to cause displacement of the substrate surface and contaminants 6708 present thereon. Cryogenic aerosol 6710 is directed toward the substrate surface from nozzle 6712.

The substrate surface can face any direction, or be in any orientation and still operate in accordance with embodiments of the present invention. In certain embodiments the substrate surface may preferably face upward, and in other embodiments may face downward or at some angle with respect to vertical.

In a similar fashion, the jet can be directed towards a substrate surface at any angle, ranging from perpendicular to parallel. During processing this angle need not remain constant. Positioning of the jet at a proper angle with respect to the substrate surface may lead to mode conversion of pulsating pressure waves exiting the jet nozzle into vibrating surface waves in the substrate.

Figure 68:
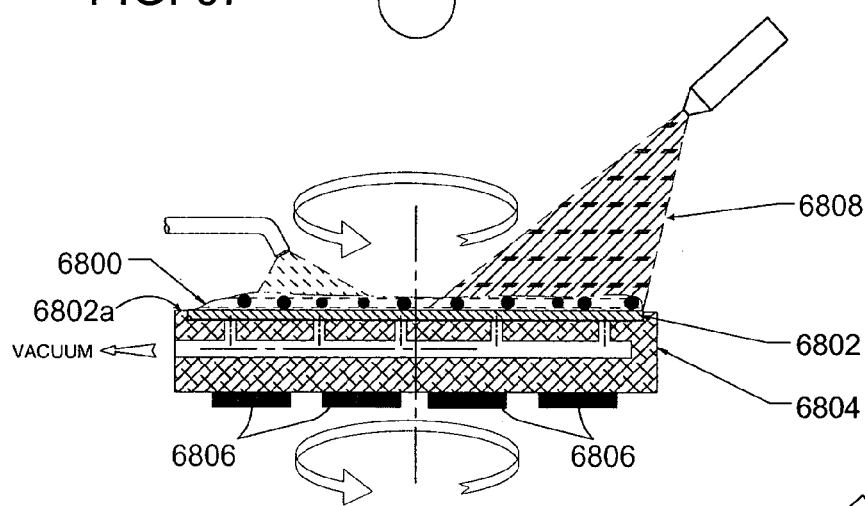
FIG. 68 shows a simplified cross-sectional view of yet another embodiment of an apparatus in accordance with the present invention, wherein a liquid layer is formed on the surface of a substrate secured on combination substrate holder/vibration member.

In another embodiment of the present invention shown in the simplified cross-sectional view of FIG. 68, liquid layer 6800 is formed on surface 6802*a* of substrate 6802 secured on combination substrate holder/vibration member 6804. Sonic energy is coupled to the backside of substrate 6802 by attaching piezoelectric crystals 6806 to the backside of combination substrate holder/vibration member 6804. Aerosol jet 6808 is directed towards front surface of substrate 6802, which is covered with thin fluid layer 6800.

While jet 6808 may be of the cryogenic aerosol type, that is not required. Jet 6808 can comprise a gas only, without inclusion of frozen solid particles, or may comprise only a liquid, or may comprise a combination of both phases. Processing can be accomplished at any pressure or temperature.

Embodiments in accordance with the present invention are not limited to the application of a jet of solid, liquid, or gaseous particles. Another processing technique which may be enhanced in accordance with embodiments of the present invention is treatment of the surface of a substrate with energy from a laser. Examples of such laser processing include shock cleaning, dry cleaning, and explosive evaporation.

Figure 65:
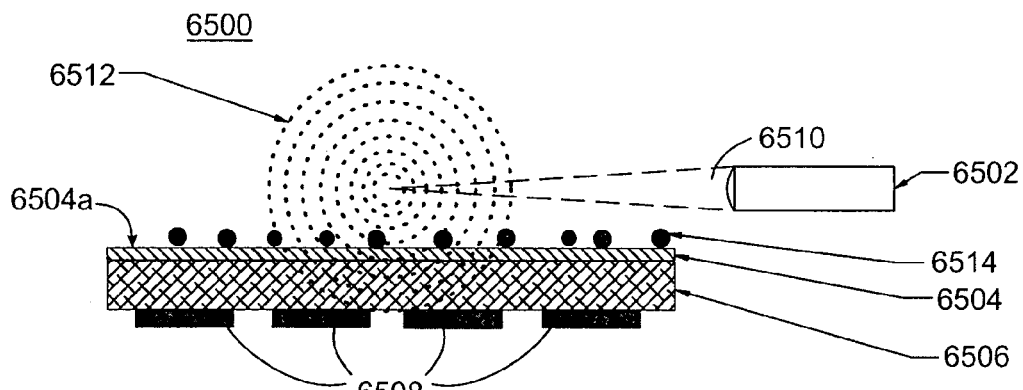
FIG. 65 shows a simplified cross-sectional view of an embodiment of an apparatus in accordance with the present invention which may be utilized to perform laser shock cleaning.

FIG. 65 shows a cross-sectional view of one embodiment of an apparatus 6500 in accordance with the present invention, which may be utilized to perform laser shock cleaning (LSC). LSC occurs when laser 6502 is focused just above surface 6504a of substrate 6504 supported on vibration member 6506 in mechanical communication with piezoelectric crystals 6508. Focused beam 6510 from laser 6502 creates a thermal shockwave 6512 by rapidly heating a localized section of the atmosphere above substrate surface 6504a. This shockwave propagates over surface 6504a of substrate 6504, displacing contaminant particles 6514 therefrom.

Again, without wishing to be bound by any particular theory, processing of a substrate with laser energy may be enhanced in accordance with the mechanism described above for processing with a jet of material. Thus for LSC, vibration of the proper frequency and intensity of the surface/contaminant could modify the dynamics of the interaction between the shockwave and contaminant particles on the substrate surface. Rapid, repetitive movement of the substrate surface/contaminant during the time period that the shockwave interacts locally with individual particles or contaminants could alter the effectiveness and efficiency of particle and contaminant removal, allowing a change in the intensity of applied energy.

Figure 73:
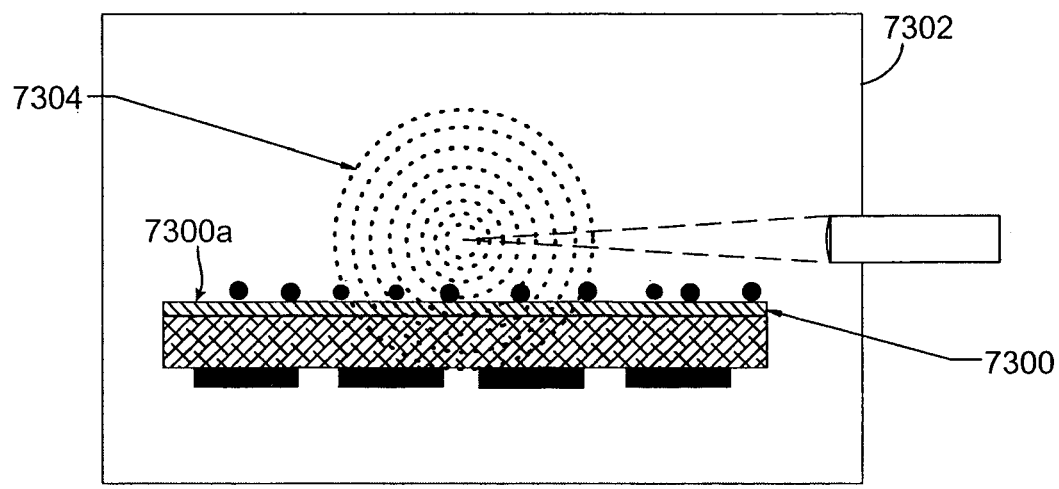
FIG. 73 shows a simplified cross-sectional view of an alternative embodiment of a processing apparatus in accordance with the present invention, wherein the substrate is contained within enclosure pressurized above atmospheric pressure during processing.

FIG. 73 shows a simplified cross-sectional view of an alternative embodiment of a processing apparatus in accordance with the present invention, wherein during LSC processing, substrate 7300 is contained within enclosure 7302 pressurized above atmospheric pressure. This elevated operating pressure changes the velocity of propagation and intensity of shockwave 7304, thereby resulting in a different dynamic interaction between shockwave 7304 and surface 7300a of substrate 7300. In still other embodiments, the enclosure could be depressurized, thereby lessening the intensity of the laser-induced shockwave.

The apparatus of FIG. 65 may be utilized to perform laser processing other than LSC. For example, laser dry cleaning, which is characterized by use of the laser to directly ablate/destroy particles directly off a substrate surface, or to modify that surface could be employed. Alternatively, explosive evaporation, which occurs when a laser is focused into a thin layer of an alcohol/water mixture on the substrate surface causing violent evaporation/explosion of the mixture, could be practiced. The resulting "explosion" wavefront propagates over the substrate surface, dislodging contaminant particles therefrom.

In accordance with another embodiment, the substrate is cooled and vibration introduced prior to the application of laser shock. While generally performed at atmospheric pressure, the laser shock can also be accomplished at either above or below atmospheric pressure depending on surface and particle characteristics and the collision dynamics desired. There is no theoretical upper or lower limit for operating pressure, other than the limits imposed by materials of construction and equipment designs. Equipment able to operate at pressures exceeding several thousand pounds per square inch are know in industry.

Still another processing technique enhanced in accordance with embodiments of the present invention is treatment of a substrate with a supercritical fluid, for example carbon dioxide ($CO_2$). At temperatures and pressures above a critical point of a particular fluid, a material becomes a supercritical fluid.

Under such conditions, the material is technically neither a gas, a liquid, nor a solid. Carbon dioxide in the supercritical state exhibits a low surface tension characteristic of the gaseous state, but also exhibits an elevated density characteristic of the liquid state. While a high velocity jet can enhance processing, even in the absence of a high velocity jet, useful processing can result from unique characteristics of a fluid present above supercritical conditions.

In certain conventional designs of processing equipment, supercritical carbon dioxide is nearly stagnant within a processing chamber. Substrates are present within the supercritical fluid, which acts as a solvent to remove contamination from the substrate surface.

In other conventional equipment designs, carbon dioxide is continuously pumped through a processing chamber in an attempt to create minimal hydrodynamic forces aiding in the removal contamination. Rather than holding the operating pressure of the system constant, the operating pressure of the system may be allowed to fluctuate or pulse during processing. These pressure pulses can either all be above the supercritical point, or can cycle between supercritical and sub supercritical levels. At sub supercritical conditions, a fluid such as carbon dioxide for example can become a gas, liquid, or solid, and then transform back into a supercritical fluid when supercritical conditions are reestablished.

It has been suggested that introduction of sonic energy into supercritical carbon dioxide may enhance substrate processing. However, because the supercritical fluid is not in a liquid or solid state, transfer of sonic energy through the supercritical fluid may be substantially reduced or attenuated. In general, attenuation within a medium varies as the square of the frequency of the sonic energy. Thus, as the semiconductor industry migrates toward application of higher frequency sonic energy to remove smaller particles, it becomes increasingly difficult to transfer significant amounts of sonic energy through a medium.

The difficulty in applying vibrational energy in the context of supercritical processing becomes even more troublesome as the size of substrates is increased. This effect is particularly evident when the sonic energy is applied in a direction parallel to the substrate surface, as has been traditionally done in batch processing. Historical attempts to transfer significant amounts of sonic energy directly across substrates has been hampered by the requirement of matching substrate thickness to an even multiple one-quarter wavelength of the pressure wave for maximum transfer. For example, because of their small thickness of semiconductor wafers, frequencies three or four time those currently used for processing would be required.

Sonic energy has been transferred over long distances parallel to substrate surfaces, in conventional batch processing and cleaning utilizing aqueous solutions at atmospheric pressure. However, such approaches are not likely to succeed in the context of supercritical processing, because of the sonic characteristics of the materials involved. Therefore it becomes even more important to maximize energy coupling between the substrate and the vibration member and to minimize distances over which sonic energy must be transferred in the fluid. Efficient transfer of energy directly across the thickness of a substrate is especially useful, allowing one surface of the substrate to be in direct contact with a vibration member or closely spaced therefrom. Such an arrangement minimizes the distance that sonic energy must travel through highly attenuating fluid.

A poor impedance match between the sonic impedance of the supercritical fluid and of the material of the vibration surface can prevent transfer of a sufficient amount of sonic energy. Thus, the selection of materials having the proper thickness, becomes important to minimize the impedance mismatch typically observed in conventional processing.

Supercritical processing enhanced in accordance with embodiments of the present invention can include the use of various gases and liquid mixtures with the supercritical fluid which may be referred to as co-solvents. Alternatively, substances other than carbon dioxide can be utilized for processing at conditions above their critical point. And while it is generally desirable for the supercritical processing fluid to comprise multiple components forming a homogeneous phase, this is not required. In accordance with alternative embodiments, the processing chemistry could comprise two or more phases. Two phase or even multiple phase chemistries could be exploited.

Sonic energy may be transferred through a medium as a series of pressure waves. Thus, whether of relatively low frequency from a mechanical vibrator, or of relatively high frequency from a piezoelectric crystal, sonic energy may be viewed as an extension of slower pressure pulses historically utilized in supercritical processing. In accordance with embodiments of the present invention, it is now possible to have pulses at multiple frequencies introduced simultaneously to even further enhance processing.

In one embodiment, sonic energy may be introduced to a processing chamber operating at supercritical conditions. A shown in the simplified cross-sectional view of FIG. 74, this may be accomplished by directly attaching piezoelectric crystals 7400 to the outside of at least one wall 7402 of the chamber 7404, with the thickness of that wall chosen to approximately equal an odd multiple one-quarter wavelength of the applied sonic energy to maximize energy coupling. As the energy in FIG. 74 is being transferred across the vessel wall instead of being generated within the vessel itself, issues associated with sealing electrical leads exiting a high-pressure environment, and with compatibility between the piezoelectric crystals 7400 and the processing chemistry are avoided.

Figure 74:
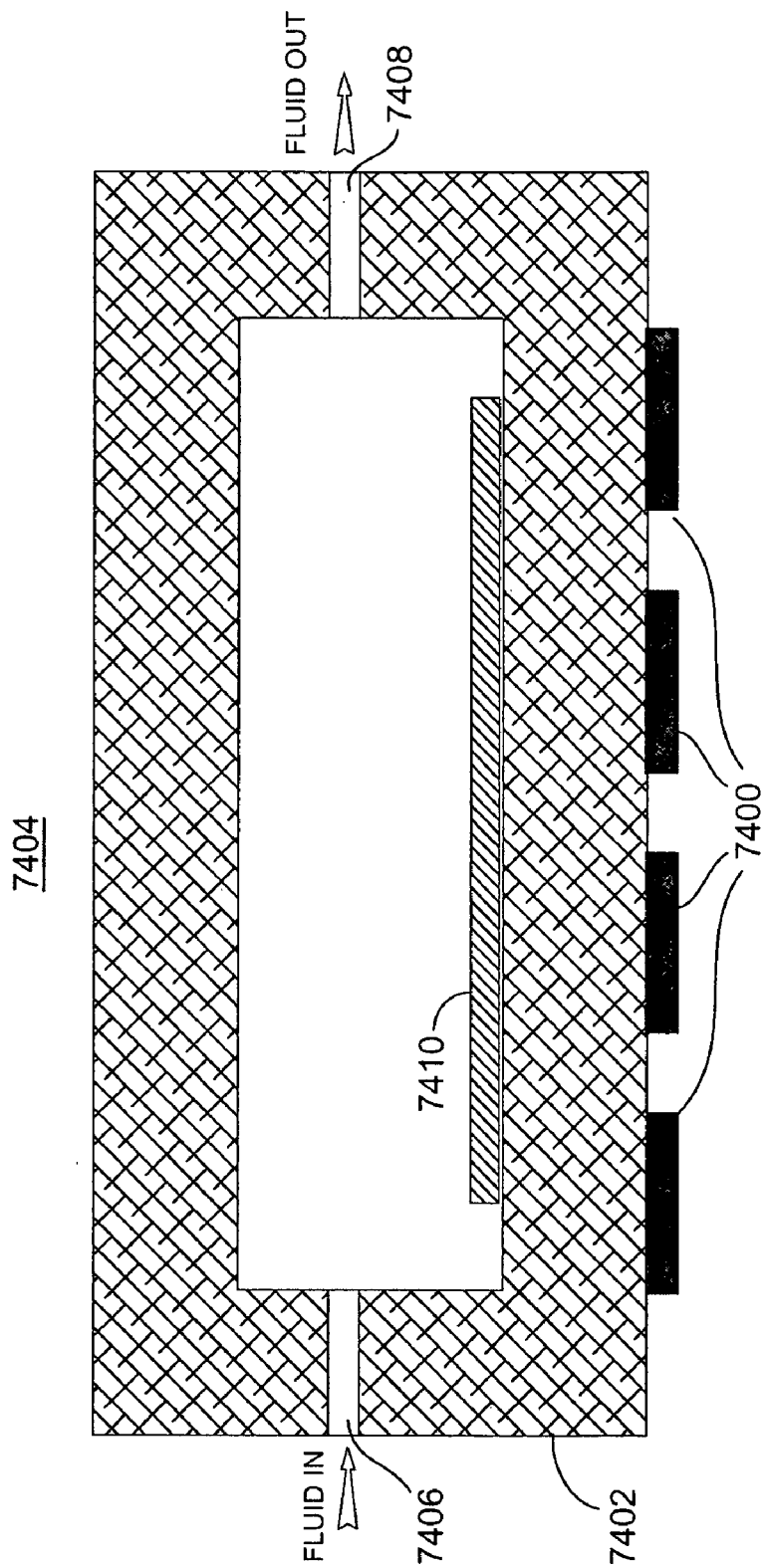
FIG. 74 shows a simplified cross-sectional view of an embodiment of a processing apparatus in accordance with the present invention featuring piezoelectric crystals attached to the outside of at least one wall of a processing chamber, with the thickness of that wall chosen to approximately equal an odd multiple one-quarter wavelength of the applied sonic energy to maximize energy coupling.

While the embodiment of FIG. 74 depicts a chamber with fluid inlet 7406 and outlet 1008 oriented such as to suggest fluid flow parallel to the surface of the substrate 7410, high velocity jets may be utilized and directed at any angle relative to the surface of the substrate.

Figure 79:
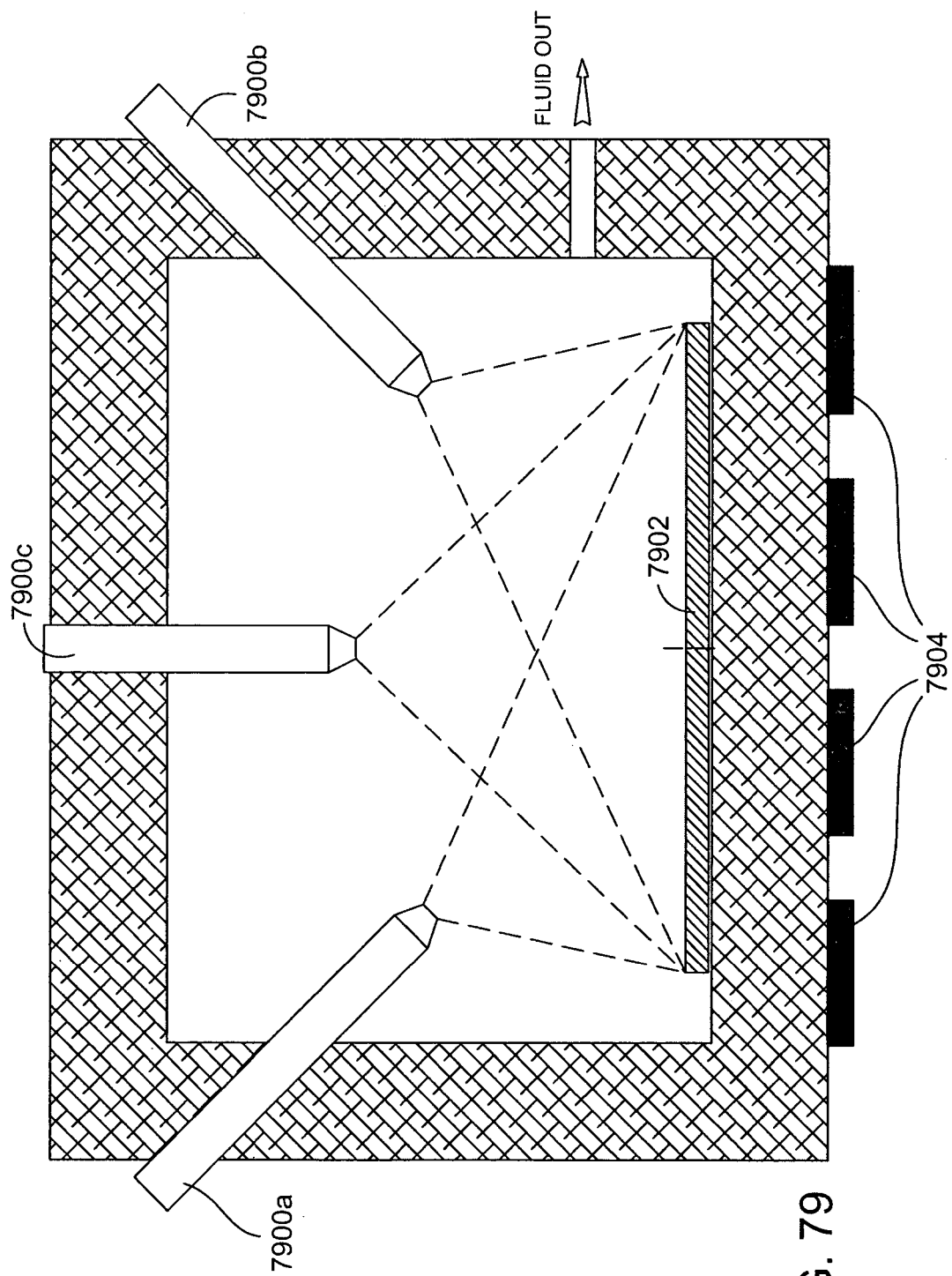
FIG. 79 shows a simplified cross-sectional view of an alternative embodiment of a processing apparatus in accordance with the present invention, featuring jets which incorporates the benefits of the unique physical and chemical properties of supercritical fluids and sonic energy with the hydrodynamic properties of a fluid jet.

FIG. 79 shows a simplified cross-sectional view of such an alternative embodiment which incorporates the benefits of the unique physical and chemical properties of supercritical fluids and sonic energy with the hydrodynamic properties of a fluid jet. As in several of the previous embodiments, jets 7900a–c provide a convenient way to transfer momentum to contaminant particles. Further, the multiple jets could be sequenced to sweep across substrate 7902 if desired. This can be combined with a megasonic system comprised of multiple piezoelectric crystals fired sequentially or continuously.

In accordance with another alternative embodiment, where the thickness of the vessel wall is determined by other constraints, the frequency of excitation of the piezoelectric crystals can be adjusted to make the given wall thickness equal the desired odd multiple one-quarter wavelength as disclosed in the above referenced application.

Figure 75:
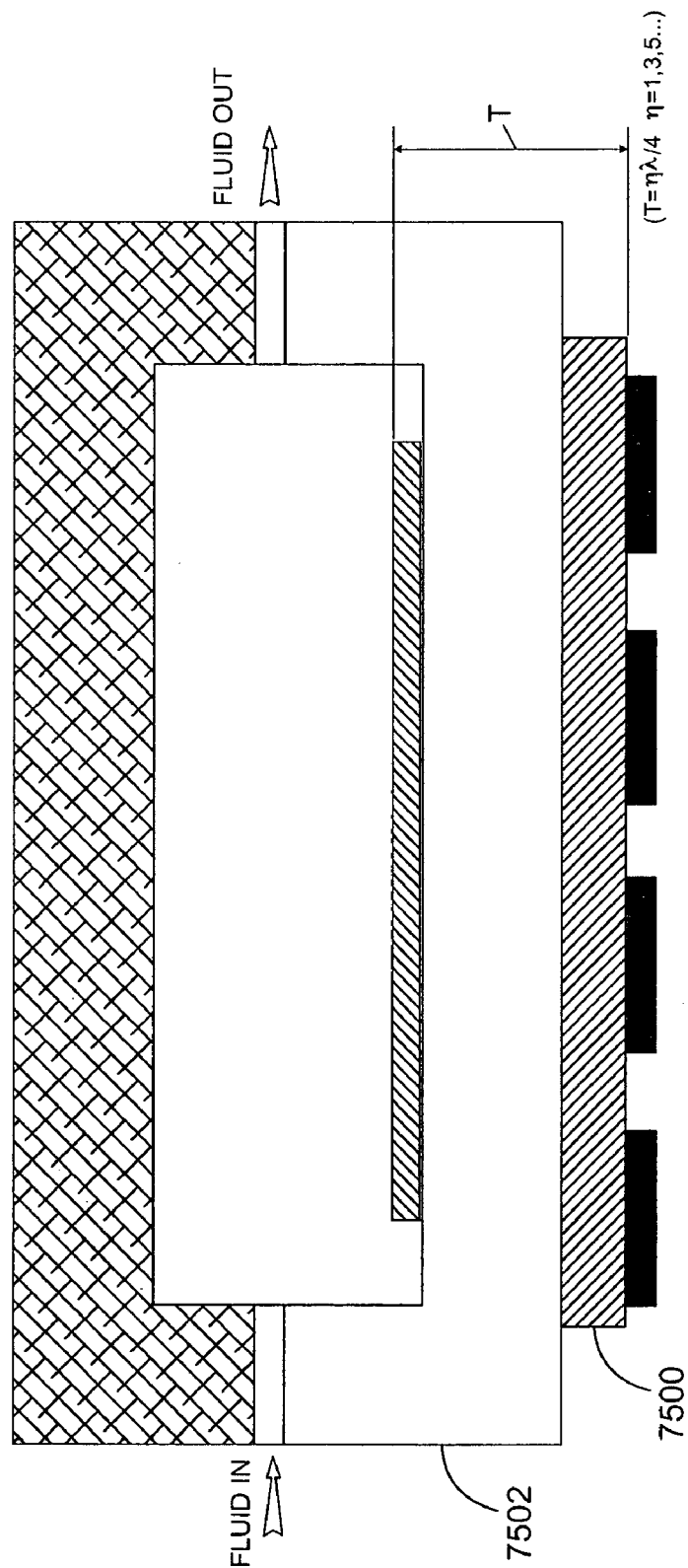
FIG. 75 shows a simplified cross-sectional view of an embodiment of a processing apparatus in accordance with the present invention, featuring crystals bonded to a vibration plate that is then rigidly attached to the chamber wall.

Further optionally, instead of bonding the crystals directly to the outside of a wall of the chamber, the crystals could be bonded to a vibration plate that is then rigidly attached to the chamber wall as shown in the simplified cross-sectional view of FIG. 75. The resulting sum of the thickness of the vibration plate 7500 in intimate contact with the tank wall 7502, and ideally including the substrate thickness as well, should equal an odd multiple one-quarter of the wavelength of the applied energy. While vibration member 7500 is shown in FIG. 75 as being bonded to the outside of chamber wall 7502, the vibration member could optionally be bonded to the inside of the chamber wall. However, such an alternative embodiment would make establishing reliable electrical connection with the vibrating element slightly more difficult, and could raise potential issues of compatibility between the material comprising the vibrating member and the surrounding processing chemistry to which it is exposed.

In such an alternative embodiment, the substrate may either be suspended in supercritical fluid within the chamber, or may be brought into direct contact with the chamber wall as was shown in FIGS. 74 and 75. When brought into direct contact or close proximity with the chamber wall, variation in the frequency or intensity of vibration can be utilized to disrupt near-field effects and enhance the uniformity of processing.

Where the substrate is in direct contact with the chamber wall (or vibration member) transmitting the sonic energy, the thickness of the substrate as well as the thickness of the chamber wall (or vibration member) may need to be taken into account in maximizing energy transfer. In such applications, the combined thickness of the substrate and the chamber wall (or vibration member), taking into account the material composition of each element, should conform to approximately an odd multiple one-quarter wavelength guideline at the operating frequency. While an exact match of thickness is not required, it is generally preferable to be within +/−50% of the guideline values.

The frequency of sonic energy or the thickness of the chamber wall (and/or vibration member) may be selected or adjusted to maximize the transfer of sonic energy across the substrate. Megasonic generators manufactured by PCT Systems Inc. of Fremont, Calif., allow for such adjustment.

Since the speed of sound can vary greatly from one material to another, each material or combination of materials will require a unique total thickness to match a selected frequency, or a unique optimal frequency to match a resulting thickness sum. For example, while the speed of sound in aluminum is approximately 6380 m/s, in stainless steel it is only 5780 m/s. Thus to ensure optimal sonic energy coupling, an aluminum plate of greater thickness than a stainless steel plate would be required.

Figure 77:
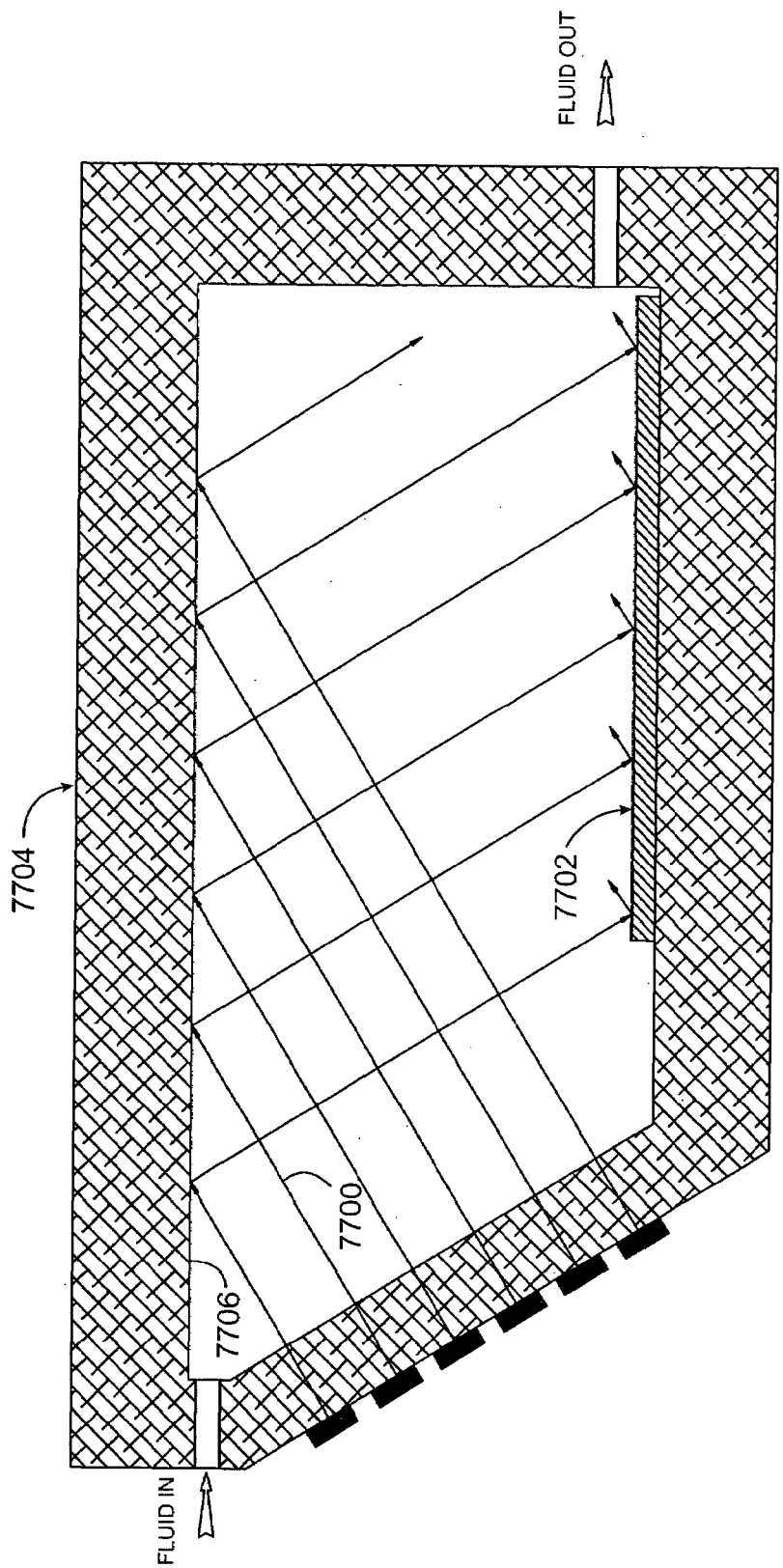
FIG. 77 shows a simplified cross-sectional view of one design of a processing apparatus in accordance with the present invention wherein sonic energy bounces off the substrate and off walls of the vessel.

When the substrate is not in direct physical contact with a chamber wall, the substrate may be oriented at any angle with respect to any of the walls. When oriented within a proper range of angles with respect to the incident sonic energy, transfer of sonic energy across the substrate can also occur. Outside this range of angles, the sonic energy may be reflected from the substrate surface. FIG. 77 shows a design for a processing apparatus wherein sonic energy 7700 bounces off substrate 7702 and off walls 7706 of vessel 7704.

While the substrate is shown in FIG. 77 as in direct contact with the vessel wall, this is not required to obtain desired reflection off the substrate surface. When the incident angle of the pressure wave is between the first and second critical angles as discussed above, energy can either be transferred across the substrate, or the incident pressure wave can be converted into a surface or shear wave, with little or no reflection.

As discussed previously, the range of angles over which significant mode conversion from dilatational to shear or surface waves occurs, perhaps including some dilatational wave diffraction, is likely to be larger than the range of angles over which cross substrate transfer of energy occurs. As with any wave interactions with multiple materials, some reflection may occur even within part of the range of angles over which significant cross substrate transfer or even mode conversion occurs.

Figure 76:
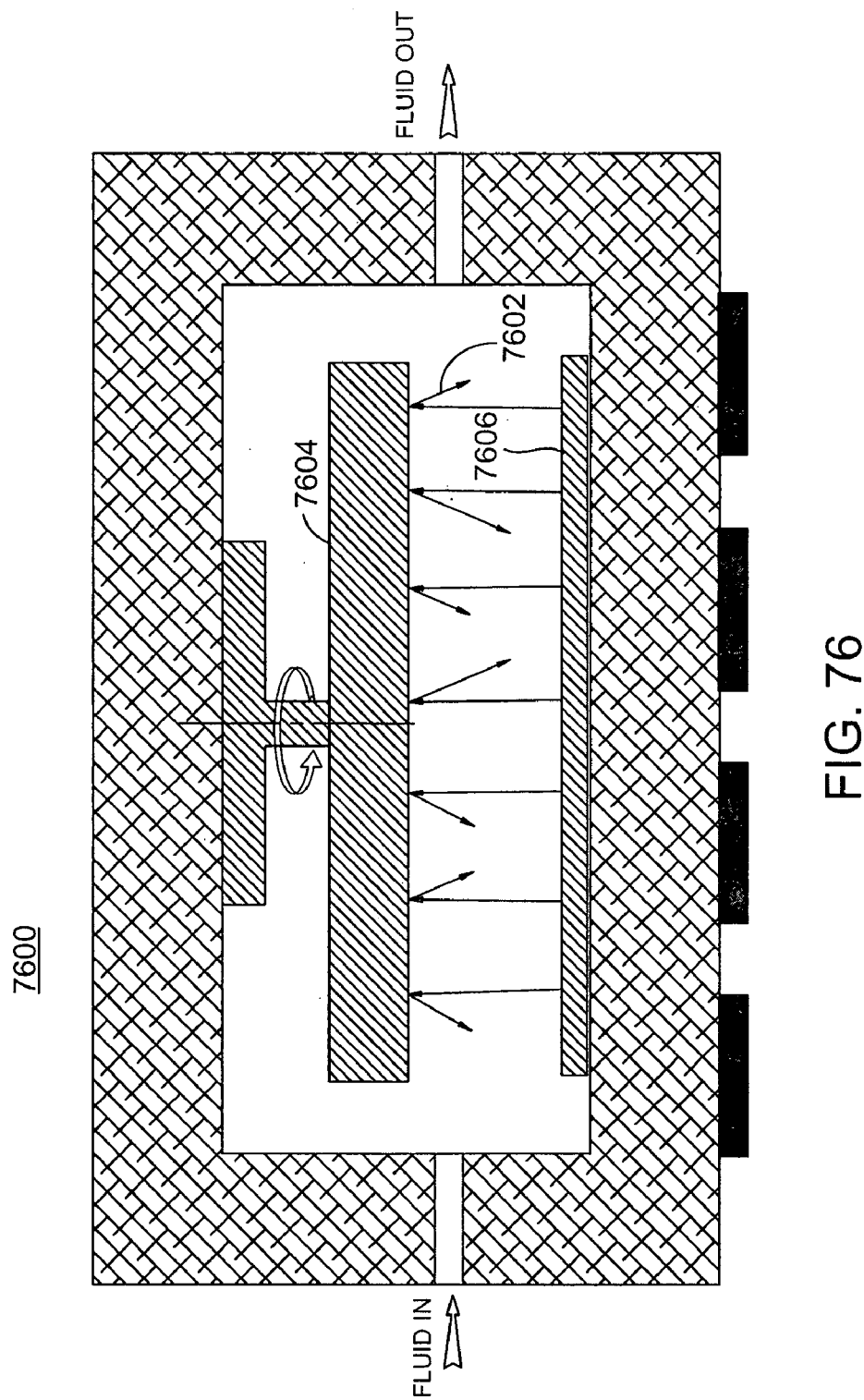
FIG. 76 shows a simplified cross-sectional view of one design of a processing apparatus in accordance with the present invention wherein reflections from a moving reflector impinge upon a stationary substrate.

When energy is transferred across a substrate, for example when the substrate is in direct contact with a surface of a vibrating member, is of a proper thickness or is oriented at an appropriate angle, the chamber may be advantageously designed to reflect transferred sonic waves back toward the substrate surface. Such reflections can be from stationary or moving surfaces. FIG. 76 shows a simplified cross-sectional view of one such design 7600, with reflections 7602 from a moving reflector 7604 impinging upon stationary substrate 7606.

Figure 78:
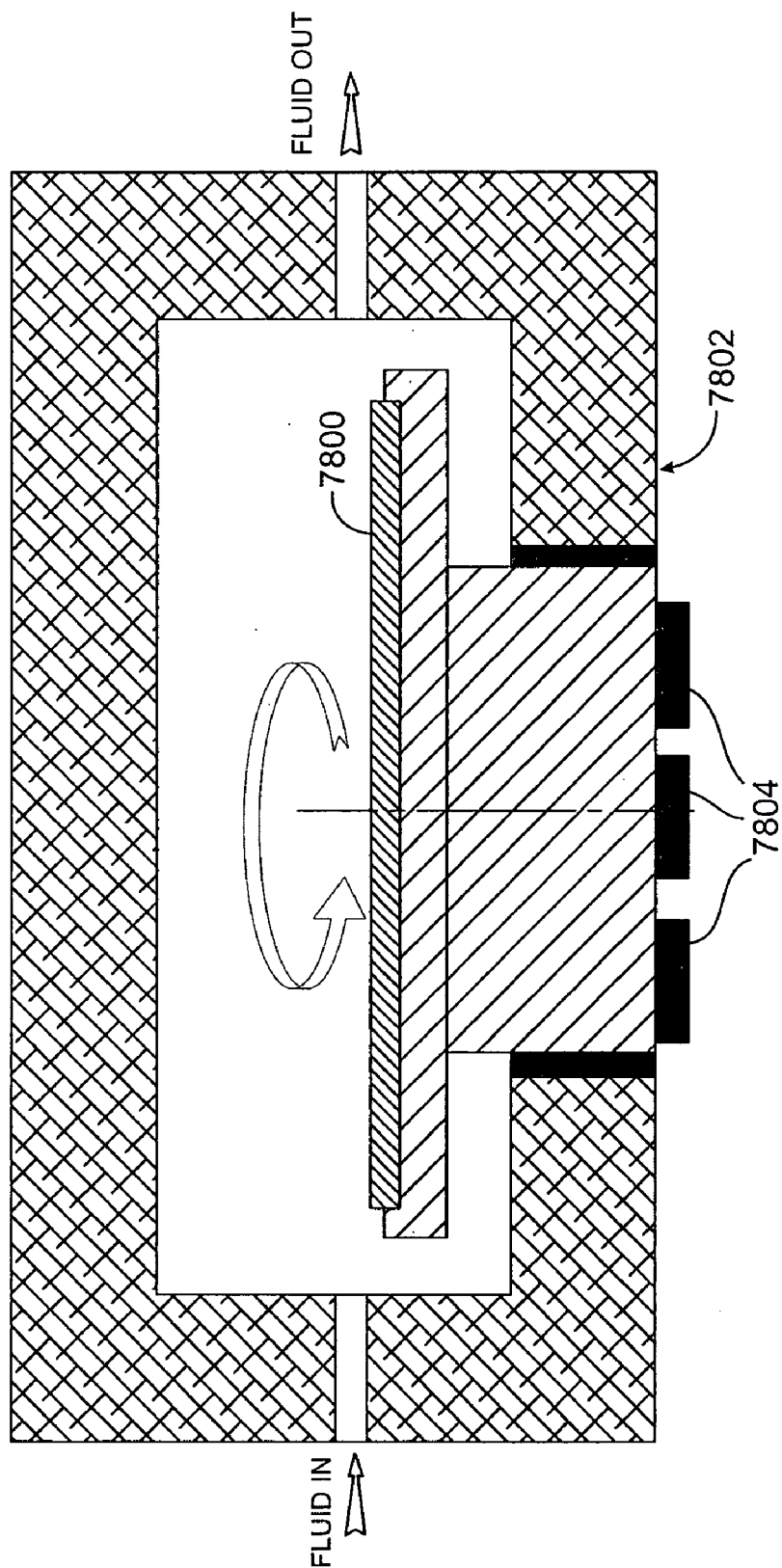
FIG. 78 shows a simplified cross-sectional view of a processing apparatus in accordance with the present invention wherein substrate is in motion and simultaneously receives sonic energy from piezoelectric crystals outside the vessel.

In accordance with an alternative embodiment, the substrate can be in motion. As shown in the simplified cross-sectional view of FIG. 78, substrate 7800 is in motion and simultaneously receives sonic energy from piezoelectric crystals 7804 outside the vessel 7802. While the specific embodiment of FIG. 78 shows the piezoelectric crystals generating the sonic energy, in accordance with other embodiments a mechanical vibrator could alternatively be utilized for such purpose. Relative motion between the substrate and the chamber or the incident sonic energy, can thus be incorporated into processing.

In another embodiment where sonic energy is added to a process chamber operating at supercritical conditions, a vibration member may be present within the process chamber. In such an embodiment, the sonic energy is not transferred across a chamber wall, and the thickness of the chamber wall need not equal an odd multiple one-quarter wavelength of the applied sonic energy. Rather, the thickness of the chamber wall need only provide adequate strength to contain the elevated pressures implicated in supercritical operation.

When sonic energy is transmitted across very thick walls or substrates, power attenuation may occur. By not requiring the sonic energy to be transferred across a thick vessel wall, more energy may be available for transfer into or across a substrate residing within the vessel.

Although the invention has been described in terms of preferred methods and structures, it will be understood to those skilled in the art that many modifications and alterations may be made to the disclosed embodiments without departing from the invention. For example, while the above description and figures have focused upon methods and apparatuses wherein the vibrating member is in direct physical contact with the substrate, this is not required by the present invention.

The substrate can either be placed into direct contact with the vibration member or be separated from it. When in direct contact, and the chamber is small, it may be desirable to have energy reflect off the chamber walls back towards the substrate surface. To enhance reflection and minimize energy loss through the chamber wall, the reflection should be conducted at the appropriate angles. This can be accomplished in either a static mode or a dynamic mode where there is relative motion between the substrate and some surface. That surface being a chamber wall or some additional energy-reflecting surface.

While the above description has emphasized enhancement in processing through the application of sonic energy, other types of energy could also be utilized. Such other types or forms of applied energy can include hydrodynamic, microwave, infrared, ultraviolet and thermal. In the case of thermal energy, you can have the addition of energy (heating) or the removal of energy (cooling).

F. Soft Megasonic Fluids

As semiconductor processing of smaller feature sizes becomes necessary, damage not posing a problem at larger feature sizes has become more of a concern.

The cavitation threshold pressure corresponds to the power density required to produce cavitation events, or to produce cavitation events that result in visible damage from those events. According to classical ultrasonic theory, most batch megasonic systems operate at a power density well below that traditionally considered the cavitation threshold pressure at these given frequencies.

The cavitation threshold pressure increases with increasing frequency of applied sonic energy. With megasonic processing, the typical power densities used in processing are far below where cavitation is expected. Even so, damage to fragile semiconductor structures is being reported at these higher megasonic frequencies.

While not wishing to be bound by any particular theory, recent ultrasonic theory addressing higher operating frequencies utilized in megasonic processing, discusses several additional parameters or possible sub-processes including microcavitation and microstreaming in addition to traditional acoustic streaming. Under some conditions, these sub-processes may lead to enhanced cleaning and processing. Under other conditions, damage may result.

Examples of megasonic processing damage may be seen with fragile polysilicon lines. Inspection after traditional batch or single wafer megasonic processing may reveal portions of a line or lines to be either broken free from the substrate, or missing entirely. This damage may be caused by cavitation, microcavitation, microstreaming, or even just the pressure waves traveling through fluid impinging on the surface of the substrate, or on the polysilicon lines directly, depending on conditions and method of introduction of sonic energy to the processing vessel.

Specifically, when cavitation events occur near a line, imperfections in a line, or the area of the line's bond with the substrate, energy released by collapse of the cavities and microcavities, may be manifested in the form of high velocity fluid jets. These high velocity jets can cause the line to be pushed or even dislodged from the substrate.

Alternatively, as gas bubbles are formed and grow between the substrate and the line, a line or other feature may be lifted or pried away from the substrate.

As a sonic energy pressure wave travels through the fluid, gas bubbles may often form from gas dissolved in the liquid, at the low pressure trailing edge of the wave. As multiple sequential bubble forming events occur, each of the newly formed and growing bubbles between the substrate and the overhanging line may cause more of the line to be lifted or dislodged from the substrate.

Generally, the higher the content of the gas in the liquid, the lower the cavitation threshold pressure and the less damage that occurs. The higher gas content of the liquid may provide more cavitation and microcavitation nucleation sites to form a larger number of smaller and more stable cavities and bubbles, each producing less energy upon collapse. For fluids containing little or no dissolved gas, a higher power density is required to form voids in the fluid. At high cavitation threshold pressures and relatively low frequencies, the voids can be filled with vapor instead of gas.

The vapor-filled cavities collapse more violently than gas filled cavities (bubbles) and can cause more severe damage. Vapor filled cavities may also likely be larger than the gas filled cavities, and can store more energy that is released during collapse. This may explain why macro-scale damage is observed at relatively low frequencies, while micro-scale damage of the type of emerging concern is observed at higher frequencies.

Ultrasonic processing in DI water can produce more damage to a thin metal foil than equivalent ultrasonic processing in acetone or an alcohol. It is theorized that water creates more damage due to high internal cohesion between adjacent packets of water molecules, as separated fluid packets are drawn back together harder under higher attraction energy. Therefore, fluids with less internal cohesive strength should produce less damage, even with the smaller microcavitation events.

Recently, semiconductor processing has utilized more dilute solutions of various processing chemicals, with the ultimate goal of processing semiconductor substrates in DI water at near room temperature. This trend is driven by the expense of preparing chemicals of the necessary purity, and of disposing of the chemicals in an environmentally-friendly way once used.

Simultaneously, the direction of the industry has been towards the manufacture of smaller and smaller device features and structures. The convergence of the trend to use ever more dilute aqueous solutions to process ever-smaller features, has enhanced the level of scrutiny regarding potential damage inflicted on features by megasonic processing.

It has also been suggested that the use of water results in greater damage than the use of a number of other fluids, because water exhibits relatively low solubility for many gases, while simultaneously possessing high thermal conductivity. Higher gas solubility provides more cavitation nucleation points for less energy intense cavitation events. And under the high temperatures generated with sonoluminesence events, fluids possessing high thermal conductivity may transfer that localized high energy to substrate surfaces more easily, leading to increased damage.

Therefore, a need exists for fluids for use in megasonic processing which impart less damage to small and fragile features on the surface of a processed substrate.

In accordance with various embodiments of the present invention, damage to small features inflicted by wet megasonic processing, may be reduced utilizing a variety of techniques, alone or in combination. According to one technique, megasonic energy may be applied to liquids that are less prone to producing cavitation and microcavitation damage, for example liquids comprising substantial components other than water, such as methanol or acetone. According to another technique, damage arising from cavitation and microcavitation events may be reduced by the presence of microbubbles within the processing fluid. According to still another technique, megasonic processing may be conducted under temperature or pressure conditions that control the void fraction and function of entrained microbubbles, controlling the degree of attenuation, the cavitation threshold pressure, and cleaning and processing performance.

Embodiments of methods, apparatuses, and compositions in accordance with the present invention utilize (1) alternative megasonic fluid types, (2) introduction of microbubbles, and (3) processing at elevated/reduced pressure or temperature conditions, alone or in combination, to reduce the damage imparted to substrate features during megasonic processing.

In ultrasonic processing, less cavitation damage is observed with some fluids than with others. For example, in fluids like methanol and acetone, applied sonic energy can produce less damage to an aluminum metal foil than water, or to a lesser extent, kerosene.

In an attempt to minimize damage inflicted during megasonic processing, it has been proposed to consider alternative fluids which do not cause as much cavitation and microcavitation damage, or which are better able to contain small or micro-sized bubbles.

Accordingly, a first technique in accordance with the present invention utilizes fluids exhibiting solubility for gases or mixtures of gases, which exceeds their solubility in traditional processing fluids such as deionized (DI) water. Components of such alternative megasonic processing fluids can include, but are not limited to, alcohols such as methanol, ethanol, and isopropyl alcohol (IPA); ketones such as acetone and MEK; other types of organic solvents such as hydrocarbons; and more exotic materials such as perfluorinated solvents, including various combinations of these various components. Many such liquid solutions may be considered, based for example on their chemical properties (reactivity with substrates), or on their physical properties (gas solubility and thermal conductivity).

The goal underlying this first approach is to obtain relatively high solubility of gas in the liquid, as compared with the solubility of the gas in DI water. Such increased gas content should facilitate cavitation and microcavitation, drop the cavitation threshold pressure, and result in less damage during processing.

Additionally, the identity of particular gases or gas mixtures dissolved in the fluid may also comprise an important processing parameter. This is so not only because alternative gases may exhibit higher solubility in the processing liquid, but because the alternative gases may lead to the formation of different ionic species in a sonic energy field, especially when sonolumunessence occurs.

A second technique in accordance with embodiments of the present invention teaches the introduction of small bubbles, preferably micro bubbles into the processing fluid near the surface of the substrate. Small or micro-bubbles introduced into the processing fluid can buffer or cushion cavitation or microcavitation events which do occur. Other theories teach that microbubbles actually facilitate the removal of small particles, or cleaning and various sonic processing.

Larger, macro-scale bubbles introduced into and dispersed within the processing fluid may attenuate sonic energy transfer, simultaneously reducing damage from cavitation shockwaves. Introduction of smaller micro-scale bubbles dispersed in the processing fluid should not attenuate sonic energy as significantly. Additionally, the small bubbles may still be able to absorb damaging shockwaves generated by microcavitation events within the fluid, particularly microcavitation events on or near the surface of the substrate.

Introduction of small bubbles into a processing fluid in accordance with embodiments of the present invention may also serve as an extension of the first approach previously described, as bubbles within the fluid may provide a dispersed gas phase reservoir allowing the concentration of dissolved gas in the fluid to be maximized.

In certain instances, the enhanced concentration of gas may also assist in cleaning. According to some theories, pressure waves of sonic energy flowing past small or microbubbles tend to cause the microbubbles to oscillate rapidly, which in turn may result in small, localized changes in fluid velocity. The resulting localized fluid velocity gradients may remove particles from surface of substrates near these oscillating bubbles. Rapid oscillation of small bubbles caused by sonic pressure waves is often referred to as microstreaming within the fluid.

There are a number of ways of generating and introducing small bubbles or microbubbles within processing fluids. Approaches for introducing small bubbles can range from vigorous high shear mixing of fluids in a vessel with a liquid/fluid interface, to introduction of gas into a rapidly accelerating fluid using a venturi mixer.

For both of the approaches discussed above, chemical characteristics of the liquid and the gases dissolved therein, may impact not only the cavitation and microcavitation threshold pressure (sonic watt density), but also the ability of the megasonic fluid to form and retain small or micro-sized bubbles for sufficient lengths of time to facilitate useful processing. Such chemical characteristics include, but are not limited to, internal cohesive force between molecules or groups of molecules, dissolved solids, dissolved gases, surface tension, surface tension lowering agents, viscosity, and density. As one or more of these parameters are varied, alone or in combination with others, the nature of the resulting processing may change.

A third technique for softening the action of megasonic fluids relates to controlling the conditions under which processing takes place. Elevated or reduced operating pressures or pressures can be used to control not only the void fraction of the entrained micro bubbles, but rates of chemical reaction as well. This will allow control to be exercised over the degree of attenuation, as well as the over the influence of cavitation and microcavitation threshold pressure upon alternative processing fluids.

The following outlines general guidelines regarding the impact of changed processing conditions on the substrate damage. First, an increase in the cavitation threshold pressure may result in the collapse of bubbles with greater violence and energy intensity. This can in turn can lead to greater damage of small, fragile device structures.

Solubility of a gas in liquid is based on the concentration and pressure (partial pressure) of that gas above the liquid. Processing above or below atmospheric pressure may also control the dissolved gas content of partially soluble gases.

This higher gas solubility may not be absolute with every conceivable gas in every liquid. Some gases are only partially soluble, and soluble to different extents (e.g. nitrogen<oxygen<ozone) in DI water. Other gases are only partially soluble, but establish a chemical equilibrium as some of the gas is converted to another species, for example as carbon dioxide is converted to carbonic acid. Still other gases are completely miscible (HCL or HF) in DI water, but may exhibit a much different solubility response in liquids other than DI water, such as benzene.

A special atmosphere may need to be maintained in a closed vessel to maintain a high concentration of a particular gas above the liquid, in order to maintain a relatively high concentration of that gas dissolved in the liquid. For example, carbon dioxide dissolved in DI water at an elevated concentration due to elevated pressure, will bubble out when the pressure is reduced, or will diffuse out if left in an open container, with air replacing some of the carbon dioxide. As with the case of dissolved ozone allowing secondary reactions with oxidizable materials, dissolved carbon dioxide may form carbonic acid which can change process fluid pH and impact processing.

Processing at pressures above or below atmospheric pressure may be used to control the size and volume fraction of small bubbles in the fluid, controlling energy attenuation and modifying cavitation and microcavitation threshold pressure and the impact of changes in surface tension of the processing fluid.

Thus, the use of elevated/reduced pressure can modify the performance of various fluids by changing their ease of cavitation, any volume fraction occupied by bubbles, and the degree of gas saturation etc. as desired.

In addition to pressure, temperature is another parameter in determining gas solubility and general fluid properties that may be controlled to soften megasonic processing in accordance with embodiments of the present invention. Thus according to embodiments of the present invention, megasonic processing can operate at higher/lower temperatures, (i.e. closer to a boil temperature or farther away) to minimize megasonic damage.

As evidenced by the damage vs. temperature curves for various fluids (particularly in the case of DI water) the trends need not be totally linear. There can be maximums that occur over the traditional temperature ranges used for semiconductor wet processing. Therefore, purely from a damage perspective, operating at temperatures approaching the boiling point of a fluid may make it easier to form cavitation and microcavitation events producing less damage. This consideration should be balanced against the tendency of higher temperatures to lead to higher rates of various chemical reactions, including undesirable reactions.

Controlling temperature can be important not only to influence gas solubility, but also because other solution characteristics such as surface tension and corrosion behavior can be a function of temperature. Therefore, in accordance with still other embodiments of the present invention, solution characteristics such as surface tension of the processing fluid may be modified with the use of additives, alone or in conjunction with the three approaches outlined above.

While most megasonic processing takes place in liquid baths, this is not required by the present invention. Alternative embodiments can be utilized in single wafer processing equipment, where a thin liquid layer is formed on the substrate surface and megasonic energy is applied through a liquid meniscus. Yet other alternative embodiments in accordance with the present invention may use spray processing as another process variable to influence the "hardness" of megasonic fluids and the resulting damage to substrate features.

Still other alternative embodiments in accordance with the present invention may use parameters of the applied sonic energy to influence the softness of a processing fluid, in combination with one of the above-described approaches. Examples of such sonic energy parameters which may be controlled include, but are not limited to, the frequency, phase, power density, and duration of the applied energy.

In accordance with further alternative embodiments of the present invention, marangoni or surface tension gradient drying may be accomplished by producing a surface layer enriched in a material having a lower surface tension (often a dissolved gas), over a bulk fluid through which the substrate is moved. This movement causes residual water droplets to be drawn off the surface of the substrate into the bulk fluid. In accordance with certain embodiments, alcohol/water mixtures could be used to not only reduce damage, but also aid in the drying of substrates without leaving watermarks, or leaving fewer watermarks.

For example, mixtures of alcohol and water, especially if on top or where the surface layer is enriched in the alcohol, will exhibit a lower surface tension than the bulk fluid. When the bulk fluid is comprised of an alcohol/water mixture, that bulk solution will exhibit a lower surface tension than pure water.

While removing a substrate from such a mixture is not exactly like moving it through an enriched layer. By virtue of the reduced surface tension alone, it is easier to pull out the substrate in a more nearly dry state than just out of water alone. The lower the surface tension, the less the tendency to leave large liquid drops behind on the substrate surface or the formation of watermarks.

The large liquid drops may take a long time to evaporate because of their relatively small surface area to volume ratio. When liquid drops stay on a surface longer, they have longer to etch surfaces. The material etched (dissolved) then is deposited back onto the substrate surface as the watermark when the drop finally evaporates. If the processing fluid tended to form more of a very thin sheet of liquid on the substrate surface, rather than large drops, the liquid could evaporate relatively quickly owing to the large ratio of surface area to liquid volume, and watermarks would be much less likely to form.

Moreover, once processing in an alcohol/water mixture in accordance with an embodiment of the present invention has occurred with less damage to the substrate, the concentration of the surface layer of the bath could be elevated when the substrate is removed. Serendipitously, better drying may thus be achieved in combination with processing with less damage.

Although the invention has been described in terms of preferred methods and structures, it will be understood to those skilled in the art that many modifications and alterations may be made to the disclosed embodiments without departing from the invention. Hence, these modifications and alterations are intended to be considered as within the spirit and scope of the invention as defined by the appended claims.

What is claimed is:

1. A method of processing a substrate, said method comprising the steps of:
   placing at least one substrate into a process vessel;
   making contact between at least a part of the substrate and at least a part of a vibration member;
   introducing at least one processing fluid into the processing vessel;
   contacting at least a part of the substrate with at least one of the processing fluids; and
   applying megasonic energy, wherein the applying megasonic energy step occurs at least one of before, during and after the introducing processing fluid step, wherein at least a part of the back side of the substrate contacts the vibration member.

2. The method of claim 1 further comprising varying a parameter of the applied megasonic sonic energy selected from a phase, a frequency, a power, and a pulse width.

3. An apparatus configured to process a substrate with megasonic energy, the apparatus comprising:
   a processing region configured to receive a processing fluid;
   a megasonic energy source; and
   a vibration member in contact with the megasonic energy source and oriented within a critical angle range of between about 18–58° relative to an element positioned within the processing region, in order to transfer the megasonic energy across the element.

4. The apparatus of claim 3 wherein the megasonic energy source comprises one of a piezoelectric crystal, a mechanical transducer, and a megasonic nozzle.

5. The apparatus of claim 3 wherein:
   the element comprises a substrate to be processed; and
   the apparatus further comprises a mechanism configured to impart motion to the substrate relative to at least one of the processing fluid and a substrate holder.

6. The apparatus of claim 3 further comprising at least one of a reflecting surface and a gas/liquid interface configured to reflect the megasonic energy toward the substrate.

7. The apparatus of claim 3 wherein the processing region is enclosed within a plurality of walls.

8. The apparatus of claim 7 wherein the plurality of walls allow processing at other than atmospheric pressure within the processing region.

9. The apparatus of claim 3 wherein the element is oriented relative to the vibration member at the critical angle range of between about 25–50°.

10. The apparatus of claim 9 wherein the element is oriented relative to the vibration member at the critical angle range of between about 30–45°.

11. The apparatus of claim 3 wherein the element comprises a substrate configured to be at least one of immersed in the processing fluid and sprayed with the processing fluid.

12. The apparatus of claim 3 wherein the megasonic energy source is configured to vary a parameter of the energy selected from a phase, a frequency, a power, and a pulse width.

13. A method of processing a substrate comprising the steps of:
    placing at least one substrate into a processing vessel;
    introducing at least one processing fluid into the processing vessel to contact at least a part of the substrate; and
    applying megasonic energy at between about 18–58° relative to a surface of the substrate such that a substantial portion of the megasonic energy is transferred across the substrate, wherein the introducing of a processing fluid step occurs at least one of before, during and after the applying megasonic energy step.

14. The method of claim 13 wherein the megasonic energy is applied at an angle of between about 30–45°.

15. The method of claim 13 wherein the introduction of processing fluid causes at least a part of the substrate to be wetted by at least one of submerging, spraying, and condensing of a vapor.

16. The method of claim 13 wherein there is relative motion between a substrate, and at least one of the processing fluid, the processing vessel and the angles of incidence of megasonic energy with a substrate.

17. The method of claim 16 wherein the relative motion comprises at least one of rotation, vibration and lateral movement.

18. The method of claim 16 wherein the relative motion of the substrate causes a change in the energy field contacting a second substrate.

19. The method of claim 13 wherein a thickness of the substrate is +/−30% of an even multiple one-quarter wavelength ($n\lambda/4$, n=2, 4, 6 . . . ) of the applied megasonic energy.

20. The method of claim 13 wherein radiation is applied at least one of prior to, during, and after the applying megasonic energy.

21. The method of claim 20 wherein the radiation is comprised of at least one of microwave, ultraviolet, infrared and electromagnetic induction.

22. The method of claim 13 wherein an electrochemical processing occurs at least one of prior to, during and after the applying megasonic energy.

23. A method of claim 13 wherein the process vessel is pressurized by at least one of a gas, a processing liquid and a fluid flow.

24. A method of claim 23 wherein the process vessel is pressurized at least one of prior to, during and after the application of megasonic energy.

25. The method of claim 23 wherein the process vessel is pressurized to a maximum pressure in the range of 1 to 500 atmospheres.

26. The method of claim 13 wherein a fluid velocity generally parallel to the substrate surface is created at least one of prior to, during and after the applying megasonic energy.

27. The method of claim 13 further comprising varying a parameter of the applied megasonic energy selected from a phase, a frequency, a power, and a pulse width.

28. A method of processing a substrate comprising the steps of:
placing at least one substrate into a processing vessel;
introducing at least one processing fluid into the processing vessel to contact at least a part of the substrate; and
applying megasonic energy at between about 18–58° relative to a surface of the substrate such that a substantial portion of the megasonic energy is transferred across the substrate, wherein the introducing of a processing fluid step occurs at least one of before, during and after the applying megasonic energy step, wherein a fluid velocity generally parallel to the substrate surface is created at least one of prior to, during and after the applying megasonic energy, and wherein the fluid velocity causes the megasonic wave to impact the substrate surface at an angle between a first critical angle and a second critical angle.

29. The method of claim 28 further comprising varying a parameter of the applied megasonic energy selected from a phase, a frequency, a power, and a pulse width.

30. A method of processing a substrate comprising the steps of:
placing at least one substrate into a processing vessel;
introducing at least one processing fluid into the processing vessel to contact at least a part of the substrate; and
applying megasonic energy at between about 18–58° relative to a surface of the substrate such that a substantial portion of the megasonic energy is transferred across the substrate, wherein the introducing of a processing fluid step occurs at least one of before, during and after the applying megasonic energy step, wherein a fluid velocity generally parallel to the substrate surface is created at least one of prior to, during and after the applying megasonic energy, and wherein the fluid velocity results from at least one of the bulk fluid movement and acoustic streaming caused by a second megasonic energy source.

31. The method of claim 30 further comprising varying a parameter of the applied megasonic energy selected from a phase, a frequency, a power, and a pulse width.

32. A method of processing a substrate comprising the steps of:
placing at least one substrate into a processing vessel;
introducing at least one processing fluid into the processing vessel to contact at least a part of the substrate; and
applying megasonic energy at between about 18–58° relative to a surface of the substrate such that a substantial portion of the megasonic energy is transferred across the substrate, wherein the introducing of a processing fluid step occurs at least one of before, during and after the applying megasonic energy step, wherein the megasonic energy is delivered to the substrate from at least one of an megasonic nozzle, a vibration member in direct contact with at least part of the substrate and a vibration member transferring megasonic energy through a fluid medium to contact the substrate.

33. The method of 32 further comprising varying a parameter of the applied megasonic energy selected from a phase, a frequency, a power, and a pulse width.

34. An apparatus configured to process a substrate with megasonic energy, the apparatus comprising:
a processing region configured to receive a processing fluid;
a megasonic energy source; and
a wedge vibration member having a first face in contact with and configured to receive energy from the megasonic energy source, and having a second face oriented at an angle relative to the first face and configured to emit energy received from the megasonic energy source to a substrate positioned within the processing region, wherein the wedge vibration member exhibits other than a triangular cross-section.

35. The apparatus of claim 34 wherein the megasonic energy source is configured to vary a parameter of the energy selected from a phase, a frequency, a power, and a pulse width.

36. An apparatus configured to process a substrate with megasonic energy, the apparatus comprising:
a processing region configured to receive a processing fluid;
a megasonic energy source; and
a wedge vibration member having a first face in contact with and configured to receive energy from the megasonic energy source, and having a second face oriented at an angle relative to the first face and configured to emit energy received from the megasonic energy source to a substrate positioned within the processing regions wherein the wedge vibration member includes an interior chamber.

37. The apparatus of claim 36 wherein the interior chamber is in fluidic communication with a orifice located in the second face.

38. The apparatus of claim 36 wherein the megasonic energy source is configured to vary a parameter of the energy selected from a phase, a frequency, a power, and a pulse width.

39. An apparatus configured to process a substrate with megasonic energy, the apparatus comprising:
a processing region configured to receive a processing fluid;
a megasonic energy source; and
a wedge vibration member having a first face in contact with and configured to receive energy from the megasonic energy source, and having a second face oriented at an angle relative to the first face and configured to emit energy received from the megasonic energy source to a substrate positioned within the processing region, wherein the wedge vibration member comprises five or greater faces.

40. The apparatus of claim 39 wherein the megasonic energy source is configured to vary a parameter of the energy selected from a phase, a frequency, a power, and a pulse width.

41. An apparatus configured to process a substrate with megasonic energy, the apparatus comprising:
a processing region configured to receive a processing fluid;
a megasonic energy source; and
a wedge vibration member having a first face in contact with and configured to receive energy from the megasonic energy source, and having a second face oriented at an angle relative to the first face and configured to emit energy received from the megasonic energy source to a substrate positioned within the processing region, the apparatus further comprising a second wedge vibration member having a first face in contact with and configured to receive energy from a second megasonic energy source, and having a second face oriented at an angle relative to the first face and configured to emit energy received from the second megasonic energy source to the substrate.

42. The apparatus of claim 41 wherein the first megasonic energy source is configured to vary a parameter selected from a phase, a frequency, a power, and a pulse width of the emitted energy, and the second megasonic energy source is configured to vary a parameter selected from a phase, a frequency, a power, and a pulse width of the emitted energy.

43. A method of processing a substrate comprising the steps of:
placing a substrate into a processing region;
introducing at least one processing fluid to the substrate;
contacting at least a part of a vibration member comprising a plate to at least part of a first face of a wedged shaped vibration member; and
applying megasonic energy to the substrate from a second face of the wedge shaped vibration member, wherein the applying megasonic energy step occurs at least one of before, during and after the introducing a processing fluid step, wherein the substrate is in contact with the second face.

44. A method of claim 43 wherein the angle between the first face and the second face of the wedge shaped vibration member is between a first critical angle and a second critical angle.

45. A method of claim 44 wherein a first critical angle is 90° or less.

46. A method of claim 43 wherein the angle between a first face and a second face of the wedge shaped vibration member causes at least one of a shear wave and a surface wave to be formed on the second face when megasonic energy is applied.

47. The method of claim 43 further comprising varying a parameter of the applied megasonic energy selected from a phase, a frequency, a power, and a pulse width.

48. A method of processing a substrate comprising the steps of:
placing a substrate into a processing region;
introducing at least one processing fluid to the substrate;
contacting at least a part of a vibration member comprising a plate to at least part of a first face of a wedged shaped vibration member; and
applying megasonic energy to the substrate from a second face of the wedge shaped vibration member, wherein the applying megasonic energy step occurs at least one of before, during and after the introducing a processing fluid step, wherein a substrate is spaced apart from the plate vibration member and held one of parallel to and at an angle to the plate vibration member.

49. A method of claim 48 wherein at least a part of the gap between the substrate and the plate vibration member is filled with a processing fluid.

50. A method of claim 48 wherein the processing fluid is comprised of at least one of a gas, a liquid, a solid and combinations thereof.

51. A method of claim 48 wherein the gap is less than 1 meter.

52. A method of claim 48 wherein the processing fluid wets at least a part of the substrate by at least one of submerging, spraying and condensing a vapor or gas onto the substrate.

53. A method of claim 48 wherein the processing region is pressurized at least one of prior to, during and after the application of megasonic energy.

54. The method of claim 53 wherein the processing region is pressurized to between about 1 to 500 atmospheres.

55. The method of claim 48 further comprising varying a parameter of the applied megasonic energy selected from a phase, a frequency, a power, and a pulse width.

* * * * *